(12) United States Patent
Ouyang et al.

(10) Patent No.: US 11,037,772 B2
(45) Date of Patent: Jun. 15, 2021

(54) METHODS FOR ANALYZING A TISSUE SAMPLE

(71) Applicant: Purdue Research Foundation, West Lafayette, IN (US)

(72) Inventors: Zheng Ouyang, West Lafayette, IN (US); Yu Xia, West Lafayette, IN (US); Xiaoxiao Ma, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 784 days.

(21) Appl. No.: 15/577,516

(22) PCT Filed: May 27, 2016

(86) PCT No.: PCT/US2016/034707
§ 371 (c)(1),
(2) Date: Nov. 28, 2017

(87) PCT Pub. No.: WO2016/196312
PCT Pub. Date: Dec. 8, 2016

(65) Prior Publication Data
US 2018/0294148 A1    Oct. 11, 2018

Related U.S. Application Data

(60) Provisional application No. 62/168,033, filed on May 29, 2015.

(51) Int. Cl.
*H01J 49/04* (2006.01)
*G01N 1/30* (2006.01)
(Continued)

(52) U.S. Cl.
CPC ............ *H01J 49/0409* (2013.01); *G01N 1/30* (2013.01); *G01N 1/405* (2013.01); *G01N 30/00* (2013.01);
(Continued)

(58) Field of Classification Search
None
See application file for complete search history.

(56) References Cited

U.S. PATENT DOCUMENTS

| 3,435,081 A | 3/1969 | Wilks et al. |
| 5,855,850 A | 1/1999 | Sittler |

(Continued)

FOREIGN PATENT DOCUMENTS

| JP | 2001-255317 A | 9/2001 |
| JP | 2005-147957 A | 6/2005 |

(Continued)

OTHER PUBLICATIONS

Ma, Xiaoxiao et al., "Identification and quantification of lipid C=C location isomers . . . ", PNAS, 2016, vol. 113, No. 10, p. 2573-2578. (Year: 2016).*

(Continued)

*Primary Examiner* — Lyle Alexander
*Assistant Examiner* — Bryan Kilpatrick
(74) *Attorney, Agent, or Firm* — Brown Rudnick LLP; Adam M. Schoen

(57) ABSTRACT

The invention generally relates to methods for analyzing a tissue sample. In certain aspects, the invention provides methods that involve obtaining a tissue sample including an unsaturated compound, conducting a radical reaction on the tissue sample that targets a carbon-carbon double bond within the unsaturated compound to thereby produce a plurality of compound isomers, subjecting the plurality of compound isomers to mass spectrometry analysis to identify a location of the carbon-carbon double bond within the unsaturated compound, and quantifying the plurality of compound isomers in order to distinguish normal tissue from diseased tissue.

20 Claims, 138 Drawing Sheets

(51) Int. Cl.
  *G01N 33/92* (2006.01)
  *G01N 30/00* (2006.01)
  *G01N 1/40* (2006.01)
  *G01N 30/72* (2006.01)
  *G01N 30/88* (2006.01)
  *H01J 49/00* (2006.01)
  *A61B 10/02* (2006.01)
  *G01N 30/02* (2006.01)

(52) U.S. Cl.
  CPC ......... *G01N 30/7233* (2013.01); *G01N 30/88* (2013.01); *G01N 33/92* (2013.01); *H01J 49/0031* (2013.01); *H01J 49/04* (2013.01); *A61B 10/0241* (2013.01); *G01N 2030/027* (2013.01); *G01N 2030/8813* (2013.01); *G01N 2458/15* (2013.01); *H01J 49/0004* (2013.01)

(56) References Cited

U.S. PATENT DOCUMENTS

| | | |
|---|---|---|
| 8,304,718 B2 | 11/2012 | Ouyang et al. |
| 8,785,846 B2 | 7/2014 | Ouyang et al. |
| 2010/0267148 A1 | 10/2010 | Blanksby et al. |
| 2013/0210917 A1 | 8/2013 | Freeman et al. |
| 2014/0256814 A1 | 9/2014 | Miller |

FOREIGN PATENT DOCUMENTS

| | | |
|---|---|---|
| WO | 2007/126141 A1 | 11/2007 |
| WO | 2014076556 A1 | 5/2014 |
| WO | 2014/120411 A1 | 8/2014 |

OTHER PUBLICATIONS

Extended European Search Report, Application No. 16804133.3, dated Oct. 24, 2018, 8 pages.
Lin, 2015, Instrumentation and development of a mass spectrometry system for the study of gas-phase biomolecular on reactions, Purdue e-Pubs.
Zhang, 2017, Ambient Ionization and Miniature Mass Spectrometry Systems for Disease Diagnosis and Therapeutic Monitoring, Theranostics, 7(12)2968-2981.
Office Action, JP Application No. 2017-561885 dated Jan. 23, 2020, 9 pages.
Akoto, 2008, Improved fatty acid detection in micro-algae meiofauna species using a direct thermal desorption interface combined with comprehensive gas chromatography-time-of-flight mass spectrometry, J. Chromatogr. A, 1186:254-261.
Allen, 2007, Lipid raft microdomains and neurotransmitter signalling, Nature Reviews Neuroscience, 8:128-140.
Artman, 1964, Interactions of Fats and Fatty Acids as Energy Sources for the Chick, Poultry. Sci, 43:994-1004.
Azrad, 2013, Current evidence linking polyunsaturated fatty acids with cancer risk and progression, Frontiers in Oncology, Cancer Molecular Targets and Therapeutics, 3(224):1-12.
Bechara, 2015, A subset of annular lipids is linked to the flippase activity of an ABC transporter, Nat Chem 7:255-262.
Blanksby, 2010, Advances in Mass Spectrometry for Lipidomics. Annual Review of Analytical Chemistry, 3:433-465.
Bond, 2016, Fatty Acid Desaturation and Elongation in Mammals, Biochemistry of Lipids, Lipoproteins and Membranes, Elsevier, Boston, 6:185-208.
Cervilla, 1983, Determination of doublebond position in monounsaturated fatty acids by mass-analyzed ion-kinetic-anergy spectrometry/collision-induced dissociation after chemical ionization of their amino alcohol derivatives, Analytical Chemistry 55:2100-2103.
Corda, 2013, Lipid signalling in health and disease, Febs Journal 280:6280-6280.
Currie, 2013, Cellullar Fatty Acid Metabolism and Cancer, Cell Metab, 18:153-161.

Eberlin, 2013, Ambient mass spectrometry for the intraoperative molecular diagnosis of human brain tumors, PNAS, 110(5):1611-1616.
Eikel, 2011, Liquid Extraction Surface Analysis Mass Spectrometry (LESA-MS) as a Novel Profiling Tool for Drug Distribution and Metabolism Analysis: The Terfenadine Example, Rapid Commun in Mass Spectrom, 25 (23):3587-3596.
Ellis, 2012, Using ambient ozone for assignment of double bond position in unsaturated lipids. Analyst, 137:1100-1110.
Fico, 2007, Miniaturization and Geometry Optimization of a Polymer-Based Rectilinear Ion Trap, Anal. Chem., vol. 79: pp. 8076-8082.
Francis, 1981, Alkylthiolation for the determination of double-bond position in unsaturated fatty acid esters, Chem. Phys. Lipids, 29:369-374.
Freilich, 1981, Observation of the 1,4 biradical in the Paterno-Buchi reaction, J. Am. Chem. Soc., 103:6255-6257.
Gao, 2006, Handheld Rectilinear Ion Trap Mass Spectrometer, Z. Anal. Chem. 78:5994-6002.
Gao, 2008, Design and characterization of a Multisource Hand-Held Tandem Mass Spectrometer, Anal. Chem., 80:7198-7205.
German, 2007, Lipidomics and lipid profiling in metabolomics, Curr. Opin. Lipidol., 18:66-71.
Groeger, 2010, "Cyclooxygenase-2 Generates Anti-Inflamatory Mediators from Omega-3 Fatty Acids" Nat Chem Biol, 6(6):433-41.
Groeger, 2010, Cyclooxygenase-2 generatesanti-inflammatory mediators from omega-3 fatty acids, Nat Chem Biol 6:433-441.
Han, 2005, Shotgun lipidomics: electrospray ionization mass spectrometric analysis and quantitation of cellular lipidomes directly from crude extracts of biological samples, Mass spectrometry Reviews, 24:367-412.
Harrison, 1996, Direct Mass Spectrometric Analysis of Ozonides:? Application to Unsaturated Glycerophosphocholine Lipids, Analytical Chemistry, 68:3224-3230.
Holloway,1964, Synthesis of fattyacids in animal tissues. II. The occurrence and biosynthesis of cis-vaccenic acid, The Journal of Biological Chemistry, 239:2489-95.
Holthuis, 2014, Lipid landscapesand pipelines in membrane homeostasis, Nature 510:48-57.
Hou, 2011, Sampling Wand for an Ion Trap Mass Spectrometer, Anal. Chem., 83:1857-1861.
Hsu, 1999, Structural characterization of triacylglycerols as lithiated adducts by electrospray ionization mass spectrometry using low-energy collisionally activated dissociation on a triple stage quadrupole instrument, J. Am. Soc. Mass Spectrom, 10:587-599.
International Preliminary Report on Patentability dated Dec. 5, 2017 for International Application No. PCT/US2016/034707, 8 Pages.
International Search Report and Written Opinion of the International Searching Authority dated Oct. 24, 2016 for International Application No. PCT/US2016/034707, 12 Pages.
Ip, 1997, Review of the effects of trans fatty acids, oleic acid, n-3 polyunsaturated fatty acids, and conjugated linoleic acid on mammary carcinogenesis in animals, Am. J. Clin. Nutr., 66:1523S-1529S.
Jacobson, 2007, Lipid rafts: at a crossroad between cell biology and physics. Nature Cell Biology 9:7-14.
Johnson, 1992, Monoenoic Fatty Acids in Human Brian Lipids: Isomer Identification and Distribution, Lipids, 27:177-180.
Kane, 1979, Fatty Acids as Energy Sources for Culture of One-Cell Rabbit Ova to Viable Morulae, Biol. Reprod, 20:323-332.
Kozlowski, 2015, Combining liquid chromatography with ozone-induced dissociation for the separation and identification of phosphatidylcholine double bond isomers. Anal. Bioanal. Chem., 407:5053-5064.
Kwon, 2011, Simple Determination of Double-Bond Positions in Long-Chain Olefins by Cross-Metathesis. Angew. Chem. Int. Ed., 50:8275-8278.
Laganowsky, 2014, Membrane proteins bind lipids selectively to modulate their structure and function. Nature 510:172-175.
Lam, 1976, M.S.F. Fatty acids, part 5*: A study of the oxymercurationdemercuration reaction of some C11-unsaturated fatty esters and methyl octadec-cis-10-en-5-ynoate, Chem. Phys. Lipids, 16:181-194.

(56) References Cited

OTHER PUBLICATIONS

Laskin, Tissue Imaging Using Nanospray Desorption Electrospray Ionization Mass Spectrometry, Anal. Chem 84:141-148.
Leslie, 2011, Do Lipid Rafts Exist? Science, 334:1046-1047.
Lingwood, 2010, Lipid Rafts as a Membrane-Organizing Principle, Science 327:46-50.
Lombard, 2012, The early evolution of lipid membranes and the three domains of life, Nat Rev Micro, 10:507-515.
Lv, 2012, Identification of possible biomarkers for breast cancer from free fatty acid profiles determined by GC-MS and multivariate statistical analysis, Clin. Biochem, 45:127-133.
Ma, 2014, Radical Mass Spectrometry as a New Frontier for Bioanalysis, Angew. Chem., 126,:2630-2634.
Ma, 2014, Pinpointing Double Bonds in Lipids by Paternò-Büchi Reactions and Mass Spectrometry, Angewandte Chemie International Edition, 53:2592-2596.
Ma, 2016, Identification and quantitation of lipid C=C location isomers: A shotgun lipidomics approach enabled by photochemical reaction, PNAS, 113:2573-2578.
Minnikin, 1978 Location of double bonds and cyclopropane rings in fatty acids by mass spectrometry. Chem. Phys. Chem. Lipids, 21:313-347.
Mulligan, 2006, Desorption electrospray ionization with a portable mass spectrometer: in situ analysis of ambient surfaces, Chem Comm, et al., Chemical Communications, 1709-1711.
Murphy, 2015, Tandem Mass Spectrometry of Lipids: Molecular Analysis of Complex Lipids, The Royal Society of Chemistry, 1-39.
Nemes, 2010, Laser Ablation Electrospray Ionization for Atmospheric Pressure Molecular Imaging Mass Spectrometry, Methods Mol Biol, 2010, 656:159-171.
Okusa, 2014. Effect of pressure on the selectivity of polymeric C18 and C30 stationary phases in reversed-phase liquid chromatography. Increased separation of isomeric fatty acid methyl esters, triacylglycerols, and tocopherols athigh pressure, Journal of Chromatography A, 1339:86-95.
Ouyang, 2009, Handheld Miniature Ion Trap Mass Spectrometers, Anal. Chem., 81:2421-2425.
Ouyang, 2009, Miniature Mass Spectrometers, Annual Review of Analytical Chemistry, 2:187-214.
Paul, Kinetics and Cidep of radicals During Photoreduction of Acetone with 2-Propanol by Effect Modulated ESR Spectroscopy, Chem. Phys., 40:265-274.
Pham, 2012, Differentiation of Complex Lipid Isomers by Radical-Directed Dissociation Mass Spectrometry, Anal Chem, 84:7525-7532.
Pham, 2013, Rapid differentiation of isomeric lipids by photodissociation mass spectrometry of fatty acid derivatives, Rapid Commun. Mass Spectrom, 27:805-815.
Phillips, 2009, Emerging roles for lipids in shaping membrane-protein function, Nature 459:379-385.
Precht, 2000, Identification and quantitation of cis/trans C16:1 and C17:1 fatty acid positional isomers in German human milk lipids by thin-layer chromatography and gas chromatography/mass spectrometry, Eur. J. Lipid Sci. Technol, 102:102-113.
Quehenberger, 2010, Lipidomics reveals a remarkable diversity of lipids in human plasma, J. Lipid. Res., 51:3299-3305.
Quehenberger, High sensitivity quantitative lipidomics analysys of fatty acids in biological samples by gas chromatography-mass spectrometry, Biochimica et Biophysica Acta (BBA)—Molecular and Cell Biology of Lipids, 1811:648-656.
Radcliffe, 2004, Fatty acid composition of serum, adipose tissue, and liver in rats fed diets containing cornoil or cottonseed oil., Plant foods for human nutrition, 59:73-77.
Roongta, 2011, Cancer Cell Dependence on Unsaturated Fatty Acids Implicates Stearoyl-CoA Desaturase as a Target for Cancer Therapy, Molecular Cancer Research, 9:1551-1561.
Rustan, 2001, Fatty Acids: Structures and Properties, eLS, John Wiley & Sons, Ltd, 1-7.

Sanders, 2009, Hand-held Mass Spectrometer for Environmentally Relevant Analytes Using a Variety of Sampling and Ionization Methods, Euro. J. Mass Spectrom,16:11-20.
Seelig, 1980, Lipid conformation in model membranes and biological membranes, Q. Rev. Biophys, 13:19-61.
Shevchenko, 2010, Lipidomics: coming to grips with lipid diversity, Nat. Rev. Mol. Cell Bio. 11:593-598.
Shiea, 2005, Electrospray-Assisted Laser Desorption/Ionization Mass Spectrometry for Direct Ambient Analysis of Solids, Rapid Communications in Mass Spectrometry, 19(24):3701-3704.
Sokol, 2011, Miniature mass spectrometer equipped with electrospray and desorption electrospray ionization for direct analysis of organics from solids and solutions, Int. J. Mass Spectrom., 306:187-195.
Stinson, 2016, A method of coupling the Paterno-Buchi reaction with direct infusion ESI-MS/MS for locating the C=C bond in glycerophospholipids, Analyst, 141:3696-3704.
Sun, 2014, Elucidationof phosphatidylcholine isomers using two dimensional liquid chromatography coupled in-line with ozonolysis mass spectrometry, J Chromatogr A 1351:37-45.
Thomas, 2005, Ozonolysis of Phospholipid Double Bonds during Electrospray Ionization:?A New Tool for Structure Determination, J. Am. Chem. Soc., 128:58-59.
Thomas, 2007, Ozone-Induced Dissociation:?Elucidation of Double Bond Position within Mass-Selected Lipid Ions, Analytical Chemistry, 80:303-311.
Tomer, 1983, Location of double-bond position in unsaturated fatty acids by negative ion MS/MS, J. Am. Chem. Soc., 105:5487-5488.
Van Meer, 2008, Membrane lipids: where they are and how they behave, Nature Reviews Molecular Cell Biology, 9:112-124.
Wang, 2013, Fatty Acidomics: Global Analysis of Lipid Species Containing a Carboxyl Group with a charge-Remote Fragmentation-Assisted Approach, Anal. Chem., 85, 9312-9320.
Wang, 2016, Novel advances in shotgun lipidomics for biology and medicine, Prog. Lipid. Res., 61, 83-108.
Wymann, 2008, Lipid signalling in disease, Nat Rev Mol Cell Biol, 9(2):162-176.
Xiong, 2014, Gas chromatography-mass spectrometry-based profiling of serum fatty acids in acetaminophen-induced liver injured rats, J. Appl. Toxicol, 34:149-157.
Xu, 2010, Miniaturization of Mass Spectrometry Analysis Systems, JALA, 15(6):433-439.
Yang, 1967, Mechanism of the Paterno-Buchi reaction, J. Am. Chem. Soc. 89,:5465-5466.
Yang, 2007, Enhancement of the LC/MS Analysis of Fatty Acids through Derivatization of Stable Isotope Coding, Anal. Chem., 79:5150-5157.
Yang, 2011, Identification and Quantitation of Unsaturated Fatty Acid Isomers by Electrospray Ionization Tandem Mass Spectrometry: A Shotgun Lipidomics Approach, Analytical Chemistry, 83:4243-4250.
Yang, 2013, Identification and Quantitation of Fatty Acid Double Bond Positional Isomers: A Shotgun Lipidomics Approach Using Charge-Switch Derivatization, Anal. Chem. 85:9742-9750.
Zahradnickova 2014 Cost effective, robust, and reliable coupled separation techniques for the identification and quantification of phospholipids in complex biological matrices: Application to insects, J. Sep. Sci. 37:2062-2068.
Zemski Berry, 2011, MALDI Imaging of Lipid Biochemistry in Tissues by Mass Spectrometry, Chem. Rev. 111:6491-6512.
Zhang, 2008, Membrane lipid homeostasis in bacteria, Nature Reviews Microbiology 6:222-233.
Zhang, 2011, Facile Determination of Double Bond Position in Unsaturated Fatty Acids and Esters by Low Temperature Plasma Ionization Mass Spectrometry. Analytical Chemistry 83:4738-4744.
Zhang, 2014, Decreased serum levels of free fatty acids are associated with breast cancer, Clinica Chimica Acta, 437:31-37.
Examination Report issued in European Application No. 16804133. 3, dated Oct. 20, 2020, 6 pages.
Jelonek, 2013, Cancer biomarkers and mass spectrometry-based analyses of phospholipids in body fluids., Clinical Lipidology, vol. 8, No. 1, pp. 137-150.

* cited by examiner

PS 18:0-18:1

FA 18:1

Before sampling     After sampling for 50 times

16:1 (n-7), 18:2 (n-6), 20:4 (n-6)
22:4 (n-6), 22:5 (n-6), 22:6 (n-3)

| | | |
|---|---|---|
| PC 16:0/16:1 | LPE 20:4 | PS 18:0/20:4 |
| PC 16:0/18:2 | PE 16:0/20:4 | PS 18:1/22:4 |
| PC 18:0/18:2 | PE 18:0/20:4 | LPS 22:6 |
| LPC 20:4 | LPE 22:4 | PS 16:0/22:6 |
| PC 16:0/20:4 | PE 22:4/22:6 | PS 18:0/22:6 |
| PC 16:0/22:4 | PE 18:0/22:4 | LPI 20:4 |
| LPC 22:6 | LPE 22:6 | PI 16:0/20:4 |
| PC 16:0/22:6 | PE 16:0/22:6 | PI 18:1/20:4 |
| PC 18:0/22:6 | PE 18:0/22:6 | |
| | LPE 22:5 | |

METHODS FOR ANALYZING A TISSUE SAMPLE

RELATED APPLICATION

The present application is a 35 U.S.C. § 371 national phase application of PCT/US16/34707, filed May 27, 2016, which claims the benefit of and priority to U.S. provisional application Ser. No. 62/168,033, filed May 29, 2015, the content of each of which is incorporated by reference herein in its entirety.

GOVERNMENT SUPPORT

This invention was made with government support under GM106016 awarded by the National Institute of Health and CHE1308114 awarded by the National Science Foundation. The government has certain rights in the invention.

FIELD OF THE INVENTION

The invention generally relates to methods for analyzing a tissue sample.

BACKGROUND

Lipids are structurally diverse molecules in that they consist of a variety of different headgroups, backbones and hydrophobic acyl chains. They serve as building blocks of the plasma membranes and play critical roles in signal transduction and energy storage in biological systems. Variations in the headgroup, acyl chain length and degree of unsaturation in lipids are exploited to modulate membrane properties and functions, such as viscosity lipid-protein interactions and lipid-lipid interactions, all of which are important to normal cellular functions. Correspondingly, lipid profiles are increasingly used as markers to probe disease states in diagnostic practices, owing to disease-bound alterations in overall lipid composition.

However, with lipid profiling using mass spectrometry, isomeric and/or isobaric lipids appear as a single peak, presenting difficulties in spectra interpretation and acquisition of detailed composition information, such as the amounts of lipid species contained within a composition. This has far-reaching significance, as existing studies show that the number and position(s) of C=C(s) in acyl chains of lipids is biologically important (Groeger et al., Nat Chem Biol 6, 433-441 (2010); Lombard et al., Nat Rev Micro 10, 507-515 (2012); and Blanksby et al., Annual Review of Analytical Chemistry 3, 433-465 (2010)). For instance, phospholipids (PLs) with omega-6 and omega-3 fatty acyls can be converted in vivo to compounds with opposite biological activities (Groeger et al., Nat Chem Biol 6, 433-441 (2010)).

Gas chromatography (GC) and liquid chromatography (LC) are the traditional method that allows quantitation of lipids (and/or their C=C isomers). However, tedious sample preparation, specialized GC columns and time-consuming optimization of chromatographic conditions are necessary. Considering the large number and various types of lipids in a lipidome, methods that allow separation-free and non-discriminative structural characterization and quantitation are highly desirable. Offering superior sensitivity and specificity, mass spectrometry (MS) has now become the method of choice in lipid analysis, but the expansion of MS methods towards simultaneous full-structure characterization ("top-down" lipidomics) and quantitation of a whole lipidome have remained elusive. Compared with profiling of saturated lipids, analysis of unsaturated lipids faces challenges in two aspects: identification of the number and position(s) of C=C(s) and quantitation of lipid C=C isomers. The past two decades have witnessed the continuous development of chemical derivatization-based methods that succeeded in characterizing lipid C=C isomers. Few of them however were attempted towards quantitation of these isomers.

SUMMARY

Unsaturated lipids constitute a large proportion of total lipids in organisms, and their physical properties, chemical reactivity and bio-transformation are closely related to a variety of physiological and physiochemical functions. However, simultaneous identification and quantification of lipid C=C isomers, especially from complex mixtures, is currently challenging. The invention provides methods that allows global characterization and quantitation of lipid C=C isomers in tissues, by coupling radical reactions (e.g., Paternó-Büchi reaction) with tandem mass spectrometry. Using those methods, it has been demonstrated that in rats fatty acid (FA) 18:1 and C18:1-containing phospholipids all exist in two C=C isomeric forms: C18:1 n-7 and C18:1 n-9, the relative ratios of which, however, varied among lipid and tissue types. Significant differences in isomeric compositions of FA 18:1 and $C_{18:1}$-containing phosphocholines were observed between normal and cancerous breast tissues in mice. The claimed methods are well suited for quantitative shotgun lipidomics and contribute to advanced biological studies through accurate quantitation of the underlying unsaturated lipids.

In other aspects, methods of the invention can be applied for shotgun lipidomics. The lipids are extracted from tissue samples and then transferred into a solvent containing PB reagent. The solvent is transferred into a nanoESI tube. A UV light of proper wavelength is provided to facilitate the reaction. A spray ionization condition, such as a high voltage applied to the solvent, is established and ions are generated for the PB reaction products, which are subsequently mass analyzed using MS and tandem MS analysis.

In certain embodiments, methods of the invention can be used for online HPLC-MS. PB reagent is mixed into the elution of the HPLC. Part of the capillary connecting HPLC and MS is exposed to the UV light of proper wavelength to enable the reaction. The products in the solution are then ionized for analysis using MS and tandem MS.

As discussed above, methods of the invention can be used for quantitative analysis. The characteristic fragment ions obtain from CID of lipid PB product ions, i.e. neutral loss of PB reagent, C=C diagnostic ions will be used for quantitation. When acetone is used as PB reagent, neutral loss scan (NLS) of 58 Da will be used for quantitation of fatty acids, glycerol lipids, and sterol lipid consisting of C=C double bond. For case of lipid C=C isomer quantitation, the ion intensity of C=C diagnostic ions are used for relative or absolute quantitation.

In certain embodiments, methods of the invention can be used for analysis of in vivo tissue. A needle is used to touch the tissue sample and then inserted into a nanoESI tube containing a solvent and PB reagent. The lipids sampled by the needle are dissolved in the solvent. A light of proper wavelength is provided to enable the PB reaction and a spray condition is established to ionize the reaction products, which are subsequently analyzed using MS and tandem MS. Such methods may be based on extraction spray, which is described for example in International patent application publication number WO 2014/120411 to Purdue Research Foundation, the content of which is incorporated by reference herein in its entirety.

Methods of the invention can also be used for MS imaging. In MALDI-MS, the reaction reagent can be mixed in the MALDI matrix or sprayed onto the tissue separately. The reaction can be enabled when the UV laser for MADLI is applied for desorption ionization. A separate light source in addition to the MALDI laser can also be provided for the PB-reaction only. The method described above applies for ambient MS methods using laser ablation for surface analysis, such as laser ablation electrospray ionization (LAESI, Methods Mol Biol. 2010; 656:159-71. doi: 10.1007/978-1-60761-746-4_9) and electrospray laser desorption ionization Rapid Commun Mass Spectrom. 2005; 19(24):3701-4). Ambient MS for surface analysis using methods such as nanoDESI (Anal Chem. 2012 Jan. 3; 84(1):141-8. doi: 10.1021/ac2021322) or liquid extraction surface analysis (LESA, Rapid Commun Mass Spectrom. 2011 Dec. 15; 25(23):3587-96. doi: 10.1002/rcm.5274). In these methods, one channel (Channel I) is used to deliver solvent to extract the chemical compounds and another channel (Channel II) is used to transfer the solvent with the analytes toward the MS inlet, where a ionization condition is established to ionize the extracted analytes. The PB reaction can be implemented by mixing the PB reagents into the extraction solvent and exposing the solvent in Channel II to a UV light of proper wavelength.

In certain aspects, the invention provides methods for analyzing a tissue sample that involve obtaining a tissue sample including an unsaturated compound. A radical reaction is conducted on the tissue sample that targets a carbon-carbon double bond within the unsaturated compound to thereby produce a plurality of compound isomers. The plurality of compound isomers are subjected to mass spectrometry analysis to identify a location of the carbon-carbon double bond within the unsaturated compound. The plurality of compound isomers are then quantified in order to distinguish normal tissue from diseased tissue. Methods of the invention can be conducted on numerous different types of unsaturated compounds. Exemplary unsaturated compounds include a lipid or a fatty acid.

Numerous different types of radical reactions can be used with methods of the invention, so long as the reaction targets a carbon-carbon double bond within the unsaturated compound. In certain embodiments, the radical reaction includes exposing the unsaturated compound and reagents for the radical reaction to ultraviolet light. In certain embodiments, the radical reaction is a Paternó-Büchi (PB) reaction. In such embodiments, the Paternó-Büchi (PB) reaction may be conducted in a solvent mixture including acetone.

The radical reaction may be conducted while the unsaturated compound is within a mass spectrometry probe. In such embodiments, at least a portion of the mass spectrometry probe may be transparent to ultraviolet light. For example, the mass spectrometry probe may be composed of a material that is transparent to ultraviolet light at approximately 200 nm wavelength. In other embodiments, the radical reaction is conducted in a vessel and subsequent to the reaction, the compound isomers are transferred to a mass spectrometry probe. In other embodiments, the radical reaction is conducted in association with a high-pressure liquid chromatography system and reagents for the radical reaction are within an elution solvent.

Other aspects of the invention provide methods for analyzing a tissue sample that involve contacting a sampling probe to a tissue including an unsaturated compound in a manner in which the unsaturated compound is retained on the sampling probe. The sampling probe is inserted into a hollow body, in which reagents for a radical reaction are present within the hollow body and the radical reaction targets a carbon-carbon double bond within the unsaturated compound. The radical reaction is conducted within the hollow body to produce reaction products. The reaction products are emitted from a distal tip of the hollow body. The emitted reaction products are then analyzed in a mass spectrometer in order to identify a location of the carbon-carbon double bond within the unsaturated compound. Methods of the invention can be conducted on numerous different types of unsaturated compounds. Exemplary unsaturated compounds include a lipid or a fatty acid.

Numerous configurations are possible for the sample probe, and analyzed probe with a distal tip is compatible with methods of the invention. In certain embodiments, the sampling probe includes a needle.

Numerous different types of radical reactions can be used with methods of the invention, so long as the reaction targets a carbon-carbon double bond within the unsaturated compound. In certain embodiments, the radical reaction includes exposing the unsaturated compound and reagents for the radical reaction to ultraviolet light. In certain embodiments, the radical reaction is a Paternó-Büchi (PB) reaction. In such embodiments, the Paternó-Büchi (PB) reaction may be conducted in a solvent mixture including acetone.

The radical reaction may be conducted while the unsaturated compound is within a mass spectrometry probe. In such embodiments, the unsaturated compound may be flowing through the hollow body while the reaction is being conducted. In such embodiments, at least a portion of the mass spectrometry probe may be transparent to ultraviolet light (e.g., at least a portion of all of the hollow body may composed of quartz glass or fused silica). For example, the mass spectrometry probe may be composed of a material that is transparent to ultraviolet light at approximately 200 nm wavelength.

Other aspects of the invention provide methods for imaging a tissue sample. Such methods may involve introducing reagents for radical reaction to a tissue including an unsaturated compound, in which the radical reaction targets a carbon-carbon double bond within the unsaturated compound. The radical reaction is conducted to produce reaction products. The tissue is scanned such that the reaction products are desorbed and ionized in a time resolved manner. The desorbed and ionized reaction products are analyzed in a mass spectrometer. An image of the tissue is produced based on results of the analyzing step. In certain embodiments, the conducting and scanning steps occur simultaneously. In other embodiments, those steps occur sequentially.

In certain embodiments, scanning includes conducting a desorption electrospray ionization technique using a desorption electrospray ionization probe at a plurality of different locations on the tissue. The reagents for the radical reaction may be introduced to the tissue via the desorption electrospray ionization probe and ultraviolet light may be applied to the tissue. In certain embodiments, the conducting and scanning steps occur simultaneously. In other embodiments, those steps occur sequentially.

In other embodiments, the introducing step includes applying reagents for the radical reaction in a MALDI matrix to the tissue. In such embodiments, scanning involves conducting a MALDI technique using a MALDI source at a plurality of different locations on the tissue. In certain embodiments, the conducting and scanning steps occur simultaneously. In other embodiments, those steps occur sequentially.

In certain embodiments, lipid and tissue analysis involves using miniature mass spectrometers. LED or LED arrays of proper wavelengths can be used to provide the light required for PB reaction. PB reaction ionization source can be combined with a DAPI-MS instrument with tandem MS capability.

Any type of mass spectrometer known in the art can be used with methods of the invention. For example, the mass spectrometer can be a standard bench-top mass spectrometer. In other embodiments, the mass spectrometer is a miniature mass spectrometer. An exemplary miniature mass spectrometer is described, for example in Gao et al. (Z. Anal. Chem. 2006, 78, 5994-6002), the content of which is incorporated by reference herein in its entirety. In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety. Miniature mass spectrometers are also described, for example in Xu et al. (JALA, 2010, 15, 433-439); Ouyang et al. (Anal. Chem., 2009, 81, 2421-2425); Ouyang et al. (Ann. Rev. Anal. Chem., 2009, 2, 187-214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082), the content of each of which is incorporated herein by reference in its entirety.

Methods of the invention can optionally involve the use of a discontinuous interface and the ionization of neutral molecules can be synchronized with the operation of the discontinuous interface. Such systems and methods are described for example in Ouyang et al. (U.S. Pat. No. 8,304,718) and Ouyang et al. (U.S. Pat. No. 8,785,846), the content of each of which is incorporated by reference herein in its entirety.

BRIEF DESCRIPTION OF THE DRAWINGS

FIG. 1A shows an exemplary setup coupling a P-B reaction with nanoESI-MS. FIG. 1B is a scheme illustrating the generation of distinct diagnostic ions specific to different lipid C=C isomers (right). +/− denotes positive/negative charge. Only charge-carrying fragments are detectable as diagnostic ions.

FIG. 2A is a scheme of a P-B reaction coupled with tandem MS to generate diagnostic ions for quantitation. FIG. 2B shows linear relationships between molar ratios and corresponding intensity ratios: PC C=C isomers (left) and FA C=C isomers (right). FIG. 2C shows calibration curves for absolute quantitation of FA 18:1 n-9 or n-7 using C18:1 n-6 (IS, 22.70 μM). FIG. 2D shows validation of the performance of two absolute quantitation methods developed in this work.

FIG. 3A shows isomeric composition of MUFAs (FA 16:1, FA 18:1, FA 19:1, FA 20:1, and FA 22:1) and PUFAs (FA 18:1, FA 20:4), with chain length ranging from 16 to 22 carbons. FIG. 3B shows isomeric compositions of C18:1-containing PLs. FIG. 3C shows isomeric composition of lysoPE 20:1. FIG. 3D shows isomeric composition of PC 1:0/16:1. FIG. 3E shows Isomeric composition of C18:2-containing PLs. FIG. 3F shows Isomeric composition of lysoPE 22:5.

FIG. 4A shows the composition of PC 16:0/18:1 isomers in rat organs. FIG. 4B shows the composition of FA 18:1 isomers in rat organs.

(FIG. 4C) FA 18:1. (FIG. 4D) PC 16:0/18:1. (FIG. 4E) PC 18:0/18:1. (FIG. 4F) PC 18:1/18:1.

FIG. 5A shows absolute intensity of precursor ions (m/z 339), ions due to a 58 Da neutral loss (m/z 281), and diagnostic ions (m/z 171/197) vs. ion injection time (10-200 ms). FIG. 5b shows relative intensities of neutral-loss fragment and diagnostic ions as a function of injection time (10-200 ms). The relative amounts of diagnostic ions (m/z 171 and 197) and neutral-loss fragments (m/z 281) were independent of ion injection time, which underwent a 20-fold increase from 10 ms to 200 ms.

FIG. 9A shows PC 18:0/18:1: CID of intact PC produces the signature ion at m/z 184.1, but with no C=C location information. After P-B reaction and tandem MS, two pairs of diagnostic ions were produced (m/z 678.5/704.6 and 706.6/732.6), suggesting the existence of PC 18:0/18:1 n9 and PC 18:0/18:1 n11. FIG. 9B shows that for lysoPE, acyl chain information (C18:1, m/z 281.3) can also be acquired via CID of its deprotonated ions. Interestingly, after P-B reaction CID of its P-B reaction products releases drivatized fatty acyls (m/z 339.3), without diagnostic ions. To acquire C=C location information, another stage of fragmentation needs to be applied to m/z 339.3 to generate informative diagnostic ions. Indeed, following MS3-CID two pairs of diagnostic ions (m/z 171.0/197.0 and 199.0/225.1) were observed, indicating that lysoPE 18:1 exists as a mixture of lysoPE 18:1 n9 and lysoPE 18:1 n11. PC 18:0/18:1 and lysoPE 18:1 used were from rat brain and kidney, respectively.

FIG. 11A shows +nanoESI mass spectrum of rat kidney FA extract added with 1% (wt) LiCl. FIG. 11B shows +nanoESI mass spectrum of the same sample after UV irradiation. FIG. 11C shows Fragmentation of P-B reaction products of lithiated FA 20:4 (m/z 311.3) produces four pairs of diagnostic ions (m/z 123/149, 163/189, 203/229, 243/269, in blue), corresponding to the four C=Cs in archidonic acid (FA 20:4 n6). FIG. 11D shows that when 20:4 n3 was added into the same FA extract sample, another distinct set of diagnostic ions emerge at m/z 165/191, 205/231, 245/271, and 285/311, which can be used for the quantitation of FA 20:4 isomers.

FIG. 25A shows MS1 spectra showing the precursor signal at m/z 760.6 before UV exposure. FIG. 25B shows 6 s cumulative UV exposure steady state reaction conditions (N2 purged solution) where m/z 818.6 is the P-B reaction product. FIG. 25C shows Beam-type CID of m/z 818.6 which shows C=C diagnostic ions at m/z 650.6 and 676.6. FIG. 25D shows XIC chromatogram of m/z 760.6 and 818.6 before, during, and after 6 s steady state UV exposure. FIG. 25E shows Precursor (m/z 760.6) and P-B reaction product (m/z 818.6) ion intensities with increased UV cumulative exposure time at 4.5 μL/min flow rate.

FIG. 26A shows MS1 spectrum of oleic acid (m/z 281.2) before UV. FIG. 26B shows MS1 reaction spectrum for 6 s UV exposure showing the P-B product at m/z 339.3. FIG. 26C shows Beam-type CID of m/z 339.3 shows monounsaturated oleic acid ion (m/z 281.2) in addition to diagnostic ions at m/z 170.1 and 197.1. FIG. 26D shows time-series graph depicting relative intensity of m/z 281.2 and 339.3 as a function of cumulative UV exposure.

FIG. 28A shows MS1 spectrum before UV. FIG. 28B shows MS1 reaction spectrum during UV (P-B products in red).

FIG. 28C shows MS2 beam-type CID of P-B product (m/z 774.5) for isomer PE 16:0_18:1 (n-9) and PE 18:0_16:1 (n-7). FIG. 28D shows MS3 ion trap CID of m/z 339.2 from FIG. 28B. FIG. 28E shows $MS^3$ ion trap CID of m/z 311.2 from FIG. 28B.

FIG. 29A shows tissue sampling by a stainless steel probe (200 µm, o.d.) and in-capillary extraction of lipids with subsequent MS analysis by nano-ESI and UV light (λ=254 nm). FIG. 29B shows Paternó-Büchi (P-B) reaction between acetone and fatty acid in association with possible fingerprint fragment ions in retro P-B reaction for localizing double bond positions.

FIGS. 30A-C show mass spectrum of lipids sampling from rat brain, kidney, and liver by extraction spray before and after P-B reaction induced by UV irradiation of –nano ESI. FIG. 30D shows MS2 CID of PS 18:0-18:1 at m/z 778.5 for identifying the head group and the length of acyl chains. FIGS. 30E-F show MS2 CID of background peaks at m/z values as same as the P-B reaction products of unsaturated lipids (FA 18:1, m/z 339.3; PS 18:0-18:1, m/z 846.5) before P-B reaction for deduction of the chemical noise. FIGS. 30G-H show MS2 CID of P-B reaction products of unsaturated lipids after P-B reaction. Double bonds of FA 18:1 in kidney can be directly identified as n-9 and n-7 according to newly generated fingerprint peaks (m/z 171.0 & 197.0 for n-9; m/z 199.0 & 225.1 for n-7). For PS 18:0-18:1, the P-B reaction products of unsaturated acyl chain 18:1 were formed and appeared in the spectrum at m/z 339.3. FIG. 30I shows MS3 CID of m/z 339.3 from P-B reaction products of PS 18:0-18:1, which indicates double positions at n-9 and n-7.

FIG. 31C shows MS2 CID of the P-B reaction products at m/z 339.3 for determination of double bonds of FA 18:1 in kidney. FIG. 31D shows MS2 CID of PS 18:0-18:1 at m/z 778.5 for identifying the head group and the length of acyl chains. FIG. 31E shows MS3 CID of m/z 339.4 from P-B reaction product of PS 18:0-18:1.

FIGS. 32D-E show effect of solvent on the signal intensity of FA 18:0 [(M-H)–, m/z 283.3], FA 18:1 [(M-H)–, m/z 281.3], and PS 18:0-18:1 [(M-H)–, m/z 788.5].

FIG. 33A shows effect of solvent on reaction time of FA 18:1 [(M-H)–, m/z 281.3, reaction product ion, m/z 339.3]. FIG. 33B shows effect of solvent on reaction yields of FA 18:1 and PS 18:0-18:1 [(M-H)–, m/z 788.5, reaction product ion, m/z 339.3]. FIG. 33C shows effect of solvent on reaction yields of FA 18:1 and PS 18:0-18:1 [(M-H)–, m/z 788.5, reaction product ion, m/z 339.3].

FIG. 35A shows molar percentages of identified fatty acids of total fatty acids. FIG. 35B shows molar percentages of identified phospholipids of total lipids. FIG. 35C shows MS2 CID spectra of FA 21:1 at m/z 381.3

FIG. 38C shows two-dimensional isomeric ratio (±SD, N=3-9) image of PA 18:1-18:1 in rat brain. FIG. 38D is a set of photographs of rat brain before and after sampling for 50 times.

FIG. 47C shows PB reaction spectrum when UV light is turned on.

FIG. 48A shows the structure of PS 16:1(9Z)/18:1(9Z) and the observed cleavage sites. FIG. 48B shows MS2 CID of P-B reaction product of PS at m/z 816.5. FIG. 48C shows MS3 CID of m/z 339.4 from P-B reaction product of PS. FIG. 48D shows MS3 CID of m/z 311.3 from P-B reaction product of PS.

FIG. 50B shows without N2 purge. FIG. 50C shows with N2 purge.

FIG. 59A shows before and FIG. 59B shows after photochemical tagging by acetone. FIG. 59C shows MS2 beam-type CID of tagged FA 17:1 (m/z 325). Loss of tag is a dominant fragmentation channel. Negative ion mode nanoESI-MS of FA extract from human plasma: FIG. 59D shows before and FIG. 59E shows after acetone tagging. FIG. 59F shows 58 Da neutral loss scan (NLS) after acetone tagging. The number of "*" signs in FA annotation standards for the number of acetone tagging to a FA.

FIGS. 60A-B show Negative ion mode nanoESI mass spectra of FA extract from 2 µL rat blood after 25 times dilution are shown in: FIG. 60A shows before tagging and FIG. 60B shows NLS (58 Da) after tagging. "#" sign indicates chemical interferences.

FIG. 61C uses acetone/water (50/50, v/v) and FIG. 61D uses ethanol/acetone/water (40/30/30, v/v/v).

FIG. 62A shows PB-MS/MS of tagged FA 18:1 (m/z 339.3). Two isomers with C=C at Δ9 and Δ11 positions are detected. FIG. 62B shows calibration curve for relative quantitation of FA 18:1 Δ9 and Δ11 isomers. FIG. 62C shows calibration curve for total FA 18:1 quantitation based on 58 Da NLS of FA 18:1 mixtures consisting of 91.5% Δ9 and 8.5% Δ11 isomers. FIG. 62D shows PB-MS/ MS of an equal molar mixture of ω-3 and ω-6 FA 18:3 isomers (m/z 343.3 lithiated). The C=C diagnostic ions of each isomer are clearly detected. FIG. 62E shows PB-MS/ MS of zoomed-in regions for C=C diagnostic ions of FA 18:3 from human plasma. ω-6 FA 18:3 is more abundant than ω-3 isomer.

In FIGS. 63A and B, error bars represent standard deviation, n=3. Differences between the FAs in RWPE1 cells and PC3 cells were evaluated for statistical significance using the two-tailed Student's t-tests (***$p<0.0005$).

FIG. 66A shows PB reaction mass spectrum of FA 20:4 using acetone/water (50/50, v/v) as the solvent. FIG. 66B shows PB reaction mass spectrum of FA 20:4 using ethanol/acetone/water (40/30/30, v/v) as the solvent. FIG. 66C shows CID spectrum of PB products of FA 20:4 at m/z 361.3, where the dominant fragmentation channels are the neutral losses of 58 Da (acetone) and 44 Da ($CO_2$).

FIG. 69A shows nanoESI-MS spectrum of FA extract added with 7.5 µM FA 17:1 as the IS. FIG. 69B shows NLS spectrum after PB reaction. Dried FA extract (from 20 µL human plasma) was reconstituted in 400 µL solvent added with 7.46 µM IS.

FIG. 70A shows nanoESI-MS spectrum of the FA extract after addition of 5 mM LiCl. Solvent is 10% ethanol in acetone/water (50/50, v/v). FIG.

70B shows nanoESI-MS spectrum of FA extract after photochemical tagging. Peaks labelled in red are tagged products of FA 18:3 (m/z 343.5), FA 18:2 (m/z 345.5), and FA 18:1 (m/z 347.5). FIG. 70C shows CID spectrum of the background ions at m/z 343.3. FIG. 70D shows CID spectrum of tagged FA 18:3 (m/z 343.3).

FIG. 72A shows nanoESI-MS spectrum of the FA extract of human plasma after AMPP derivatization. FIG. 72B shows precursor ion scan spectrum of m/z 183.1 of the same extract after AMPP derivatization. FA 18:2-d11 and FA 18:1-d17 were added before extraction to evaluate recovery.

FIG. 73A shows nanoESI-MS spectrum of FAs in normal prostate cells (RWPE1 cells). FIG. 73B shows nanoESI-MS spectrum of FAs in cancerous prostate cells (PC3 cells). FA 17:1 (10Z) was used as the IS.

FIG. 74A shows trap CID spectrum of PB reaction products (m/z 339.3) of FA 18:1 in normal prostate cells. FIG. 74B shows trap CID spectrum of PB reaction products of FA 18:1 in prostate cancer cells. The trap CID conditions in FIGS. 74A-B were: Q3 entry barrier, 2V; activation time, 200 ms; AF2 (fragmentation energy), 50 (arbitrary unit). Diagnostic ions at m/z 171.1/197.2 are unique to the Δ9 isomer, while diagnostic ions at m/z 199.2/225.2 are unique to Δ11 isomer. The relative amount of the Δ9 isomer is higher in prostate cancer cells.

DETAILED DESCRIPTION

Methods of the invention combine photochemical derivatization with tandem mass spectrometry (PCD-MS"), which allows global characterization and quantitation of lipid C=C isomers from complex lipid mixtures in a shotgun lipidomics approach. Methods of the invention use radical reactions (e.g., Paternò Büchi (P-B) reaction) to pinpoint C=Cs in unsaturated lipids. The working principle comprises three central components (FIG. 1A): (1) C=C bonds are first converted to their corresponding P-B reaction products via P-B reaction with acetone (used as nanoESI solvent as well) under 254 nm UV irradiation. (2) Reaction products are then sequentially isolated and CID-fragmented (tandem MS), to rupture oxetane rings formed at the original C=C bonds to preferentially produce isomer-specific diagnostic ions (diagnostic ions). (3) The relative abundances of diagnostic ions are then used to develop powerful methodologies capable of relative and absolute quantitation of C=C isomers of various lipid species. The methods of the invention show that PCD-MS" improved lipid targeting, led to the identification of 96 unique lipid species including lipid C=C isomers in rat brain, with 35 unsaturated lipids quantified. It also revealed the heterogeneity in isomeric compositions of unsaturated lipids in rat organs. In cancerous tissues, significant changes in relative amounts of C=C isomers of FA 18:1 and C18:1-containing phosphocholines (PCs) were detected, demonstrating the usefulness of the methods of the invention as diagnostic methods, e.g., cancer diagnostic methods. Considering the different biosynthetic pathways responsible for the production of lipid C=C isomers, the methods find wide applications in research fields involving lipid C=C isomers, such as cell biology and disease diagnostics.

In certain embodiments, methods of the invention can be used for: (1) quantifying compositions of FA and PL C=C isomers in rat brain; (2) determining and comparing isomeric compositions of PLs across different rat tissues; (3) comparing isomeric compositions of PLs between normal and cancerous tissues. It is shown herein that a P-B reaction coupled with nanoESI-MS/MS allows efficient and confident characterization of lipid C=C isomers via abundant and distinct diagnostic ions. That methodology can be extended for accurate quantitation of lipid C=C isomers by comparing the relative intensities of their diagnostic ions.

Principle of Photochemical Derivatization Coupled with Tandem MS Strategy

Figures 1A, 1B:
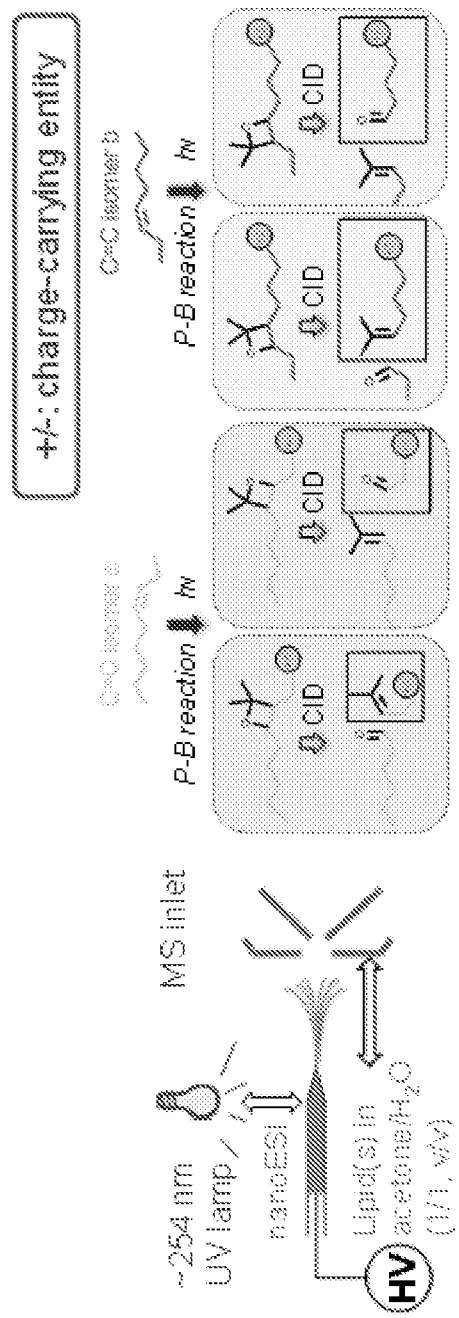
FIGS. 1A-B show the principle of photochemical derivatization-tandem MS to identify and quantify unsaturated lipids.
Figure 1C:
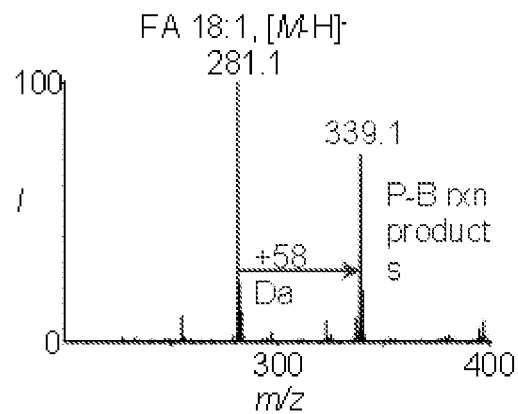
FIG. 1C is a P-B reaction spectrum of a 4:1 mixture of FA 18:1 n-9 and FA 18:1 n-7, where the formation of P-B reaction products was observed (m/z 339.3).
Figure 1D:
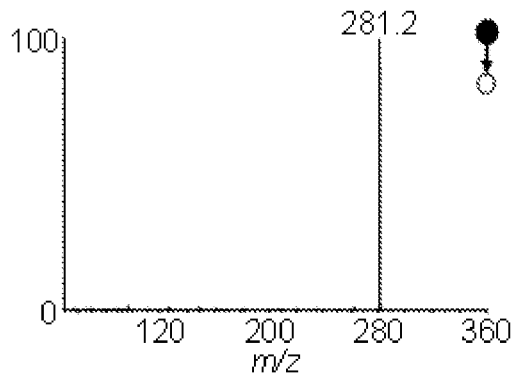
FIG. 1D is a CID mass spectrum of intact FA 18:1 n-9. No C=C position information can be retrieved.
Figure 1E:
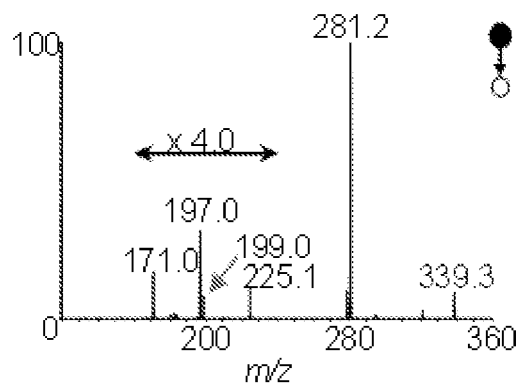
FIG. 1E is a mass spectrum showing that upon CID, P-B reaction products of the FA 18:1 mixture release two distinct pairs of diagnostic ions at m/z 171.1/197.2 and m/z 199.1/225.2, clearly showing the presence of two FA 18:1 n-9 and n-7 isomers.
Figure 1F:
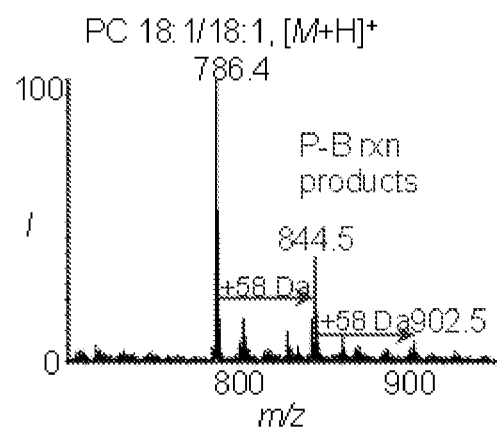
FIG. 1F is a reaction mass spectrum of equimolar PC 18:1 n-9/18:1 n-9 and PC 18:1 n12/18:1 n12 (m/z 786.6).

A schematic of an experimental setup where a P-B reaction is coupled with nanoESI-MS is illustrated in FIG. 1A. A low-pressure mercury (LP-Hg) lamp with a major emission at 254 nm as the UV source was used for P-B reaction.[35] The reaction kinetics are fast in that after 0.3~0.5 minute the stable state is reached (See Examples below). For a lipid containing one C=C, reaction products are a mixture of two oxetane regio-isomers, as there is no regio-selectivity when UV-activated carbonyl in acetone is added to C=C in the lipid. Consequently, upon CID P-B reaction products produce two diagnostic ions, with each one originating from one regio-isomer (FIG. 1B). The preferential formation of abundant C=C-specific diagnostic ions following CID benefits from CID-susceptible high-energy oxetane rings, as reaction products of the fragmentation-resistant C=C. In addition, the characteristic 26 Da mass difference within a pair of diagnostic ions is useful in identifying diagnostic ions, especially in cases where interferences exist. To demonstrate the power of PCD-MS" towards mixture analysis of lipid C=C isomers, a 4:1 mock mixture of oleic acid (C18:1 n-9) and cis-vaccenic acid (C18:1 n-7) was prepared and analyzed. Fragmentation if intact FAs at m/z 281 (deprotonated form) generates no informative ions useful to pinpoint the C=C. By contrast, following P-B reaction and tandem MS, two distinct pairs of diagnostic ions appeared at m/z 171.1/197.2 (FA 18:1 n-9) and m/z 199.1/225.1 (FA 18:1 n-7) (FIG. 1E). Because each pair of diagnostic ions are unique to their specific lipid C=C isomer, PCD-MS" can simultaneously analyze an unlimited number of isomers.

Figure 1G:
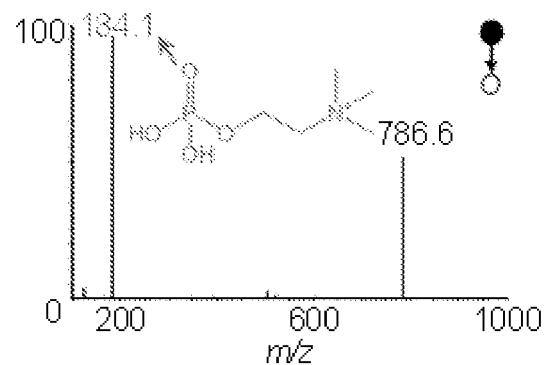
FIG. 1G is a CID mass spectrum of intact of intact PCs (m/z 786.6), with no C=C position information retrievable.
Figure 1H:
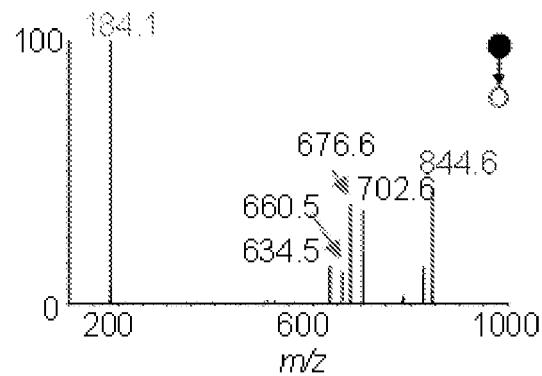
FIG. 1H is a CID mass spectrum of P-B reaction products (m/z 844.6) from the above PC mixture. Two pairs of diagnostic ions (m/z 634.5/660.5 and m/z 676.6/702.6), corresponding to the position of C=Cs in each PC isomer, were formed in high abundance.

Subsequently, PCD-MS" was extended to structurally characterize polar lipids by +nanoESI. As an example, an equimolar mixture of two PC C=C isomers, i.e. 1,2-dipetroselenoyl-sn-glycero-3-phosphocholine (PC 18:1 n-12/18:1 n-12) and 1,2-dioleoyl-sn-glycero-3-phosphocholine (PC 18:1 n-9/18:1 n-9) was prepared. Each PC contains two identical acyl chains, C18:1 n12 or n-9. Similar to unsaturated FAs, no diagnostic ions can be formed following CID of intact PCs, except the signature ion at m/z 184 (the phosphocholine headgroup in PCs or sphingomyelins, FIG. 1G). Following P-B reaction and tandem MS, two pairs of diagnostic ions at m/z 634.5/702.6 and m/z 676.5/702.6 were generated, consistent with C18:1 n-12 and C18:1 n-9 in each PC 18:1/18:1 species. Therefore, using FA (−nanoESI) and PC isomers (+nanoESI) as examples, it was demonstrated that methods of the invention can analyze all polar lipids regardless of the charge they carry, and such an advantage is attributed to the radical nature of P-B reaction.[36,37] Besides, it is worth pointing out that P-B reaction is unselective towards C=Cs at different locations, and all C=Cs have a possibility to be derivatized. By this reason, for PLs containing more than one C=C, CID mass spectra of first-step P-B reaction products contains information of all C=Cs present. Because such spectra are much easier to interpret than those of later-stage reaction products, the former were always chosen to facilitate tandem MS analysis.

Validation of PCD-MS$_n$ for Quantitative Analysis of Lipid C=C Isomers

Figure 2A:
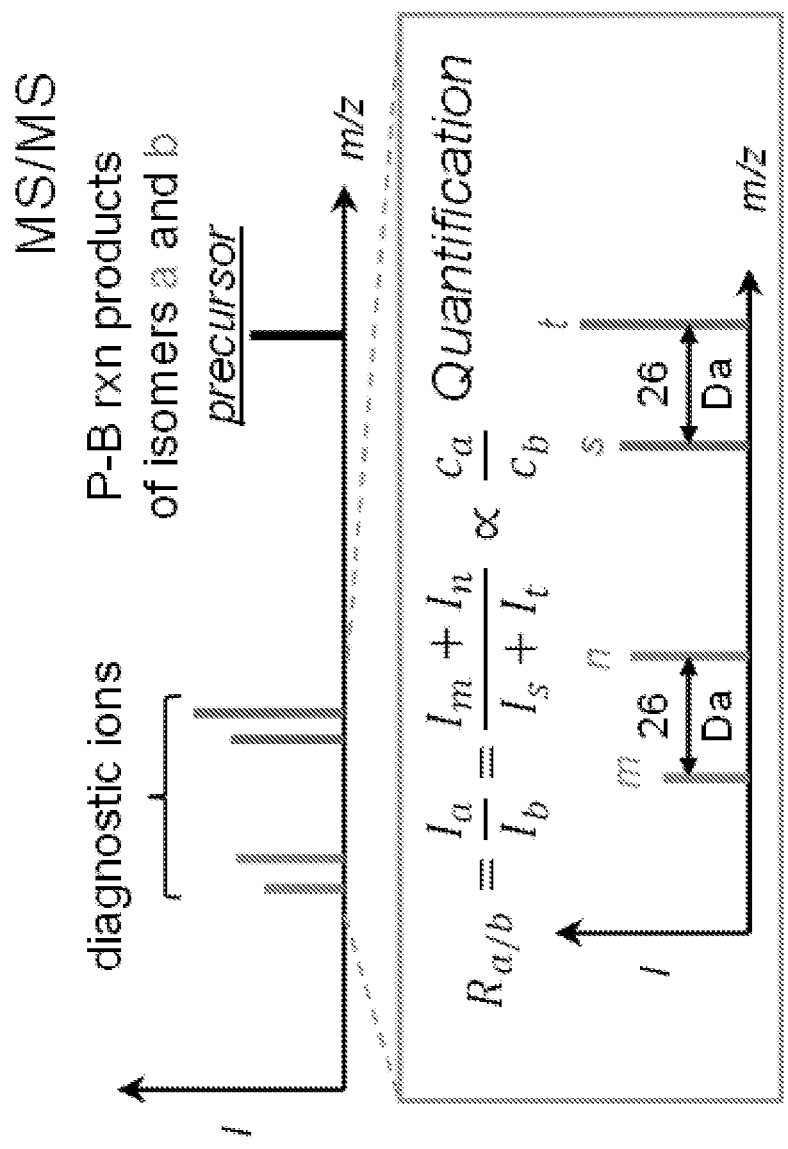
FIGS. 2A-D show principles for relative and absolute quantitation of lipid C=C isomers.
Figure 2B:
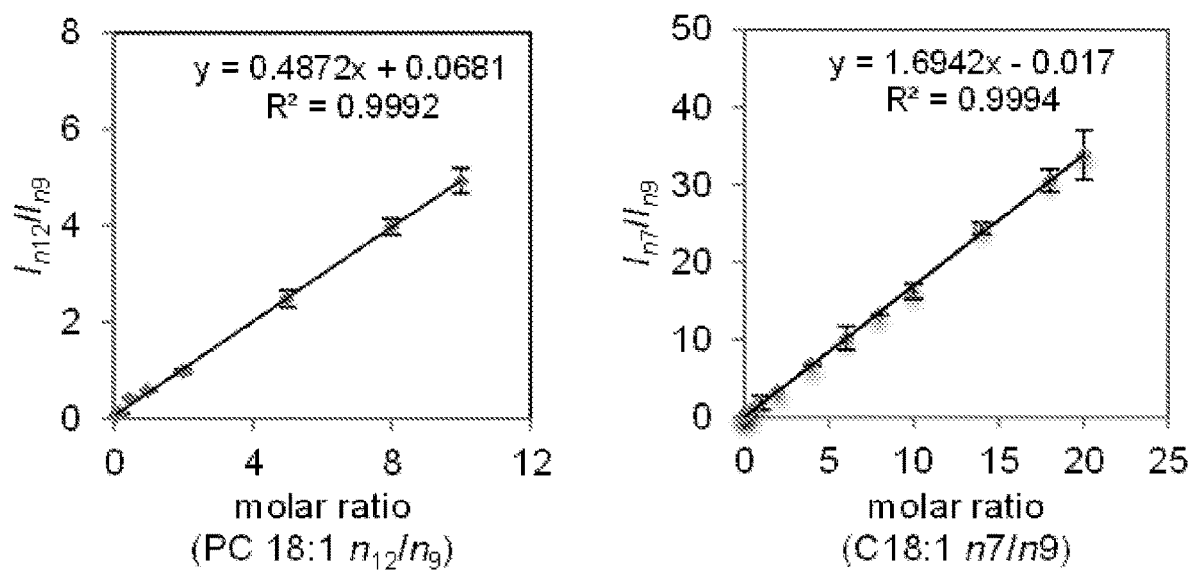

To validate PCD-MS″ as a method to quantify lipid C=C isomers, isomer mixtures at different molar ratios were prepared and subjected to analysis (for typical CID mass spectra, see Examples below). For all PC 18:1/18:1 or FA 18:1 isomers, an excellent linearity of the molar ratio of isomers vs. the intensity ratio between their corresponding diagnostic ions (FIG. 2A) was observed ($R^2$=0.9992 and 0.9994), suggesting the robustness of PCD-MS$_n$ in lipid C=C isomers (FIG. 2B). The intensity ratio is defined as the ratio between the intensity of diagnostic ion(s) for one isomer to those for another, i.e.

$$\text{intensity ratio} = \frac{\Sigma_1 \text{ intensity of diagnostic ions from isomer 1}}{\Sigma_2 \text{ intensity of diagnostic ions from isomer 2}}.$$

The accuracy is over 90% and 95% (mol) in the relative quantification of PC 18:1/18:1 and FA 18:1, respectively. According to reaction mass spectra, unsaturated lipids were not converted to their corresponding reaction products completely. However once the reaction becomes stable, so does the intensity ratio between pairs of diagnostic ions (See Examples below). Such a unique and extremely useful feature of PCD-MS″ is attributed to the high specificity of P-B reaction towards C=Cs, which allows rapid, reproducible and quantitative analysis of lipid C=C isomers.

Absolute Quantitation of FA C=C Isomers

Figure 2D:
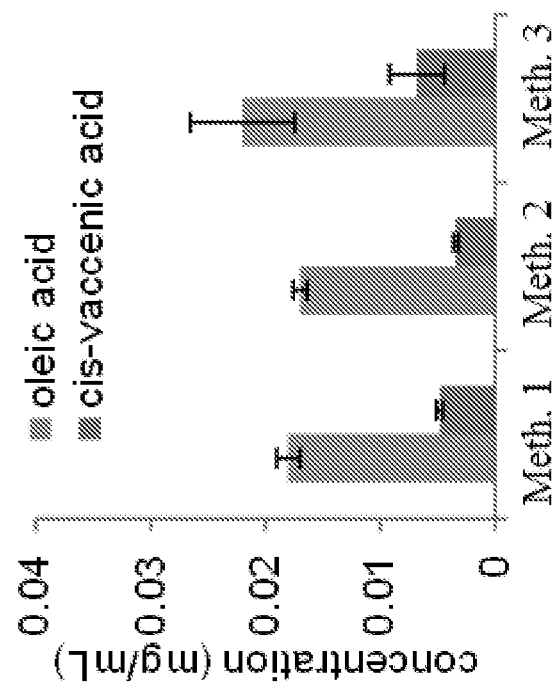
Figure 2C:
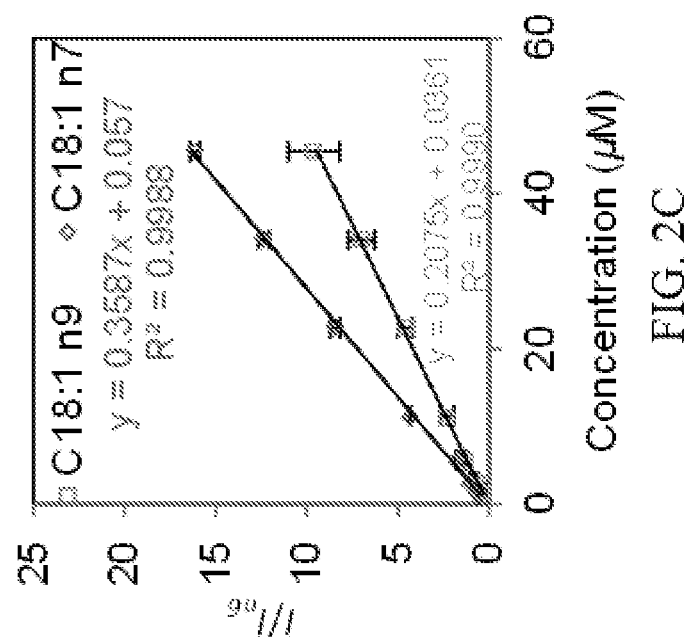

Once the basis for relative quantitation of C=C isomers was established, methods were developed for absolute quantitation. If two isomers (oleic acid and cis-vaccenic acid) need to be quantified, and a third isomer (petroselenic acid, FA 18:1 n12) is available, two calibration curves (for oleic acid and cis-vaccenic acid) can be constructed for absolute quantitation (FIG. 2C). Here, FA 18:1 n12 was used as the common internal standard (IS). Calibration curves were prepared by keeping the IS concentration constant (22.7 μM) while the concentration of oleic acid or cis-vaccenic acid varies in the range of 1.4~45.4 μM. Since the IS is mixed with both FAs, it is important to explore whether the co-existence of oleic acid and cis-vaccenic acid will influence the quantitative performance. The calculated slope from calibration curves of cis-vaccenic/IS and oleic acid/IS (0.3587/0.2075=1.729, FIG. 2D) was compared with that (A=1.694) measured directly using cis-vaccenic/oleic acid mixtures (FIG. 2B). It was found that these two slope are consistent. Therefore, it was concluded that co-existence of multiple isomers has no detectable effects on their mutual quantitative relationships. This feature enables PCD-MS″ to characterize and quantify unlimited number of lipid C=C isomers.

In cases where a third isomer is unavailable, alternative methods for absolute quantitation can be developed. These include standard addition (See Examples below) and use of an IS in nanoESI combined with relative quantitation by PCD-MS″ (See Examples below). Analytical performances of these three methods were demonstrated through analysis of a mock mixture of FA 18:1 n-9/n-7 at a molar ratio of 4:1 ($c_{FA\ 18:1\ n-7}$=0.0032 mg/mL) and a FA extract from rat brain. The quantitative capability of the PCD-MS″ method is evidenced by consistency among different methods and its accuracy in quantifying FA isomers. Overall, the analytical performances of the first two methods (experimental error <7%, s.e. <15%) are better than the third method, possibly due to the fluctuation of ionization efficiency in the latter.

Relative Quantitation of FA and PL C=C Isomers in Rat Brain

Figure 3A:
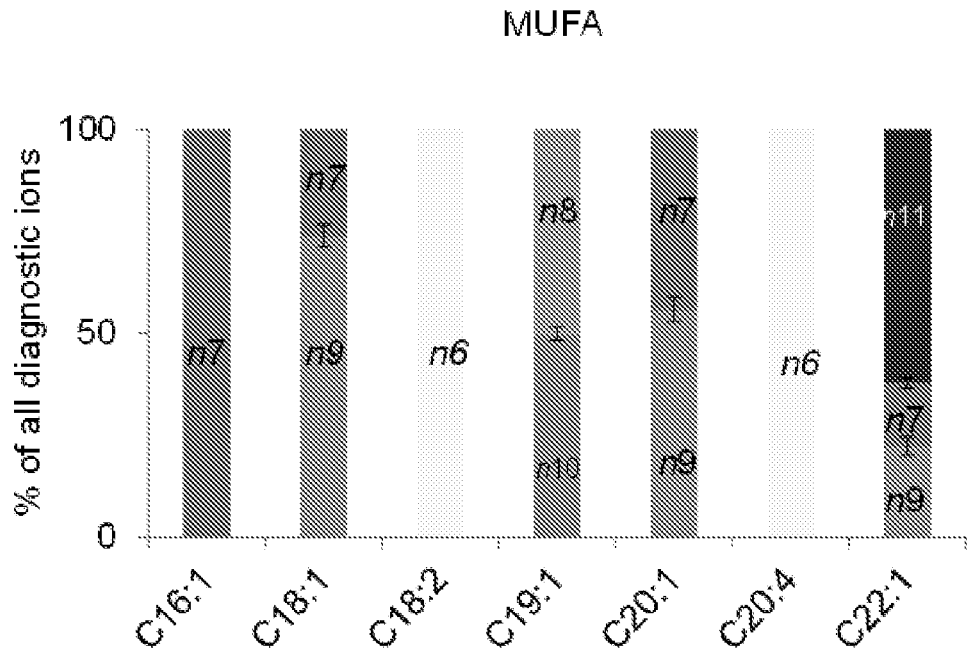
FIGS. 3A-F show relative quantitation of unsaturated lipids in rat brain.
Figure 3B:
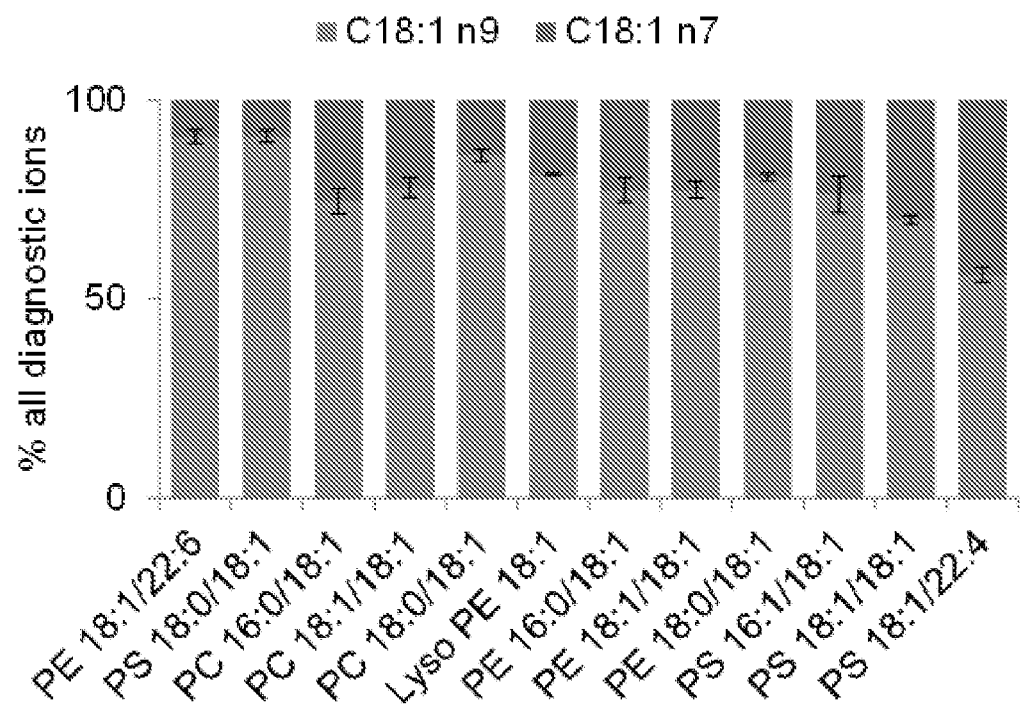
Figures 3C, 3D:
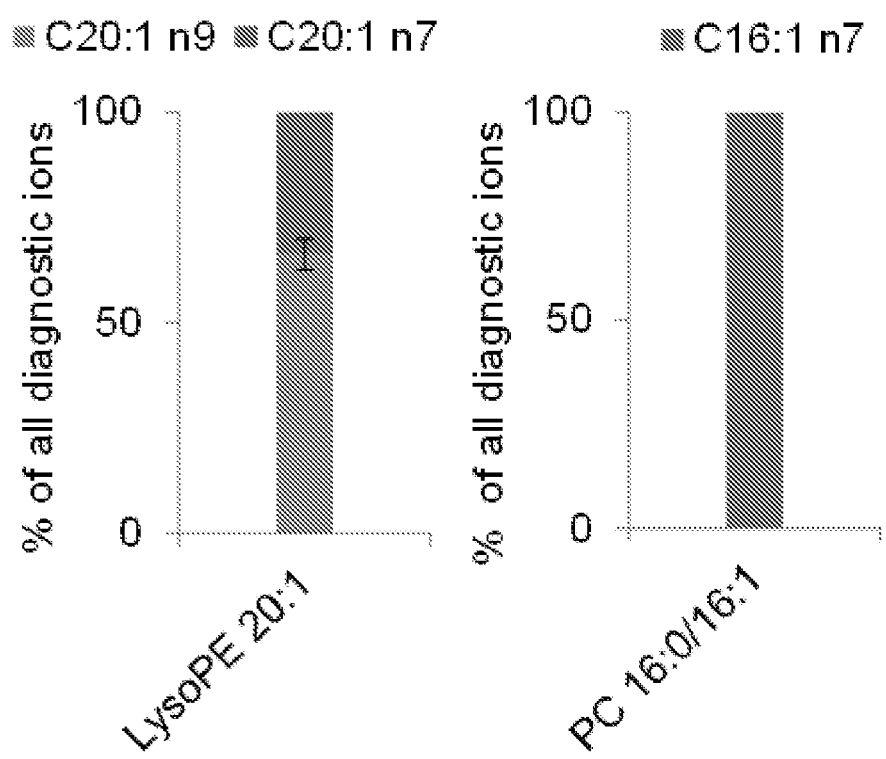
Figures 3E, 3F:
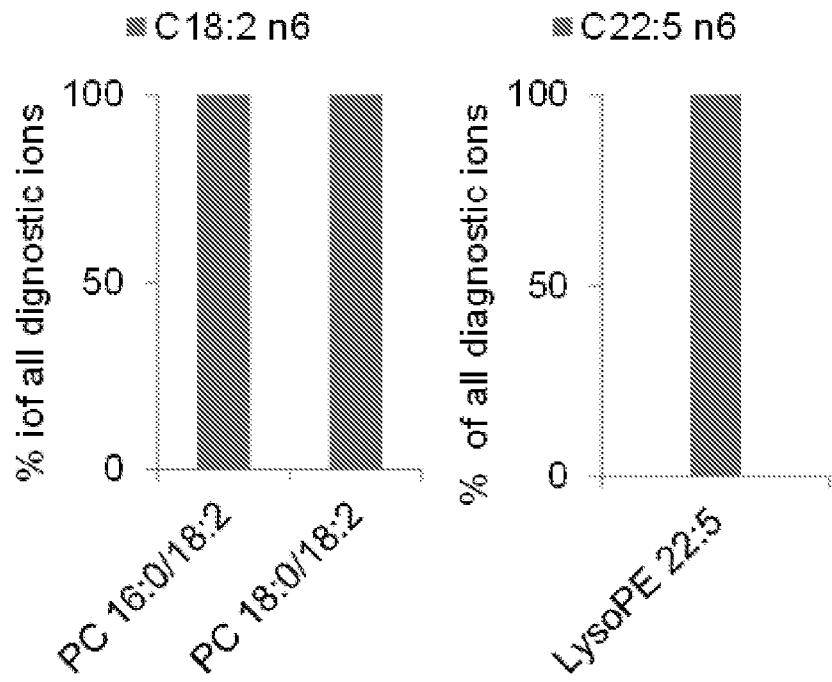
Figure 3G:
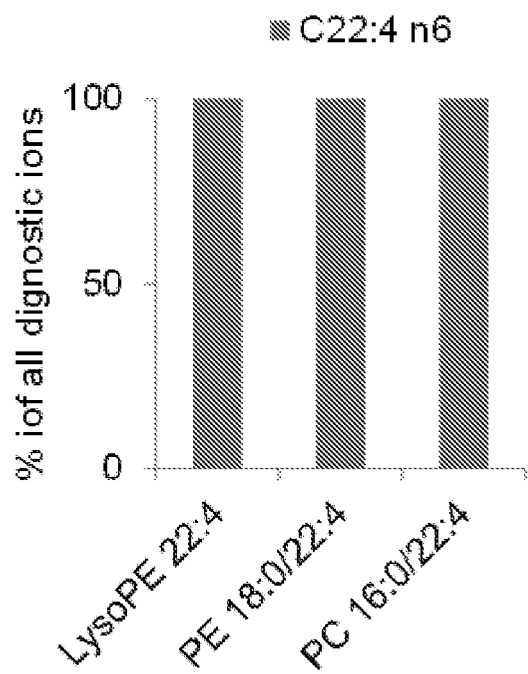
FIG. 3G shows Isomeric composition of C22:4-containing PLs.
Figure 3H:
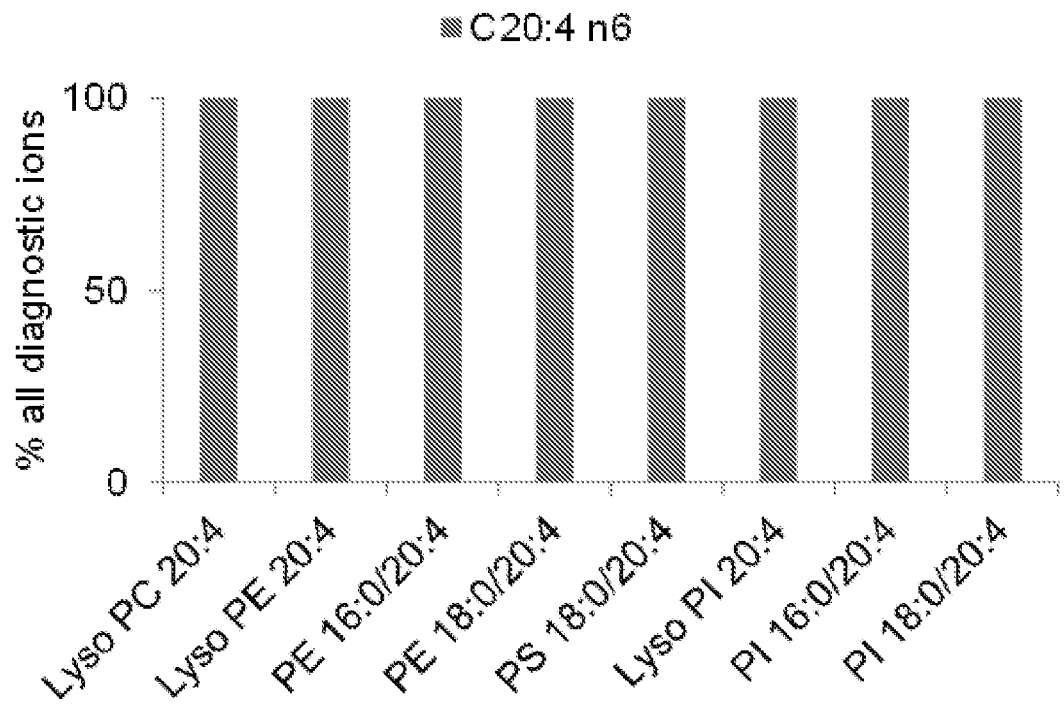
FIG. 3H shows Isomeric composition of C20:4-containing PLs.
Figure 3I:
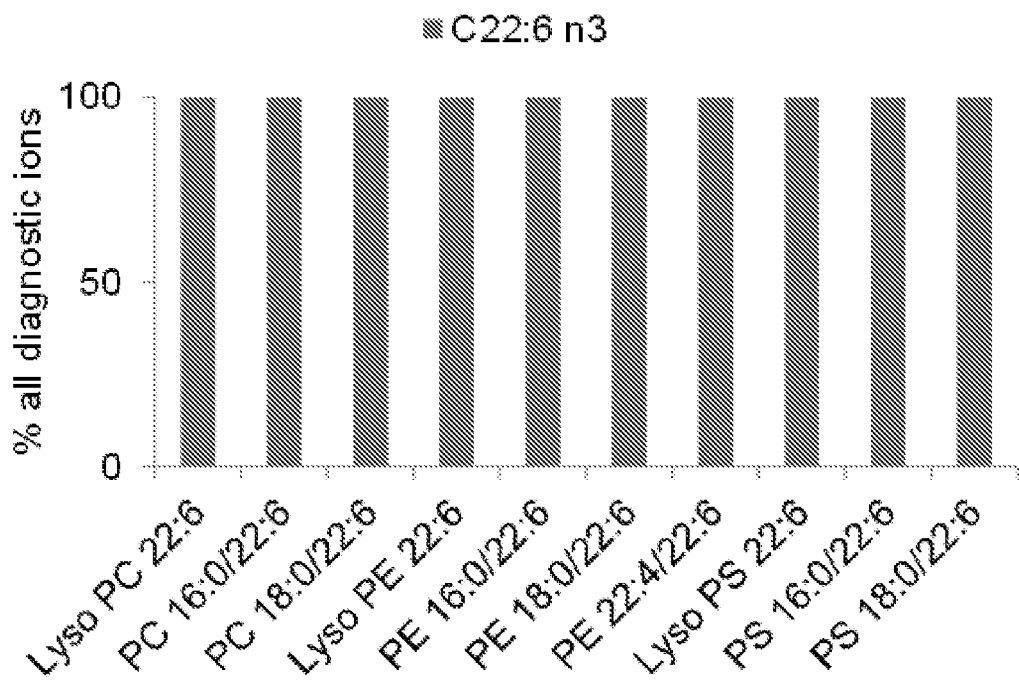
FIG. 3I shows Isomeric composition of C22:6-containing PLs. Isomeric composition is represented as the percentage of the total intensity of diagnostic ions for one isomer in that of diagnostic ions from all isomers.

Once established, PCD-MS″ was applied to quantify lipid C=C isomers from complex FA and PL extracts from the rat brain. Until recently, few papers reported the existence of C=C isomers in PL species by coupling chromatography with methods capable of locating C=Cs, such as ozone-induced dissociation (OzID). In addition to characterization of lipid C=C isomers, methods of the invention can also provide lipid C=C isomer composition information by relative quantitation. Analysis was performed by hyphenating PCD-MS″ with shotgun lipidomics, without any chromatographic separation. For unsaturated FAs, they include monounsaturated fatty acids (MUFAs) and polyunsaturated fatty acids (PUFAs). Except for FA 20:4, fragmentation of their P-B reaction products releases abundant diagnostic ions. It was found that of unsaturated FAs in rat brain, FAs 16:1, 18:2 and 20:4 are pure, in forms of FA 16:1 n-7, FA 18:2 n-6 and FA 20:4 n-6. By contrast, FA 19:1 is a mixture of n-8 and n-10 isomers, FAs 18:1 and 20:1 are also mixtures of n-7 and n-9 isomers, and FA 22:1 consists of three n-7, n-9 and n-11 isomers (FIG. 3A). P-B reaction yield of FA 20:4 is high, however no diagnostic ions was produced due to the dominant $CO_2$ loss (−44 Da) upon CID of PUFAs and their reaction products. To circumvent this problem, $Li^+$ was used as the charge carrier and succeeded in suppressing $CO_2$ loss by forming $[PUFA+Li]^+$ adducts. Such a strategy is also compatible with PCD-MS″ and makes quantitation of PUFA C=C isomers possible (See Examples below). CID of P-B reaction products of lithiated FA 20:4 releases four pairs of lithiated diagnostic ions abundantly, (See Examples below). Subsequently, a global analysis of all unsaturated PLs detected was performed, including phosphatidylcholines (PCs), lyso PCs (LPCs), phosphatidylethanolamines (PEs), lyso PEs (LPEs), phosphatidylinositols (PIs), lyso PIs (LPIs), phosphatidylserines (PSs), and lyso PSs (LPSs). The principle of quantifying unsaturated PL isomers by negative CID is detailed in the Examples below (refer to FIG. 1G for the principle of quantitation by positive CID). In agreement with the co-existence of FA 18:1 n-7 and n-9 isomers, all C18:1-containing PLs in rat brain are also identified to mixtures of n-7 and n-9 isomers. This is universally true for other FAs and their corresponding PLs that contain the corresponding fatty acyls (C18:2, C20:1, C20:4 and C22:6) (FIG. 3A, and Examples below). Such observations are in accordance with the well-established PL synthesis mechanism where free FAs are used as substrates.

Heterogeneous Compositions of Lipid C=C Isomers in Rat Tissues

Figure 4A:
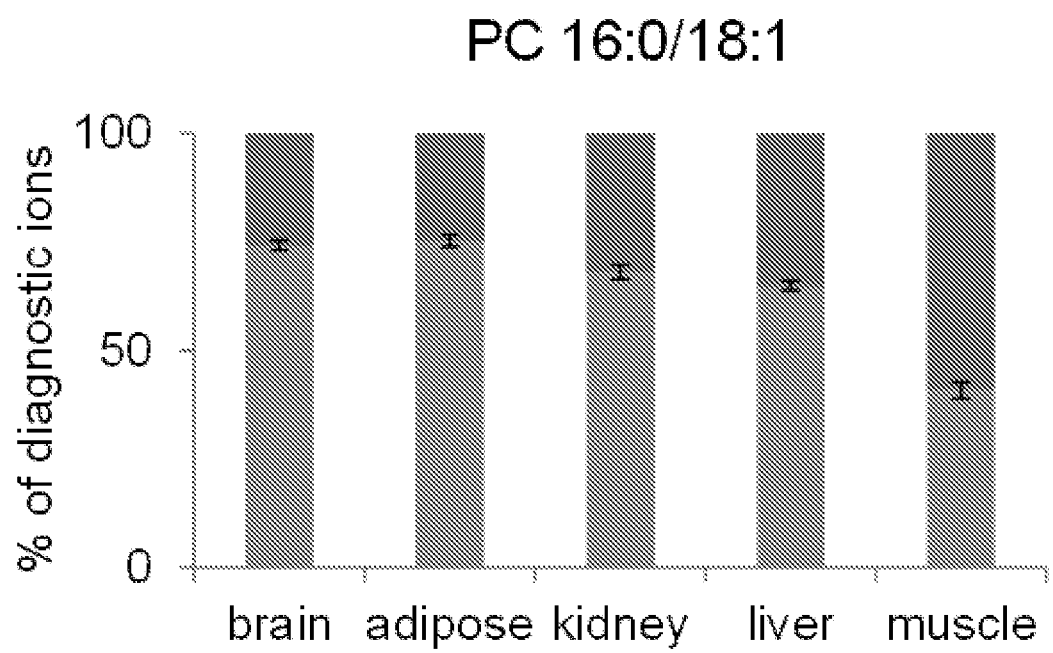
FIGS. 4A-B show variations in isomeric composition of C18:1-containing PCs and FA 18:1 isomers in rat organs (including brain, adipose, kidney, liver and muscle) and mouse breast cancer tissues.
Figure 4B:
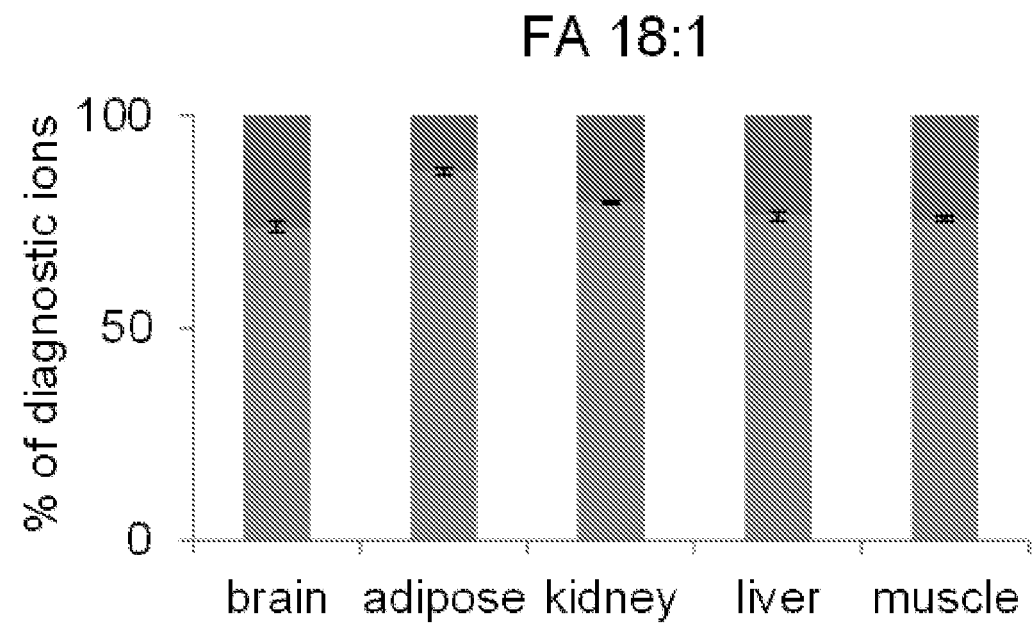
Figure 4C:
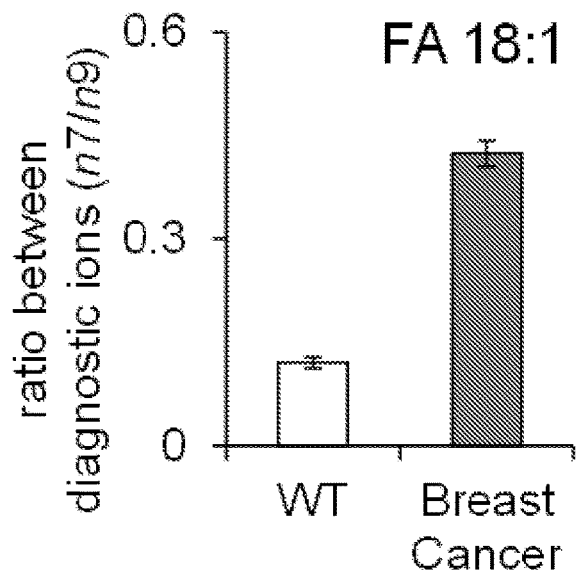
FIGS. 4C-F show comparison of isomeric compositions of FA 18:1 and C18:1-containing PCs (PC16:0/18:1, PC 18:0/18:1, PC 18:1/18:1) between normal (WT) and cancerous mouse breast tissues.
Figure 4D:
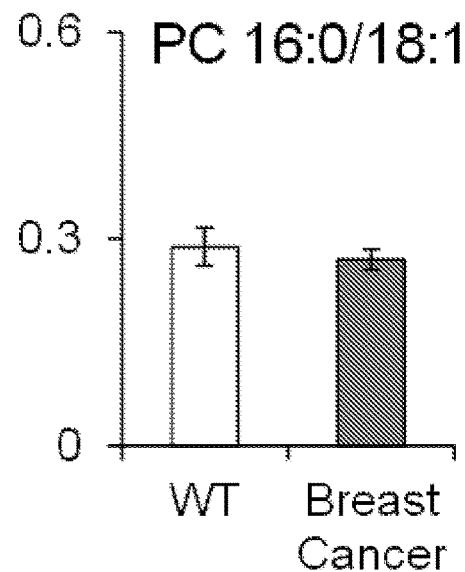
Figure 4E:
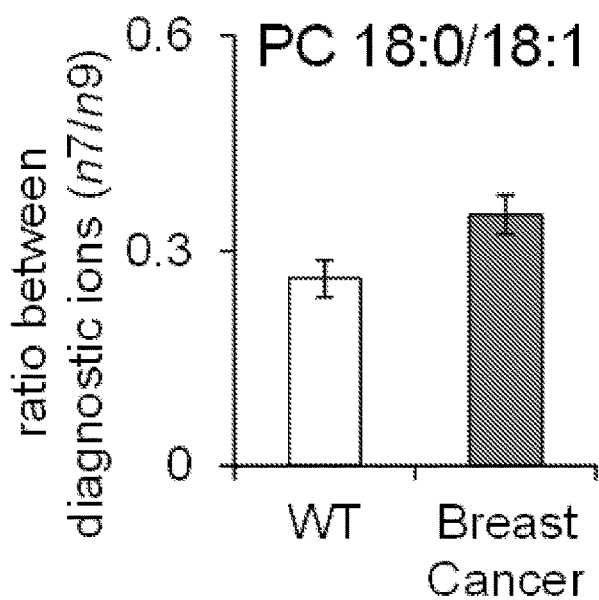
Figure 4F:
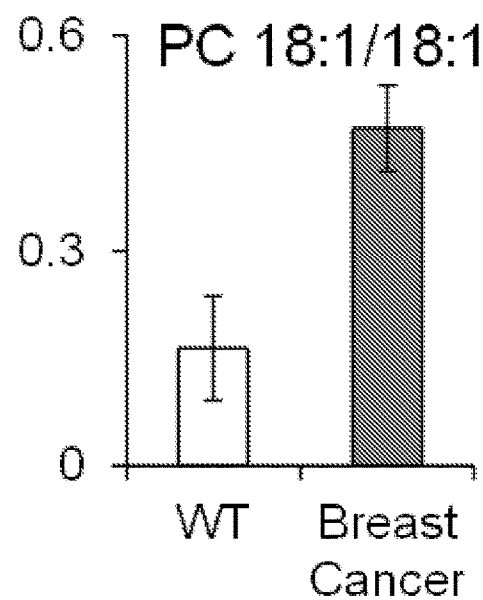

To investigate and compare the isomer compositions of lipid C=C isomers across different rat organs, FA and PL extracts from tissues of five rat organs were analyzed. Abundant PC species common to all organs were the initial focus of methods of the invention, PC 16:0/18:1. Tandem MS of its P-B reaction products generates two pairs of diagnostic ions (at m/z 650.5/676.6 and 678.5/704.5) that strongly indicates the presence of PC 16:0/18:1 n-7 and n-9 isomers (FIGS. 4A-B). Surprisingly, the isomeric composition of PC 16:0/18:1 showed large variations in rat organs. The variation is most significant between brain and muscle: in brain, diagnostic ions of n-9 isomer were more abundant than those from n-7 isomer, while the reverse is true in muscle. The relative amount of PC 16:0/18:1 n-7 in all rat organs analyzed follows the sequence of brain<adipose<kidney<liver<muscle. The data show that there is a correlation between free FAs and corresponding fatty acyls in PLs. FA 18:1 and C18:1-containing PLs were analyzed. In all organs except brain, consistent increases in the relative amounts of FA 18:1 n-9 and C18:1 n-9-containing PLs was observed, from adipose, kidney, liver to muscle. Brain, muscle kidney and liver contain 24-26% and adipose contains 13% FA 18:1 n-7. These results demonstrate that compositions of FA isomers play a role in determining the isomeric compositions of PLs, which are major components of plasma membranes and critical to normal protein functions. Heterogeneities in rat kidney, liver and muscle, were observed in terms of isomeric compositions of three sets of C18:1-containing PLs from each organ (See Examples below). In general n-7 isomers were found to increase in relative amounts from brain, kidney, liver, to muscle, although many PLs cannot be detected in all three organs.

Altered Compositions of PL C=C Isomers in Cancerous Tissues

Following the confirmed changes in lipid C=C isomers' compositions in different rat organs, it was investigated as to whether similar differences may exist between normal and cancerous cells/tissues. Methods of the invention were validated by choosing mouse breast cancer as the model of study, with normal mouse breast tissues used as controls (wild type, WT). From all polar lipid extracts, PCs were the most abundant lipid species detected by +nanoESI. Therefore, PCs containing C18:1, including PC 16:0/18:1, PC 18:0/18:1, PC 18:1/18:1, were then subjected to P-B reaction and tandem MS to determine their isomeric compositions (see Examples below). FAs were extracted using a different protocol, and isomers of FA 18:1 were quantified to compare with C18:1-containing PCs.

As expected, all C18:1-containing PCs and FA 18:1 studied consist of n-9 and n-7 isomers (see Examples below). Of most interests is the phenomenon that, as FIGS. 4C-F show, relative amounts of FA 18:1 n-7 and C18:1 n-7-containing PCs were elevated in rat breast cancer tissues (except for PC 16:0/18:1). The most significant n-7 isomer increases were seen in FA 18:1 and PC 18:1/18:1. For PC 18:1/18:1. Another isomer was also observed, i.e. PC 18:0/18:2 n-6. Converse to FA 18:1 n-7 and C18:1 n-7-containing PCs, the relative amount of PC 18:0/18:2 n-6 was drastically down-regulated in breast cancer tissues (see Examples below). The possible mechanism underlying these observations can be altered synthesis, transformation and metabolism of FA and PL C=C isomers in cancer cells. Such differences offer a novel perspective to identify malignancies and disease states, by focusing on detailed lipid composition information such as lipid C=C isomer composition.

Quantitative Methods

The data herein show the power of PCD-MS$^n$ strategy towards efficient and accurate quantitation of lipid C=C isomers in complex tissue extracts. The method can be used as a routine technique for quantitative analysis of unsaturated lipids for the following reasons: (1) The method possesses both structural characterization and isomer quantitation capabilities, thereby allowing analysis of unlimited number of lipid C=C isomers. (2) Very high signal-to-noise ratios (S/Ns) can be achieved for diagnostic ions, which are extremely desirable for quantitative analysis. First, CID is applied to produce diagnostic ions, during which most interference in MS1 was removed. Second, the oxetane ring is a high-energy structure that can be preferentially cleaved to produce abundant diagnostic ions. (3) P-B reaction is radical-based that is very selective towards C=Cs, but irrespective of C=C locations, so all types of unsaturated lipids can be derivatized and analyzed, in both positive and negative modes. (4) Because diagnostic ions were produced in tandem MS, they can be easily mapped to their precursor lipids, enabling direct analysis of complex mixtures. Therefore, PCD-MS$_n$ is compatible and can be easily coupled with shotgun lipidomics for large-scale quantitative analysis, and no front-end chromatographic separation or back-end instrumental modification is required.

Lipid C=C isomer composition, maintained by a network of sensors and pipelines evolved by cells, is critical for membrane hemostasis integral to a range of cellular processes. However, as a consequence of the lack of sensitive and robust methods, systematic monitoring and profiling of lipid C=C isomer compositions are very challenging. The present methods provide a suitable approach for such analyses, which is capable to supply important evidence to enigmatic problems in biochemical studies, such as: What is the underlying mechanism used to maintain the heterogeneity in lipid C=C isomer composition in organs? How do changes in relative amounts of C=C isomers of lipids affect cell metabolism and relate to pathogenesis? Can C=C isomer compositions be exploited for disease diagnostics, or exogenous lipid C=C isomers be used as therapeutics to intervene, halt or even reverse disease progression? The results acquired from PCD-MS$_n$ and shotgun lipidomics already show that the isomeric compositions of FA and PLs are significantly different between normal and cancerous cells/tissues. PCD-MS$_n$-based lipidomics, therefore, provides new opportunities for investigating the roles of lipid C=C isomers in biological processes as well for discovering biomarkers towards disease diagnosis.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Materials and Methods

Fatty acid extraction protocol: 1 mL of MeOH and 25 mM HCl (1% v) were added into 50 mg of tissue prior to sample homogenization in a glass tube. The sample was then vortexed for 30 s before centrifugation at 2700 rpm for 10 min. The supernatant was subsequently removed and evaporated until dry.

Phospholipid extraction protocol: Into 50 mg of tissue was added 300 µL of deionized water prior to sample homogenization in a glass tube. Prepare extraction solvent, chloroform/methanol (1/1; v/v) (solvent A), and 10 and 50 nM LiCl solutions. Chloroform was obtained from VWR (IL, USA) and LiCl was from Alf Aesar (MA, USA). After homogenization, 4 mL solvent A was added to a glass tube for extraction, and an appropriate volume of 50 mM LiCl to bring the aqueous phase to a final volume of 2 mL. Then the tubes and were capped and samples were vortexed for 20 sec. After that samples are centrifuged at 2700 rpm for 10 min. The bottom layer was collected to a new borosilicate glass tube and 2 mL chloroform was added to individual glass tubes with the residual top layer. Tubes were then capped and vortexed for 20 sec. Samples are again centrifuged at 2700 rpm for 10 min. The bottom layer was collected and combined with that collected in the last step. The combined bottom layer was evaporated under a nitrogen stream with a nitrogen-evaporator until totally dried. The individual residue was suspended with 4 mL of solvent A, followed by addition of 2 mL of 10 mM LiCl. Tubes were capped and vortexed for 20 sec. and then centrifuged at 2700 rpm for 10 min. The above two steps were repeated. The individual lipid extract residue was re-suspended in solvent A. Lipid extracts were finally flushed with nitrogen, capped, and stored at −20° C. for MS analysis.

GC-MS analysis: Fatty acid sample were first dried under vacuum and then reconstituted in ethyl acetate.

Before GC-MS analysis, 25 uL of sample was mixed 25 uL of derivatizing reagent. Then 0.5 uL of the final solution was injected at a split ratio of 10:1.

NanoESI-MS, online Paternó-Büchi reaction and tandem MS analysis: FAs (Sigma-Aldrich, MO, USA), PLs (Sigma-Aldrich, MO, USA) and rat tissue extracts were all dissolved in 50/50 (v/v) acetone/water before MS analysis. To facilitate detection of FAs by −nanoESI, 0.5% NH$_4$OH was added into the sample. For P-B reaction between acetone and C=Cs, a low-pressure mercury (LP-Hg) lamp with an emission at 254 nm (Model No.: 80-1057-01, BHK, Inc., CA, USA) was used. All MS experiments were performed on a 4000 QTRAP triple quadrupole/linear ion trap (LIT) hybrid mass spectrometer (Applied Biosystems/Sciex, Toronto, Canada). This instrument allows PIS and NLS, as described in the paper. The instrument parameters used are as follows: ESI voltage, ±1200-1800V; curtain gas, 10 psi; interface heater temperature, 40 C; declustering potential: ±20. Precursor ion isolation width was set to 1.0 Th. The precursor ion intensity was kept at around 4×106 counts for MS/MS, by keeping ion injection time within 10-200 ms. The collision energy used for P-B reaction products is 35 V (beam CID) or 50 a.u. (trap CID).

Figure 5A:
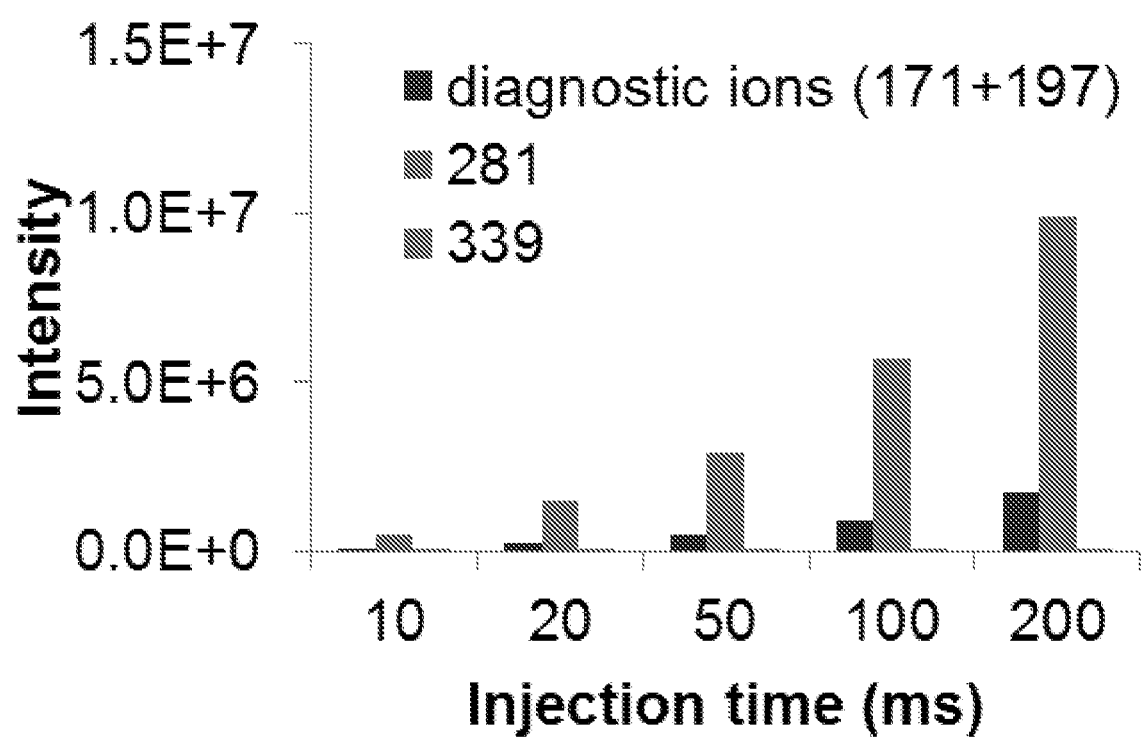
FIGS. 5A-B show precursor ion injection time has negligible effects on different retro-P-B reaction channels (those leading to production of diagnostic ions and those leading to m/z 281, due to a neutral loss of acetone).
Figure 5B:
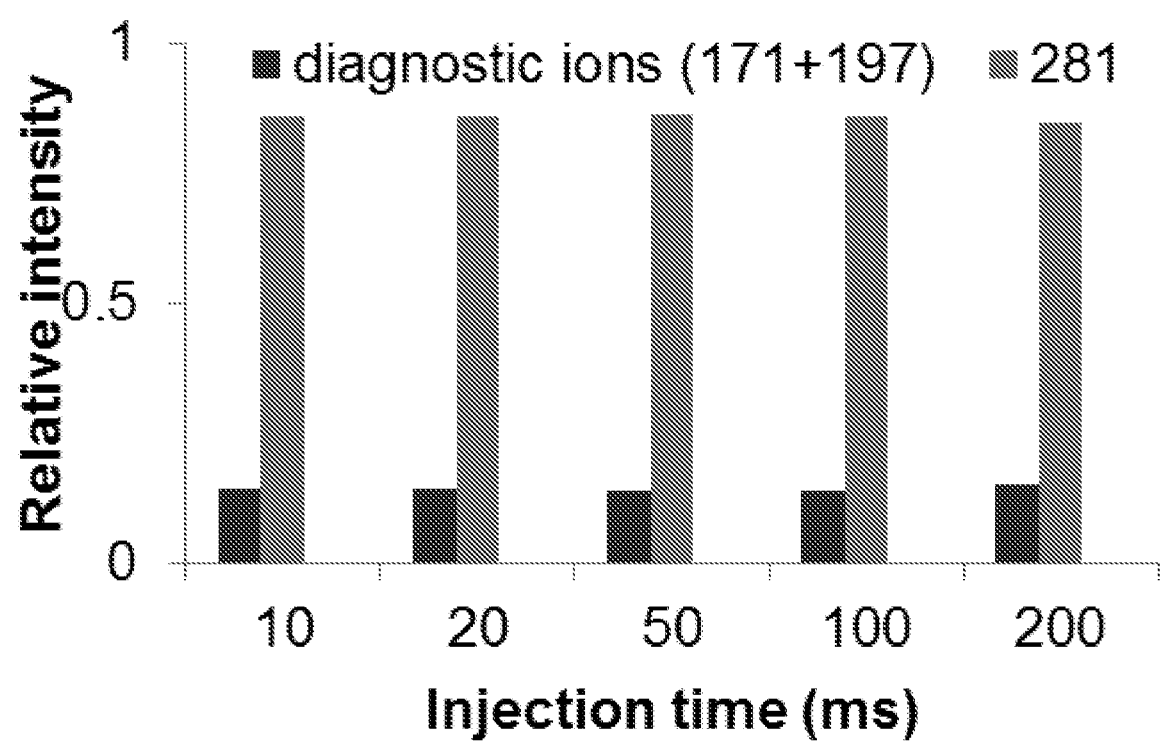

Example 2: Effects of Ion Injection Time on the Relative Intensities of Diagnostic Ions after Tandem MS The data in FIGS. 5A-B and Table 1 illustrate that with increased ion injection time (from 10 to 200 ms), the absolute intensities of precursor ions (P-B reaction products), ions after a 58 Da neutral loss and DIs all increase as well. However, the relative intensities of DIs and ions after a 58 Da neutral loss are very stable although the injection time is increased 20 times. Since the production of DIs and neutral loss ions are two retro P-B reaction pathways, the results indicate that the branching between the two retro-pathways are not dependent upon injection time. Such an important feature makes it unnecessary to carefully control the amount of precursor ions admitted into the ion trap for CID analysis.

TABLE 1

| Ion injection time (ms) | % of diagnostic ions (m/z 171/197) | % of neutral loss ions (m/z 281) |
|---|---|---|
| 10 | 0.14 | 0.86 |
| 20 | 0.14 | 0.86 |
| 50 | 0.14 | 0.86 |
| 100 | 0.14 | 0.86 |
| 200 | 0.15 | 0.85 |

Example 3: P-B Reaction Kinetics

A mixture of PC 18:1 n9/18:1 n9 and 18:1 n12/18:1 n12 was used to study the P-B reaction kinetics by +nanoESI. The amount of P-B reaction products were represented by their extracted ion current (EIC). Once the LP-Hg lamp was warmed up, a rapid increase in the amount of reaction products was observed. The reaction became stable after about 0.3-0.5 minute to reach a plateau.

Figure 6:
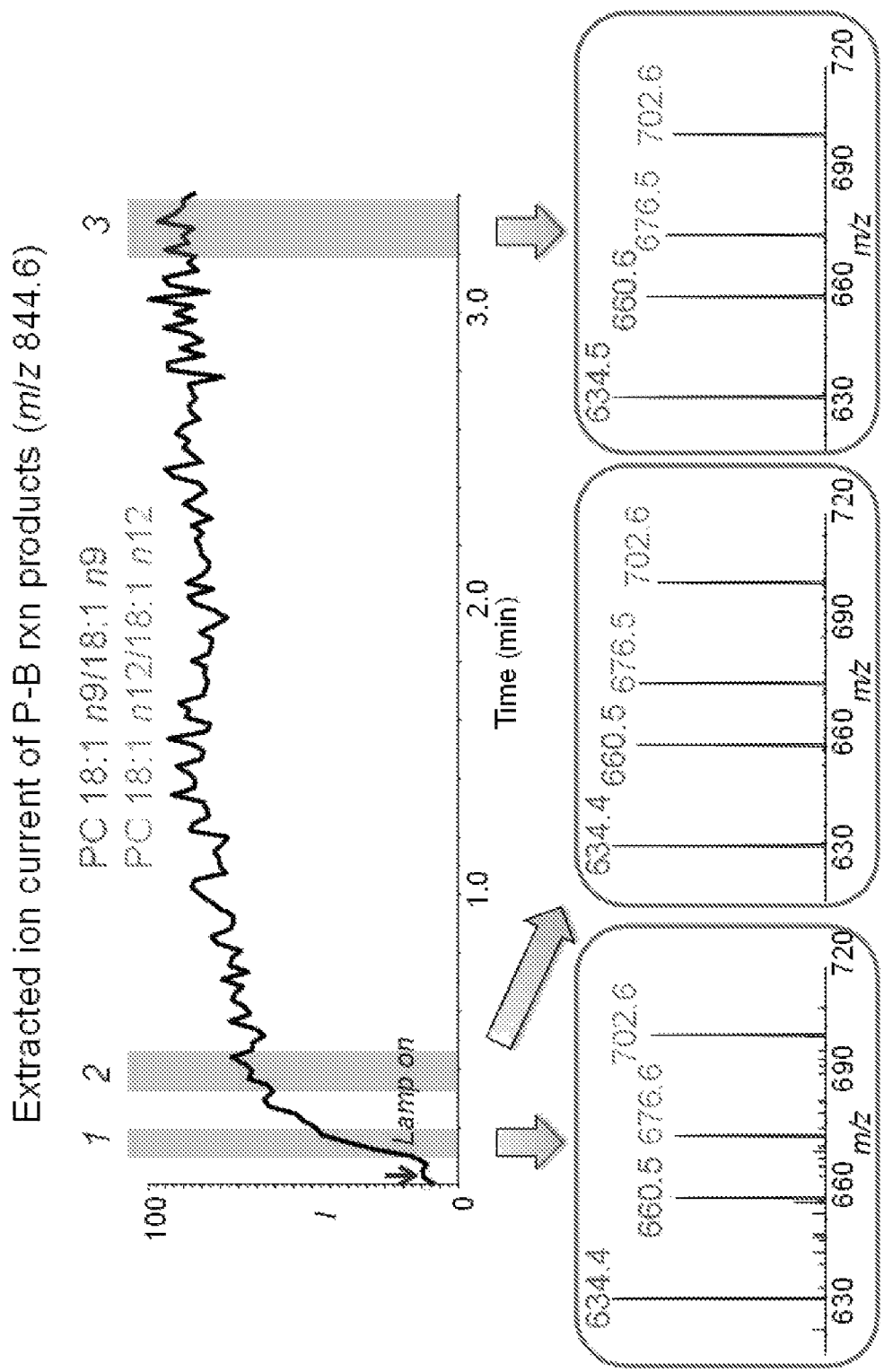
FIG. 6 show kinetics of P-B reaction between PC 18:1/18:1 (a mixture of two C=C isomers) with acetone under 254 nm UV irradiation. Fast reaction rate was observed: Within 0.4 min the reaction became stable. After that, the ratio between diagnostic ions for each isomer became constant, which lays the foundation for quantitative analysis (see the three tandem spectra at time points 1, 2 and 3).
Figure 7A:
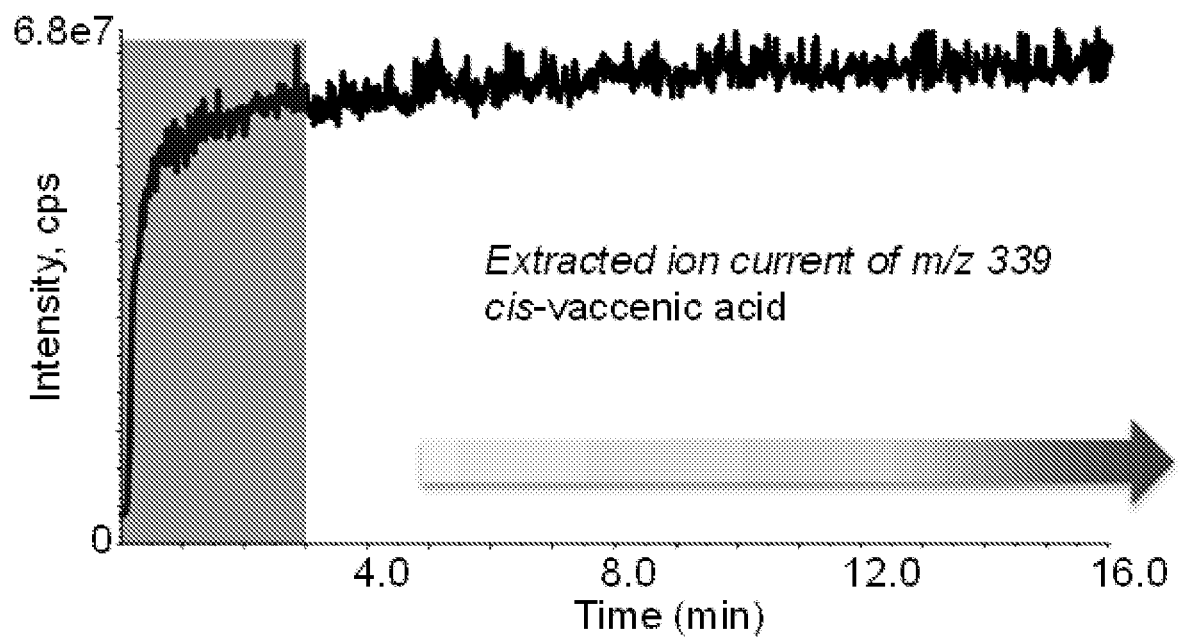
FIGS. 7A-D are CID mass spectra of P-B reaction products of oleic acid/cis-vaccenic acid mixture solutions (at different molar ratios).
Figure 7B:
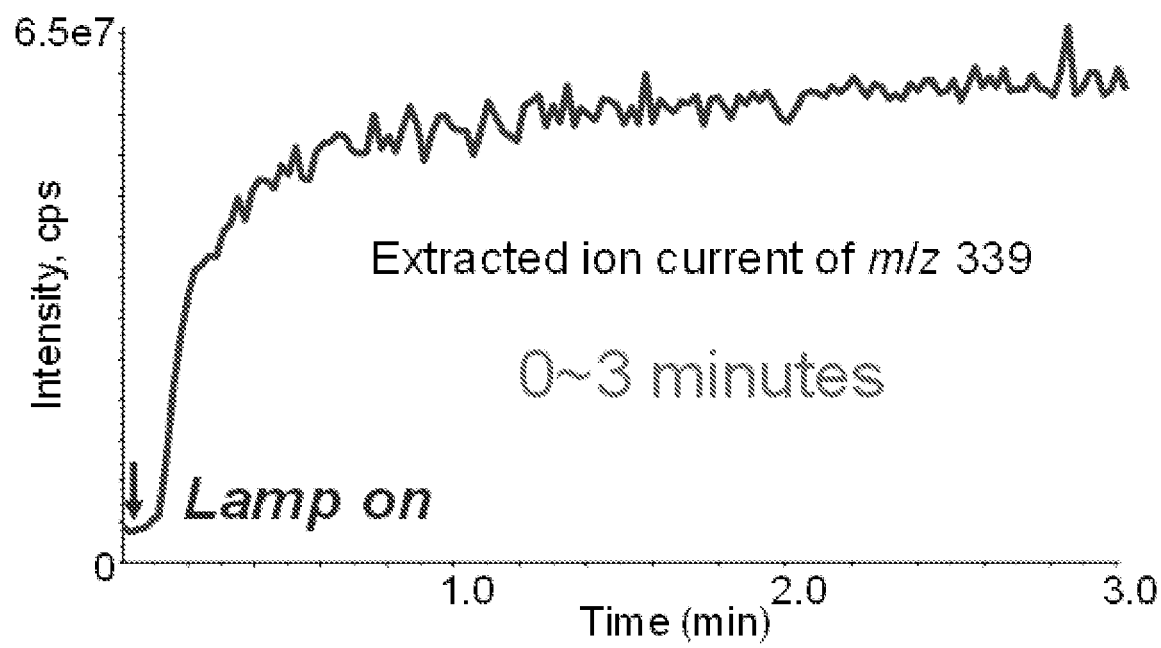
Figure 7C:
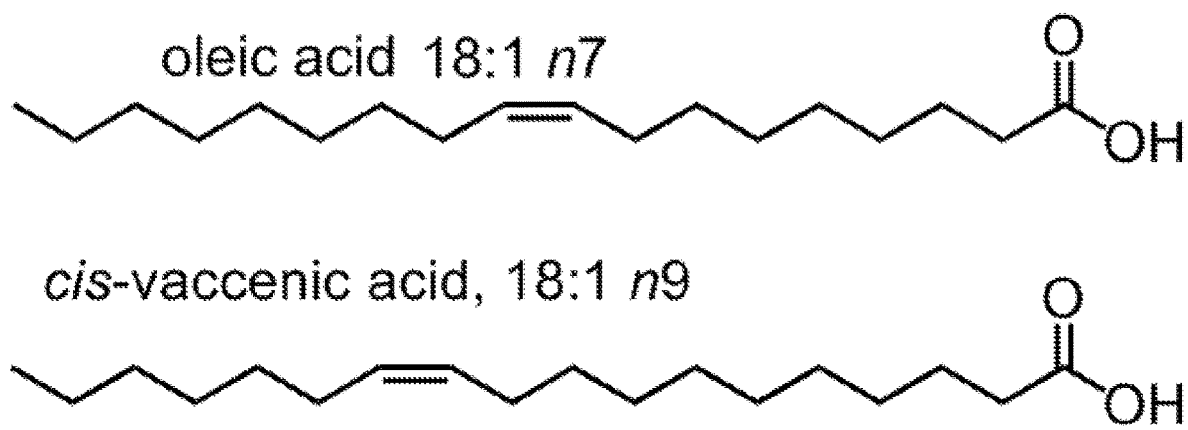
Figure 7D:
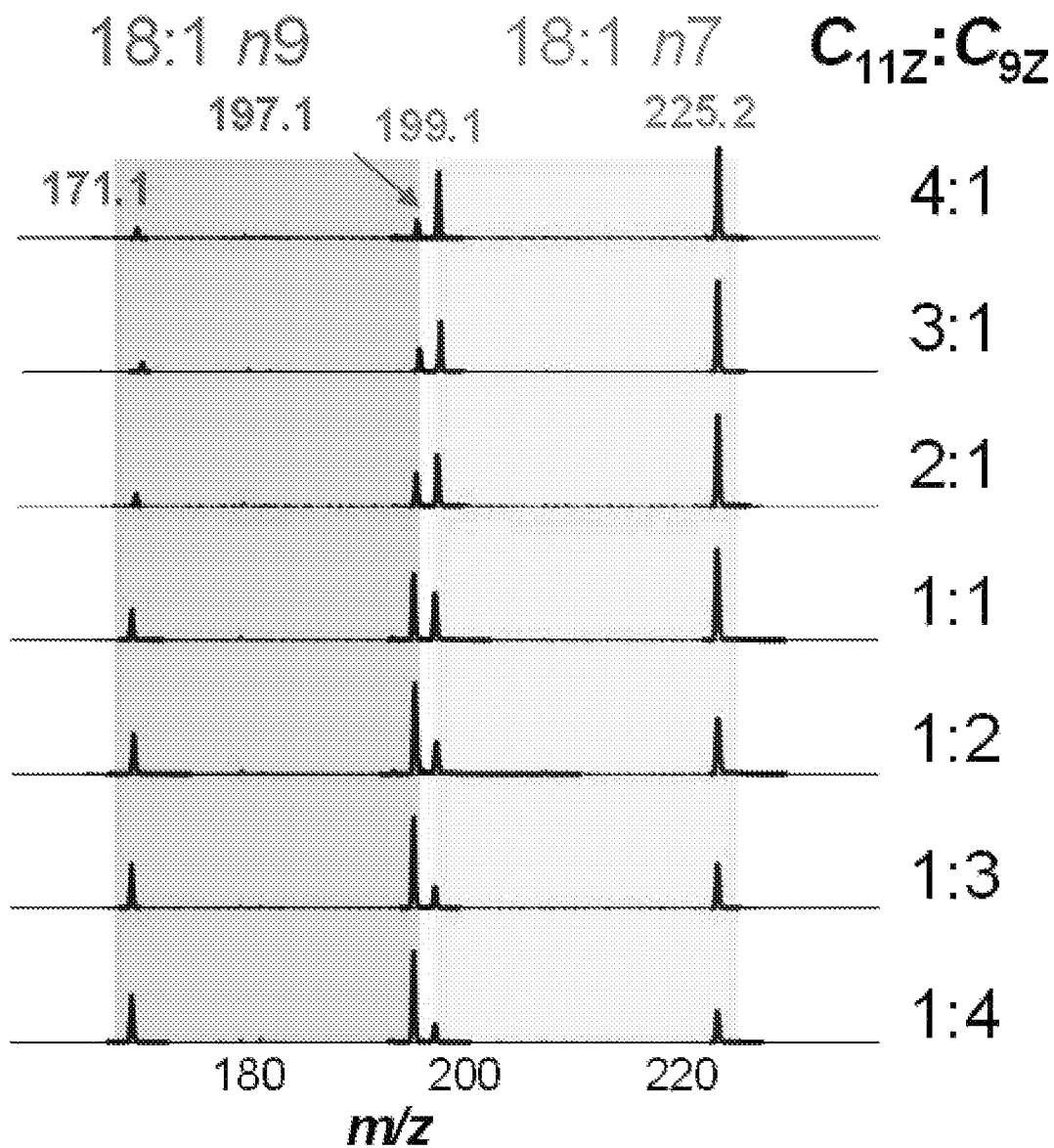
Figure 8A:
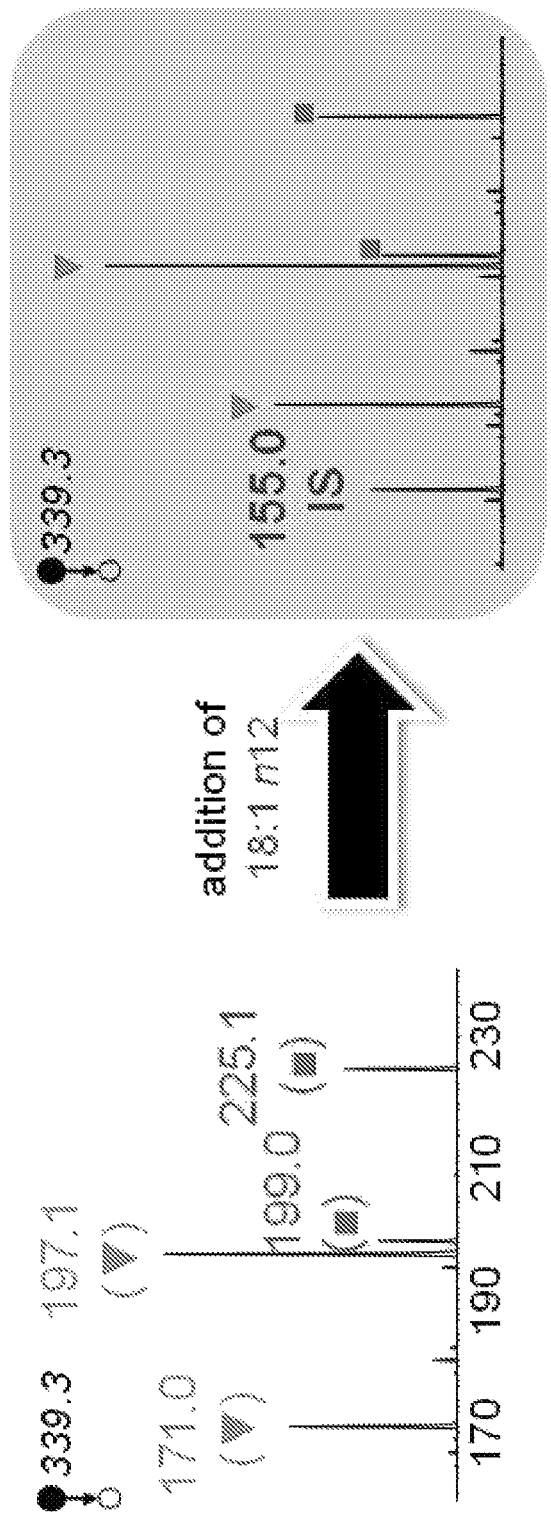
FIGS. 8A-C show three methods that allow absolute quantitation of lipid C=C isomers. FA 18:1 isomers were used as an example to demonstrate the principles. IS: internal standard.
Figure 8B:
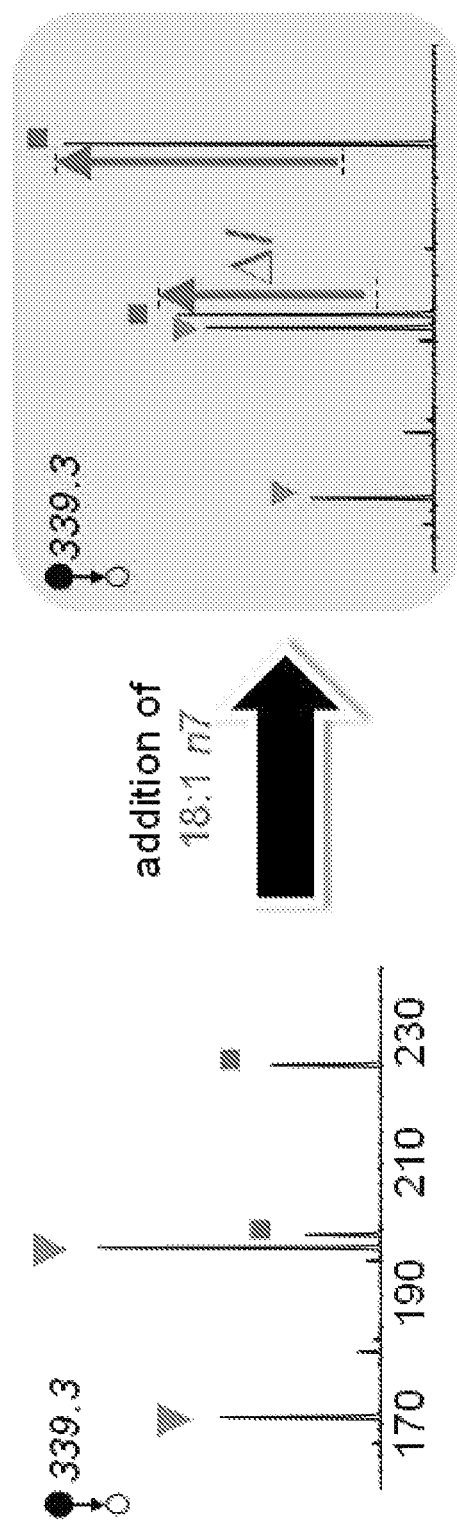
Figure 8C:
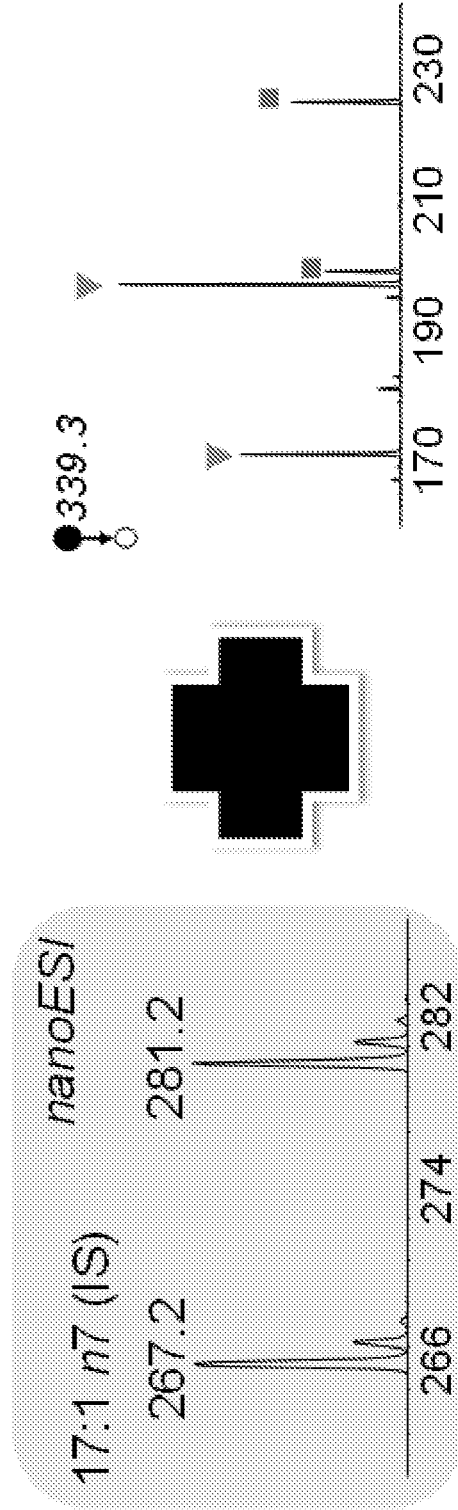

FIG. 6 show kinetics of P-B reaction between PC 18:1/ 18:1 (a mixture of two C=C isomers) with acetone under 254 nm UV irradiation. Fast reaction rate was observed: Within 0.4 min the reaction became stable. After that, the ratio between diagnostic ions for each isomer became constant, which lays the foundation for quantitative analysis (see the three tandem spectra at time points 1, 2 and 3).

Similar results were observed for unsaturated fatty acids by −nanoESI. Shown in FIGS. 7A-D are EIC of P-B reaction products of a cis-vaccenic acid solution (m/z 339.3), as well as a magnified view of EIC (3 minutes after P-B reaction was initiated).

Example 4: Principles of Three Methods that Allow Absolute Quantitation of Lipid C=C Isomers, Based on P-B Reaction and Tandem MS Method 1: Absolute quantitation using a third isomer as IS: One C=C isomer, different from those to be quantified, was used as the internal standard (IS). Ratios of diagnostic ions of the IS to those from C=C isomers to be analyzed in the sample can then be calculated. The absolute amounts of C=C isomers can be found out from calibration curves prepared for each isomers using the IS.

Method 2: Standard addition: A known amount of one isomer (present in the sample for analysis, for example FA 18:1 n11) was added into the mixture. As a result of standard addition, the intensity ratio between the two pairs of diagnostic ions will be changed.

Let us define the following parameters:

$I_1$ as the intensity ratio between the two pairs of diagnostic ions before standard addition, $I_2$ as the intensity ratio between the two pairs of diagnostic ions after standard addition, $\Delta c$ as the increase in isomer concentration (in this case the concentration of FA 18:1 n11), $c_1$ as the concentration of FA 18:1 n11, $c_2$ as the concentration of FA 18:1 n9.

Since the calibration curve between C18:1 n11 and C18:1 n9 is I=1.6942x−0.017 (x is concentration ratio (FA 18:1 n11 to FA 18:1 n9)), we have, $$\frac{c_1}{c_2} = \frac{I_1 + 0.017}{1.6942}$$

$$\frac{\Delta c + c_1}{c_2} = \frac{I_2 + 0.017}{1.6942}$$

Therefore, the original concentrations of FA 18:1 n11 and FA 18:1 n9 can be readily found out, $$c_1 = \frac{I_1 + 0.017}{I_2 - I_1}\Delta c$$

$$c_2 = \frac{1.6942}{I_2 - I_1}\Delta c$$

Figure 9A:
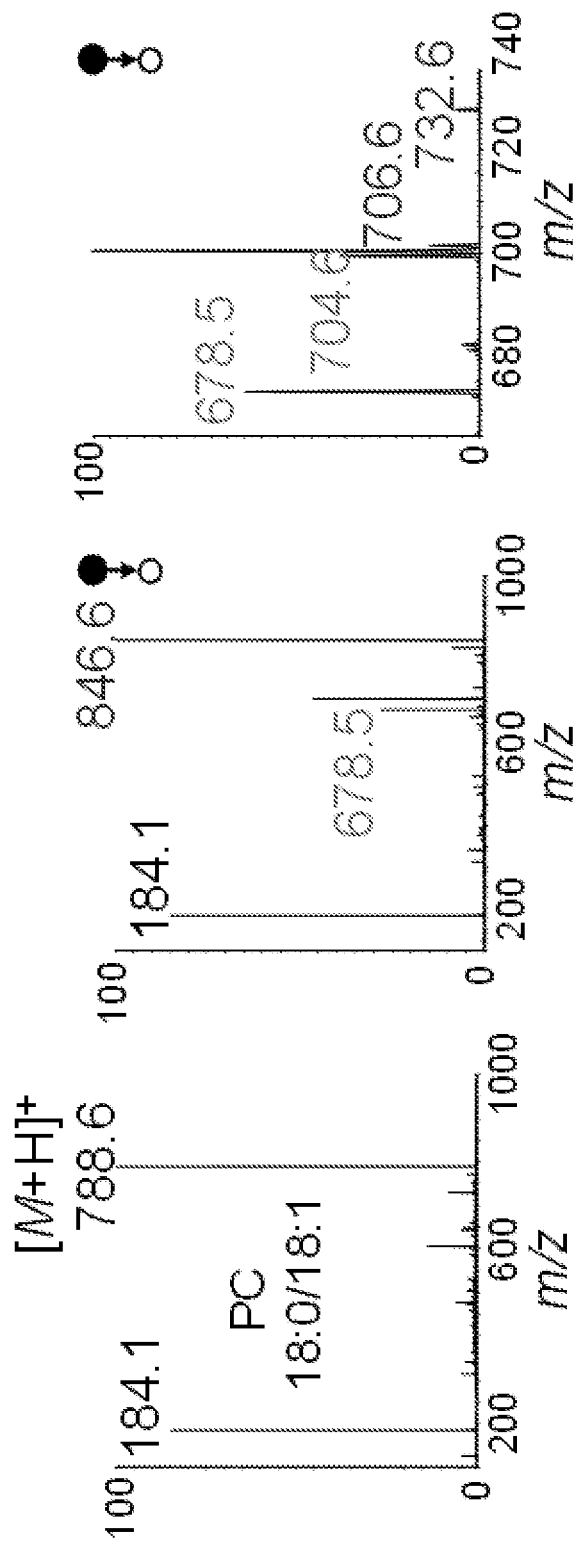
FIGS. 9A-B show relative quantitation of PLs by CID in positive and negative modes (using PC 18:0/18:1 and lysoPE 18:1 as examples).
Figure 9B:
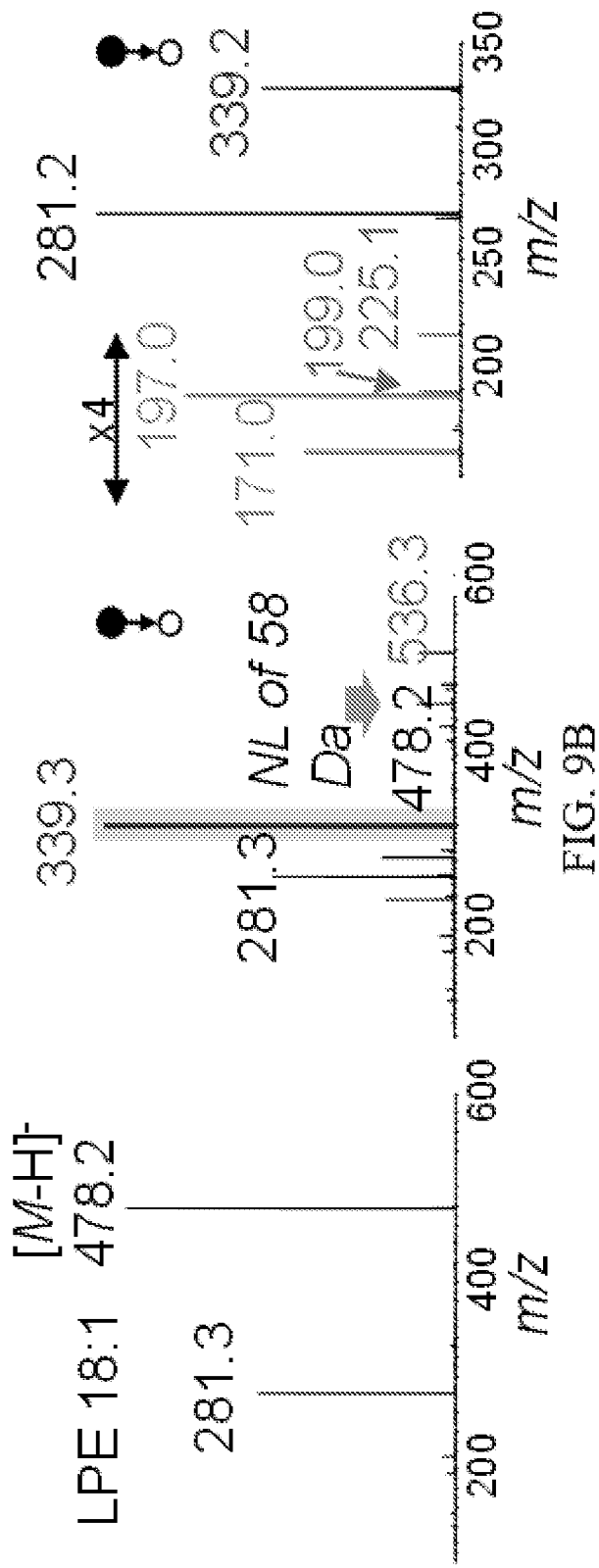

Example 5: Relative Quantitation of C=C Isomers of Phospholipids of Different Types Depending on the polarity of the PL headgroup, PLs can be analyzed in either positive or negative ion mode. Accordingly, PCs were analyzed by +nanoESI, while PAs, PIs, PEs and PSs were analyzed by −nanoESI. Here we use two examples (PC 18:0/18:1 and lyso PE 18:1) to demonstrate the relative quantitation of PLs using P-B reaction/tandem MS. Acyl chain information in PLs can be acquired via (−)CID of their formate, acetate, or chloride adducts (See FIGS. 9A-B).

Example 6: Structural Characterization and Quantification of PUFAs

Figure 10:
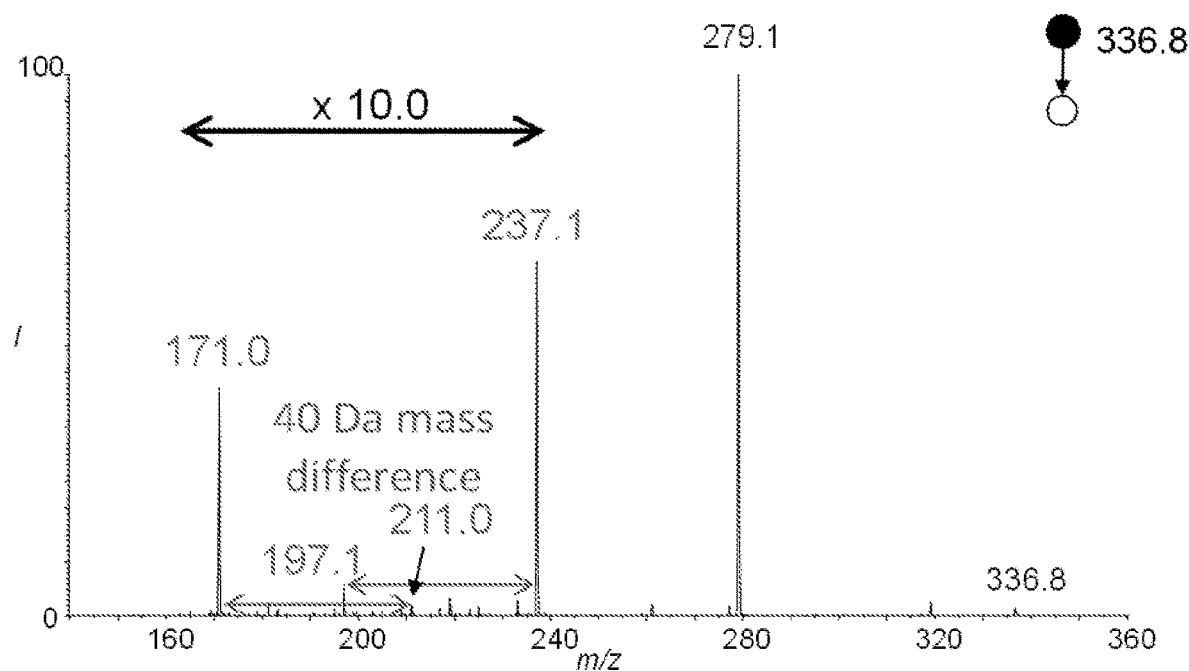
FIG. 10 shows MS2 ion trap CID mass spectrum of P-B reaction products of FA 18:2 in rat adipose tissue. Two pairs of diagnostic ions at m/z 171.0/197.1 and 211.0/237.1 were detected. The 40 Da mass difference between the two pairs indicate that the two C=Cs in FA 18:2 are methylene-separated.
Figure 11A:
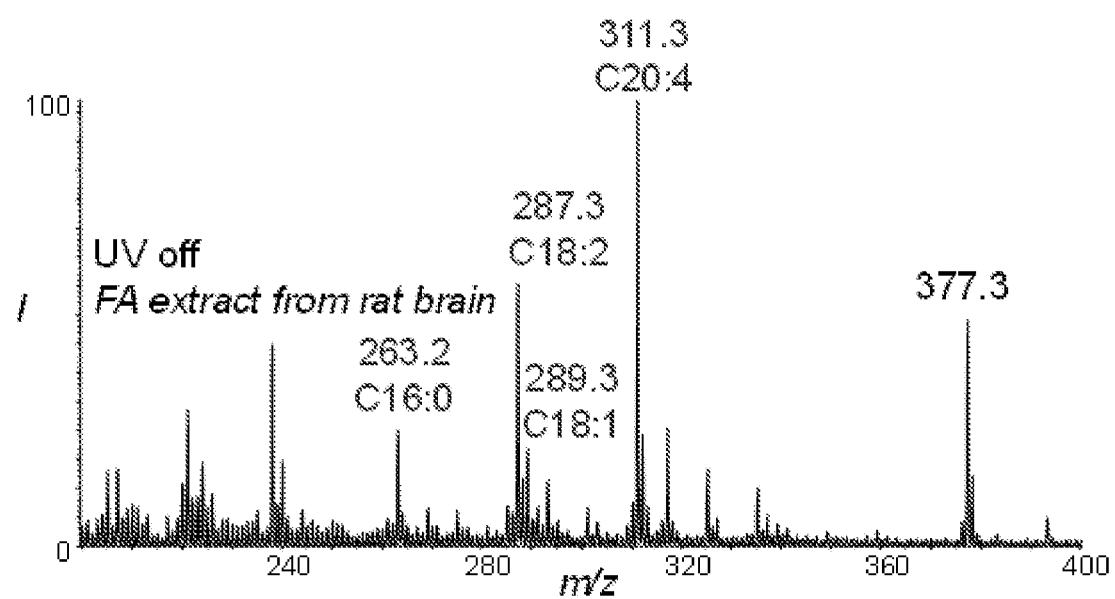
FIGS. 11A-D show structural characterization of FA 20:4 in rat kidney.
Figure 11B:
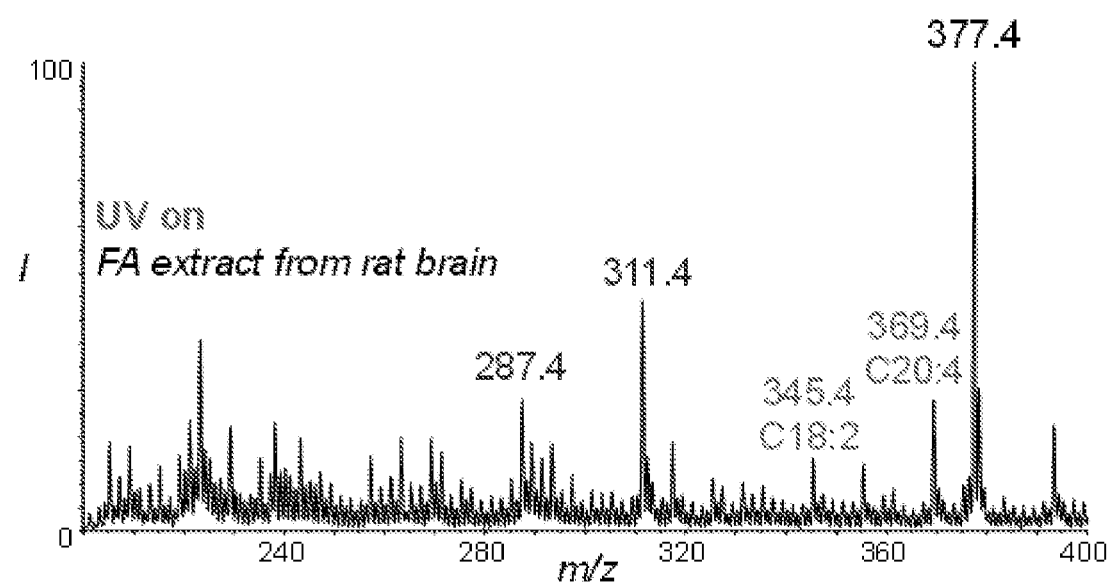
Figure 11C:
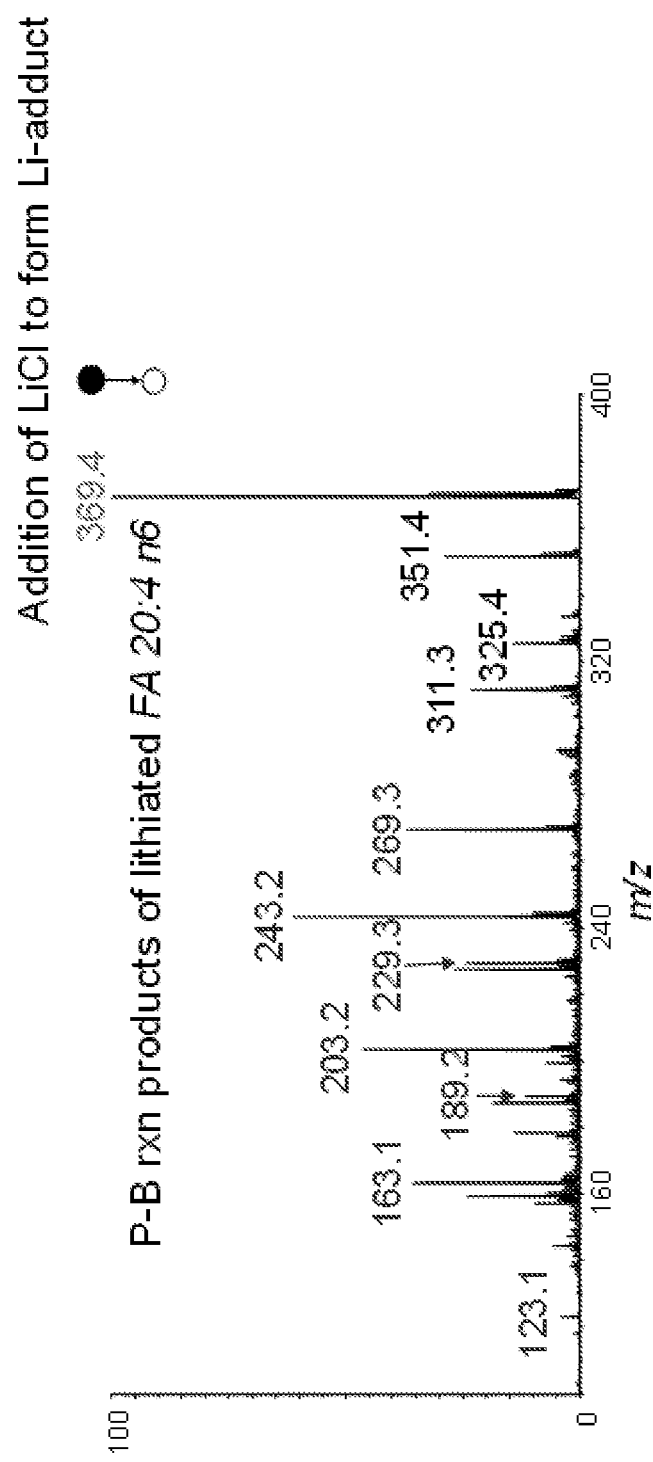
Figure 11D:
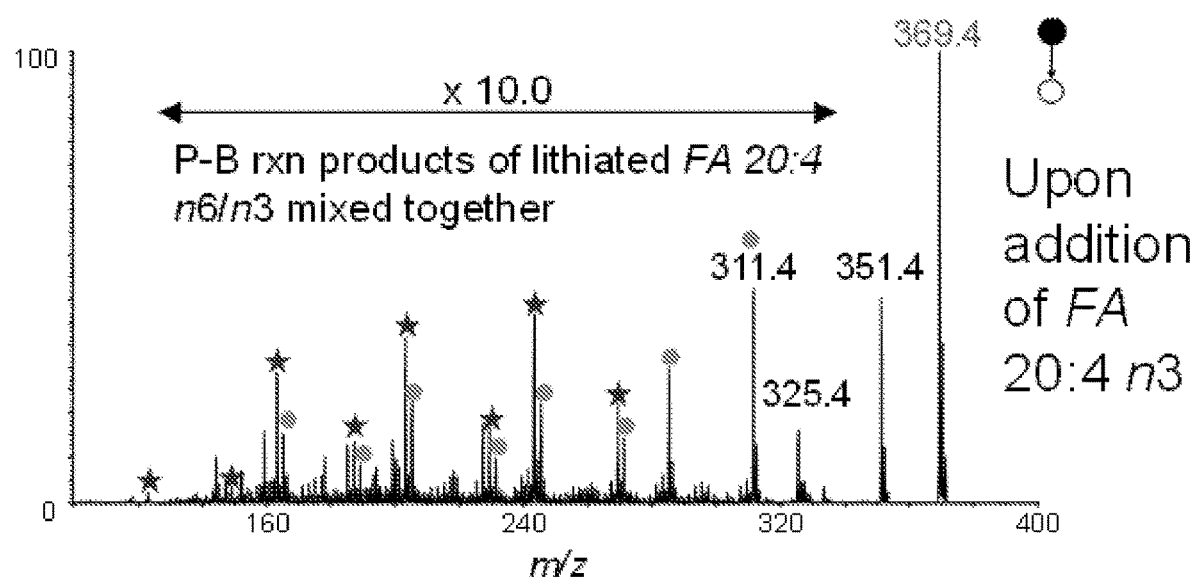
Figure 11E:
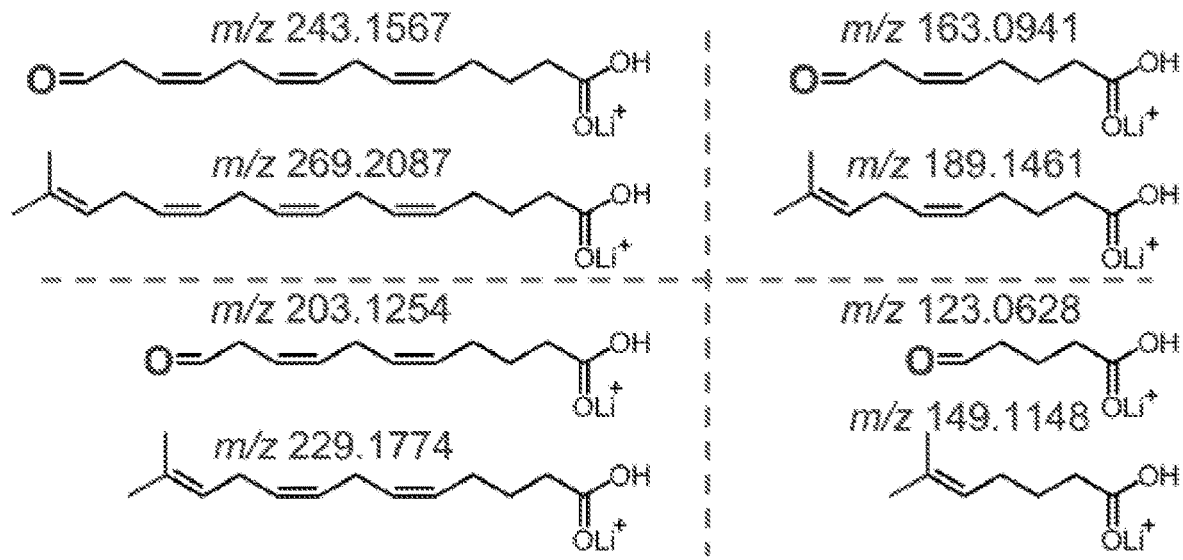
FIG. 11E shows diagnostic ions of Ω6 archidonic acid and Ω3 archidonic acid.
Figure 11E:
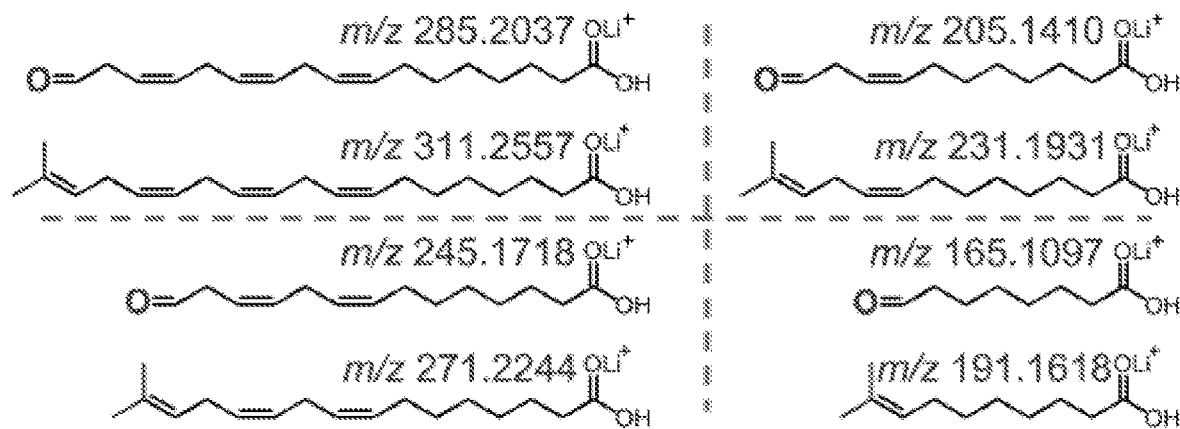

For FA 18:2 in all rat organs, CID of its P-B reaction products releases two pairs of diagnostic ions that are in line with the two methylene-separated C=Cs at C9 and C12 (FA 18:2 n6). See FIG. 10.

However, for PUFAs containing even larger number of C=Cs, the fragmentation pathway of $CO_2$ loss (−44 Da) during fragmentation of both intact PUFAs and their P-B reaction products becomes predominant. Other fragmentation pathways become suppressed and assignment of C=C positions turns out difficult. To circumvent this problem, lithium was deliberately added to render FAs detectable as [FA+Li]+ by +nanoESI. As shown in FIGS. 11A-D, tandem MS of lithiated P-B reaction products produced abundant diagnostic ions (in lithiated forms), with $CO_2$ loss now completely suppressed. Such a strategy allows versatile and effective characterization and quantitation of PUFA isomers.

Figure 12:
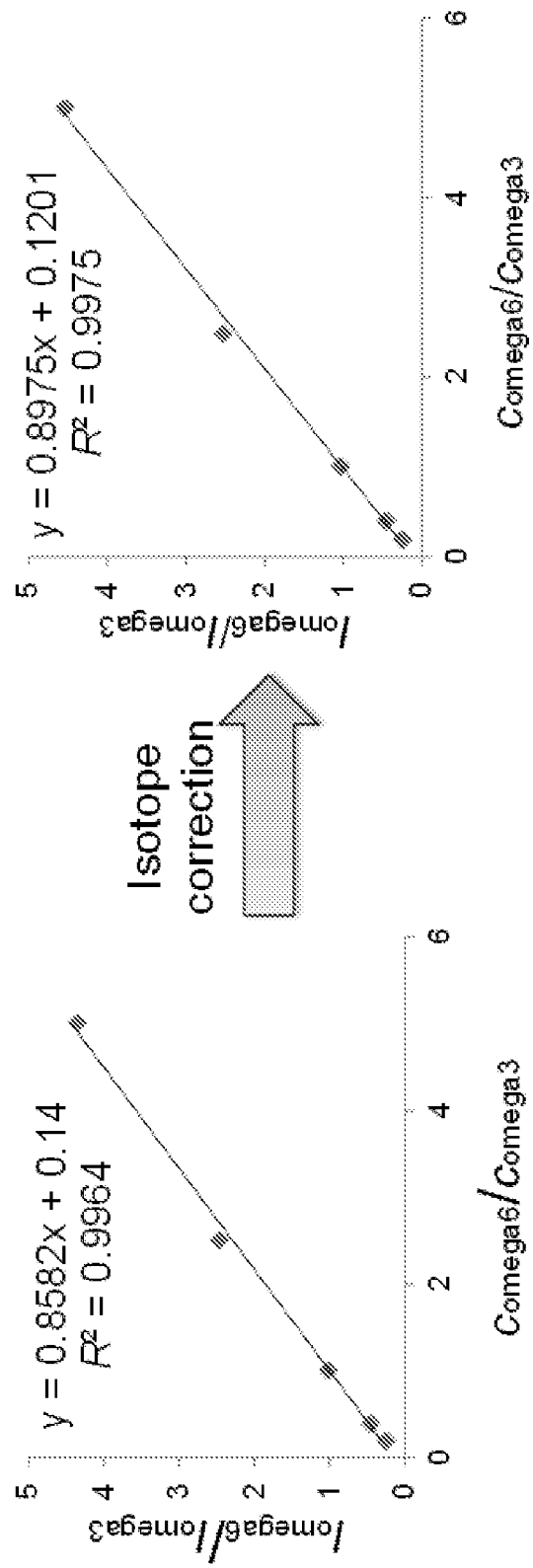
FIG. 12 shows calibration curves illustrating the linear relationship of IFA 20:4 n6/IFA 20:4 n3 vs. cFA 20:4 n6/cFA 20:4 n3.

FIG. 12 shows calibration curves illustrating the linear relationship of IFA 20:4 n6/IFA 20:4 n3 vs. cFA 20:4 n6/cFA 20:4 n3. Data also shown below in Table 2.

TABLE 2

| | Diagnostic ions (m/z) | | | | | |
|---|---|---|---|---|---|---|
| | 163 | 189 | 203 | 229 | 243 | 269 |
| Contribition to +2 Da isotope | 0.0062 (165) | 0.0065 (191) | 0.0065 (205) | 0.0107 (231) | 0.0107 (245) | 0.016 (271) |

Example 7: Polyunsaturated Fatty Acyls (C18:2, C20:4, C22:6 et al) in PLs Exist as Pure n6 Isomers in Rat Organs PL extracts were analyzed from rat organs, and results thereof lead to the conclusion that polyunsaturated fatty acyls exist as pure isomers (C18:2 and C20:4 as C18:2 n6 and C20:4 n6; and C22:6 as C22:6 n3), consistent with PUFAs previously identified.

Figure 13:
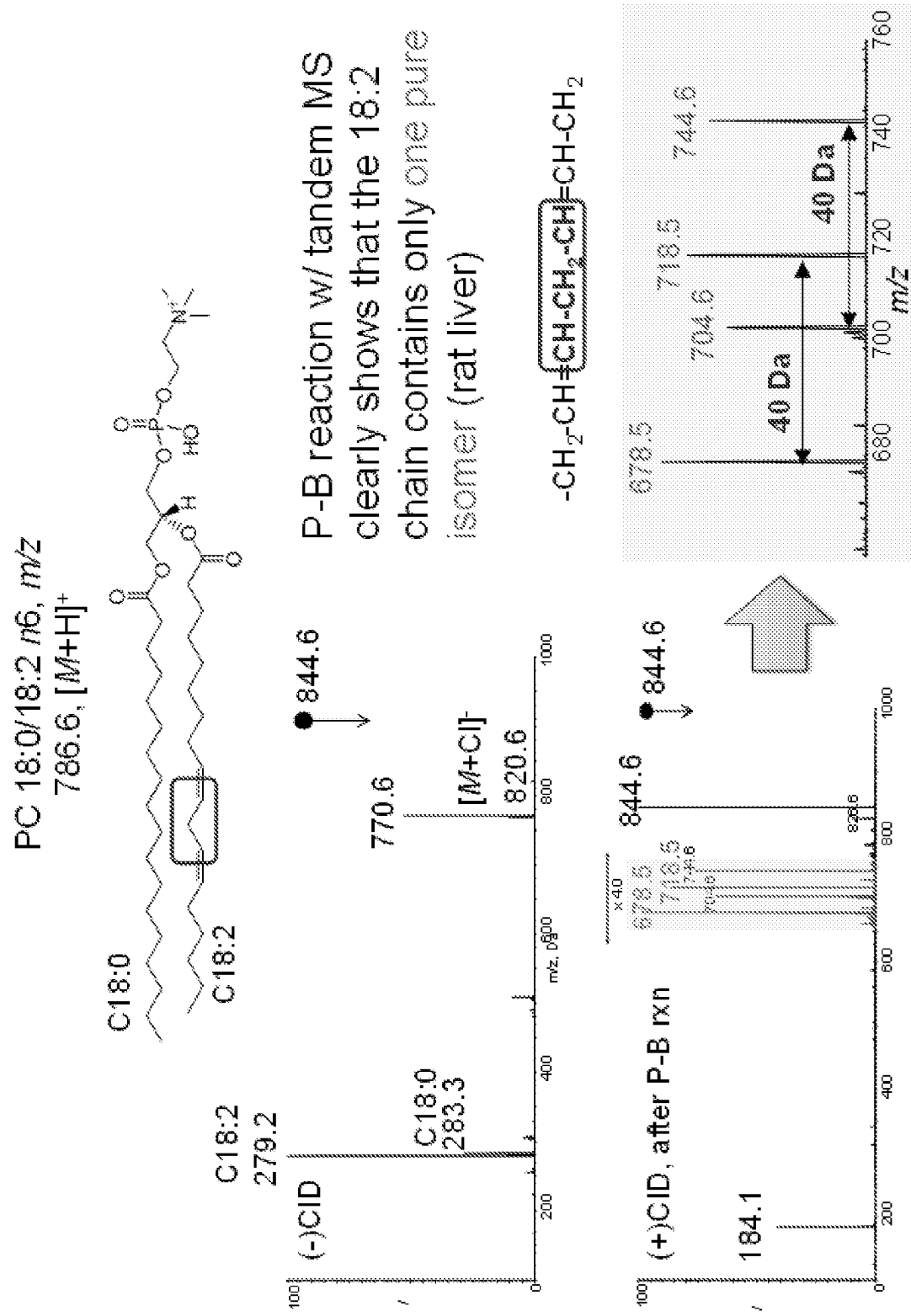
FIG. 13 shows that C18:2 is pure in the form of C18:2 n6 in PC 18:0/18:2. Acyl chain information of PC 36:2 was acquired via CID of [PC 36:2+Cl]−. In this case, PC 36:2 (from rat liver) was characterized as PC 18:0/18:2. Following P-B reaction and tandem MS, C=C positions in C18:2 can be assigned to be at 9Z and 12Z.

C18:2 fatty acyl (FIG. 13): Ions at m/z 786.6 (+nanoESI) were identified to be PC 18:0/18:2 (via −nanoESI-MS/MS of [PC+Cl]−). Double bond locations were identified after fragmentation of the corresponding P-B reaction products. Since PC 18:0/18:2 has two C=Cs, two pairs of diagnostic ions were observed, at m/z 678.5/704.6 and m/z 718.5/744.6. The 40 Da mass difference between the two pairs suggests the presence of two methylene-separated C=Cs, as shown in the box. In addition, the absence of any other pair of diagnostic ions confirms that no other isomer(s) of PC 18:0/18:2 exist.

C20:4 fatty acyl: The ions at m/z 782.6 (+nanoESI) were identified as a mixture of PC 16:0/20:4 and PC 18:2/18:2 (a smaller amount). Fatty acyl information were acquired via −MS/MS of [PC+Cl]−. For PC 16:0/20:4, four pairs of diagnostic ions were observed, in agreement with the presence of four C=Cs in C20:4. The two pairs of diagnostic ions for PC 18:2/18:2 happen to overlap with two out of the four pairs for PC 16:0/20:4 n6, at 674.6/692.6 and 714.6/740.6. As such, C18:2 in PC 18:2/18:2 was identified to be C18:2 n6, which is the same isomeric form as characterized for C18:2 within PC 18:0/18:2. In fact, for a polyunsaturated fatty acyl (exemplified by C20:4 here), no matter within what types of PL species it presides, is in the same pure isomeric form (data not shown for other polyunsaturated fatty acyls).

Figure 14A:
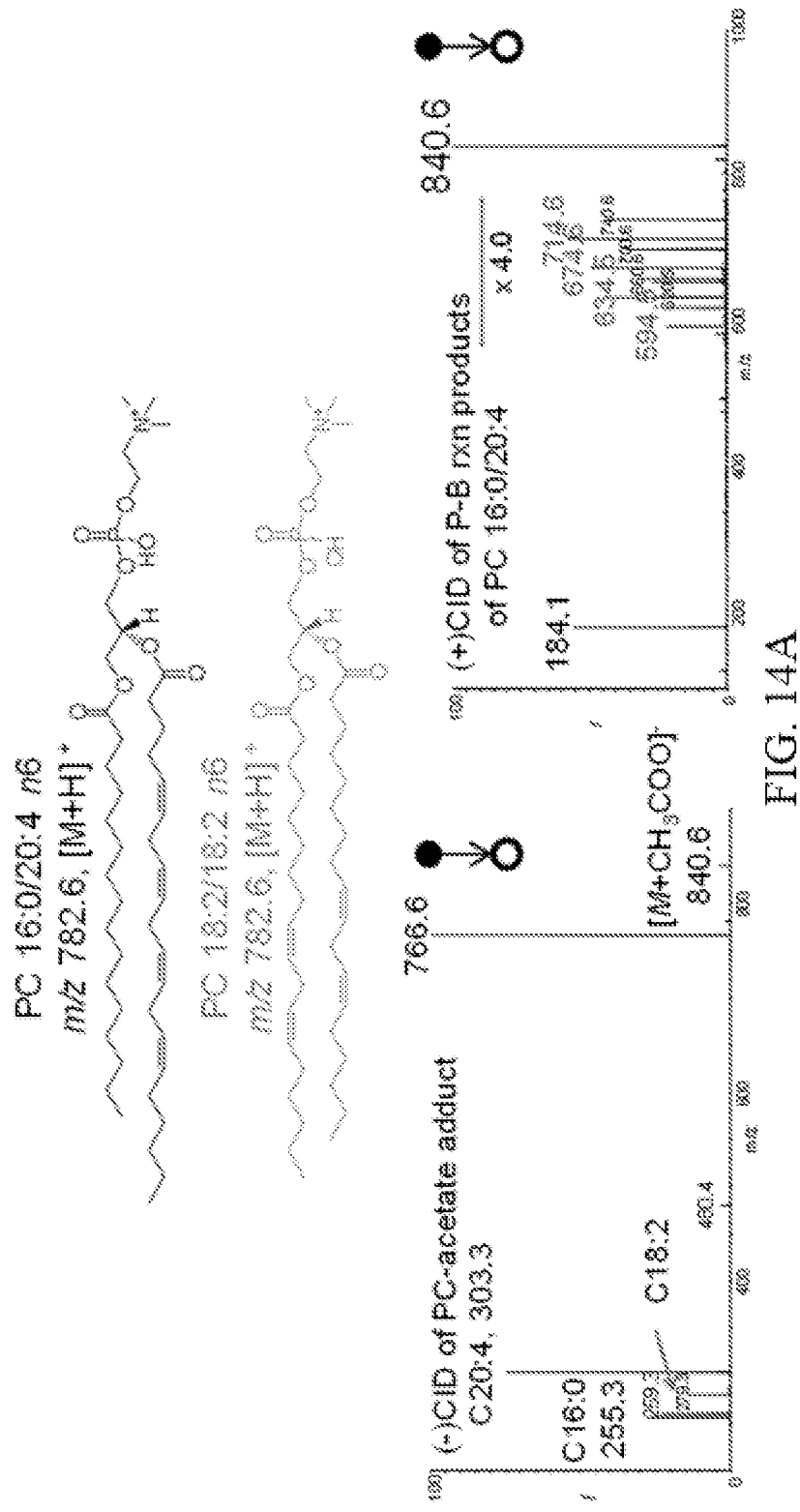
FIGS. 14A-B show that C20:4 fatty acyl in PE 16:0/20:4 is pure in the form of C20:4 n6.
Figure 14B:
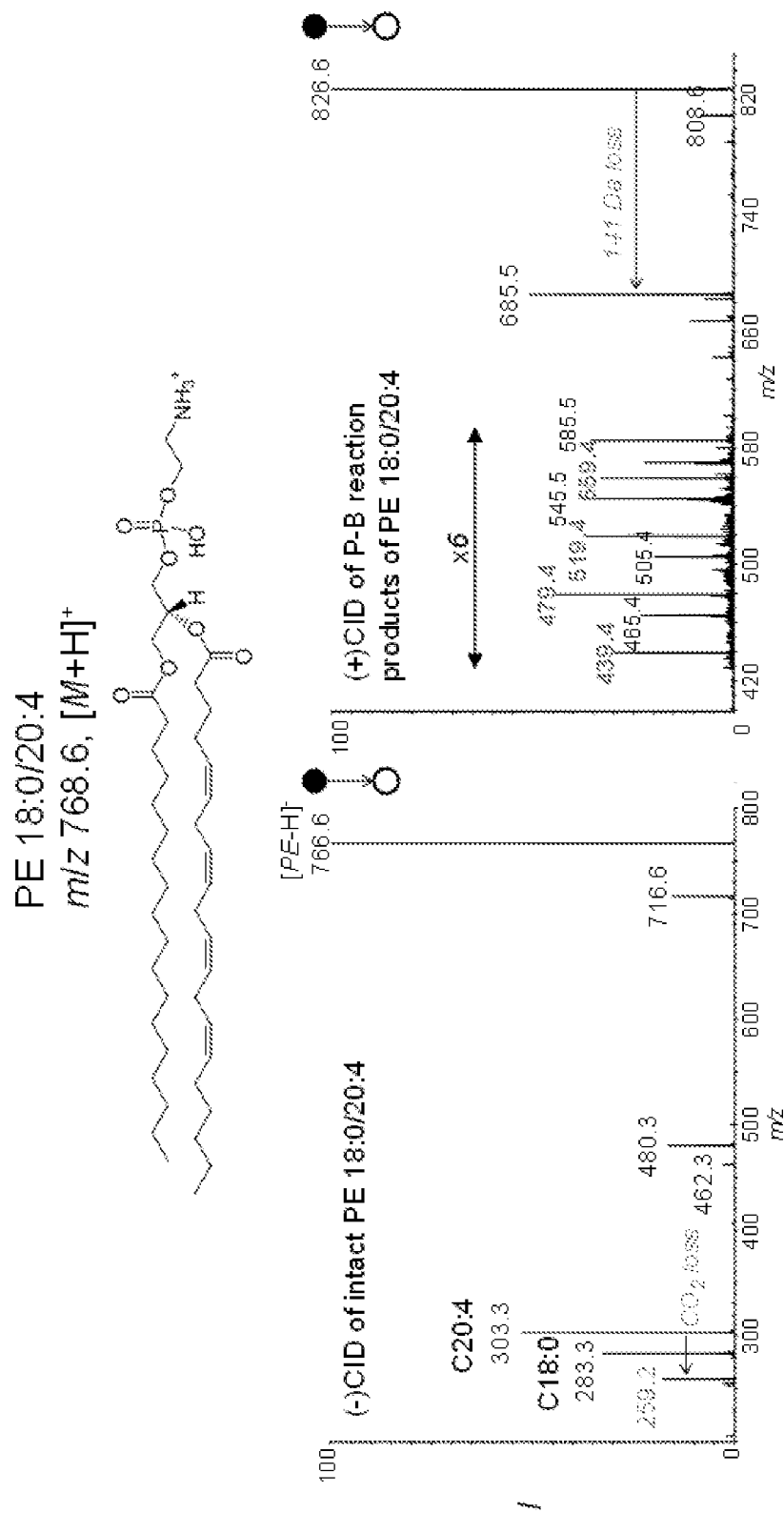
Figure 14C:
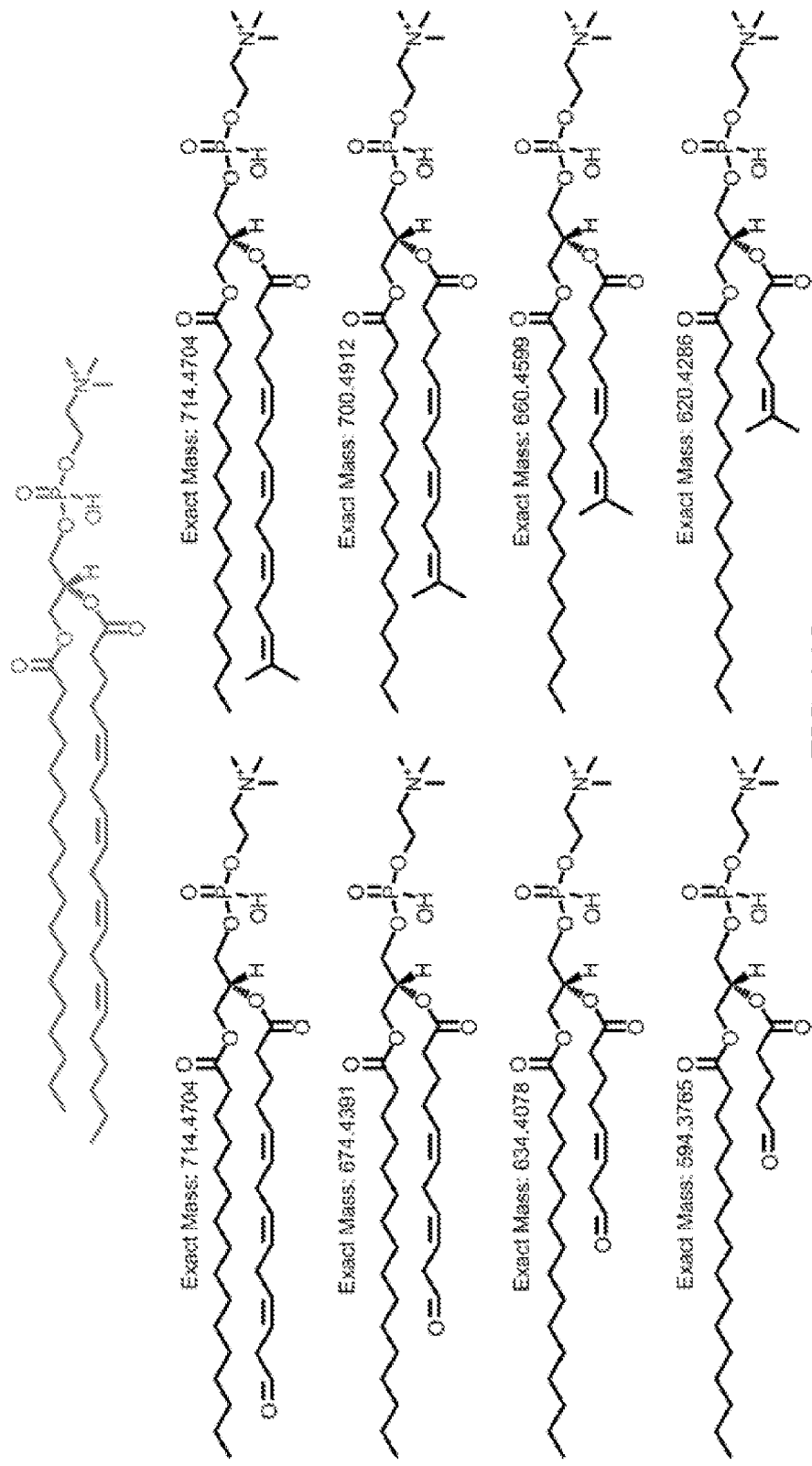
FIG. 14C shows the chemical structures of diagnostic ions for PC 16:0/20:4 n6.

PC 16:0/20:4 n6 (rat brain; FIG. 14A): Left panel: CID mass spectrum of [PC 36:4+$CH_3COO$]−, clearly suggesting Method 3 (absolute quantitation of total concentration by nanoESI combined with relative quantitation via P-B reaction/tandem MS): An internal standard (IS) containing a different number of carbons (e.g. FA 17:1) is added into the mixture of FA 18:1 isomers. NanoESI-MS analysis is performed for absolute quantitation of FAs to be quantified. (1. A calibration curve needs to be prepared in advance. 2. FA C=C isomers are assumed to have equal ionization efficiency). The total concentration of C18:1 isomers is calculated. The relative amount of each FA isomer is determined by P-B reaction/tandem MS, following which the absolute concentration of each isomer can be determined.

the presence of two PC species, PC 16:0/20:4 and PC 18:2/18:2. Right panel: CID mass spectrum of P-B reaction products of PC 36:4. Double bond locations in each PC species can be readily assigned by using the diagnostic ions. FIG. 14C shows the chemical structures of diagnostic ions for PC 16:0/20:4 n6.

PC 16:0/20:4 n6 (rat liver; FIG. 14B): By similar analysis, C20:4 fatty acyl in PE 16:0/20:4 (from rat liver) was also characterized as C20:4 n6.

C22:6 fatty acyl: The ions at m/z 806.6 (+nanoESI) were identified to be PC 16:0/22:6, where fatty acyl information were acquired via −MS/MS of [PC+CH3COO]− adducts. Similarly, C=C positions can be deduced by +nanoESI-MS/MS of the corresponding P-B reaction products. We observed six pairs of diagnostic ions, in agreement with the presence of six C=Cs in C22:6. The mass-to-charge ratios of these six pairs of diagnostic ions (580.5/606.6, 620.5/646.6, 660.4/686.6, 700.5/726.6, 740.5/766.6, 780.6/806.6; co-existing ions, with an odd m/z, were possibly fragments from PLs other than PC 16:0/22:6) can be used to unambiguously assign the positions of the six C=Cs to be at 4, 7, 10, 13, 16, and 19. Therefore, C22:6 is pure in the form of C22:6 n3.

Figure 15:
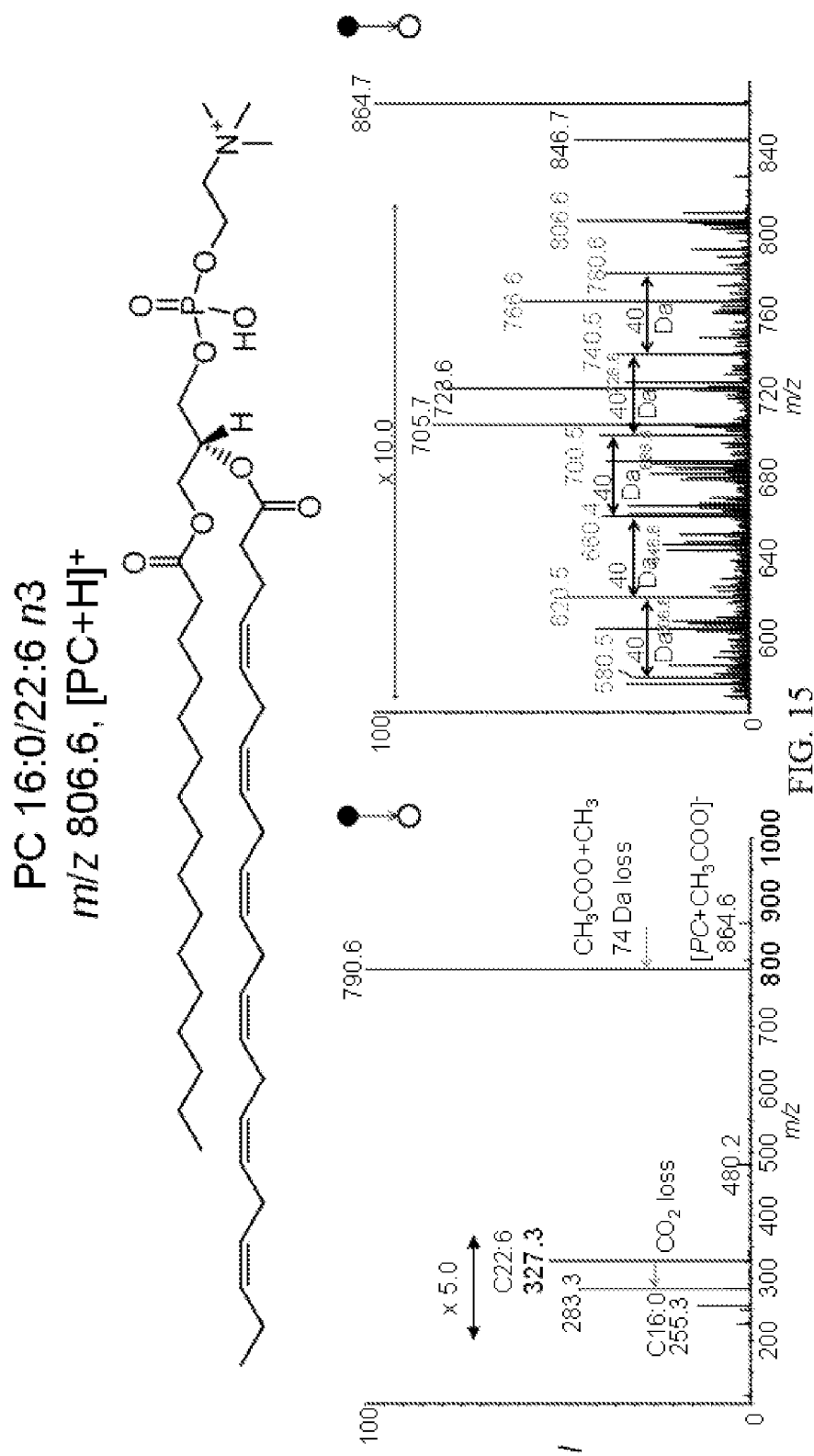
FIG. 15 shows that C22:6 fatty acyl within PC 16:0/22:6 is pure in the form of C22:6 n3.

PC 16:0/22:6 n3 (rat brain; FIG. 15): Left panel: CID mass spectrum of [PC 38:6+CH3COO]−, showing C22:6 at sn-2 position, and C16:0 at sn-1 position within PC 38:6. Right panel: CID mass spectrum of P-B reaction products of PC 16:0/22:6.

Figure 16:
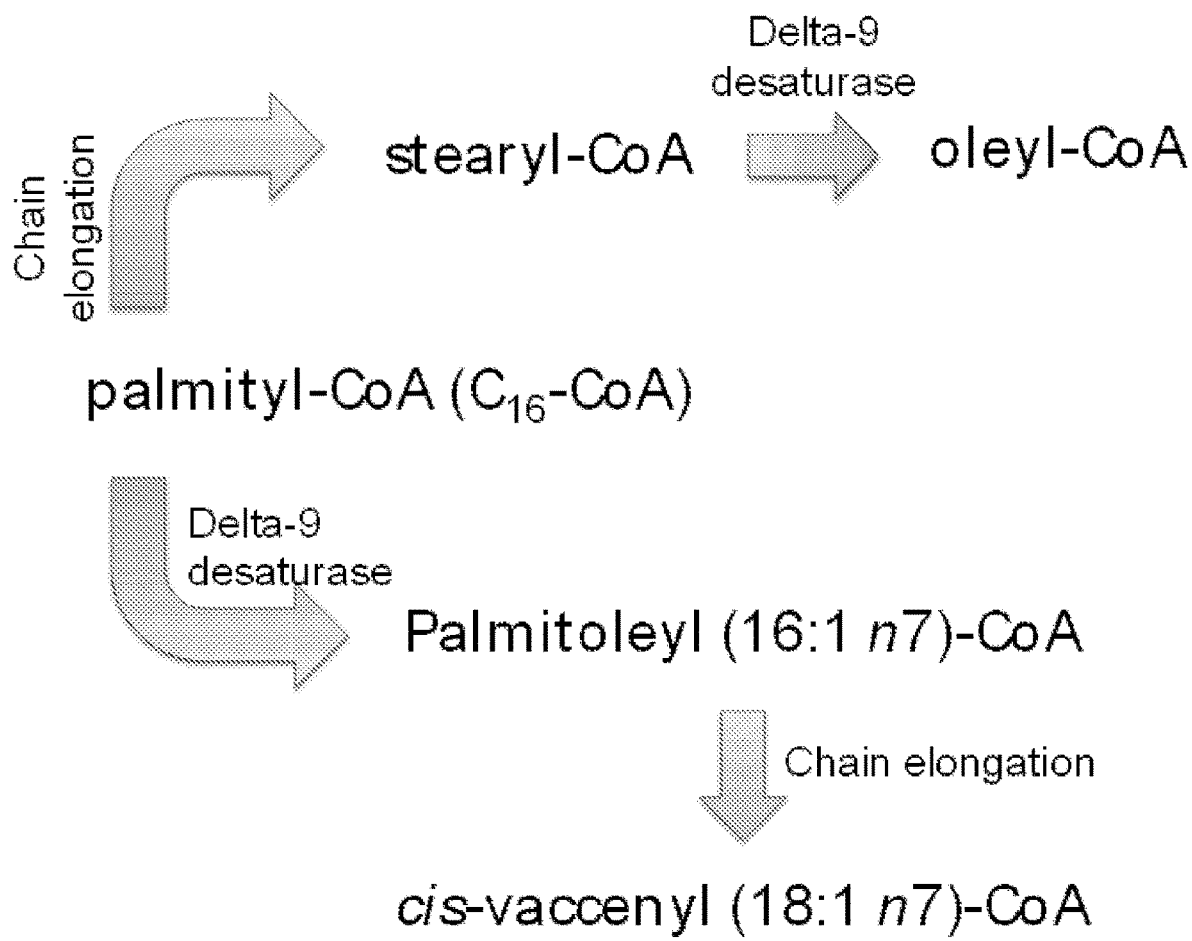
FIG. 16 shows the biosynthetic pathways for oleic acid and cis-vaccenic acid in rat tissues.
Figure 17A:
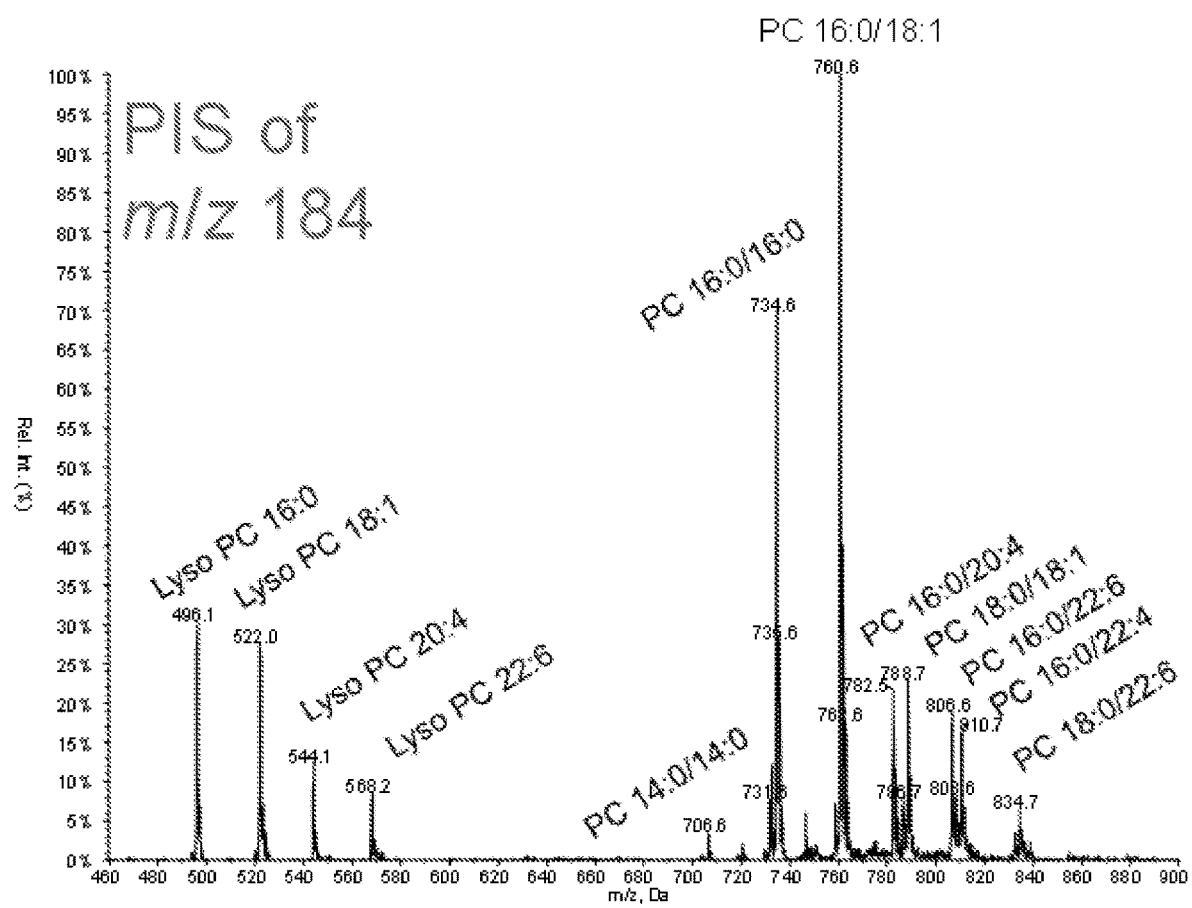
FIGS. 17A-D show representative PIS and NLS mass spectra of a complex lipid extract sample from rat tissues.
Figure 17B:
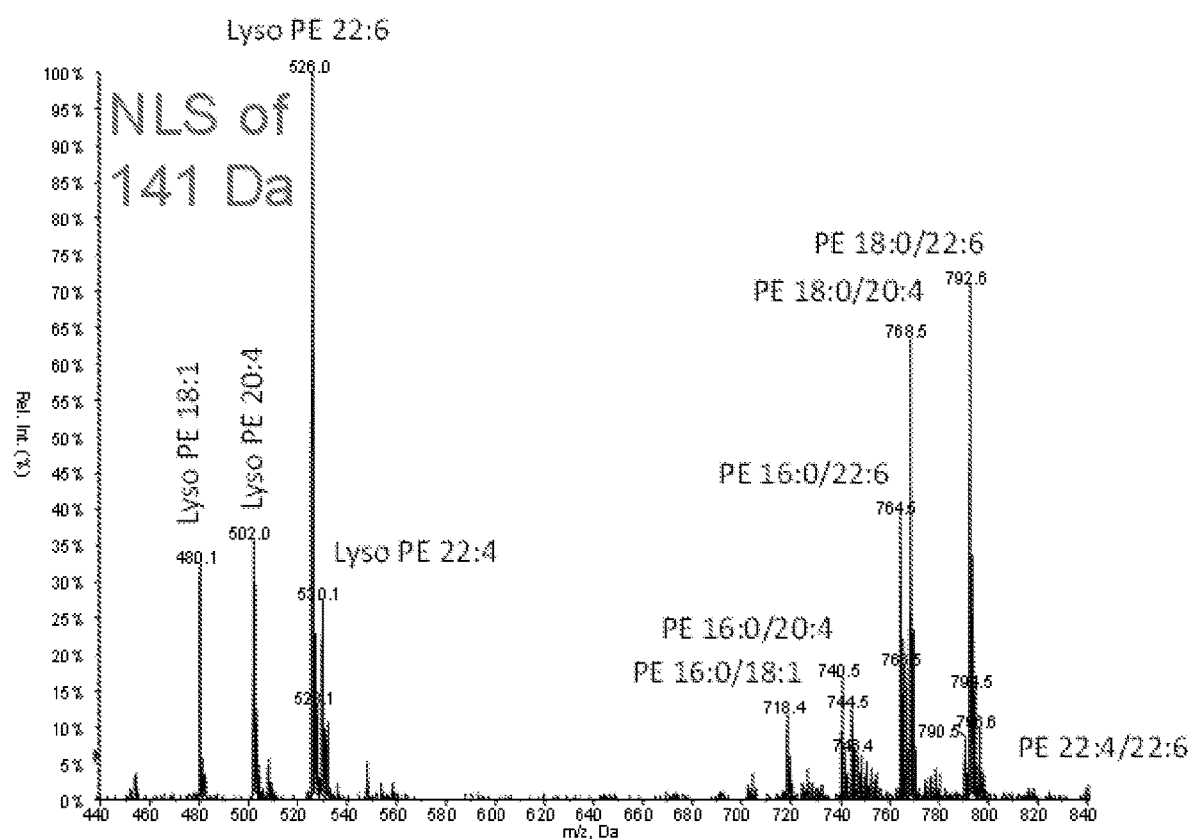
Figure 17C:
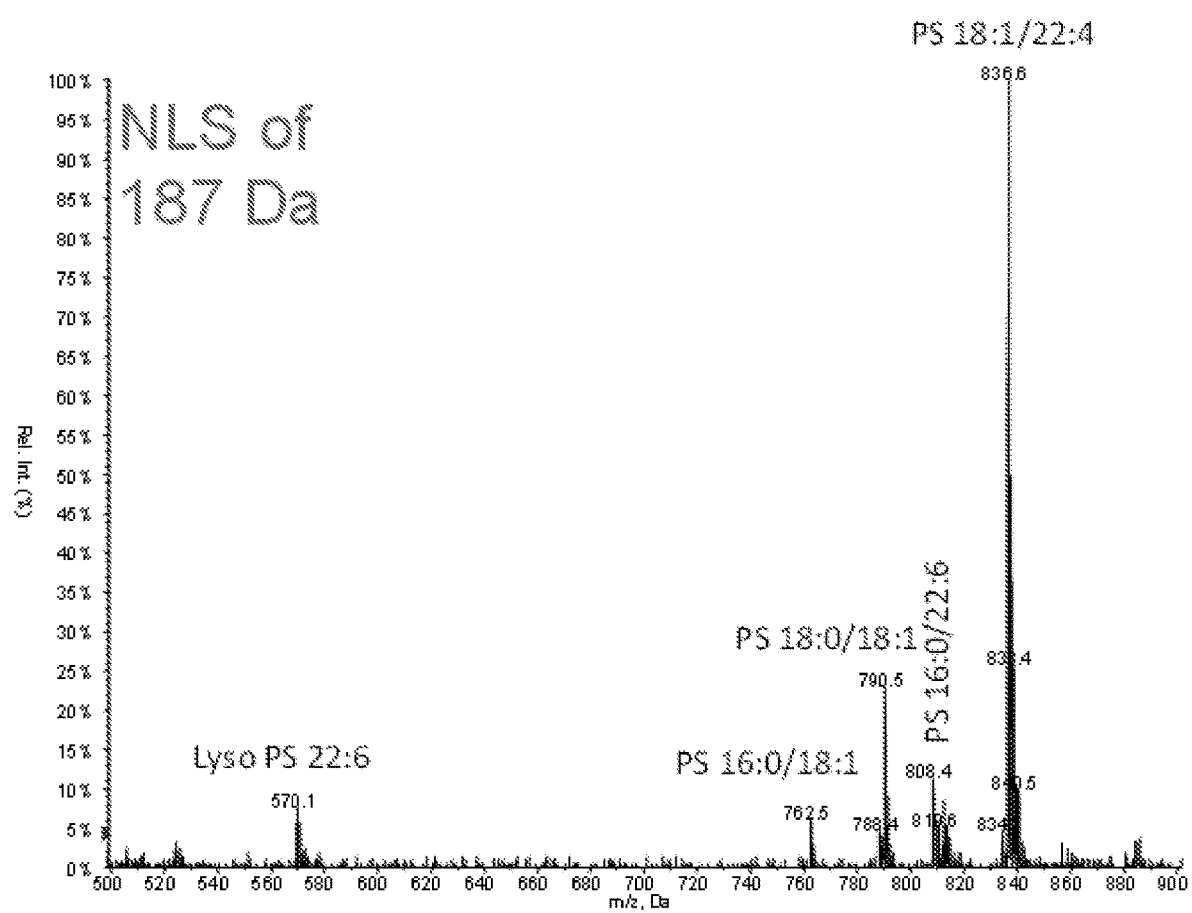
Figure 17D:
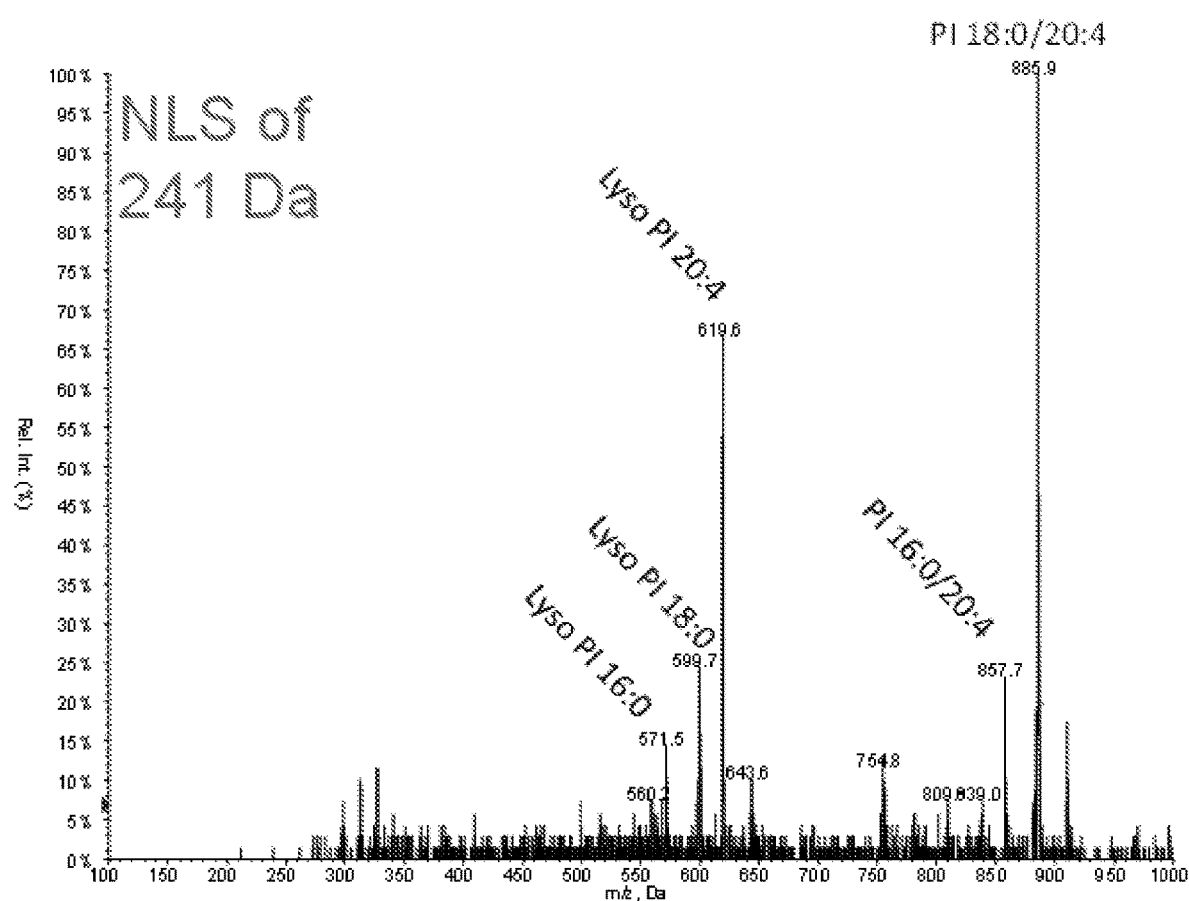
Figure 18A:
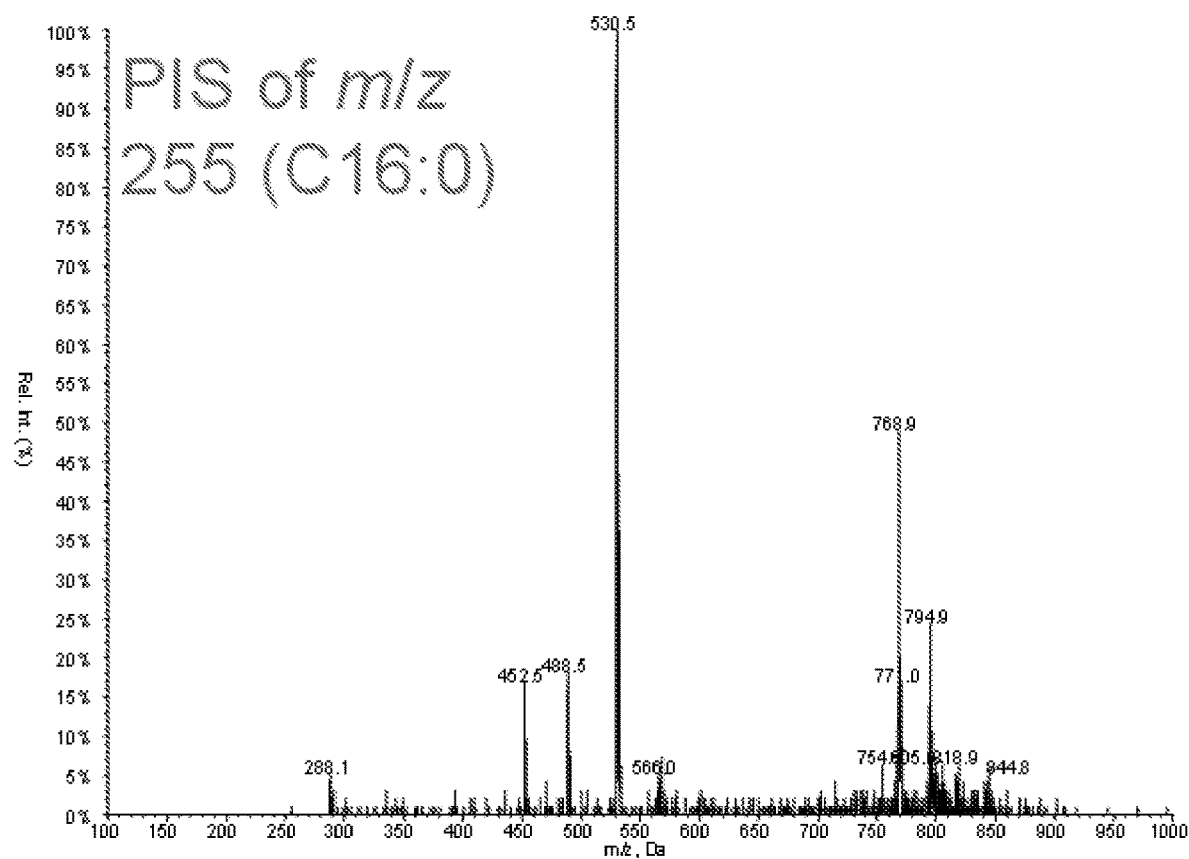
FIGS. 18A-F show PIS mass spectra where the ensemble of lipids containing C16:0, C18:1, C18:0, C20:4, C22:6, or C22:4 were displayed.
Figure 18B:
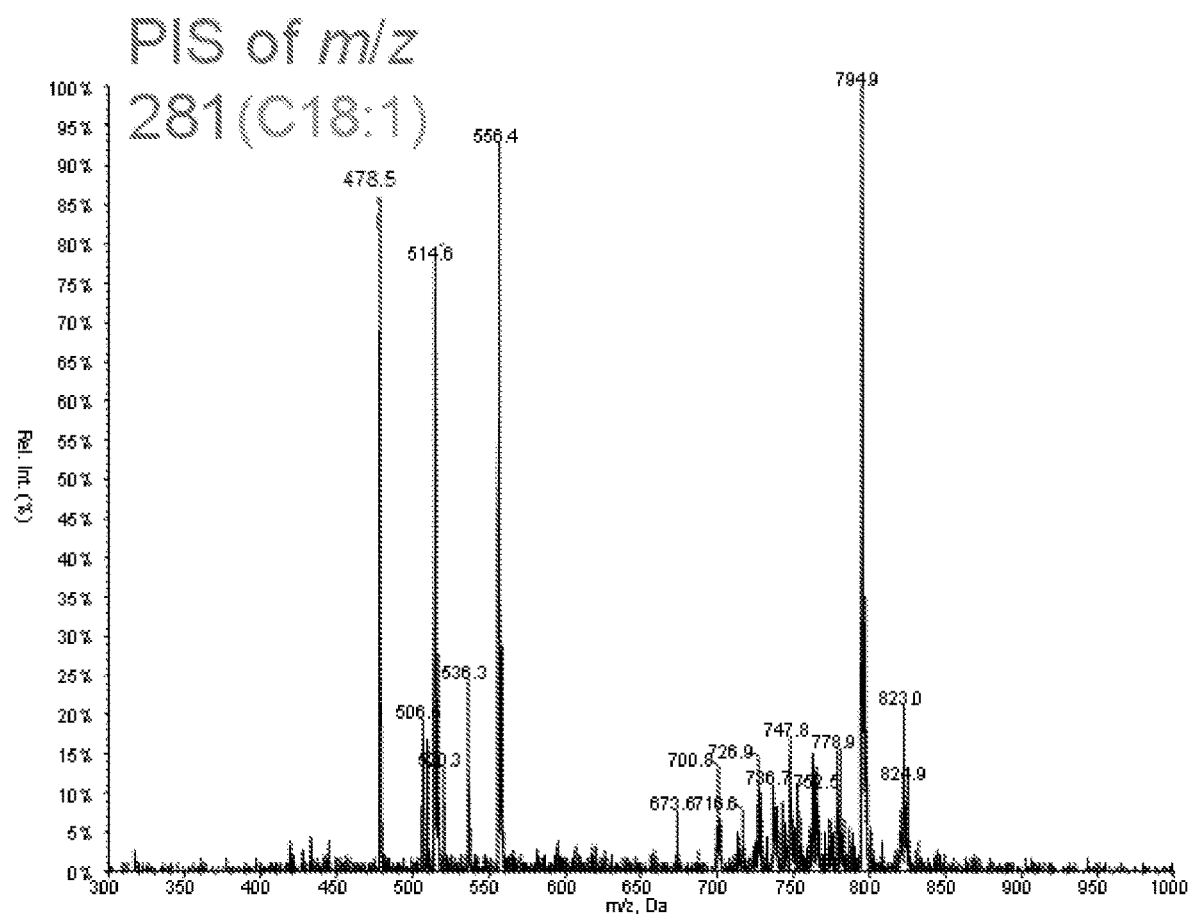
Figure 18C:
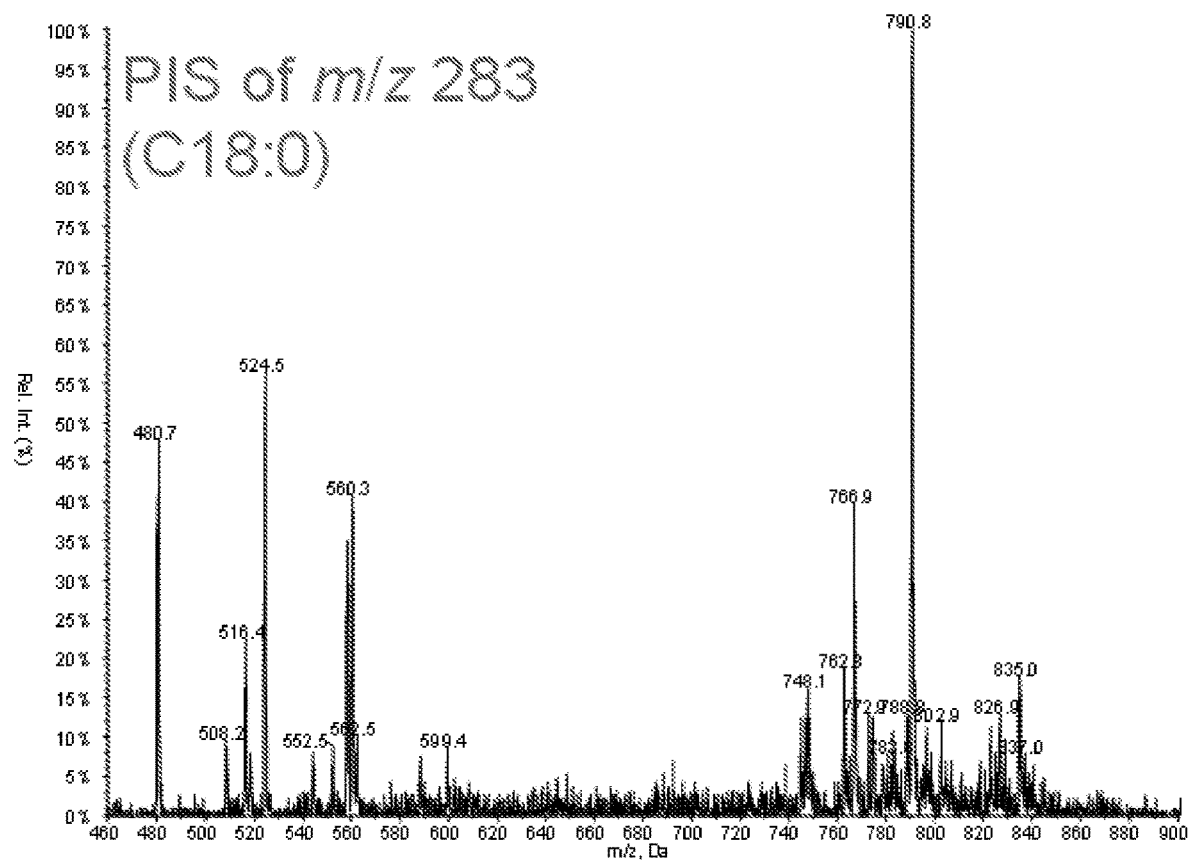
Figure 18D:
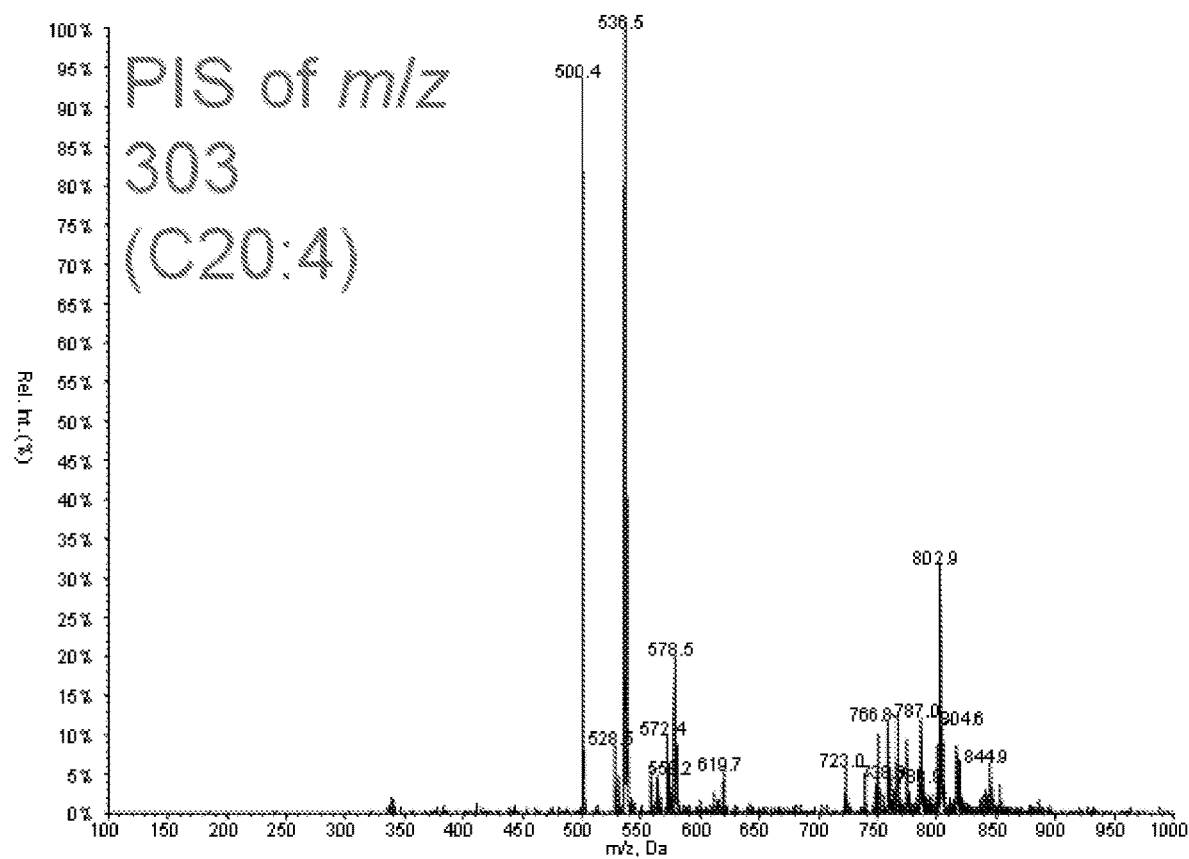
Figure 18E:
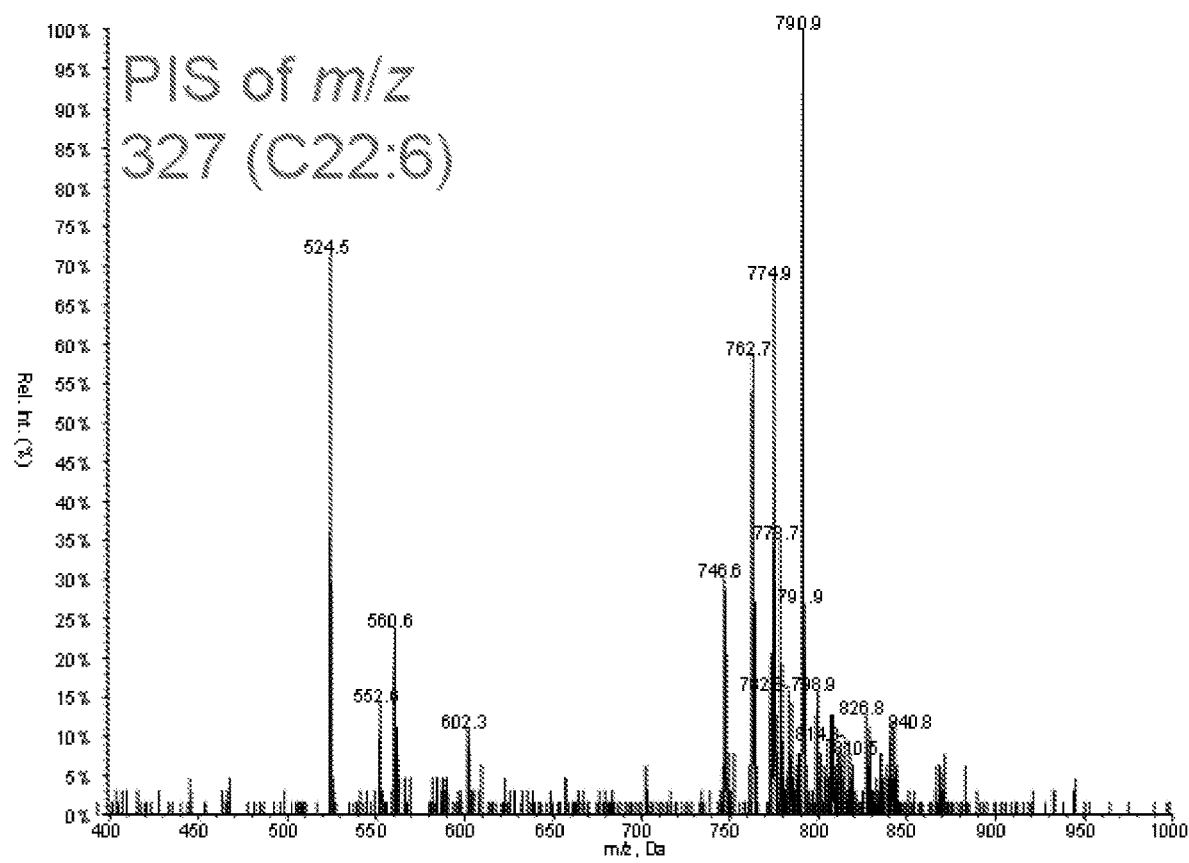
Figure 18F:
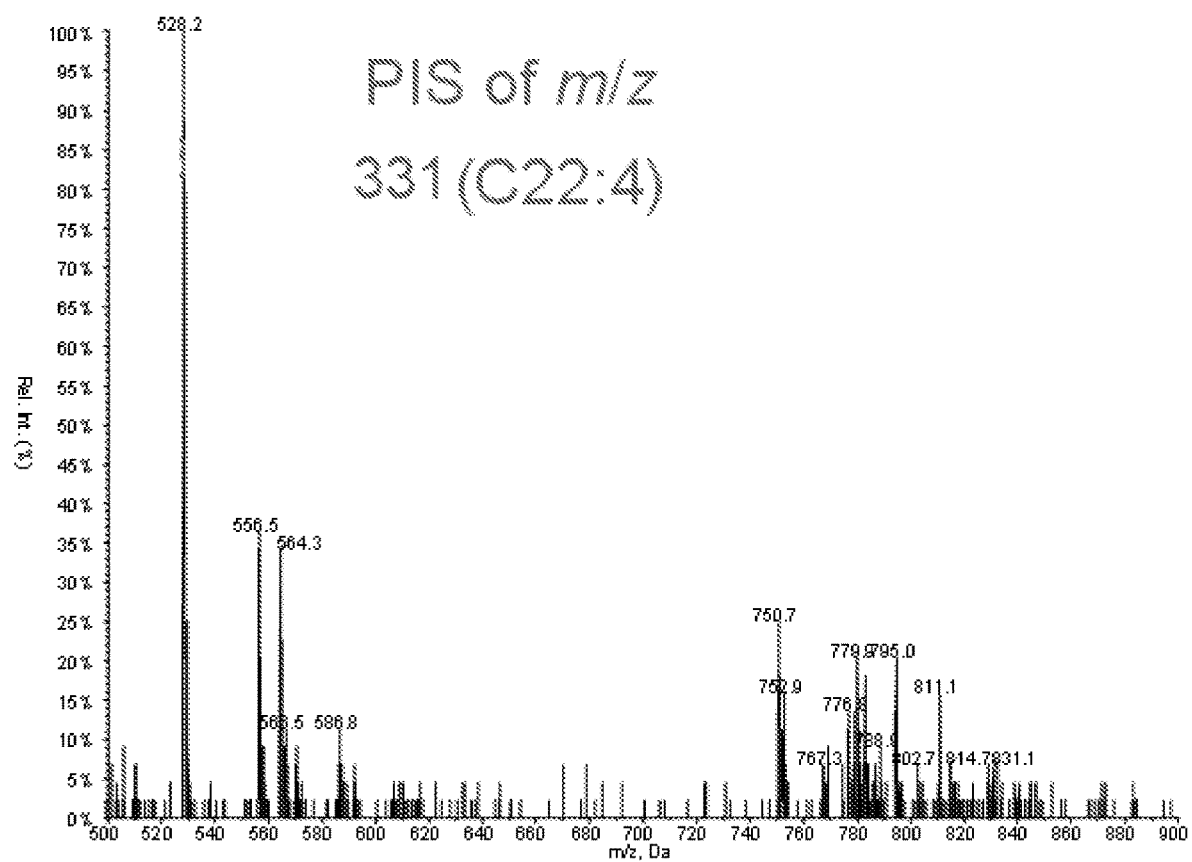

Example 8: Precursor Ion Scan (PIS) and Neutral Loss Scan (NLS) Speed Analysis of Certain Types of Lipids in Complex Mixtures FIG. 16 shows the biosynthetic pathways for oleic acid and cis-vaccenic acid in rat tissues. In consideration of the compositional complexity of PL extracts from rat tissues, precursor ion scan (PIS) and neutral loss scan (NLS) can be utilized to speed the identification of PLs belonging to a specific class and their fatty acyls. For instance, the ion at m/z 184 (under +MS/MS) can be used to specifically extract the information of all PCs, lysoPCs, and SMs, while the ion at m/z 241 (under −MS/MS) can be used to extract the information of all PIs from a complex lipid mixture. Neutral losses of 187 Da and 141 Da are characteristic of PSs and PEs, respectively. Representative PIS and NLS spectra of the rat brain are shown in FIGS. 17A-D.

Fatty acyl composition of a PL can be acquired by −MS/MS. To make this process more efficient, PIS of the m/z of each common fatty acyl can be performed to give a profile of all PLs containing the fatty acyl scanned. Shown in FIGS. 18A-F are PIS mass spectra for C16:0, C18:1, C18:0, C20:4, C22:6, and C22:4. Because each PL contains two fatty acyls, if a common m/z signal appears in two of these spectra, the two fatty acyls within a PL can be readily identified.

Figure 19:
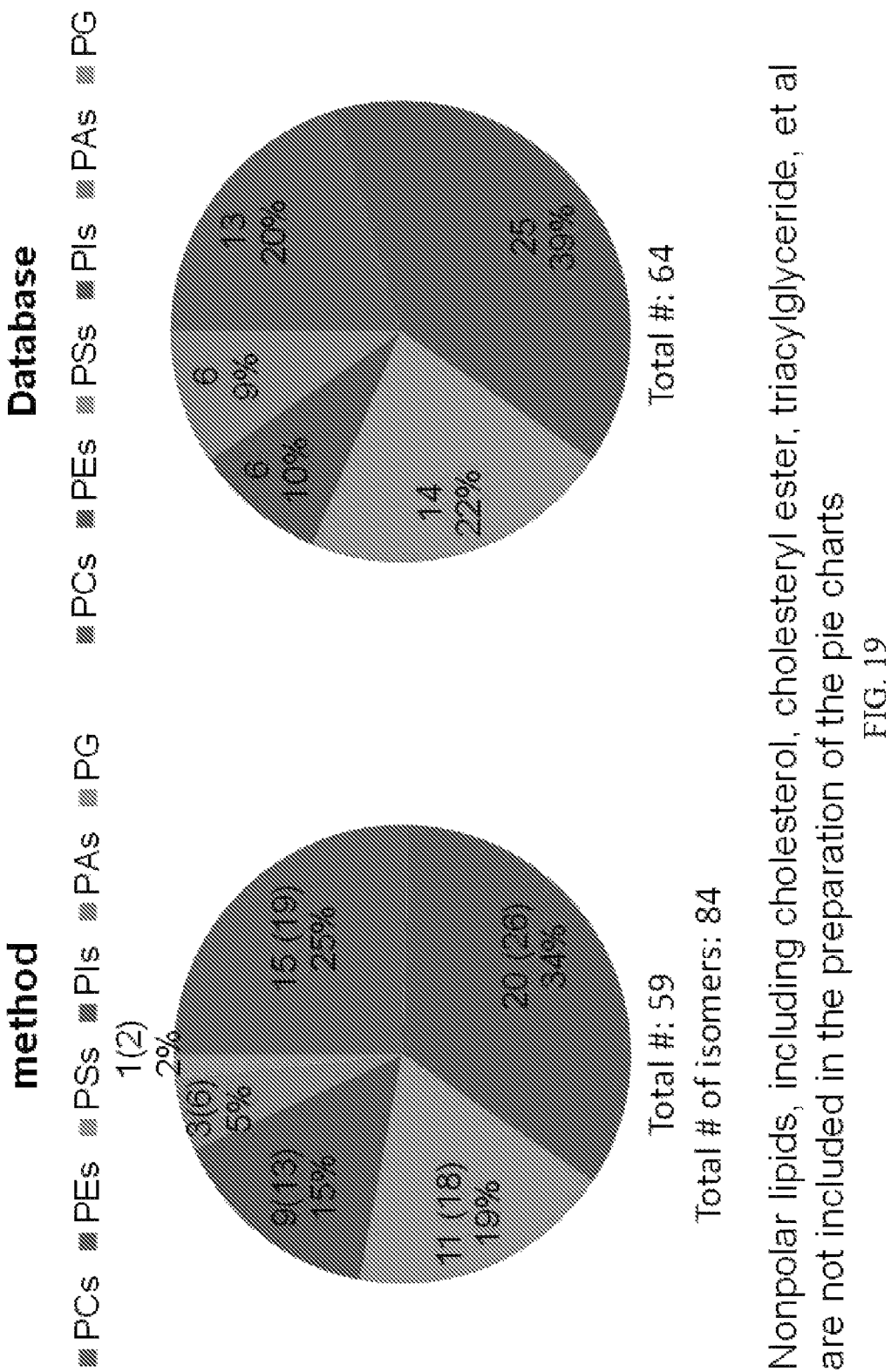
FIG. 19 is a set of pie charts providing a summary of PLs and their C=C isomers identified in rat brain. The charts show a comparison of the present method (left) with literature reports (right) in the number and types of phospholipids identified.

FIG. 19 and Table 3 below provides a summary of the number and structures of PL isomers identified from rat brain.

TABLE 3

| phospholipid | # of isomer(s) | structure of isomers |
|---|---|---|
| Lyso PC & PC | | |
| Lyso PC 18:1 | 2 | Lyso PC 18:1 (n7); Lyso PC 18:1 (n9) |
| Lyso PC 20:4 | 1 | Lyso PC 20:4 (n6) |

TABLE 3-continued

| phospholipid | # of isomer(s) | structure of isomers |
|---|---|---|
| Lyso PC 22:6 | 1 | Lyso PC 22:6 (n6) |
| PC 16:0/16:1 | 1 | PC 16:0/16:1 (n7) |
| PC 16:0/18:1 | 2 | PC 16:0/18:1 (n7); PC 16:0/18:1 (n9) |
| PC 16:0/20:4 | 1 | PC 16:0/20:4 (n6) |
| PC 18:1/18:1 | 4 | PC 18:1 (n7)/18:1 (n7); PC 18:1 (n9)/18:1 (n7); PC 18:1 (n7)/18:1 (n9); PC 18:1 (n9)/18:1 (n9) |
| PC 18:0/18:1 | 2 | PC 18:0/18:1 (n7); PC 18:0/18:1 (n9) |
| PC 16:0/22:6 | 1 | PC 16:0/22:6 (n6) |
| PC 16:0/22:4 | 1 | PC 16:0/22:4 (n6) |
| PC 18:0/22:6 | 1 | PC 18:0/22:6 (n6) |
| Lyso PE & PE | | |
| Lyso PE 18:1 | 2 | Lyso PE 18:1 (n7); Lyso PE 18:1 (n9) |
| Lyso PE 20:4 | 1 | Lyso PE 20:4 (n6) |
| Lyso PE 20:1 | 2 | Lyso PE 20:1 (n7); Lyso PE 20:1 (n9) |
| Lyso PE 22:6 | 1 | Lyso PE 22:6 (n6) |
| LysoPE 22:4 | 1 | LysoPE 22:4 (n6) |
| PE 16:0/18:1 | 2 | PE 16:0/18:1 (n7); PE 16:0/18:1 (n9) |
| PE 16:0/20:4 | 1 | PE 16:0/20:4 (n6) |
| PE 18:1/18:1 | 4 | PE 18:1 (n7)/18:1 (n7); PE 18:1 (n9)/18:1 (n7); PE 18:1 (n7)/18:1 (n9); PE 18:1 (n9)/18:1 (n9) |
| PE 18:0/18:1 | 2 | PE 18:0/18:1 (n7); PE 18:0/18:1 (n9) |
| PE 16:0/22:6 | 1 | PE 16:0/22:6 (n6) |
| PE 18:0/20:4 | 1 | PE 18:0/20:4 (n6) |
| PE 18:1/22:6 | 2 | PE 18:1 (n7)/22:6 (n6); PE 18:1 (n9)/22:6 (n6) |
| PE 18:0/22:6 | 1 | PE 18:0/22:6 (n6) |
| PE 18:0/22:4 | 1 | PE 18:0/22:4 (n6) |
| PE 22:4/22:6 | 1 | PE 22:4 (n6)/22:6 (n6) |
| Lyso PS & PS | | |
| Lyso PS 22:6 | 1 | Lyso PS 22:6 (n6) |
| PS 16:1/18:1 | 1 | PS 16:1 (n7)/18:1 |
| PS 16:0/18:1 | 2 | PS 16:0/18:1 (n7); PS 16:0/18:1 (n9) |
| PS 18:1/18:1 | 4 | PS 18:1 (n7)/18:1 (n7); PS 18:1 (n9)/18:1 (n7); PS 18:1 (n7)/18:1 (n9); PS 18:1 (n9)/18:1 (n9) |
| PS 18:0/18:1 | 2 | PS 18:0/18:1 (n7); PS 18:0/18:1 (n9) |
| PS 16:0/22:6 | 1 | PS 16:0/22:6 (n6) |
| PS 18:0/20:4 | 1 | PS 18:0/20:4 (n6) |
| PS 18:1-20:1 | 4 | PS 18:1 (n7)/20:1(n7); PS 18:1 (n9)/20:1 (n7); PS 18:1 (n7)/20:1(n9); PS 18:1 (n9)/20:1 (n9) |
| PS 20:1/18:1 | 2 | PS 20:1/18:1 (n7); PS 20:1/18:1 (n9) |
| PS 18:0/22:6 | 1 | PS 18:0/22:6 (n6) |
| PS 18:1/22:4 | 2 | PS 18:1 (n7)/22:4 (n6); PS 18:1 (n9)/22:4 (n6) |
| Lyso PI & PI | | |
| Lyso PI 18:1 | 2 | Lyso PI 18:1 (n7); Lyso PI 18:1 (n9) |
| Lyso PI 20:4 | 1 | Lyso PI 20:4 (n6) |
| PI 16:0/20:4 | 1 | PI 16:0/20:4 (n6) |

TABLE 3-continued

| phospholipid | # of isomer(s) | structure of isomers |
|---|---|---|
| PI 18:1/18:1 | 4 | PI 18:1 (n7)/18:1 (n7); PI 18:1 (n9)/18:1 (n7); PI 18:1 (n7)/18:1 (n9); PI 18:1 (n9)/18:1 (n9) |
| PI 18:0/18:1 | 2 | PI 18:0/18:1 (n7); PI 18:0/18:1 (n9) |
| PI 18:1/20:4 | 2 | PI 18:1 (n7)/20:4 (n6); PI 18:1 (n9)/20:4 (n6) |
| PI 18:0/20:4 | 1 | PI 18:0/20:4 (n6) |
| Lyso PA & PA | | |
| Lyso PA 18:1 | 2 | LPA 18:1 (n7); LPA 18:1 (n9) |
| PA 16:0/18:1 | 2 | PA 16:0/18:1 (n7); PA 16:0/18:1 (n9) |
| PA 18:1/18:1 | 4 | PA 18:1 (n7)/18:1 (n7); PA 18:1 (n9)/18:1 (n7); PA 18:1 (n7)/18:1 (n9); PA 18:1 (n9)/18:1 (n9) |
| Lyso PG | | |
| Lyso PG 18:1 | 2 | Lyso PG 18:1 (n7); Lyso PG 18:1 (n9) |

Example 9: Changes in PL C=C Isomer Compositions Across Different Rat Tissues

Figure 20:
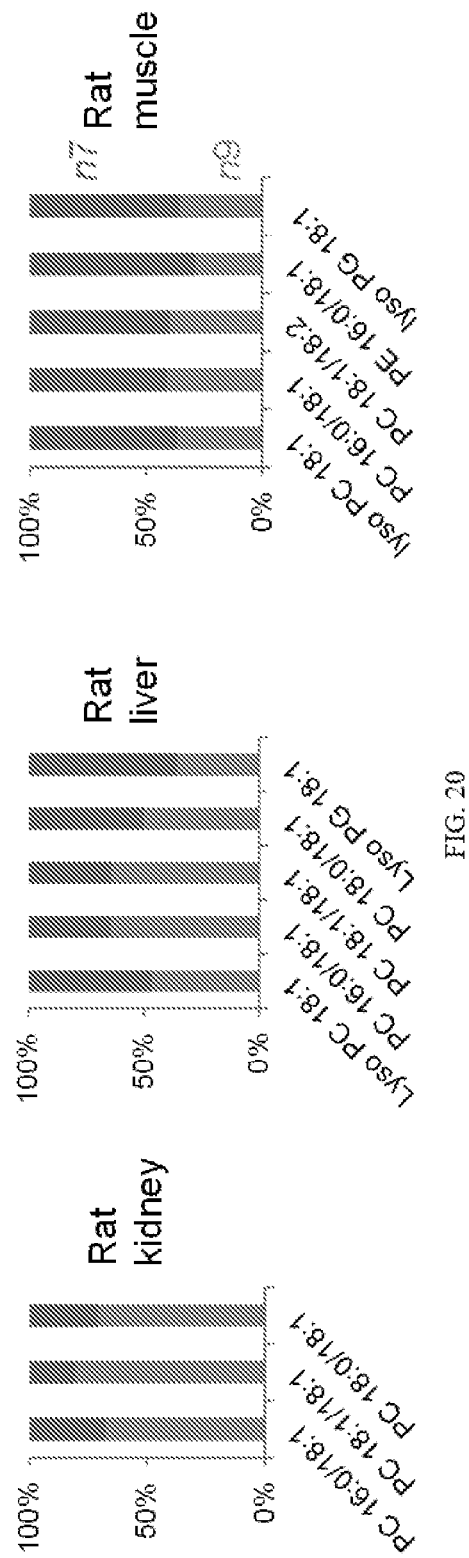
FIG. 20 shows isomeric composition of C18:1-containing PLs in rat kidney, liver and muscle.

The data herein show that the isomeric composition of PC 16:0/18:1, in all rat tissues analyzed, varies across different organs. A natural question to ask is: Does the trend observed for PC 16:0/18:1 apply to other PLs? To answer this question, C18:1-containing PLs in other rat tissues, including kidney, liver and muscle were analyzed. Since the lipid composition in these tissues were different, as evidenced from nanoESI mass spectra of PL extracts (FIG. 20), few abundant PL species were common to organs studied. This fact, however, does not prevent one from gaining insights into the heterogeneity of PL isomeric compositions in different organs. C18:1-containing PLs that were most abundant in each organ were selected, and it was observed that their isomeric compositions appear to be similar. More interestingly, inter-organ variation in PL isomer compositions is evident and in agreement with the isomeric compositions of PC 16:0/18:1 (FIG. 4), as shown in FIG. 20. It appears that the relative amounts of C18:1 n7 isomers were highest in muscle lowest in kidney.

Figure 21:
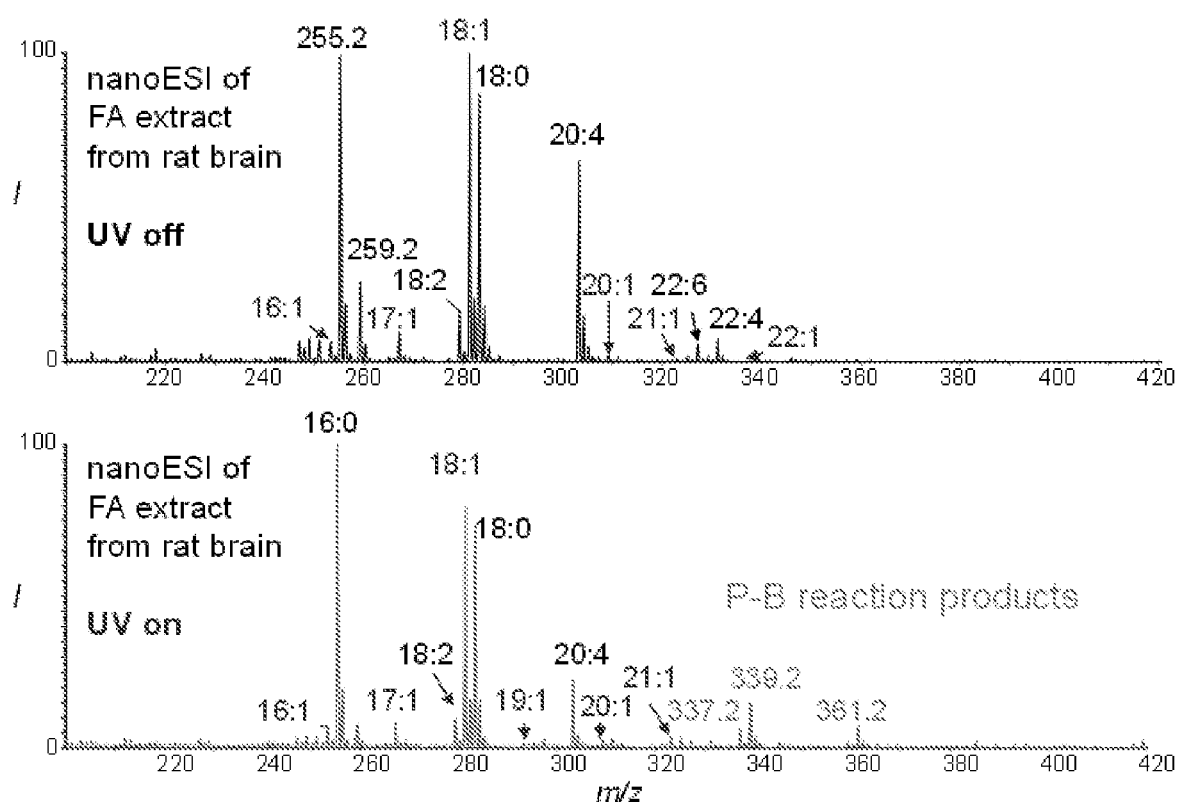
FIG. 21 show nanoESI mass spectra of a FA extract sample from rat brain before (top) and after (bottom) P-B reaction.
Figure 22:
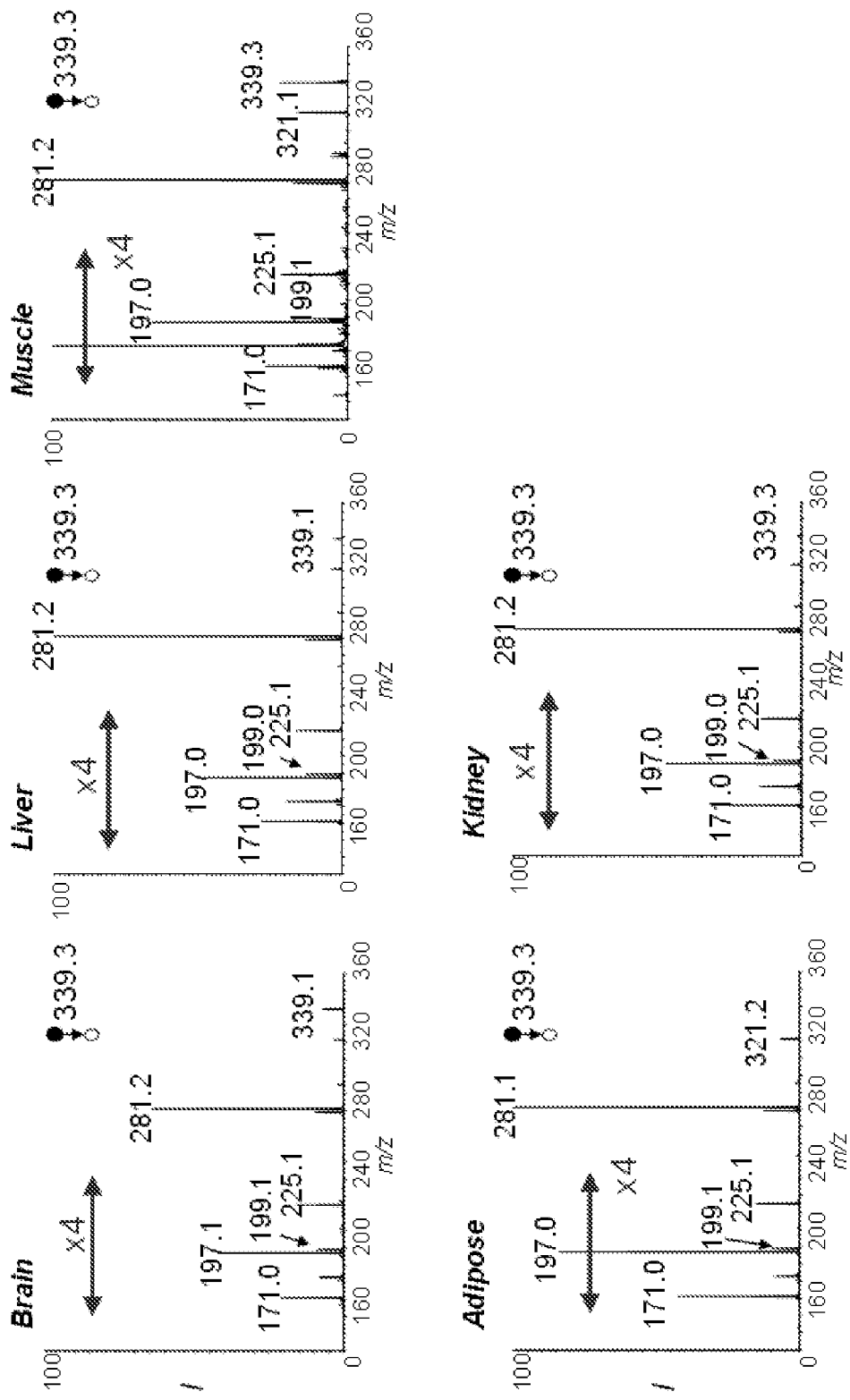
FIG. 22 shows relative quantitation of FA 18:1 isomers via tandem MS of P-B reaction products (m/z 339.3) of FA 18:1 (rat brain, liver, muscle, adipose and kidney).
Figure 23A:
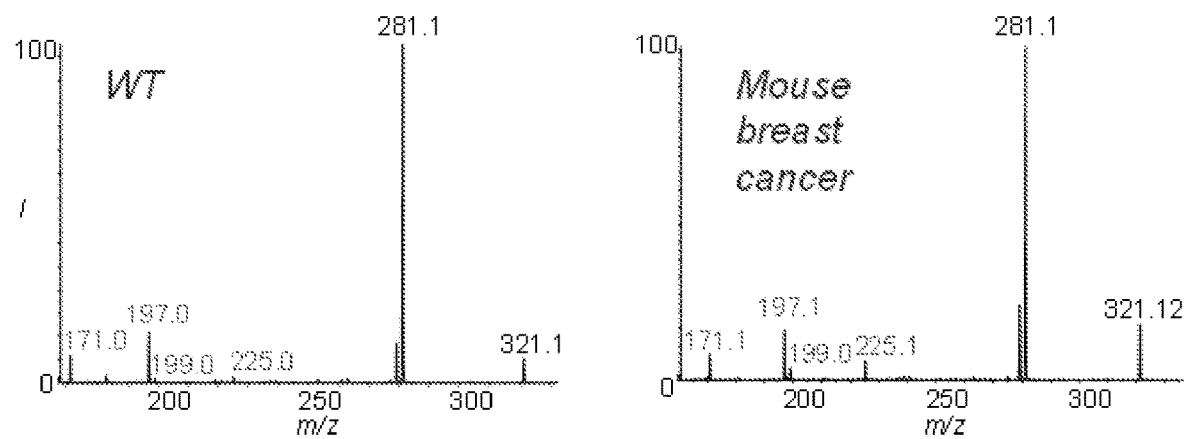
FIGS. 23A-D show that consistent increases in FA 18:1 n7 and C18:1 n7-containing PCs were observed in mouse breast cancer tissues, compared with results from normal mouse breast tissues (WT). CID mass spectra of P-B reaction products of (FIG. 23A) FA 18:1, (FIG. 23B) PC 34:1, (FIG. 23C) PC 36:1, and (FIG. 23D) PC 36:2 from normal (left in each panel) and cancerous tissues (right in each panel). In (FIG. 23D), a decrease in the relative amount of PC 18:0/18:2 was clearly observed as well. The diagnostic ions that lead to the identification of PC 18:0/18:2 were m/z 678.5/704.5 and 718.5/744.6.
Figure 23B:
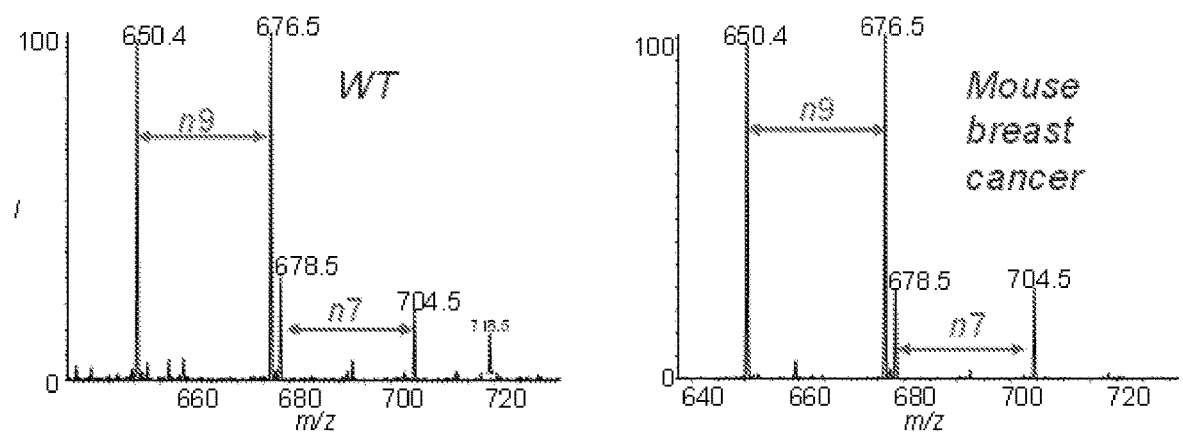
Figure 23C:
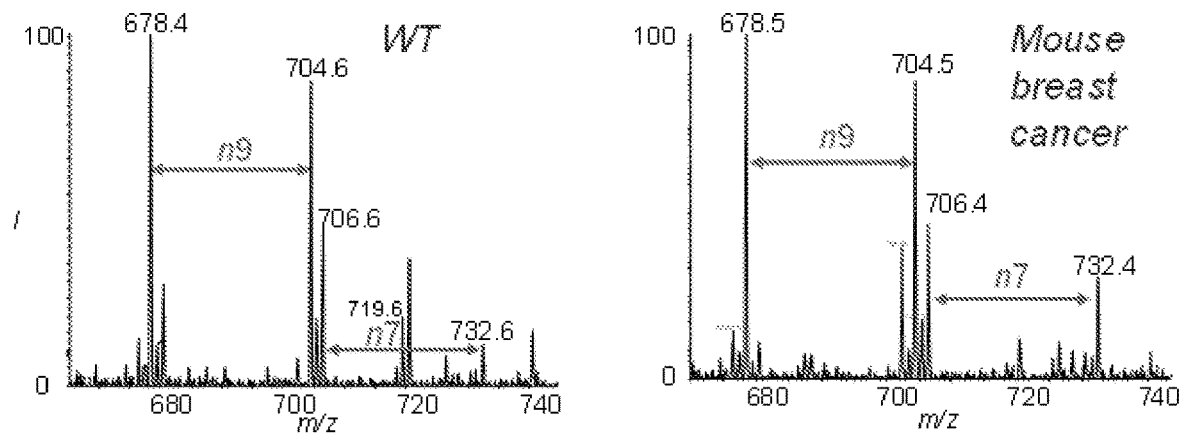
Figure 23D:
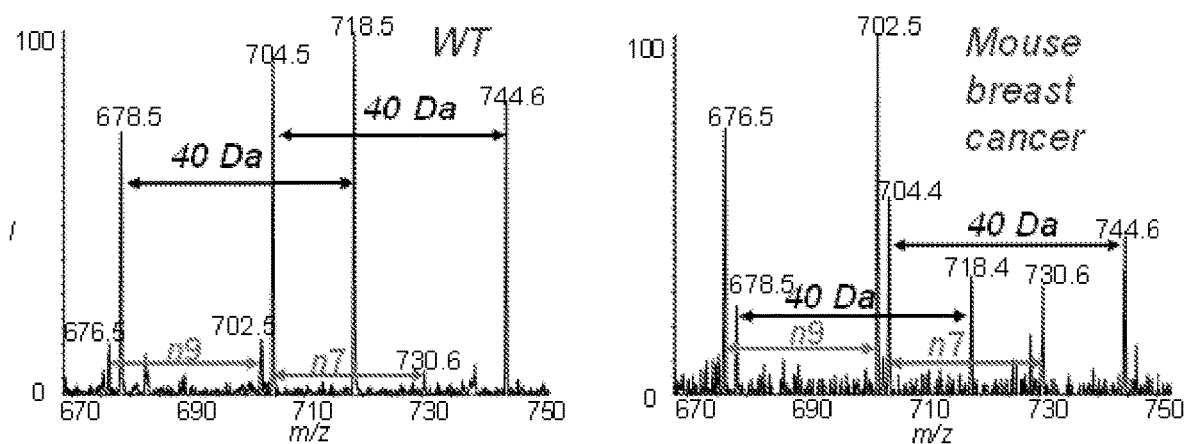

FIG. 21 shows the composition of FA 18:1 isomers in rat organs. FIG. 22 shows relative quantitation of FA 18:1 isomers via tandem MS of P-B reaction products (m/z 339.3) of FA 18:1 (rat brain, liver, muscle, adipose and kidney).

Example 10: Analysis of Normal and Cancerous Mouse Breast Tissues

As shown in FIG. 23, consistent increases in FA 18:1 n7 and C18:1 n7-containing PCs were observed in mouse breast cancer tissues, compared with results from normal mouse breast tissues (WT). CID mass spectra of P-B reaction products of (FIG. 23A) FA 18:1, (FIG. 23B) PC 34:1, (FIG. 23C) PC 36:1, and (FIG. 23D) PC 36:2 from normal (left in each panel) and cancerous tissues (right in each panel). In (FIG. 23D), a decrease in the relative amount of PC 18:0/18:2 was clearly observed as well. The diagnostic ions that lead to the identification of PC 18:0/18:2 were m/z 678.5/704.5 and 718.5/744.6. See also Tables 4-5 below.

TABLE 4

| Lipid Species | Intensity of diagnostic ions (C18:1 n9, a.u.) | | Intensity of diagnostic ions (C18:1 n7, a.u.) | | WT |
|---|---|---|---|---|---|
| FA 18:1 | 171 | 197 | 199 | 225 | $Ratio_{n7:n9}$ |
| Sample #1 | 130000 | 240000 | 18000 | 23000 | 0.111 |
| Sample #2 | 140000 | 240000 | 20000 | 30000 | 0.132 |
| Sample #3 | 130000 | 250000 | 20000 | 25000 | 0.118 |
| Sample #4 | 116000 | 210000 | 16000 | 22000 | 0.117 |
| Sample #5 | 115000 | 220000 | 18000 | 23000 | 0.122 |
| | | | | Average | 0.120 |
| | | | | STD | 0.008 |
| PC 16:0/18:1 | 650 | 676 | 678 | 704 | $Ratio_{n7:n9}$ |
| Sample #1 | 19000 | 18000 | 6500 | 4599 | 0.300 |
| Sample #2 | 25000 | 24000 | 10000 | 4500 | 0.296 |
| Sample #3 | 16000 | 15000 | 6951 | 2913 | 0.318 |
| Sample #4 | 18000 | 17000 | 5000 | 4808 | 0.280 |
| Sample #5 | 20000 | 18000 | 5398 | 3977 | 0.247 |
| | | | | AVERAGE | 0.288 |
| | | | | STD | 0.027 |
| PC 18:0/18:1 | 678 | 704 | 706 | 732 | $Ratio_{n7:n9}$ |
| Sample #1 | 23000 | 22000 | 7000 | 3906 | 0.242 |
| Sample #2 | 22000 | 18000 | 7661 | 3500 | 0.279 |
| Sample #3 | 48000 | 40000 | 20000 | 4375 | 0.277 |
| Sample #4 | 59000 | 50000 | 18000 | 6000 | 0.220 |
| Sample #5 | 49000 | 38000 | 20567 | 3800 | 0.280 |
| | | | | AVERAGE | 0.260 |
| | | | | STD | 0.027 |
| PC 18:1/18:1 | 676 | 702 | 704 | 730 | $Ratio_{n7:n9}$ |
| Sample #1 | 14130 | 12000 | 61000 | 1800 | 0.150 |
| Sample #2 | 10340 | 8880 | 60000 | 2289 | 0.258 |
| Sample #3 | 14000 | 10000 | 69000 | 2174 | 0.217 |

TABLE 4-continued

| Lipid Species | Intensity of diagnostic ions (C18:1 n9, a.u.) | | Intensity of diagnostic ions (C18:1 n7, a.u.) | | WT |
|---|---|---|---|---|---|
| Sample #4 | 15990 | 19999 | 80000 | 2120 | 0.106 |
| Sample #5 | 16000 | 25000 | 75000 | 2100 | 0.084 |
| | | | | AVERAGE | 0.163 |
| | | | | STD | 0.073 |

TABLE 5

| Lipid Species | Intensity of diagnostic ions (C18:1 n9, a.u.) | | Intensity of diagnostic ions (C18:1 n7, a.u.) | | Breast Cancer |
|---|---|---|---|---|---|
| FA 18:1 | 171 | 197 | 199 | 225 | $\text{Ratio}_{n7:n9}$ |
| Sample #1 | 60000 | 107000 | 20000 | 51000 | 0.425 |
| Sample #2 | 78000 | 140000 | 39000 | 57000 | 0.440 |
| Sample #3 | 110000 | 210000 | 58000 | 84000 | 0.444 |
| Sample #4 | 160000 | 300000 | 77000 | 110000 | 0.407 |
| Sample #5 | 116000 | 250000 | 58000 | 90000 | 0.404 |
| | | | | AVERAGE | 0.424 |
| | | | | STD | 0.018 |
| PC 16:0/18:1 | 650 | 676 | 678 | 704 | $\text{Ratio}_{n7:n9}$ |
| Sample #1 | 51000 | 49000 | 14000 | 13000 | 0.270 |
| Sample #2 | 50000 | 48000 | 13000 | 16000 | 0.396 |
| Sample #3 | 170000 | 160000 | 44000 | 40000 | 0.255 |
| Sample #4 | 240000 | 230000 | 61000 | 59000 | 0.255 |
| Sample #5 | 230000 | 220000 | 63000 | 60000 | 0.273 |
| | | | | AVERAGE | 0.270 |
| | | | | STD | 0.017 |
| PC 18:0/18:1 | 678 | 704 | 706 | 732 | $\text{Ratio}_{n7:n9}$ |
| Sample #1 | 66000 | 50000 | 28000 | 16000 | 0.379 |
| Sample #2 | 79000 | 58000 | 26000 | 20000 | 0.336 |
| Sample #3 | 98000 | 100000 | 45000 | 30000 | 0.379 |
| Sample #4 | 93000 | 78000 | 34000 | 22000 | 0.327 |
| Sample #5 | 92500 | 79000 | 33000 | 24000 | 0.332 |
| | | | | AVERAGE | 0.351 |
| | | | | STD | 0.026 |
| PC 18:1/18:1 | 676 | 702 | 704 | 730 | $\text{Ratio}_{n7:n9}$ |
| Sample #1 | 22000 | 36000 | 34000 | 19000 | 0.528 |
| Sample #2 | 27000 | 43000 | 31000 | 17000 | 0.395 |
| Sample #3 | 76000 | 92000 | 70000 | 50000 | 0.543 |
| Sample #4 | 25000 | 35000 | 36000 | 15000 | 0.429 |
| Sample #5 | 28000 | 34000 | 32100 | 15800 | 0.465 |
| | | | | AVERAGE | 0.472 |
| | | | | STD | 0.063 |

Example 11: Coupling Paterno-Buchi Reaction with Direct Infusion ESI-MS

Tandem mass spectrometry ($MS^n$, where n is the number of mass analysis steps) coupled with soft ionization is emerging as the preferred platform for lipid analysis. As already discussed, determining C=C bond location unambiguously continues to be an analytical challenge. The above illustrates that by applying a variant of the Paterno-Buchi (P-B) reaction (cycloaddition between UV excited acetone and the C=C bond within unsaturated lipids) with online nanoelectrospray ionization (nanoESI) MSn, C=C bond location for phospholipids and fatty acids in complex mixtures can be confidently determined. The P-B reaction can be effected via UV illumination of a borosilicate nanoESI emitter and the spray plume. In this Example, the above methods have been modified by effecting the reaction in a fused silica capillary "microreactor" prior to ESI. A syringe pump propelled the solution through the capillary which was coiled for extended photochemical reaction times. Parametric studies showed that within 6 s UV exposure at 4.5 μL/min 50% and 40% P-B reaction yields were achieved for PC 16:0_18:1(n-9Z) and oleic acid (n-9Z), respectively, in 7:3 acetone:$H_2O$ 1% modifier solvent conditions. The reaction was successfully implemented over 0.1-4.5 μL/min flow rate range and was also compatible with a variety of LC solvents in the lipid solution. Finally, the utility of this method was tested by analyzing yeast polar lipid extract to demonstrate its application to biological extraction mixtures, where C=C location was revealed for a total of 35 unsaturated phospholipids.

Introduction

Lipids are diverse molecules with hydrophobic characteristics and as a primary biomolecule lipids perform critical biological functions such as formation of cellular membranes, cell signaling, and energy storage. To enhance an understanding of lipids in biological systems the field of lipidomics has emerged as a powerful tool with the goal of fully characterizing lipid species in biological systems in terms of structural identification, spatial, and time distribution. State of the art lipid analysis, with few exceptions, utilizes atmospheric pressure "soft" ionization sources, e.g. electrospray ionization (ESI), coupled with mass spectrometry (MS) due to its sensitivity at low concentrations and selectivity in obtaining high level structural information via tandem MS (MS$^n$, where n is the number of mass analysis steps).

One application of MS lipid analysis is in disease biomarker discovery, e.g., for type II diabetes and autism. As the search for more effective biomarkers progresses the need for high level lipid structural information with minimal sample preparation is becoming increasingly important, which creates challenging problems for the analytical chemist. For example, C=C bond location on fatty acyls (FA) is emerging as an integral factor in phospholipid (PL) interaction with cholesterol and protein binding, yet most commercially available MS platforms can provide data for the degree of saturation and location of C=C is often assumed or not reported.

Several methods exist for determining C=C location using MS methods and can be broadly categorized as utilizing tandem MS or chemical derivatization. Examples of tandem MS include high energy CID (>1 keV) tandem time of flight (TOF), linear ion trap (LIT) tandem MS, and LC-ion mobility tandem MS. Chemical derivatization strategies involve bond specific reactions which are used to directly identify C=C bonds. Prominent methods in the literature involve ozone reactions where several variants have been reported including: solution-phase ozonolysis post LC-separation, ozonolysis within an electrospray plume (OzESI), and on mass selected ions under vacuum, called ozone-induced dissociation (OzID).

The methods of the invention herein may involve online derivatization for C=C bond analysis of unsaturated FAs and PLs using a form of the Paterno-Buchi (P-B) reaction. The P-B reaction can be effected by ultraviolet (UV) irradiation~250 nm) of a nanoESI plume and subsequent intermolecular [2+2] cycladdition between photoexcited acetone and fatty acyl olefin functional group(s) to form oxetane products. Low energy CID on the oxetane reaction products produced two diagnostic fragment ions with 26 dalton (Da) spacing at the original C=C location (see Scheme 1 for reaction schematic).

This Examples focuses on implementing the methods of the invention using a continuous flow photochemical microreactor. In analytical chemistry, photochemical reactors have been used extensively to enhance sensitivity and selectivity in electrochemical detection via post-column reactions in liquid chromatography. Flow photochemistry is also a developing field in organic synthesis where traditional batch reactors are replaced or enhanced with continuously flowing solutions primarily in <1 mm i.d. capillaries. There are a few examples in the flow chemistry literature of intramolecular [2+2] continuous flow photochemical reactions in addition to intermolecular photoaddition. Continuous solution flow, in combination with microreactor dimensions, enables precise control of solution UV exposure which can increase product yields by reducing unwanted side products from over or uneven UV exposure.

In this Example, monounsaturated phosphatidylcholine (PC) 16:0_18:1(n-9Z) was used as a model system to explore reaction yield under a variety of experimental conditions, including exposure time, flow rate, and solvent composition. A maximum yield of 50% was achieved for 5 μM PC 16:0_18:1(n-9Z) in 7:3 acetone: H$_2$O 1% acetic acid for 6 seconds cumulative UV exposure and 4.5 μL/min flow. Comparative yields were also obtained for oleic acid (n-9Z) and phosphatidic acid (PA) 18:0_18:1(n-9Z) in negative ionization mode under basic conditions containing NH$_4$OH in place of acetic acid. In addition, the reaction was successfully implemented at flow rate range of 0.1-4.5 μL/min and under a variety of solvent conditions that are relevant to liquid chromatography separations of PLs. Finally, the P-B reaction was applied to the complex mixture analysis of a commercially purchased yeast polar lipid extract, where C=C location was identified for 35 unsaturated PLs via ESI tandem MS.

Figure 76:
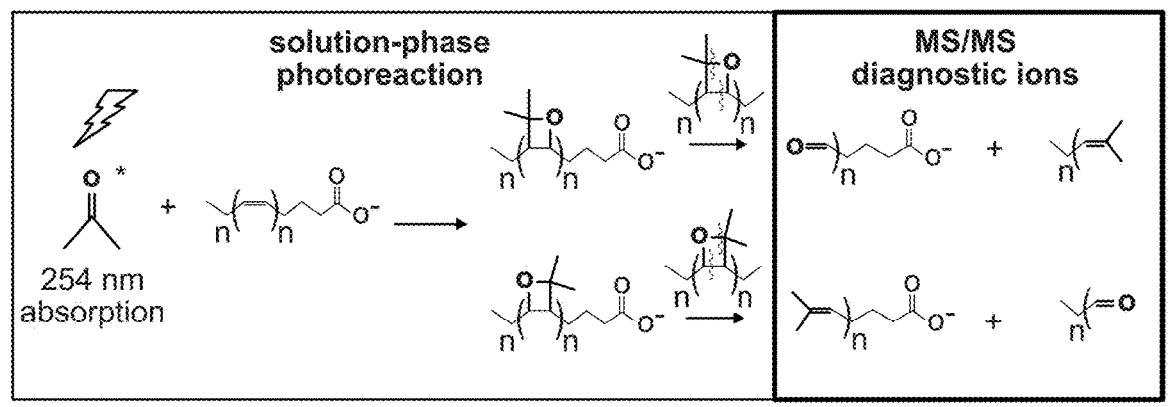
FIG. 76 shows a reaction between UV excited acetone and monounsaturated fatty acid.

Scheme 1 in FIG. 76 shows a reaction between UV excited acetone and monounsaturated fatty acid. An oxetane ring is formed and upon MS/MS collision induced dissociation (CID) diagnostic ions are produced which identify C=C bond location.

Lipid Nomenclature: Shorthand notation from the Lipid Maps project (Fahy et al., J. Lipid Res. 2009, 50, S9) and recent work by Blanksby and Mitchell (S. Anal. Bioanal. Chem. 2015, 1) were used for lipid structural identification. For PL standards the head group, fatty acyl stereo position, carbon number, degree of unsaturation, and C=C stereo orientation were specified. For example, PC 16:0_18:1(n-9Z) signifies the glycerophosphocholine head group with 16 and 18 carbon fatty acyl chains on the sn1 and sn2 glycerol positions, respectively. The "0" and "1" after the carbon number refers to the degree of unsaturation of the fatty acyl. C=C bond location was identified by counting sequential carbons starting from the terminal carbon and proceeding towards the ester of the acyl chain, i.e. C=C bond at the n-9 position is located between carbon 9 and 10 of the fatty acyl. Z and E nomenclature for C=C bond stereo configuration follows the C=C location identifier. For PL analysis in the yeast extract sn1 and sn2 fatty acyl positions were arbitrarily assigned and alkene Z and E stereo configurations were not assigned.

Chemicals: All standard lipids and yeast polar extract were purchased from Avanti Polar Lipids, Inc. (Alabaster, Ala., USA) at either 10 or 25 mg/mL in chloroform. 1-palmitoyl-2-oleoyl-sn-glycero-3-phosphocholine (PC 16:0_18:1 (n-9Z)), 1-stearoyl-2-oleoyl-sn-glycero-3-phosphate (PA 18:0_18:1 (n-9Z)), and cis-9-octadenoic acid (oleic acid (n-9Z)) were used as standards. Stock solutions in chloroform were diluted with isopropanol (LC grade; Macron Fine Chemicals; Center Valley, Pa., USA) before diluting to the final working solution. Primary organic solvents used in ESI working solutions were all LC grade and consisted of acetone (Macron Fine Chemicals), methanol (Macron Fine Chemicals), acetonitrile (Sigma Aldrich; St. Louis, Mo., USA), hexane (95% n-hexane; Avantor; Center Valley, Pa., USA), and isopropanol. Ultrapure H$_2$O was obtained from a purification system at 0.03 μS·cm (model: CASCADA AN MK2; Pall Life Sciences; Port Washington, N.Y., USA). Ammonium hydroxide (28-30% as NH3; Macron Fine Chemicals; Center Valley, Pa., USA) and glacial acetic acid (Mallinckrodt Chemicals; Hazelwood, Mo., USA) were used as solution modifiers to enhance lipid ionization in the negative and positive ESI modes, respectfully.

P-B reaction and Direct Injection ESI: A 20 mA, 2.54 cm lamp length, 0.95 cm diameter, double bore tubing low pressure mercury (LP Hg) lamp with the 185 nm emission filtered (model number: 80-1057-01; BHK, Inc.; Ontario, Calif.) was utilized to initiate the PB reaction. Lamp specifications from the manufacturer state the primary emission intensity at 20 cm distance for 254 nm is 60 µW/cm$^2$.

A syringe pump (pump 11 Elite; Harvard Apparatus; Holliston, Mass., USA) was used to infuse a syringe (Gastight syringes, 1700 series; Hamilton Company; Reno, Nev., USA) filled with lipid solution. Fluorinated ethylene propylene (FEP) tubing, FEP tubing sleeves, polyether ether ketone (PEEK) fittings, and PEEK junctions (IDEX Health and Science; Oak Harbor, Wash., USA) were used to connect the syringe to the fused silica which was then connected to the ESI source. The fused silica (part 1068150140; 363 µm o.d. 100 µm i.d.; Polymicro Technologies/Molex; Phoenix, Ariz., USA) consisted of a fluoropolymer coating which enabled UV transparency >10% at 310 nm according to the specifications provided by the manufacturer. A commercial ESI source was used for experiments with flow rates ≥1 µL/min (Turbo VTM; Applied Biosystems/Sciex; Toronto, Canada). Gas 1, Gas 2, and interface heater were set to zero for all experiments. Fused silica nanoESI tips (New Objective; Woburn, Mass.; USA) with tip i.d. of 8 µm were used for flow rates <1 µL/min. A stainless steel union (Valco; Houston, Tex., USA) was used to join the fused silica nanoESI tips and UV transparent fused silica and was also the location for applied high voltage DC. More details for solution preparation and MS conditions can be found in the Supporting Information.

Results

Figure 24:
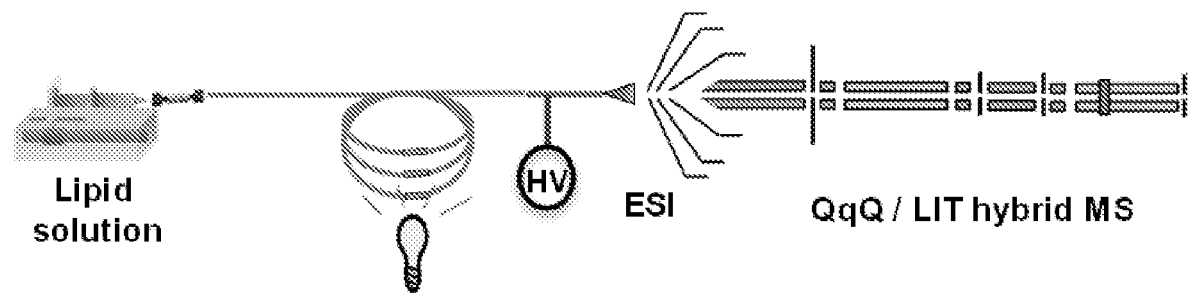
FIG. 24 shows a depiction of a discontinuous UV exposure reaction setup used for exploring rate of photochemical product formation.

A setup for this Example for effecting P-B reaction via discrete exposure with online ESI MSn is shown in FIG. 24. This arrangement was deemed optimal for exploratory studies due to the minimal disturbance to experimental conditions as extent of UV exposure was varied. Fluoropolymer coated fused silica capillary (100 µm i.d.) with a surface area: volume ratio of 20,000 m$^2$/m$^3$ (microreactor dimensions) was connected to an ESI source and utilized as UV transparent material. The fused silica was coiled around a 2.5 cm diameter high density polyethylene tube and aluminum foil was used to permanently cover the fused silica so that a 1 cm length for each coil was exposed to the lamp. The lamp was positioned 0.5 cm distance from each exposure and cumulative exposure time was controlled by covering/uncovering discrete sections with aluminum foil. Cumulative exposure time was determined by the total volume of the fused silica tubing exposed to UV divided by the sample flow rate.

Figure 25A:
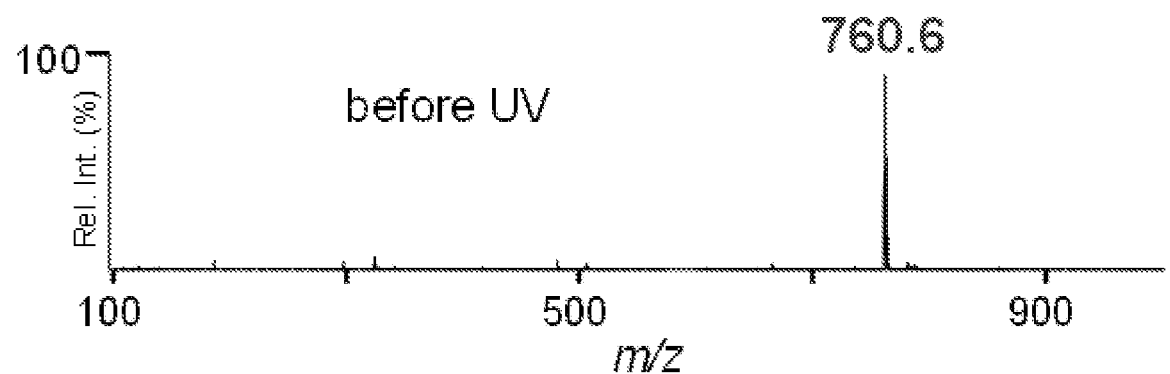
FIGS. 25A-E show mass spectra and time series graphs depicting UV exposure to solution containing N2 purged 5 μM PC 16:0_18:1(n-9Z) in 7:3 acetone:H2O 1% acetic acid.
Figure 25B:
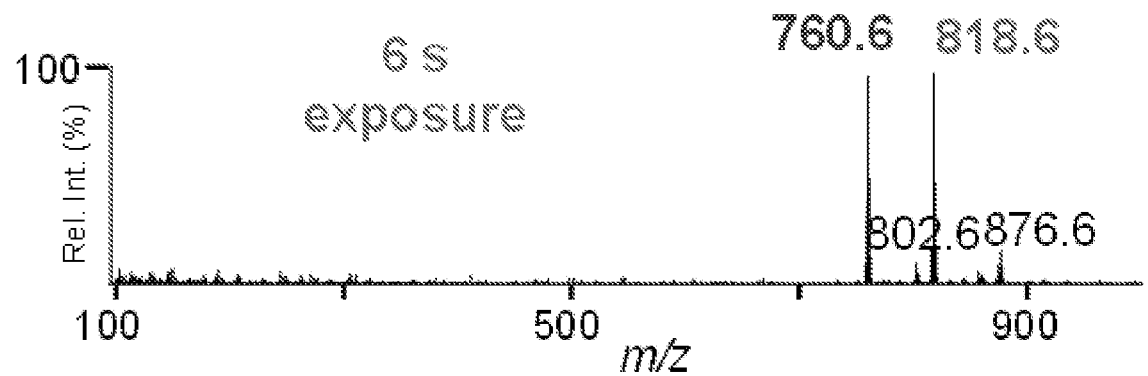
Figure 25C:
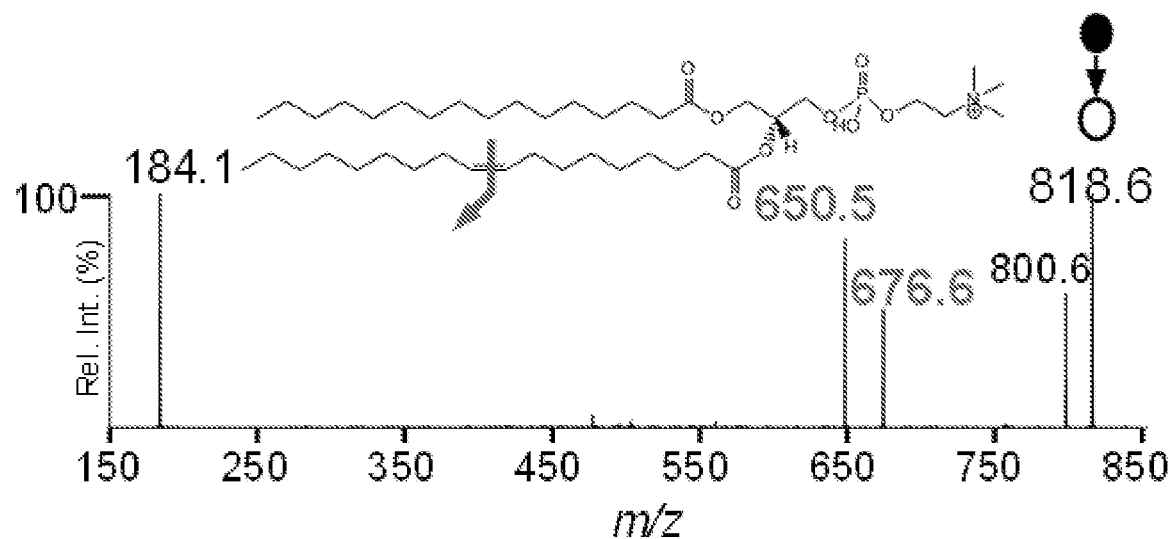

To investigate the rate of P-B product formation using the set up in FIG. 24, an N$_2$ purged solution containing 5 µM monounsaturated PC 16:0_18:1(n-9Z) in 7:3 acetone:H$_2$O 1% acetic acid was used as a model system. For each exposure time the reaction was effected for several minutes and the reported ion intensities were obtained from the averaged spectra from steady state reaction conditions. Reaction yield was estimated by dividing the P-B intensity during reaction by the precursor intensity prior to reaction, assuming the same ionization efficiency for the product and precursor. The MS$^1$ spectrum before the sample was exposed to UV light showed precursor signal at m/z 760.6 (FIG. 25A) and upon 6 s cumulative UV exposure the P-B reaction product at m/z 816.6 was observed as the dominant reaction product (FIG. 25B). Beam-type CID of m/z 816.6 revealed the phosphocholine head group at m/z 184.136 in addition to diagnostic ions for C=C localization at m/z 650.6 and 676.5 (FIG. 25C). The diagnostic ions correspond to a loss of C$_9$H$_{18}$ from the monounsaturated fatty acyl replaced with an aldehyde (m/z 650.6) or C(CH$_3$)$_2$ (m/z 676.5) from acetone. These ions clearly show the location of C=C to be between the 9 and 10 carbons on the 18 C fatty acyl.

In the MS$^1$ reaction spectrum, relatively low intensity side reactions were observed at m/z 802.6 and 876.6, in addition to low abundance chemical noise from m/z 100-300. m/z 802.6 is believed to be associated with Norrish type reactions arising from photo-induced homolytic cleavage of acetone and subsequent covalent reaction with C=C bond in the fatty chain. The reaction product of m/z 876.6 is currently not known but could potentially be from a non-covalent acetone adduct on the P-B product. An experimental setup was implemented for continuous UV exposure to verify that the observed reaction phenomenon was not due to the experimental apparatus in FIG. 24. A comparison of MS$^1$ spectra between discrete and continuous UV exposure for ~9 s reaction reveals similar reaction phenomenon, confirming the side reactions were not an artifact of discrete UV exposure.

Figures 25D, 25E:
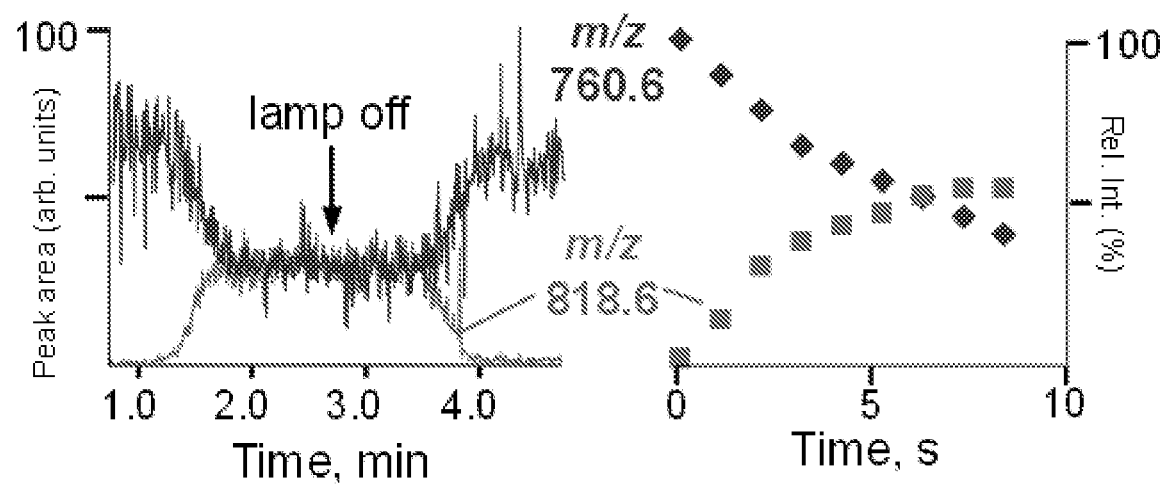

One advantage of flow photochemistry relative to batch conditions is the enhanced control of sample UV exposure, which can minimize unwanted side reactions and maintain steady ion intensities over an extended period of time. This has important implications for shotgun lipidomics studies where extended infusion times are often required for purposes of low abundance ion signal averaging. The capability for extended reaction times for the flow photochemistry setup is shown in FIG. 25D via an extracted ion chromatogram (XIC) of precursor and P-B product peak area for 6 s cumulative exposure. For a typical experiment using the apparatus in FIG. 24 the total residence time from the point of UV exposure to the MS inlet was ~1.2 min at 4.5 µL/min flow. The timing of the reaction products could therefore be predicted which confirmed that photons initiated the PB reaction and was quenched with the lamp off. Once the P-B reaction product was observed ~1 min was required to reach steady state reaction conditions, which was approximately the total residence time within all loops for 6 s discrete sample exposure. The low fluctuation in ion current for ~2 min during steady state reaction conditions demonstrates the feasibility of extended analysis times for low abundance ion signal averaging.

To explore the limits of P-B product formation as a function of UV exposure, precursor and P-B product intensities were recorded in ~1 s increments (FIG. 25E). The values for intensity were obtained from peak height of reaction spectra averaged for over 1 min steady state reaction conditions. For the conditions, a linear increase in P-B reaction yield was observed up to 4 s and began to decrease in slope until a plateau was observed at 7 s for 50% reaction yield. The yields for similar acetone systems were reported for cyclopentene (28%) and cyclohexene (8%) in excess acetone and extended reaction times (>2 hours). Accordingly, it was found that the yields herein for olefin production were reasonable compared to previous reports in the literature.

Figure 26A:
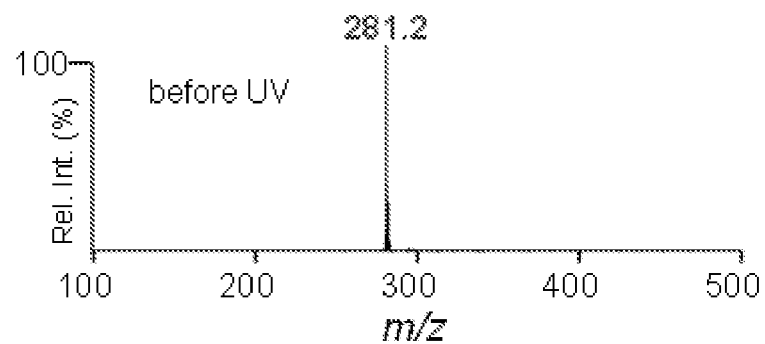
FIGS. 26A-D show online P-B reaction applied to N2 purged 5 μM oleic acid (n-9Z) in 7:3 acetone:H2O 1% NH4OH using the experimental apparatus from FIG. 24.
Figure 26B:
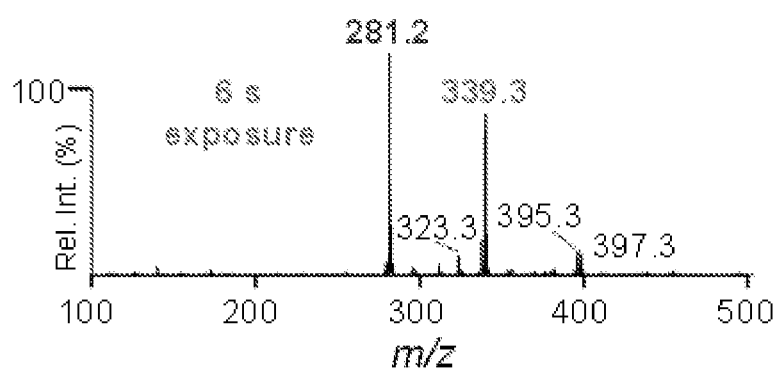
Figure 26C:
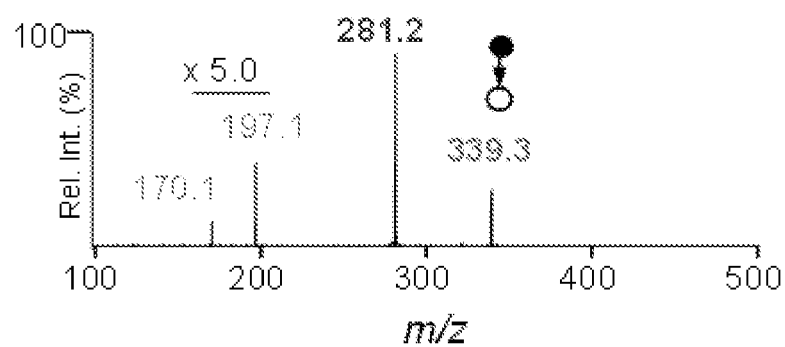
Figure 26D:
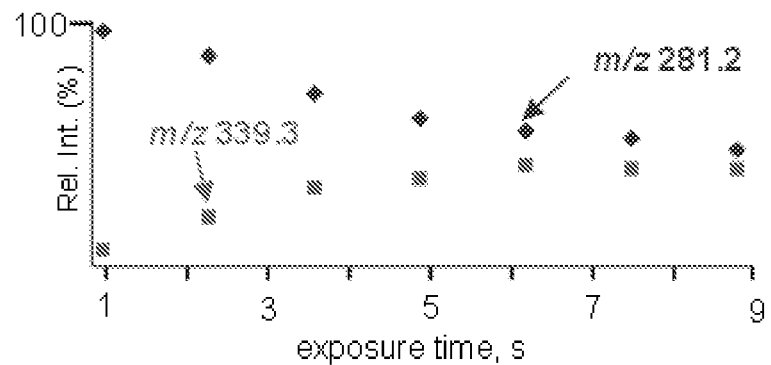

In addition to positive ionization under acidic conditions, many lipids are analyzed in negative ionization ESI MS under basic solution conditions due to facile deprotonation of phosphate. To investigate the P-B reaction under negative ionization, oleic acid (n-9Z) was used as a model compound in an N$_2$ purged solution of 7:3 acetone:H$_2$O 1% NH$_4$OH (5 µM) using the same experimental setup as FIG. 24. FIG. 26A was the MS$^1$ spectrum showing the precursor signal at m/z 281.2 and FIG. 26B was the MS$^1$ reaction spectrum after 6 s cumulative UV exposure. Abundant P-B product at m/z 339.3 was observed in addition to small peaks at m/z 323.3, 395.3, and 397.3. Beam-type CID on the P-B reaction product (m/z 339.3) showed C=C diagnostic ions at m/z 170.1 and 197.1 which locate the C=C bond between carbons 9 and 10 on the FA. The m/z values correspond to a loss of $C_9H_{18}$ from the monounsaturated fatty acyl replaced with an aldehyde (m/z 170.1) or $C(CH_3)_2$ (m/z 197.1) from acetone. Observation of the time-series graph of oleic acid and P-B product intensities for the given experimental conditions revealed a P-B product plateau at ~6 s UV exposure for a 40% yield (FIG. 26D). In addition, negative ionization experiments with PA 18:0_18:1(n-9Z) also produced yields of 40%. This demonstrates that the P-B reaction yield for monounsaturated PLs and FAs is independent of relevant solution pH and ionization polarity.

To obtain increased yields of P-B product, solutions were $N_2$ purged prior to direct infusion. $N_2$ purging is an established method for eliminating oxygen from solution and is routinely used in quantitative fluorescence measurements. Ground state molecular oxygen in solution is an efficient triplet radical scavenger via collisional transfer of energy and results in reduced fluorescence intensity measurements. The presence of oxygen in solution also proved to reduce P-B reaction yields. In the absence of $N_2$ purging of 5 µM PC 16:0_18:1(n-9Z) in 7:3 acetone:$H_2O$ 1% acetic acid side reaction peaks are observed at m/z 650.4, 622.4, and 606.4 in addition to chemical noise observed at low m/z values. P-B reaction yield reaches a maximum of ~10% after ~2 s of exposure time. This data shows that purging solutions of oxygen prior to implementing the on-line P-B reaction is important in maximizing P-B yield under the given experimental conditions.

Figure 27A:
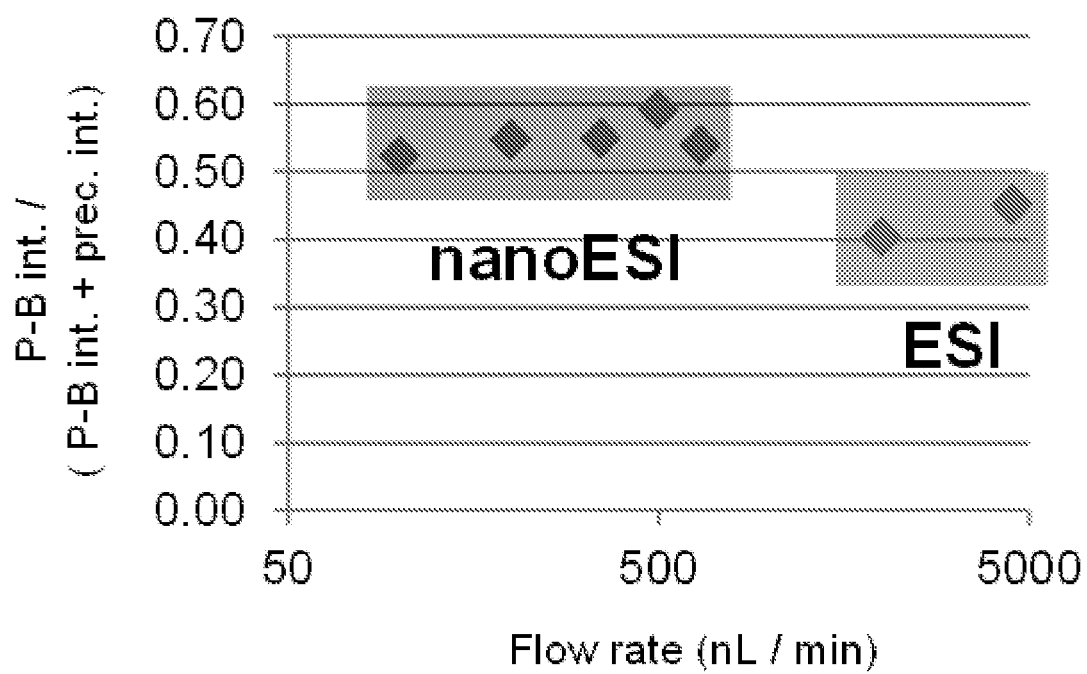
FIG. 27A shows intensity ratio of precursor to P-B product for N2 purged 5 μM PC 16:0_18:1(n-9Z) in 7:3 acetone:H2O 1% acetic acid with 5 s UV exposure at progressively increasing flow rates.

To further examine the performance of the continuous flow P-B reaction experimental setup, yield was determined as a function of flow rate at a fixed exposure time of 5 s (FIG. 27A). The intensity ratio [P-B int./(P-B int.+Prec. int.)] during reaction steady-state conditions was used on the y-axis as absolute ion intensities vary with flow rate and therefore are not directly comparable within the same graph. On the same graph fused silica nanoESI tips (8 µm i.d.) were used for 100-750 nL/min and the commercial ESI source was used for higher flow rates. Extreme values for the intensity ratio range from 0.4-0.6 however the majority are between 0.45-0.55 which gives good agreement for consistent P-B product formation for almost two orders of magnitude flow rate range.

One trend observed in the data is a slight decrease in intensity ratio with lower flow rates for each source. It is speculated that the decrease is a result of increased diffusion of atmospheric oxygen into the solution line at lower flow rates, which was previously demonstrated to reduce P-B yield. In addition, different intensity ratios are observed between the two ionization sources, which can be attributed to differences in experimental apparatus and conditions, e.g. exposure length and lamp position. Nonetheless, the data show that the intensity ratio is relatively steady over almost two orders of magnitude flow rate range which expands the range of potential analytical applications.

Thus far reaction conditions have been explored for a fixed solvent condition of 7:3 acetone:$H_2O$ 1% acetic acid. In practice, however, a variety of solvent conditions are used for ESI MS lipid analysis. $CHCl_3$ is the most common direct injection lipid solvent as it is used as solvent for biological extraction and also provides good lipid ionization efficiency. Unfortunately, the presence of $CHCl_3$ is deleterious to P-B reaction yields, and therefore other relevant solvent systems were investigated.

Figure 27B:
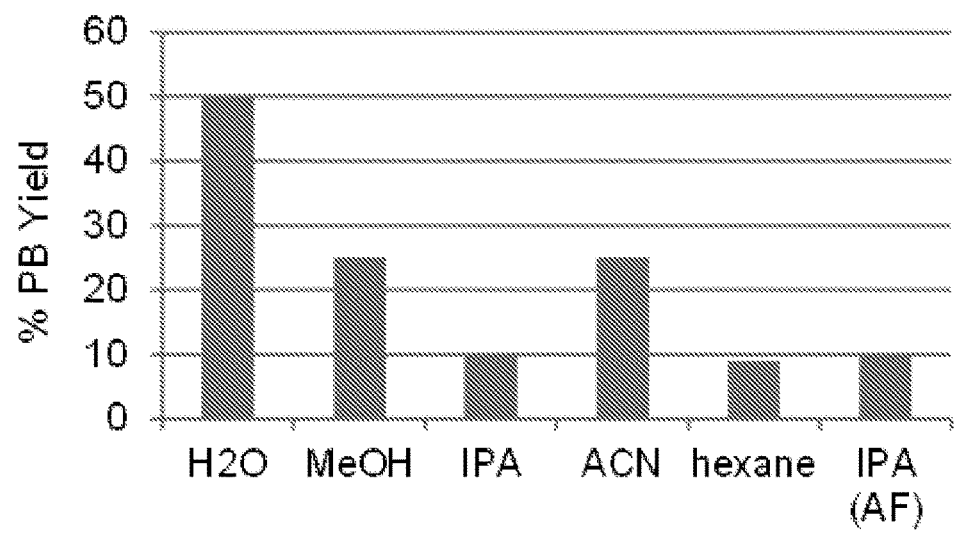
FIG. 27B shows P-B yields after 6 s UV exposure for 5 μM PC 16:0_18:1(n-9Z) solution composed of 70:15:15 acetone:H2O:solvent 1% acetic acid, where solvent is indicated on the x-axis of the bar graph. Ammonium formate (AF) (2 mM) was used in place of acetic acid for data in the last column.

The systematic investigation reported herein involved addition of methanol, isopropanol, acetonitrile, and hexane as solvent to 5 µM PC 16:0_18:1(n-9Z) in 70:15:15 acetone:$H_2O$:solvent 1% acetic acid and 6 seconds UV exposure (FIG. 27B). All solvents are relevant for both normal and reversed phase LC separations of phospholipids and ammonium formate, which was used in place of acetic acid, is a common LC-MS mobile phase salt. Results showed that smaller and more polar solvents, e.g. acetonitrile and methanol, produced higher P-B yields (25%) relative to the larger and less polar solvents (IPA and hexane) which produced yields ~10% when added to the PL solution containing $H_2O$ and acetone. It is speculated that the reduced yield observed with IPA and hexane involves competition with acetone for solvation of the fatty acyl chain, thus reducing the chances for excited acetone to react with the olefin functional group. In addition, competing reaction pathways such as hydrogen abstraction from hexane are known to occur with UV excited acetone thus reducing P-B yield. Investigations into minimum acetone solvent ratios revealed a 10% P-B yield for 1% acetone in 1:1 $H_2O$:acetonitrile 1% acetic acid. For acetone:$H_2O$ ratio<1 with modifier the ionization efficiency was poor for PC 16:0_18:1(n-9Z) but with addition of acetonitrile the ionization efficiency was greatly increased. These experiments demonstrate the feasibility of coupling the P-B reaction with LC solvents which enables the potential for coupling the P-B reaction with online LC-MS.

Observations of the P-B reaction in this Example have thus far have been performed under controlled conditions with standard lipids. In lipidomics applications of biological samples, a prominent method is to directly inject a lipid extract into the mass spectrometer with little sample preparation. The lipid extract of biological material has orders of magnitude more chemical complexity relative to standard solutions which could potentially reduce the effectiveness of the P-B reaction. However, an advantage of the P-B reaction is that diagnostic ions are produced during tandem MS which enables high selectivity and sensitivity in C=C identification in individual PL species.

P-B reaction applied to a biological extract was demonstrated by direct injection of a commercially purchased yeast polar lipid extract diluted in 7:3 acetone:$H_2O$ 1% acid/base modifier (0.1 mg/ml). According to the manufacturer, acetone and diethyl ether were added to the chloroform:methanol total extract with the PL content in the diethyl ether phase, which was concentrated and dissolved in chloroform. For PL analysis triple quadrupole precursor ion and neutral loss scans were first employed to identify PL species head group via characteristic fragmentation pathways. LIT $MS^3$ scans were then utilized to identify fatty acyl chain length and degree of saturation. Finally, the sample was exposed to 6 s of UV irradiation and the predicted m/z for P-B products of unsaturated lipids were subjected to LIT $MS^3$ scans for C=C diagnostic ion detection.

Figure 28A:
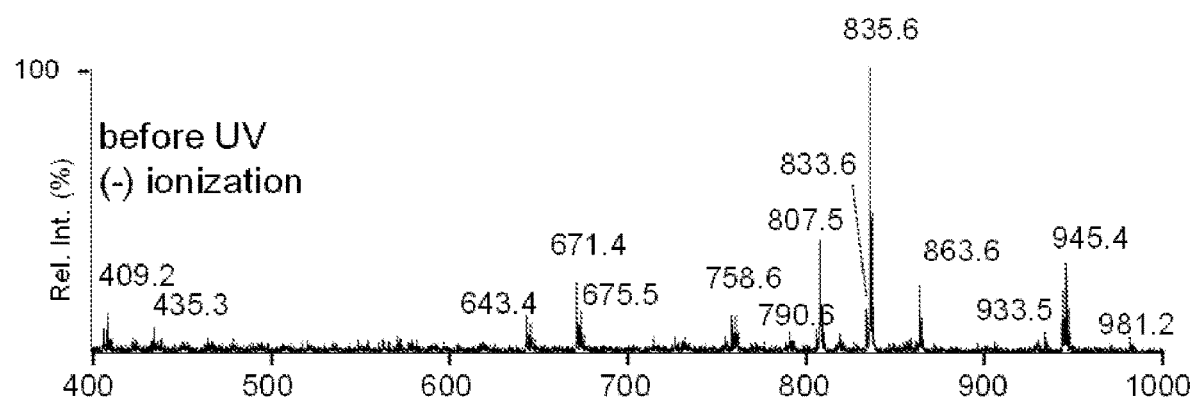
FIGS. 28A-E show application of direct injection P-B reaction to a commercially purchased yeast polar lipid extract analyzed in negative ionization mode.
Figure 28B:
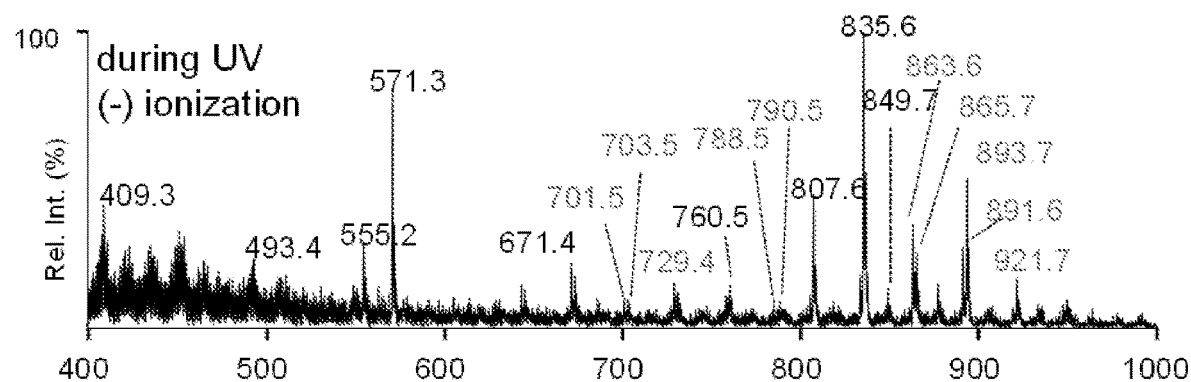
Figure 28C:
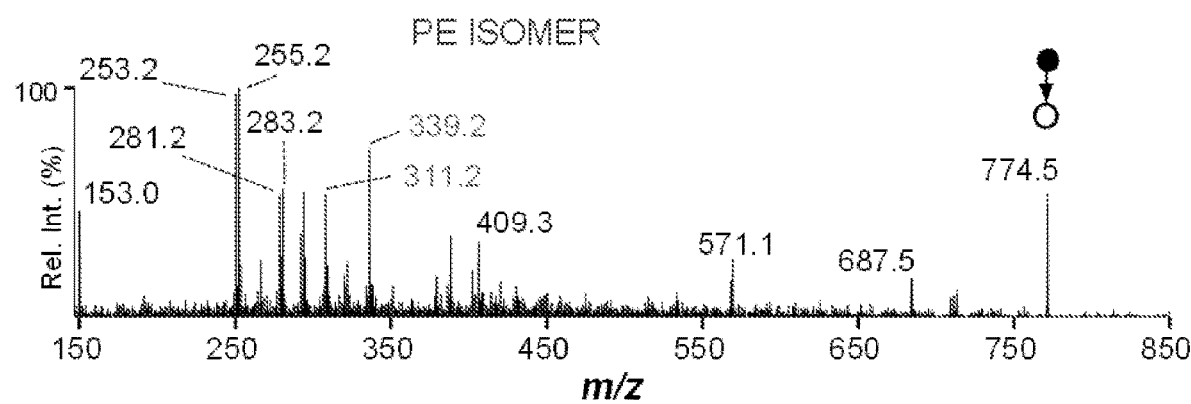
Figure 28D:
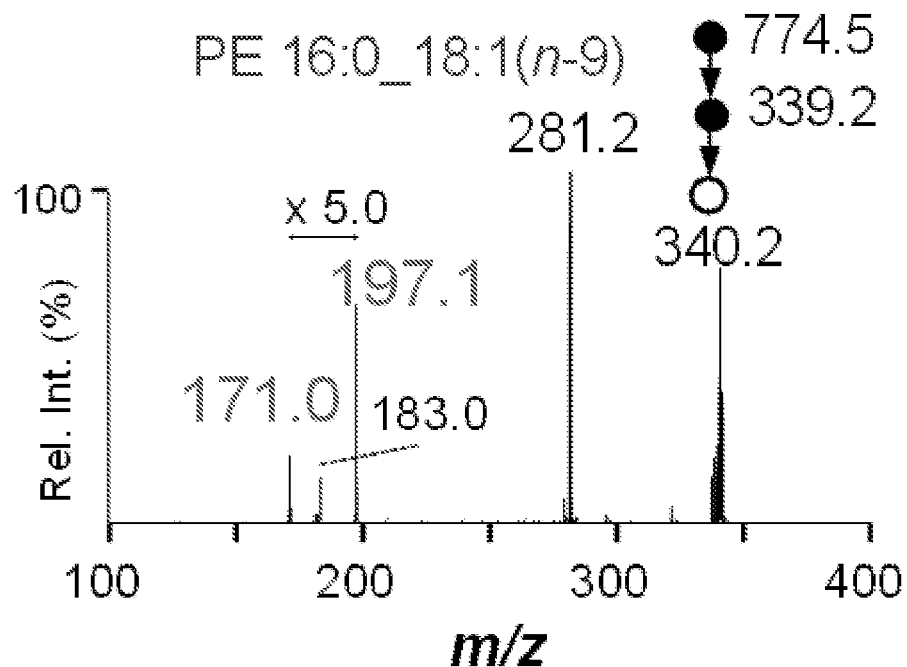
Figure 28E:
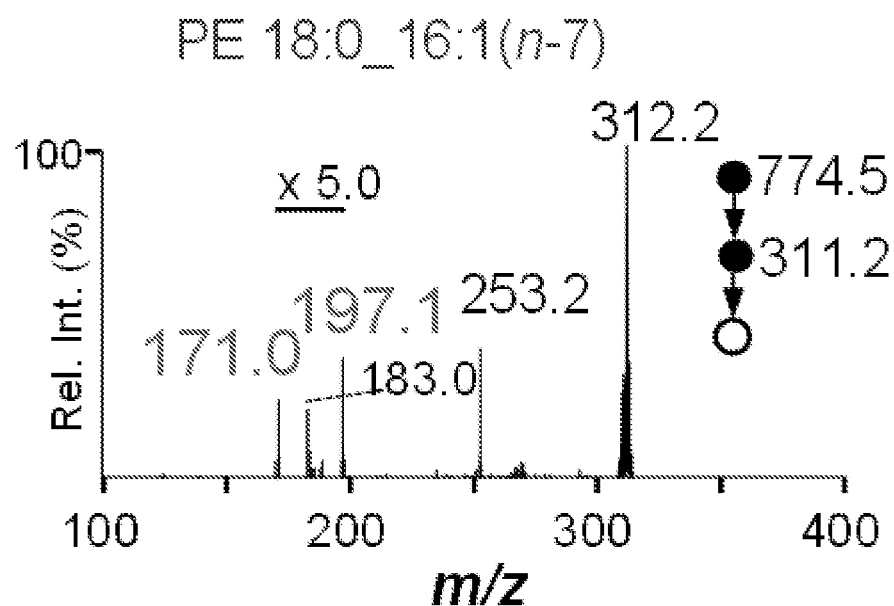

$MS^1$ LIT spectra for the yeast lipid extract are shown in FIGS. 28A-B for negative ionization. Before exposure to UV abundant signal is observed for PL species (FIG. 28A) and during UV irradiation several P-B reaction peaks are observed in the spectrum indicated by red font (FIG. 28B). Reaction products not clearly observed in the $MS^1$ reaction spectrum could still be analyzed via predicted m/z values for P-B reaction products based on PL identification from the triple quadrupole and product ion scans. For example, FIGS. 28C-E show tandem MS spectra for the isomers PE 18:0_16:1 (n-7) and PE 16:0_18:1 (n-9) at P-B reaction product m/z 774.5. Beam-type CID of m/z 774.5 produced fragment ions at m/z 311.2 and 339.2 in addition to saturated and monounsaturated fatty acyl fragment ions (m/z 283.2, 255.2 and 281.2, 253.2, respectively) (FIG. 28C). $MS^3$ ion trap CID of m/z 339.2 from FIG. 28B showed fragment ions of the 18-C monounsaturated fatty acyl (m/z 281.2) with diagnostic ions at m/z 171.0 and 197.1 indicating C=C bond at the n-9 location (FIG. 28D). In addition, $MS^3$ ion trap CID of m/z 311.2 from FIG. 28B showed fragment ions of the 16-C monounsaturated fatty acyl (m/z 253.2) with diagnostic ions at m/z 171.0 and 197.1 indicating C=C bond at the n-7 location (FIG. 28E). Table 6 is a summary of 35 unsaturated PLs with C=C location identified in the yeast polar extract analyzed as described. These results show the power of $MS^3$ CID in reducing background noise resulting in sensitive detection of C=C diagnostic ions.

TABLE 6

| Phospholipid | monoisotopic mass |
| --- | --- |
| PC 16:0_16:1(n-7) | 731.6 |
| PC 16:1(n-7)/16:1(n-7) | 729.5 |
| PC 16:1(n-7)/18:1(n-9) | 757.6 |
| PC 16:0_18:1(n-9) | 759.6 |
| PC 18:0_16:1(n-7) | 759.6 |
| PC 18:1(n-9)/18:1(n-9) | 785.6 |
| PE 16:1(n-9)/16:1(n-7) | 687.5 |
| PE 18:0_16:1(n-7) | 717.5 |
| PE 16:0_18:1(n-9) | 717.5 |
| PE 16:1(n-7)/18:1(n-9) | 715.5 |
| PI 16:0_16:1 (n-7) | 808.5 |
| PI 16:1(n-7)/16:1 (n-7) | 806.5 |
| PI 16:1(n-7)/18:1(n-9) | 834.5 |
| PI 16:0_18:1(n-9) | 836.5 |
| PI 18:0_16:1(n-7) | 836.5 |
| PI 18:0_18:1(n-9) | 864.6 |
| PI 18:1(n-9)/18:1(n-9) | 862.6 |
| PA 16:0_16:1(n-7) | 646.5 |
| PA 16:1(n-7)/16:1(n-7) | 644.4 |
| PA 16:0_18:1(n-9) | 674.5 |
| PA 16:1(n-7)/18:1(n-9) | 672.5 |
| PS 16:0_16:1(n-7) | 705.5 |
| PS 16:1(n-7)/16:1(n-7) | 703.4 |
| PS 18:0_16:1(n-7) | 733.5 |
| PS 16:0_18:1(n-9) | 733.5 |
| PS 16:1(n-7)/18:1(n-9) | 731.5 |
| LPC 16:1(n-7) | 493.3 |
| LPC 18:1(n-9) | 522.4 |
| LPE 16:1(n-7) | 451.3 |
| LPE 18:1(n-7) | 479.3 |
| LPI 16:1(n-7) | 570.3 |
| LPI 18:1(n-9) | 598.3 |
| LPA 18:1(n-9) | 436.3 |
| LPS 16:1(n-7) | 495.3 |
| LPS 18:1(n-9) | 523.3 |

Conclusions

A method for coupling the classic [2+2] Paterno-Buchi reaction to online ESI $MS^n$ for locating C=C bond in unsaturated lipids was presented. Reaction limits were explored for a range of ESI MS conditions including flow rate, solvent composition, and UV exposure time. A maximum yield of 50% was achieved for 5 μM PC 16:0_18:1 (n-9Z) in 7:3 acetone:$H_2O$ 1% acetic acid with 6 s cumulative UV exposure. Yields of 40% were obtained for basic solutions of oleic acid and PA 18:0_18:1(n-9Z) in negative ion mode. Solutions were $N_2$ purged prior to analysis as the presence of molecular oxygen in solution reduced P-B reaction yield. The reaction was successfully implemented at flow rate range of 0.1-4.5 μL/min and showed relatively constant reaction product formation. In addition, the P-B reaction was also effected with the addition of alternative solvents such as acetonitrile, methanol, isopropanol, and hexane routinely used in LC separations. Finally, application of the method was demonstrated for online analysis of a complex mixture of yeast polar extract. Although the reaction environment was much more complicated relative to the model system a C=C location for total of 35 unsaturated phospholipids were identified. Such works allows for the invention herein to encompass coupling of the P-B reaction to online LC-MS via tee junction post-column separation, for lipid C=C determination in complex mixtures.

Example 12: Profiling Unsaturated Lipids in Tissue

Direct tissue analysis by mass spectrometry (MS) with simple procedures represents a key step in accelerating lipidomic analysis, especially for the study of unsaturation of isomeric lipids. In this Example, isomeric structures of unsaturated lipids from tissue were first directly determined with systematic structure profiles in a single step by ambient mass spectrometry, which was implemented by on-line Paternó-Büchi (P-B) reaction and extraction spray mass spectrometry. Lipids were directly extracted by sticking a stainless steel wire into a chunk tissue and then immersing into a nanoESI capillary preloaded with solvent for extraction, reaction and detection by ESI-MS. UV light (λ=254 nm) was used to facilitate the P-B reaction to form reaction product ions (+58 Da) added with an oxetane ring at the original location of the C=C bound, which is subsequently cleaved by CID to produce characteristic fragment ions. The unsaturation of lipids in a broad dynamic range of concentrations (0.0013%-0.5% of total lipids in rat brain) can be identified with good reproducibility (isomeric ratios of lipids detected: RSD<10%, sampling in the same region of one tissue; RSD<21%, sampling in the same region of tissues in the same type). Since the sample consumption of the present method can achieve as low as 10 μg/sample, isomeric ratios of unsaturated lipids were also first mapped for rat brain and kidney. Significant differences in isomeric ratios of lysophosphatic acid (LPA) 18:1 and phosphatic acid (PA) 18:1-18:1 were observed in different regions of rat brain, while isomeric ratios of fatty acid (FA) 18:1 was relatively stable in both rat brain and kidney.

The present work first directly determined structures of lipids from tissues with positions of C=C bonds by integration of Paternó-Büchi reaction and extraction spray mass spectrometry. Since the sample consumption is as low as ~10 μg, isomers of lipids in a small region (0.5 mm×0.5 mm) can be quickly measured and first profiled as a two-dimensional (2D) map of isomeric ratios in brain and kidney. This technique provides a powerful platform to monitor unsaturated lipids for understanding impacts of unsaturation of lipids on tissue biological functions, biosynthetic pathways, and thereby the disease states of the tissues.

Introduction

Lipids are a group of naturally occurring molecules that display emergent physic-chemical properties in cell membrane development, energy production and storage, hormone production, insulation and protection of membrane proteins in hydrophobic environment, and cellular signaling process through their self-assembly and collective behaviors. Unsaturation of lipids, viz. the number and locations of C=C bonds, as one of important parameters determining the shape of a lipid, is closely related to the biological function and the disease state of a tissue by affecting the cell membrane curvature in the context of membrane permeability, trans-membrane structure, and enzymatic action. For example, the ordering within a membrane was found to be weakest when the C=C bond was located in the middle of an acyl chain, and therefore enhances the fluidity of the membrane. In addition, the omega-3 fatty acids, containing 18-22 carbons with a signature C=C bond positioned in the third place from the methyl end of a lipid, were found to be important in brain development and employ cardioprotective functions in both primary and secondary coronary heart disease preventions trails. However, the localization of C=C positions is still a big challenge and requires reliable analytical platforms to profile molecular structures and distinguish isomers of a lipid from many possibilities.

Mass spectrometry (MS), in contrast, is capable of providing detailed molecular information and thus has been widely used in determining identities and quantities of individual lipids due to its high sensitivity, selectivity and broad mass range. A series of MS-based methods were developed for determination of C=C bonds employing either direct fragmentation of lipids by high energy collisional-induced dissociation (CID) or chemical derivatization before MS analysis. Typically, lipids needs to be extracted, separated, and purified in several steps before MS analysis, which may require intensive labor work for up to one day. This type of multi-step procedure works well for analysis of large batches of samples. Meanwhile, ambient ionization mass spectrometry as a single-step based strategy has been shown good performance in analyzing target analytes.

In ambient ionization mass spectrometry, the analytes are directly ionized from a sample in its native state and transferred into the gas phase for MS analysis with minimal sample preparation. Many ambient ionization methods were developed and applied in direct lipid analysis as well as two-dimensional (2D) imaging of its distribution on tissues, such as desorption electrospray ionization mass spectrometry (DESI), matrix-assisted secondary ion mass spectrometry, probe electrospray ionization (PESI), matrix-assisted laser desorption electrospray ionization (MALDESI), easy ambient sonic-spray ionization (EASI), atmospheric pressure infrared matrix-assisted laser desorption ionization (AP IR-MALDI), paper spray, as well as needle biopsy and spray ionization. The application of ambient ionization mass spectrometry in determination of double bond positions was first achieved in microbial fatty acid ethyl ester mixtures from bacterial samples by low temperature plasma ionization mass spectrometry (LTP-MS). However, little headway has been made in direct localization of double bonds in tissue samples. At the same time, although distributions of lipid concentrations were well profiled in high resolutions by many powerful imaging platforms, the relationship between proportions of isomeric lipids with regions of a tissue was still not clear.

In this Example, isomeric structures of unsaturated lipids from tissue samples were first directly determined with systematic structure profiles by ambient mass spectrometry, which was implemented by extraction spray and on-line Paterno-Buchi (P-B) reaction. The spatial distributions of isomeric ratio of lipids were also first imaged in the rat brain and kidney.

Sample Collection: Rats were obtained from Harlan Laboratory (Indianapolis, Ind., USA) housed and were decapitated upon cessation of respiration. All the surgeries were performed in accordance with the Purdue University Animal Care and Use Committee guidelines and ARRIVE guidelines. The tissues, including brains, kidneys, and livers, were removed from the bodies and immediately frozen at −80° C. Before analysis, the tissue was gradually thaw in a −20° C. freezer and then in a 4° C. for 1 hour, respectively. The tissue was then transferred onto a glass slide and stored in an ice box for the experimental use.

Figure 29A:
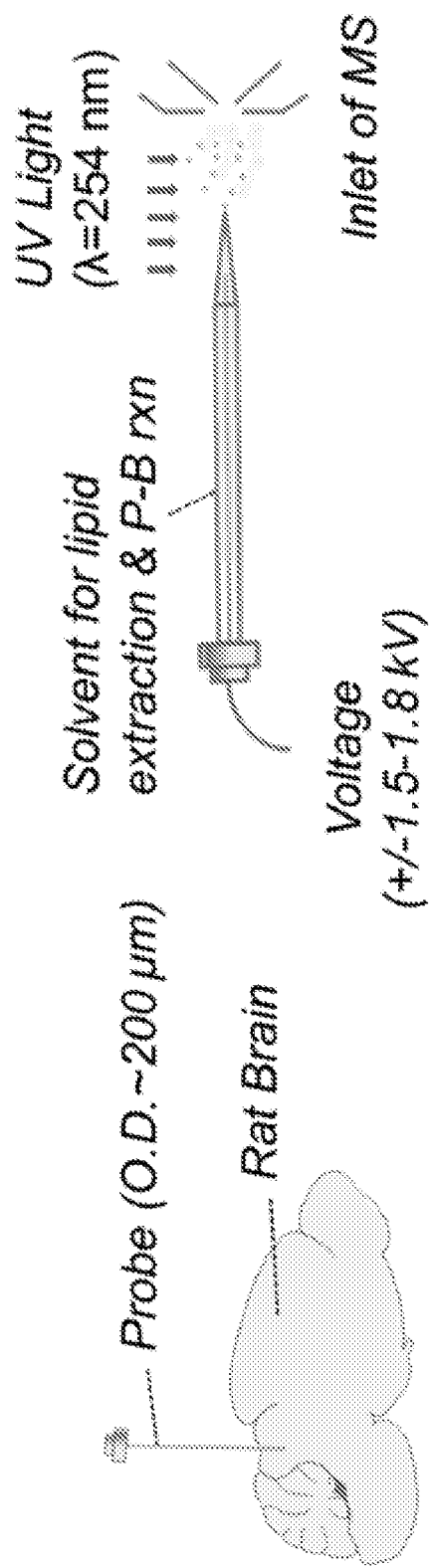
FIGS. 29A-B show a schematic overview of direct identifying C=C bond positions of lipids in tissue with combination of extraction spray and P-B reaction.

Sampling, Extraction, and Ionization of Lipids: The extraction spray was implemented for the direct analysis of tissue as shown in FIG. 29A. Using a procedure similar to tissue biopsy, a stainless steel wire (200 m o.d.) was inserted into a tissue at a depth of ~2 mm, and then immersed into 20 μL solvent in a glass capillary (1.5 mm o.d. and 0.86 mm i.d.) with a pulled tip for nanoESI. The solvent was prepared as acetone:acetonitrile:water (v:v:v=70:20:10) for phospholipids, while acetone:water (v:v:v=70:30) for fatty acids. The sampled lipids were then transferred into the solvent and a 1.8 kV DC was applied on the wire to generate nanoESI.

Mass Spectrometry: All the mass spectra were recorded by a QTrap 4000 triple quadrupole/linear ion trap hybrid mass spectrometer (Applied Biosystems/Sciex, Toronto, Canada). Typically, instrument settings of the 4000 QTRAP MS were as following: curtain gas, 8 psi; declustering potential, ±20V; interface temperature heater, 40° C.; and scan rate, 1000 Da/s with the use of Q3 as a linear ion trap.

For locating C=C bonds on unsaturated fatty acids by tandem mass spectrometry, Paternó-Büchi (P-B) reaction products lipids were isolated by Q1 quadrupole array and then were transferred to Q3 linear ion trap for on-resonance activation (ion trap CID). The excitation energy (AF2) was set in the range of 30-70 V in accordance of each fatty acid. For unsaturated phospholipids, lipids or their P-B reaction products were isolated by Q1 quadrupole array and then were accelerated to Q2 quadrupole array for beam-type collision-induced dissociation (CID). The collision energy (CE) varied from 25 to 50 V in different molecular species. The determination of C=C locations of phospholipids was according to the spectra in MS3 CID, in which one of fragments of product ions was formed by bream-type CID and isolated in Q2; a further fragmentation was then performed in Q3 linear ion trap by applying AF2 of 30-70 V.

Lipid Identification: Identification of lipids was performed by comparing the tandem MS spectra patterns with reported literatures.

Paternó-Büchi (P-B) Reactions: A low-pressure mercury lamp (BHK Inc., Ontario, Calif.) was used to apply a UV irradiation at 254 nm to facilitate the Paternó-Büchi reaction between the unsaturated lipids and the acetone. It was positioned orthogonally to the nanoESI tip in a distance of 0.5-1.0 cm. The lipids and the reaction products were analyzed by QTrap 4000.

Results

Figure 29B:
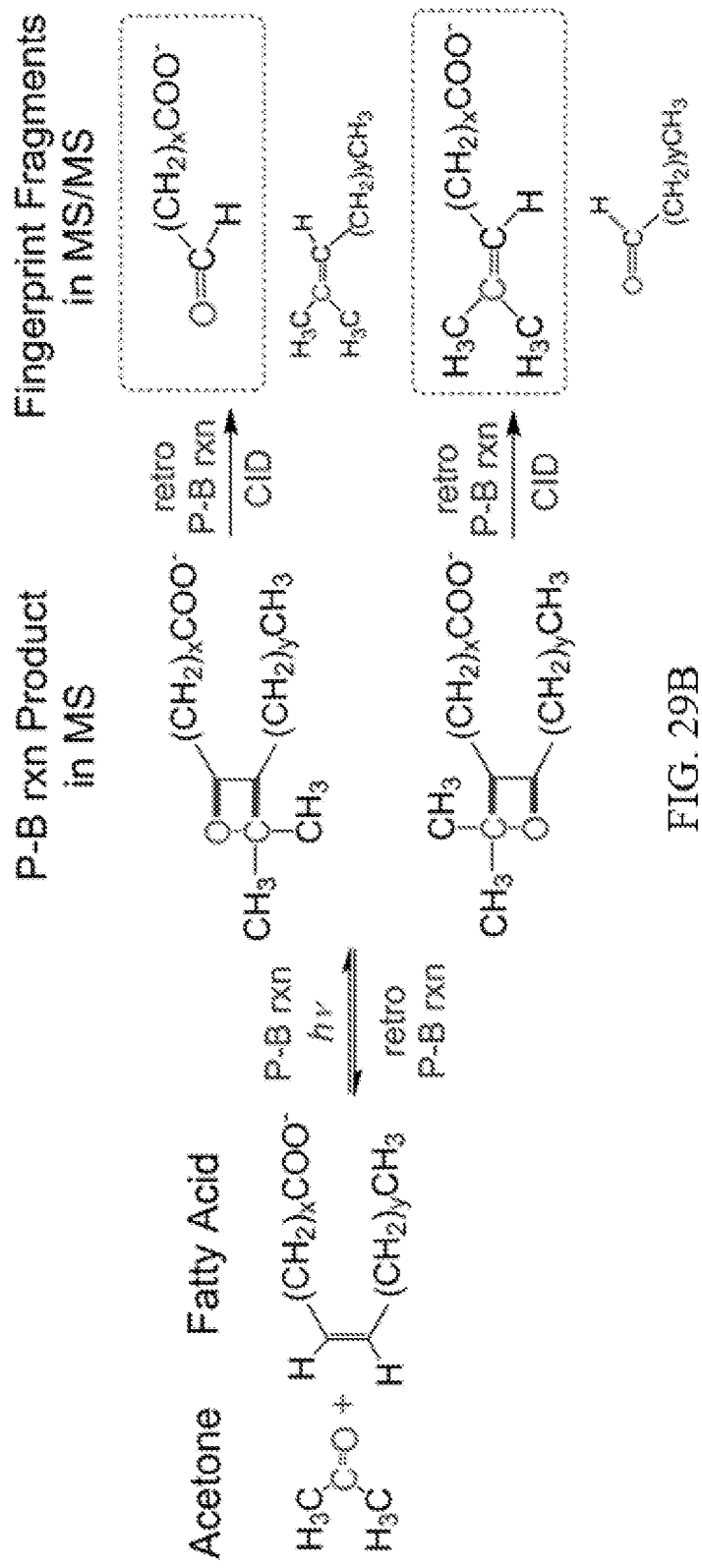
Figure 30A:
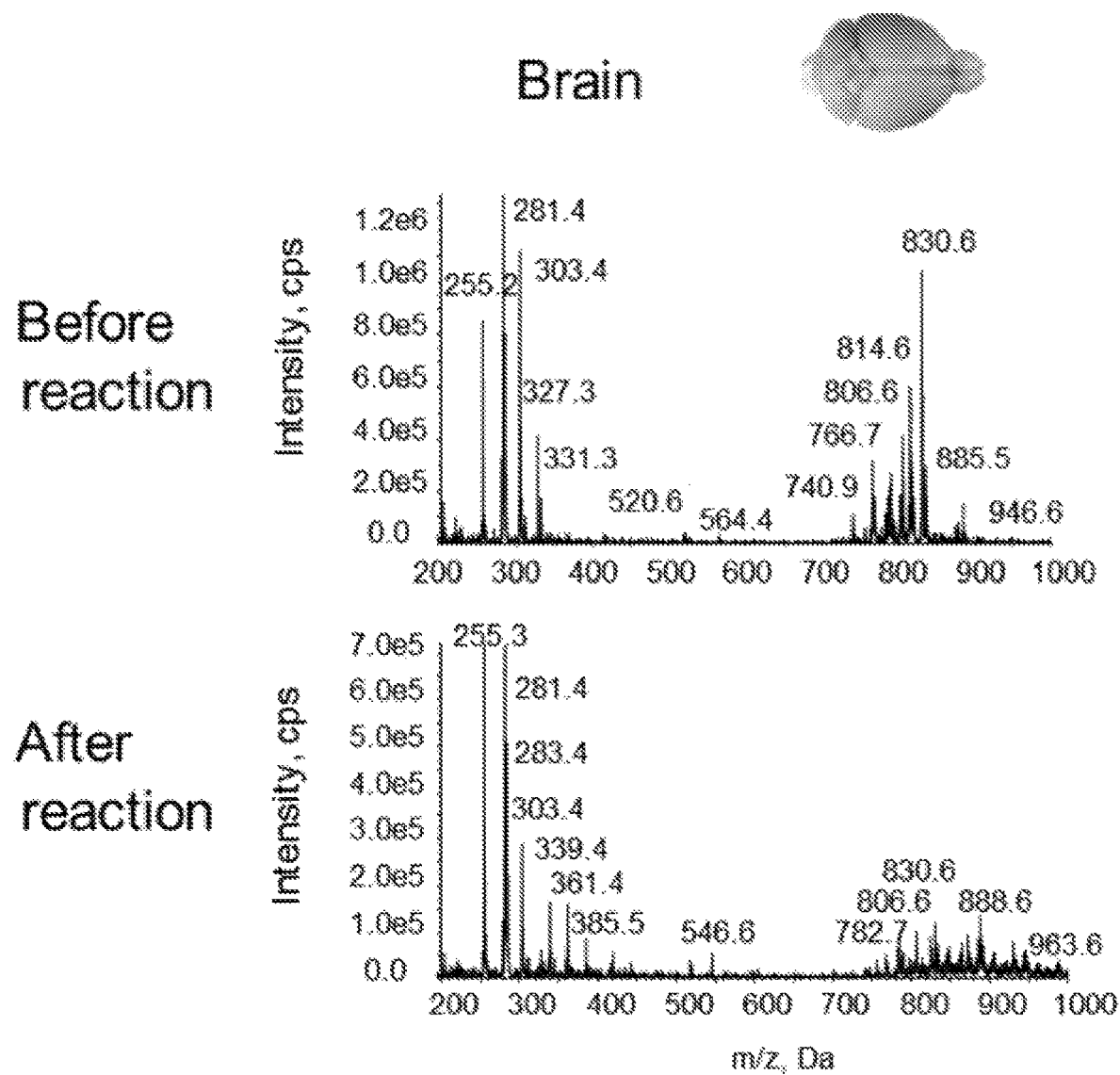
FIGS. 30A-I show direct lipid analysis with combination of on-line P-B reaction and extraction spray mass spectrometry.
Figure 30B:
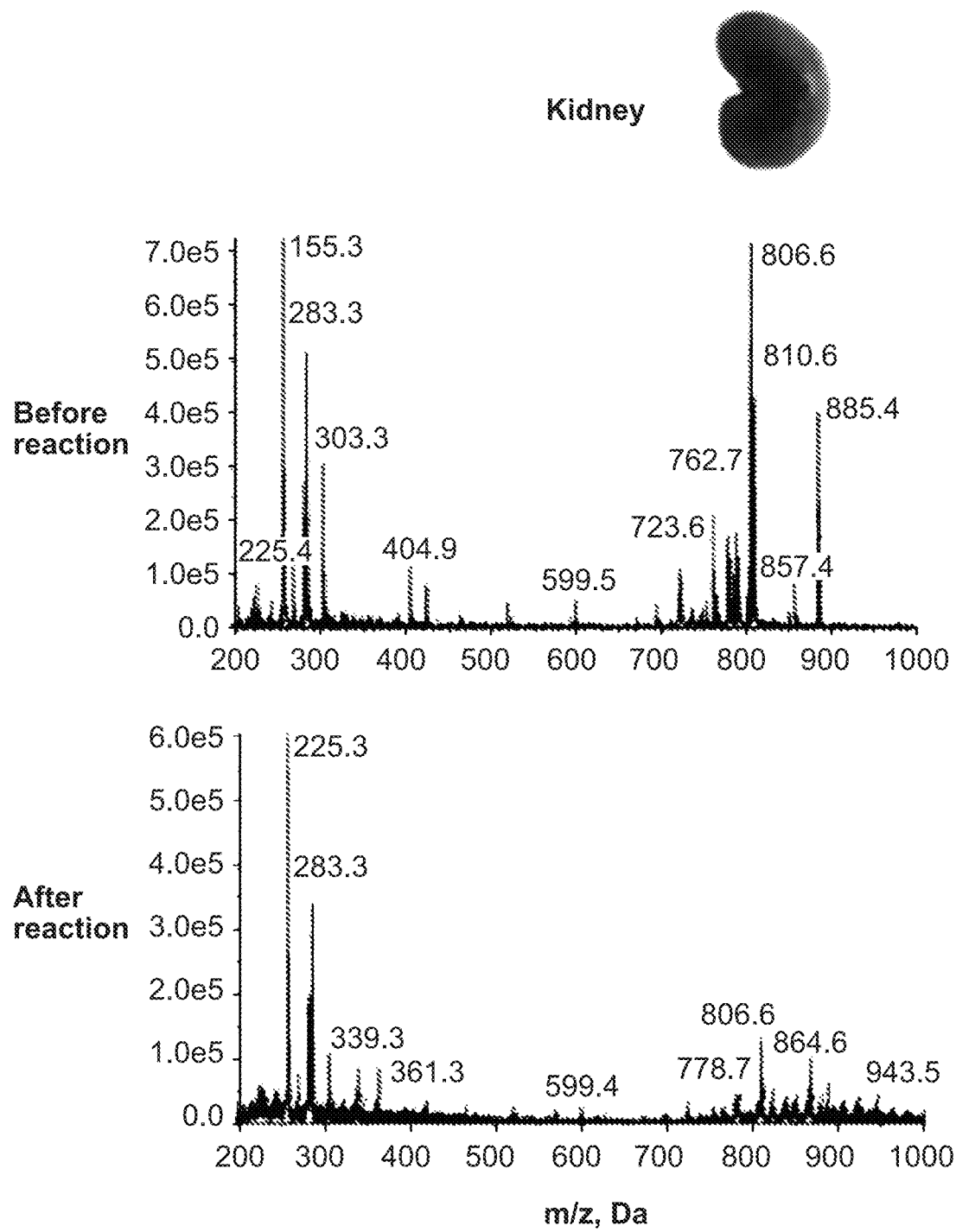
Figure 30C:
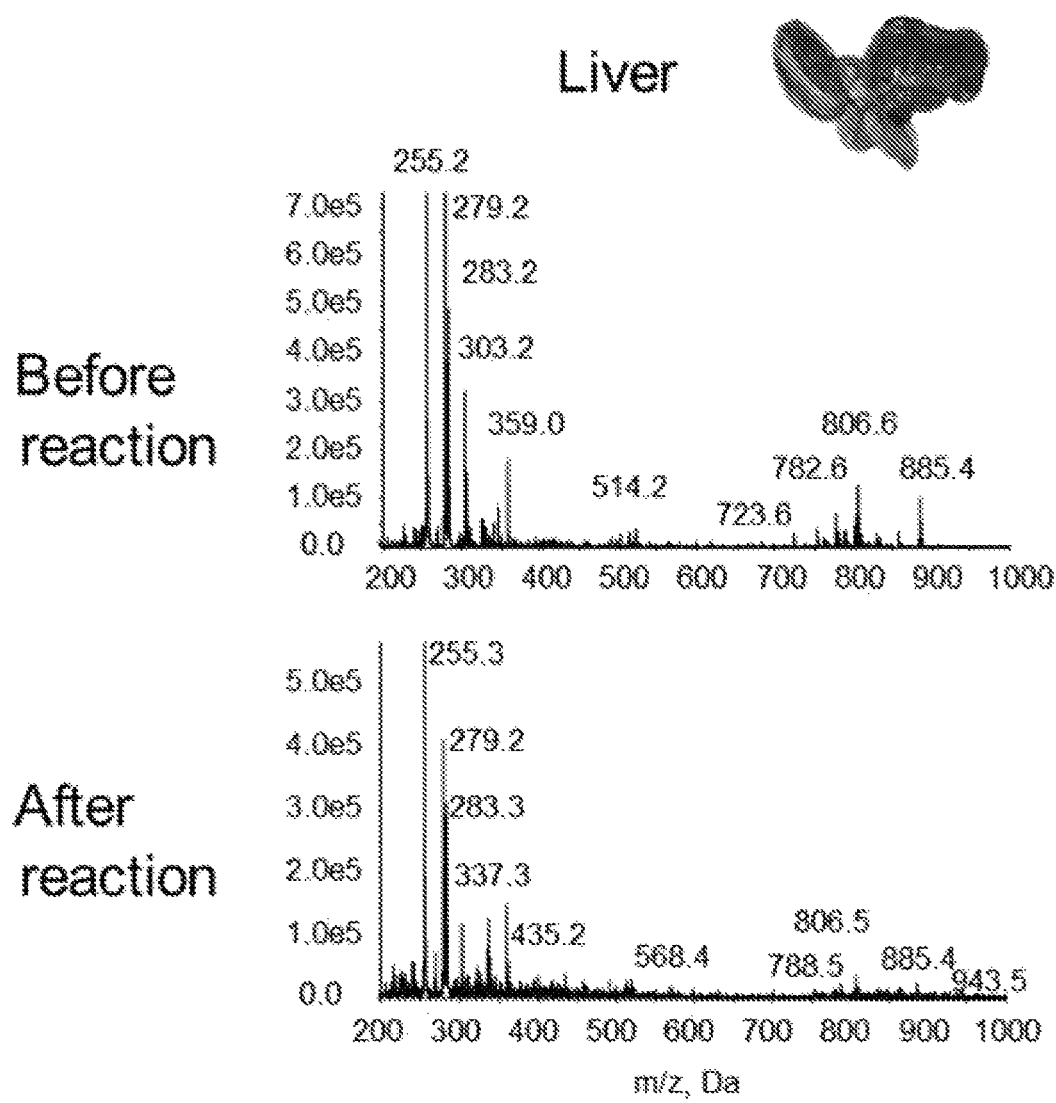
Figure 30D:
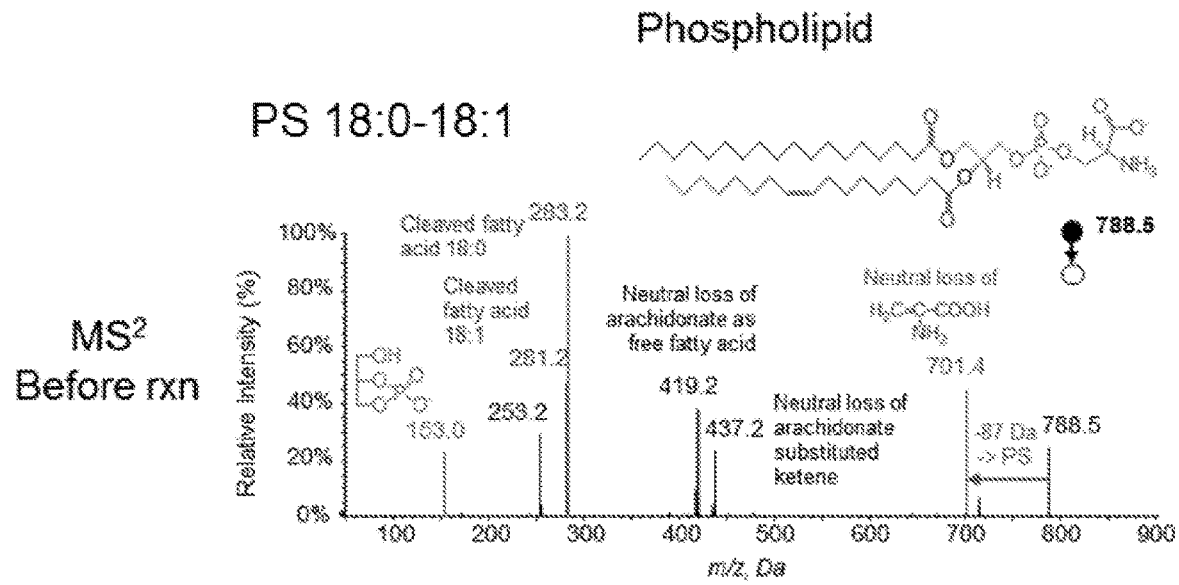
Figure 30E:
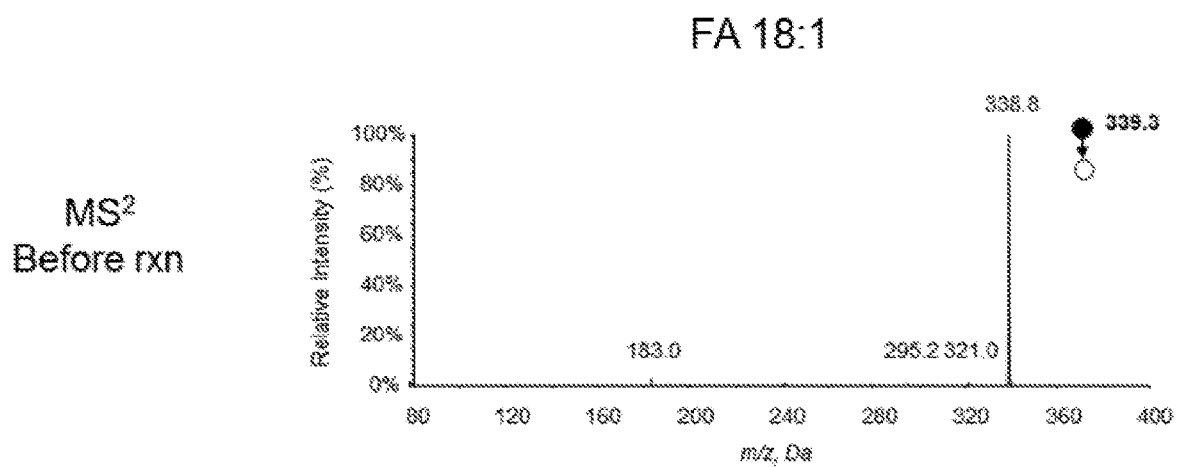
Figure 30F:
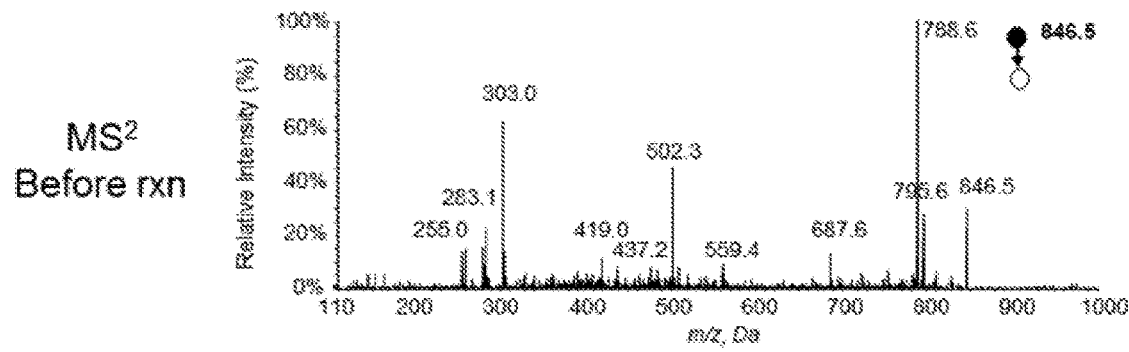
Figure 30G:
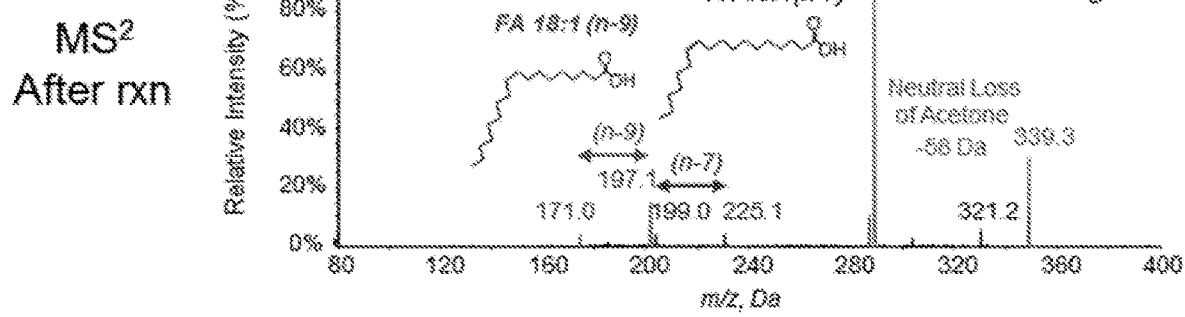
Figure 30H:
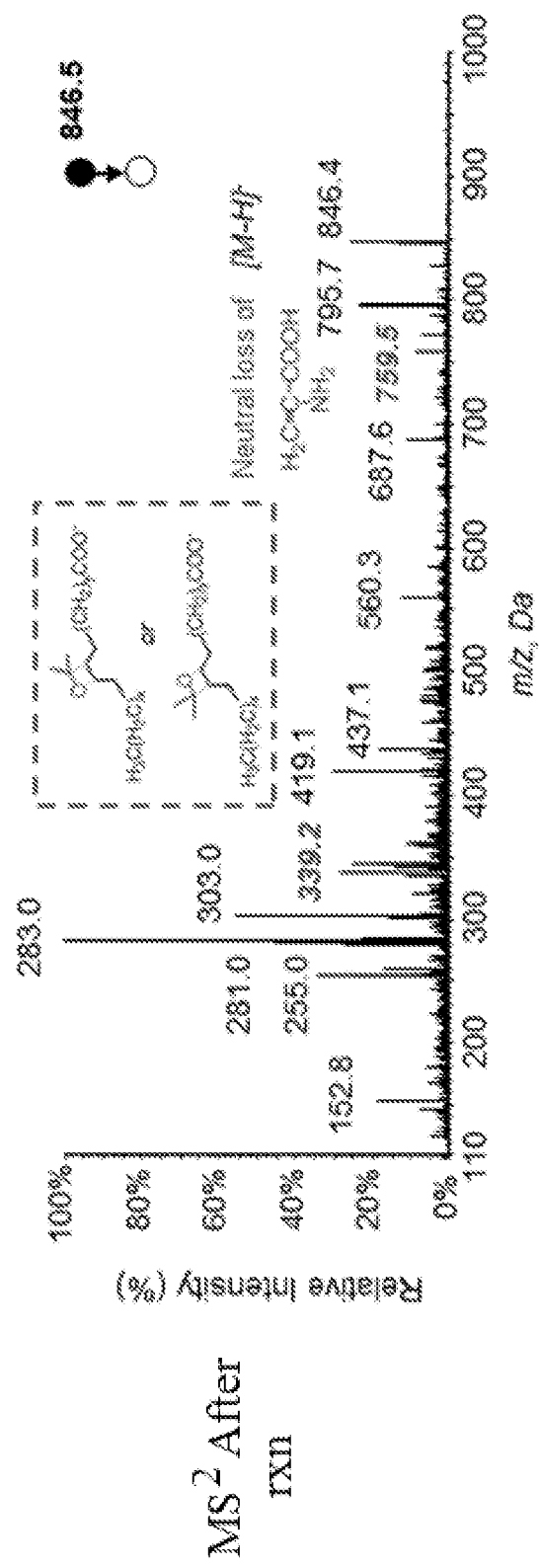
Figure 30I:
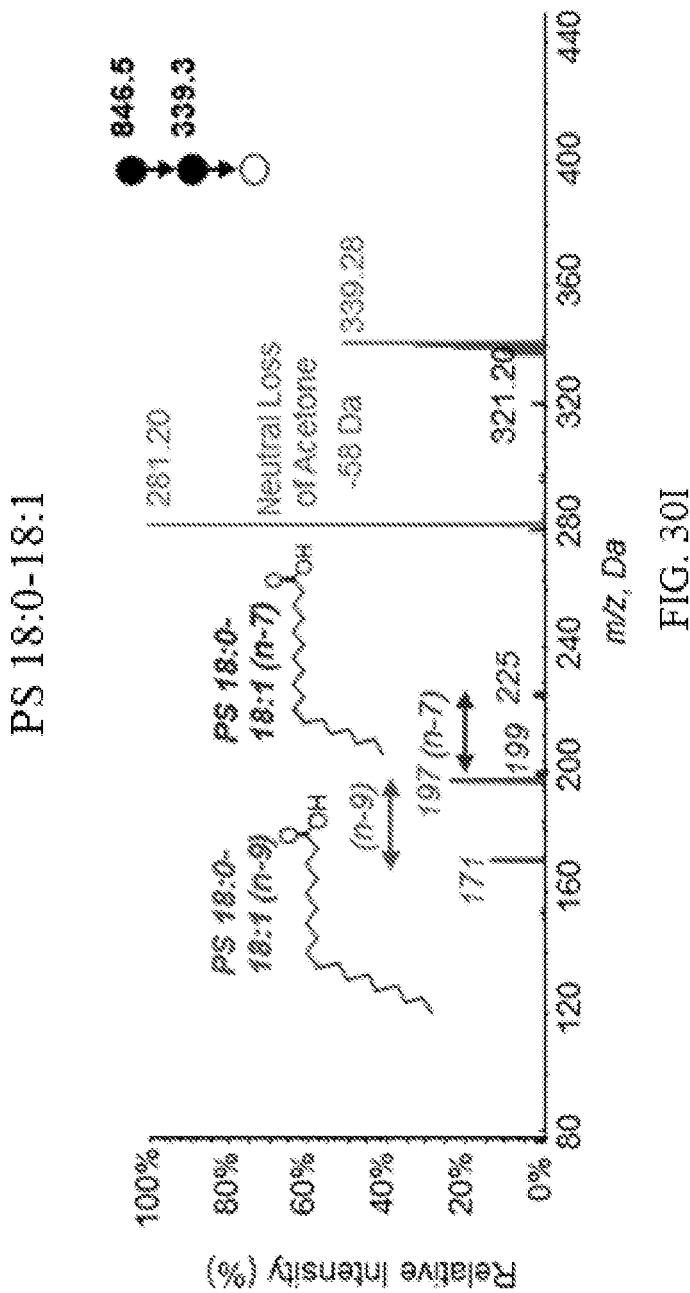

The design and the procedure were shown in FIG. 29A. Lipids were directly extracted by sticking a stainless steel wire into a chunk tissue and then immersing into a nanoESI capillary preloaded with solvent for extraction and reaction. A high voltage was applied on the wire to generate nanoESI. A low-pressure mercury lamp with 254 nm of UV light was used to facilitate the P-B reaction for the formation of reaction product ions (+58 Da) adding with an oxetane ring at the original location of the C=C bound, which is subsequently cleaved by CID to produce characteristic fragment ions (FIG. 29B).

The extraction process of lipids from tissue has been shown to be very efficient by extraction spray, as demonstration in rat brain, kidney, and liver tissues. Fatty acids and phospholipids quickly appeared in the mass range from m/z 200 to 900, and reached an equilibrium of intensity within 20 s when a high voltage was applied to the ESI-tip. A good reliability of lipid extraction was also proven for similar MS peak patterns as spectra of conventional lipid extracts. Meanwhile, the MS peak patterns differ with diverse types of tissues (FIGS. 30A-I). The head group and acyl chains of each phospholipid or lyso-phospholipid can be easily identified by tandem mass spectrometry (FIG. 31A-E). The selection of the organic solvent is critical. It needs to have good solubility of lipids, be suitable for electrospray and ensure high reaction efficiency of lipids. Several formulations of solvents were tested (FIGS. 32A-E). Solvents of 70% acetone: 30% $H_2O$ (v:v) as well as 70% acetone: 20% ACN: 10% $H_2O$ (v:v:v) were found to provide the optimal performance for the analysis of fatty acids and phospholipids, respectively.

Figure 31A:
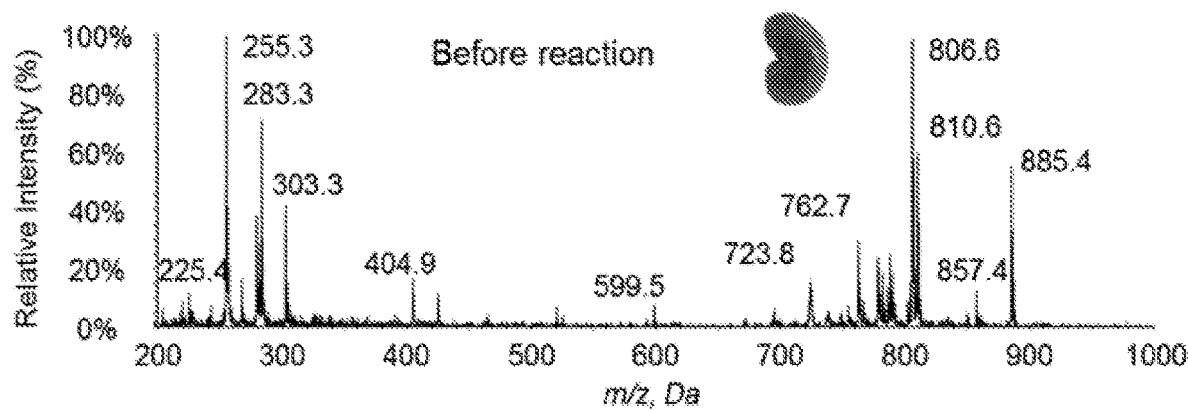
FIGS. 31A-E show direct lipid analysis with combination of on-line P-B reaction and extraction spray mass spectrometry. Mass spectrum of lipids sampling from rat kidney by extraction spray in negative ion mode before (FIG. 31A) and after (FIG. 31B) P-B reaction induced by UV irradiation.
Figure 31B:
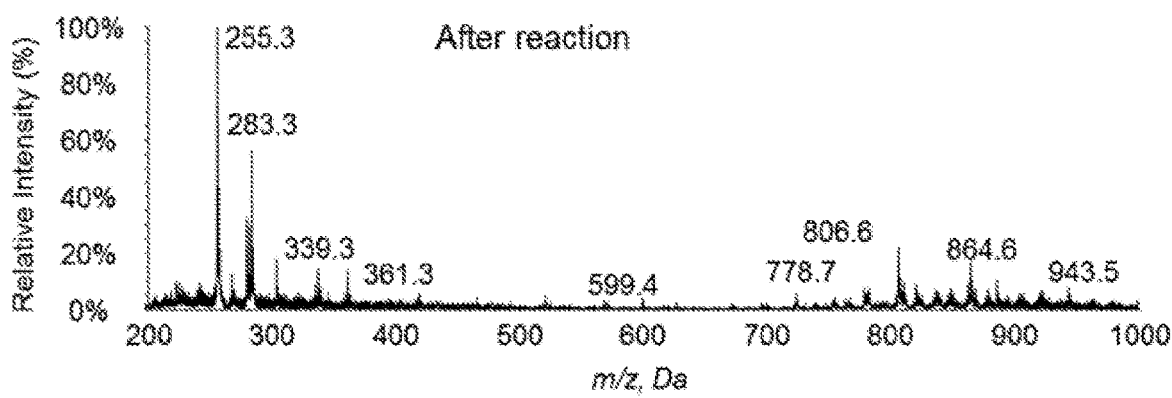
Figure 31C:
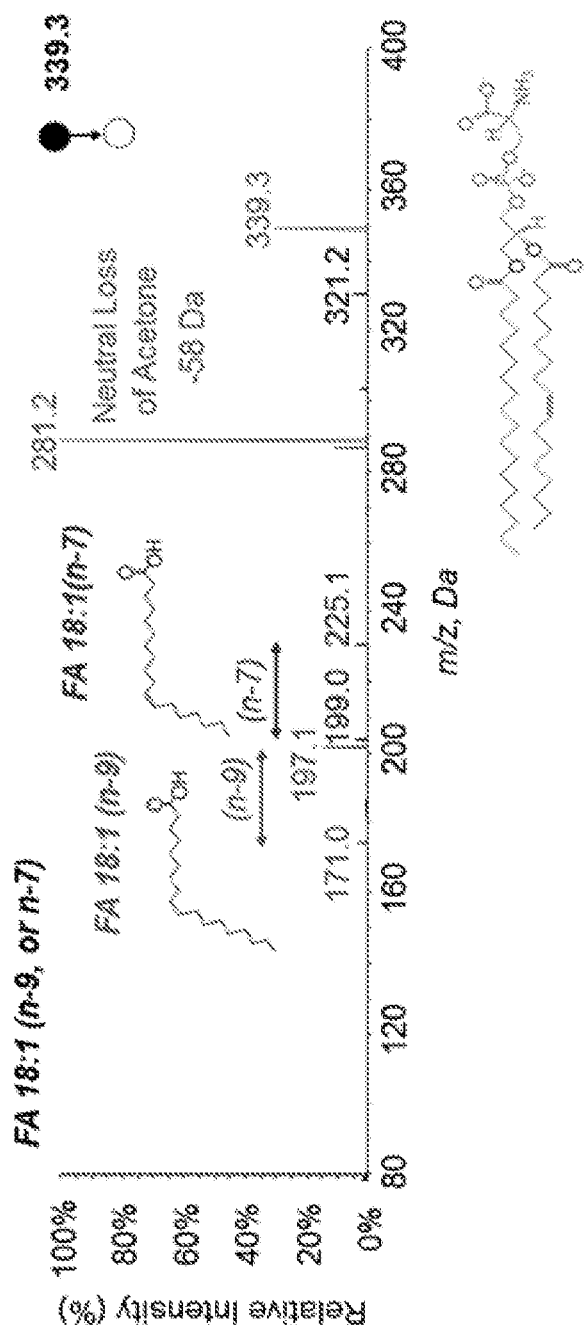
Figure 31D:
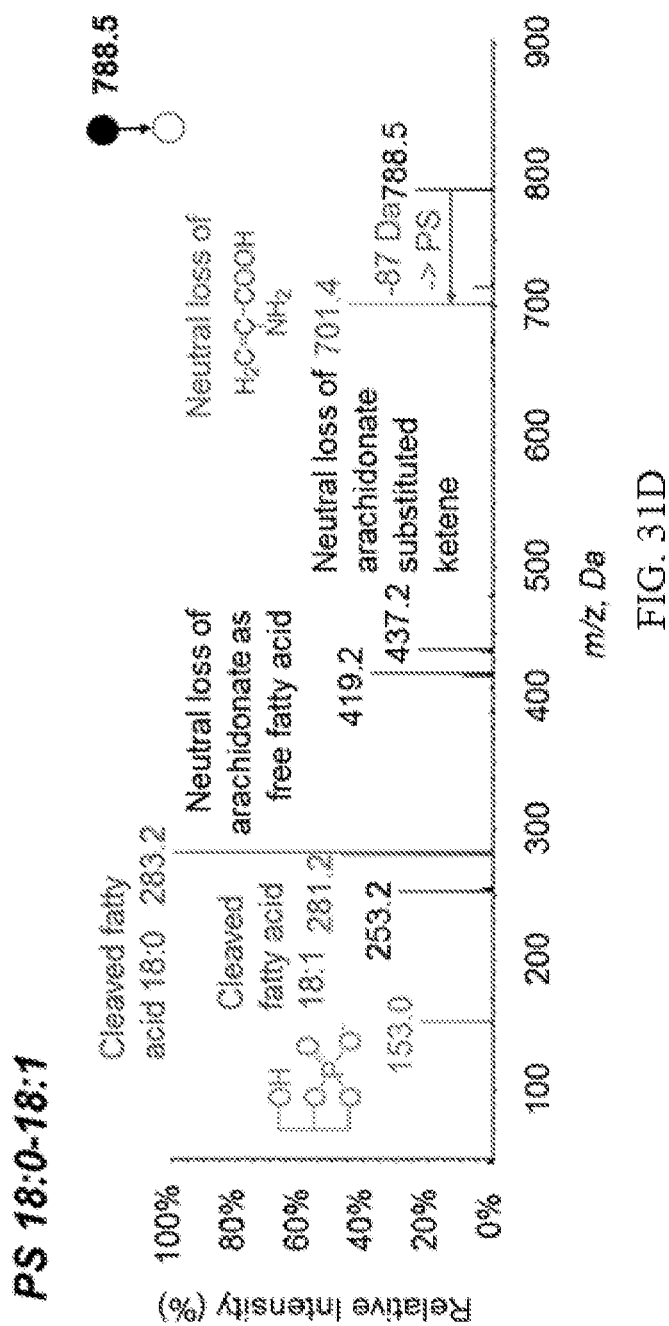
Figure 31E:
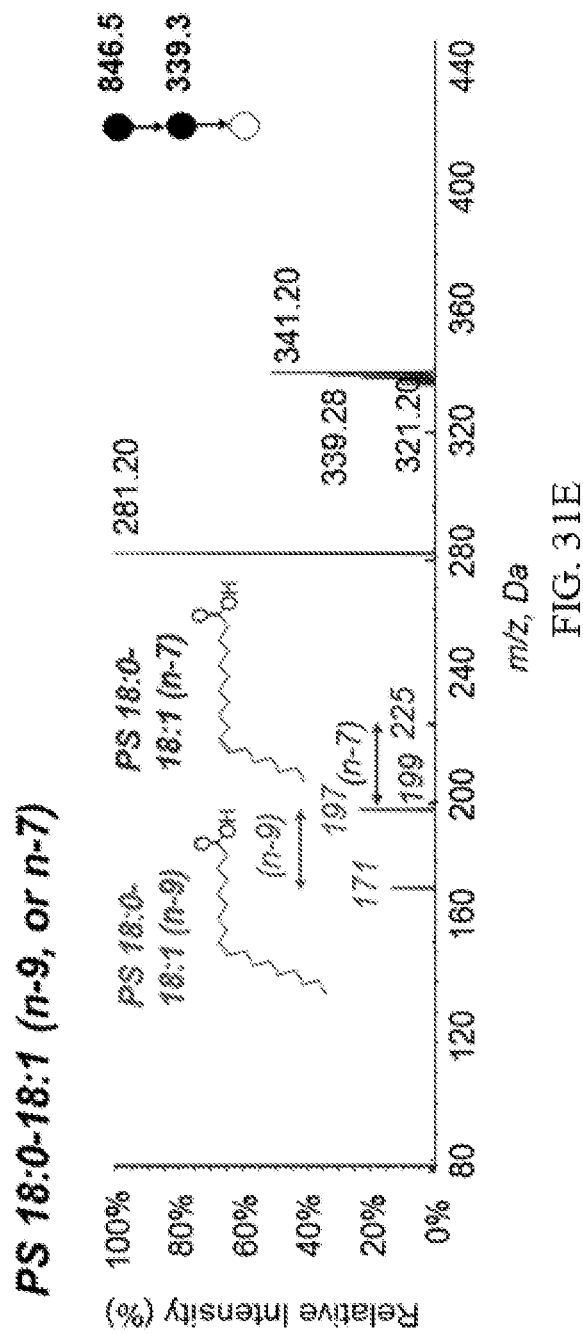
Figure 32A:
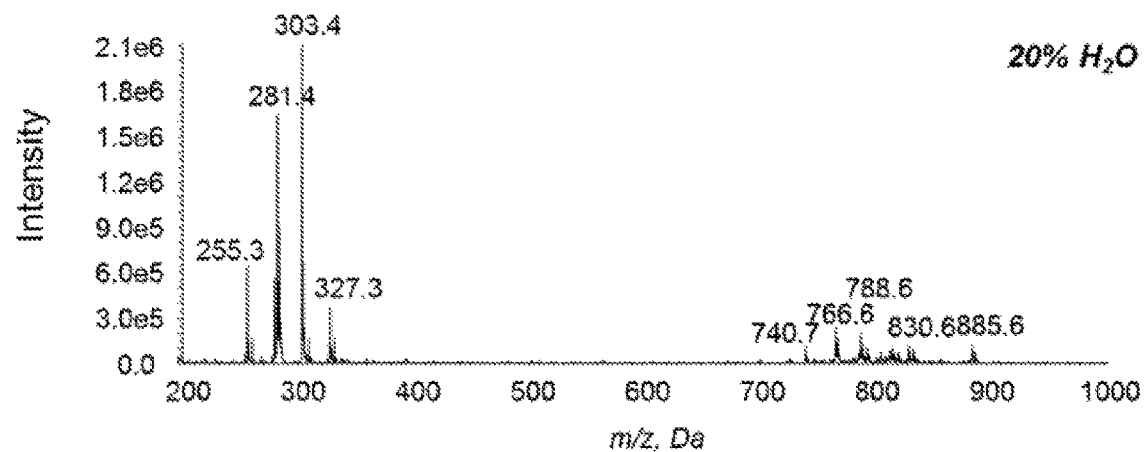
FIGS. 32A-E show optimization of solvents for lipid extraction. MS spectra of lipids directly extracted in a formulation with 70% acetone+10% H2O+20% X, X=(FIG. 32A) H2O, (FIG. 32B) Isopropanal (IPA), (FIG. 32C) acetonitrile (ACN).
Figure 32B:
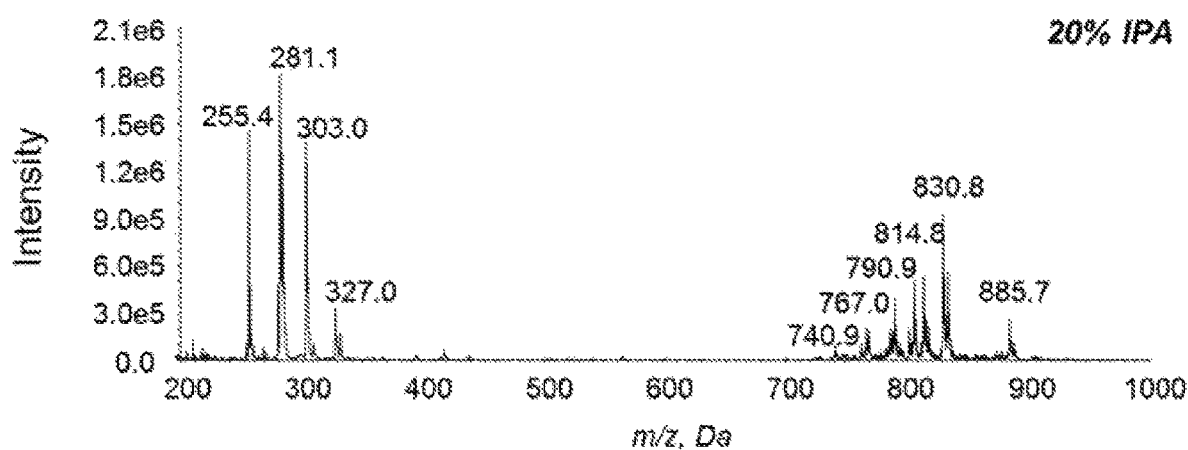
Figure 32C:
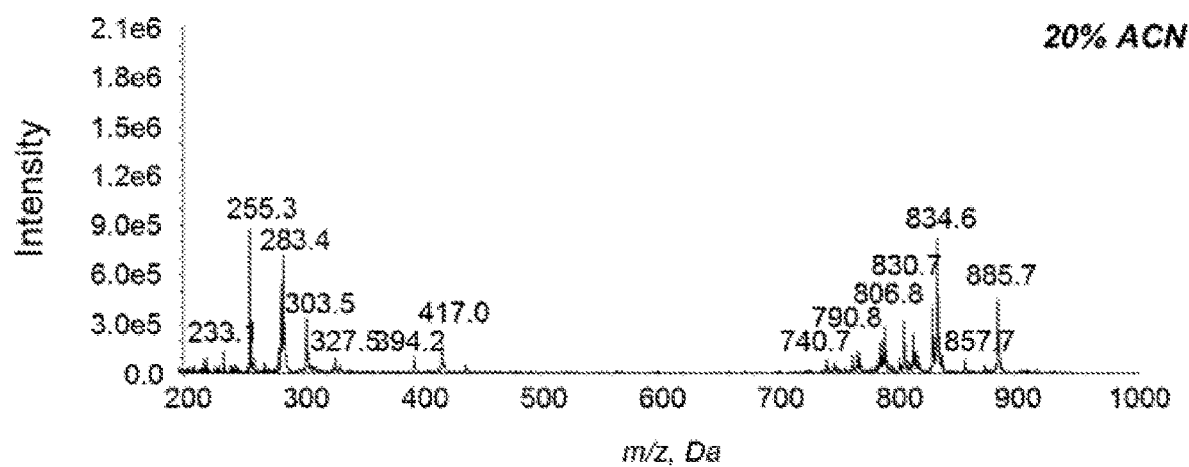
Figure 32D:
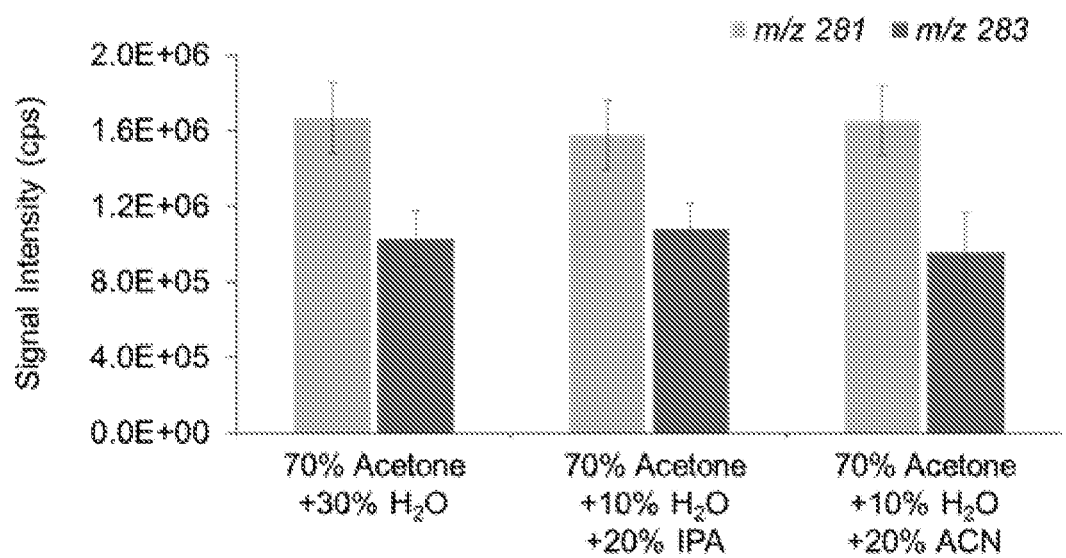
Figure 32E:
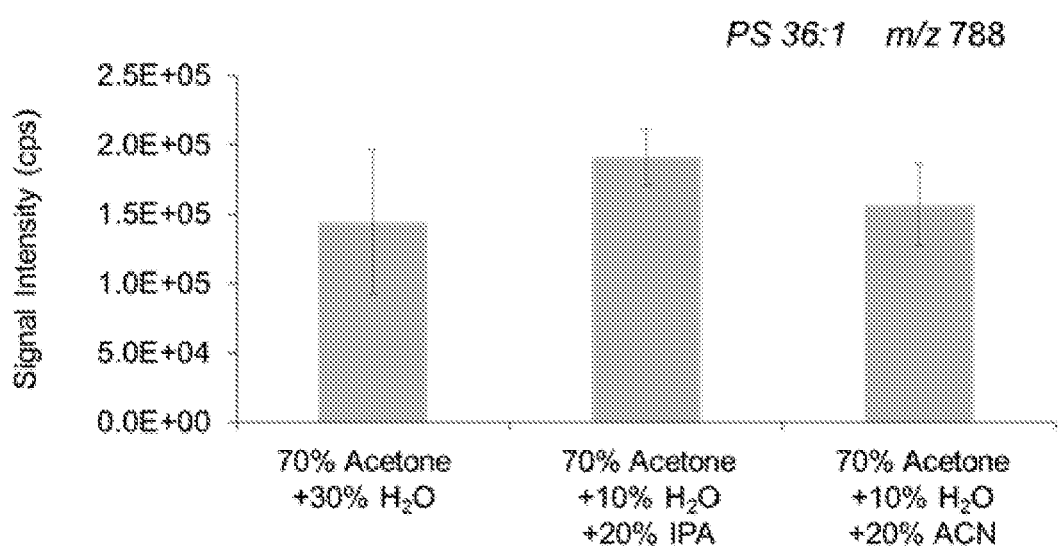
Figure 33A:
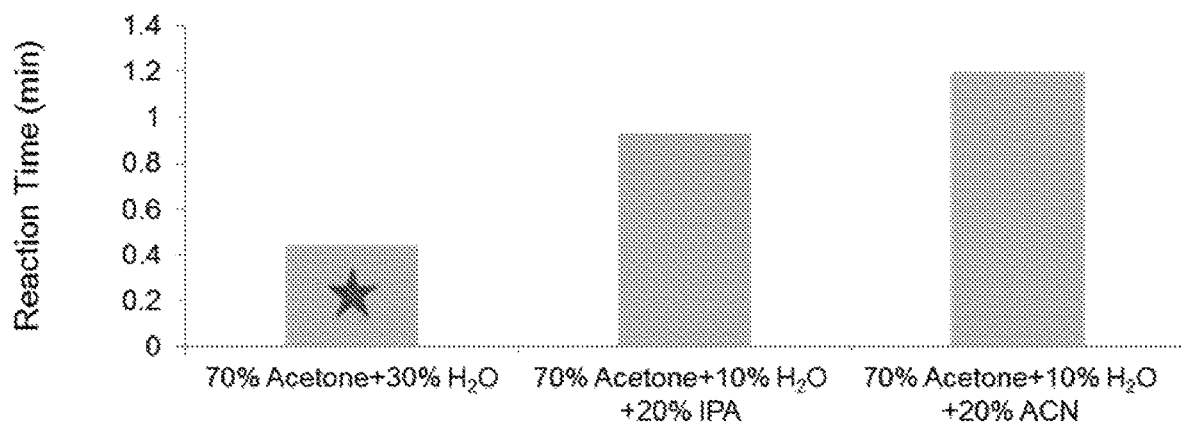
FIGS. 33A-C show optimization of solvents for P-B reaction of lipids and acetone.
Figure 33B:
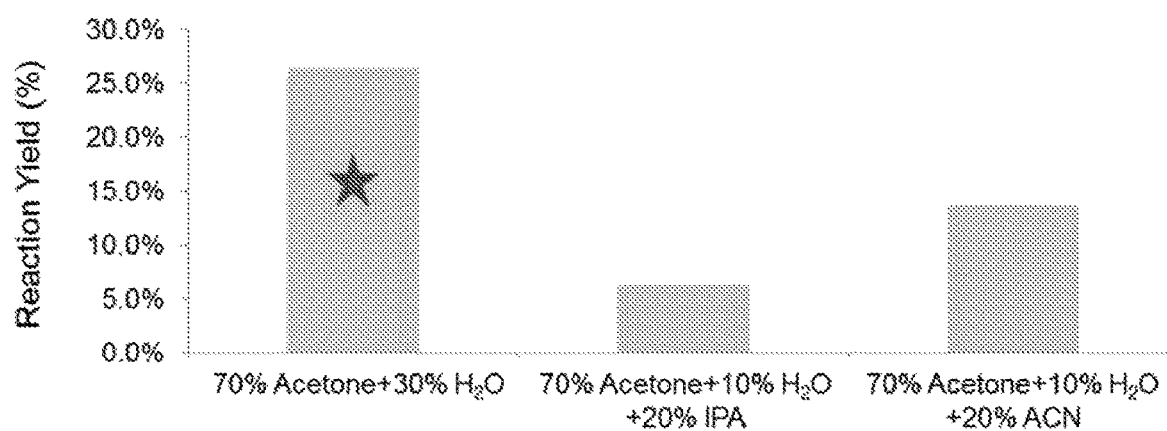
Figure 33C:
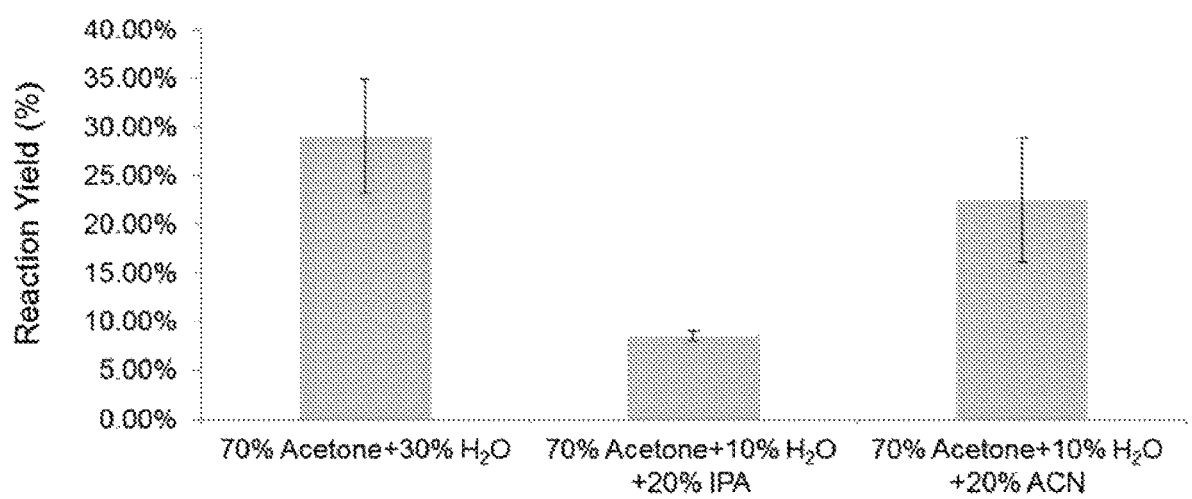
Figure 34A:
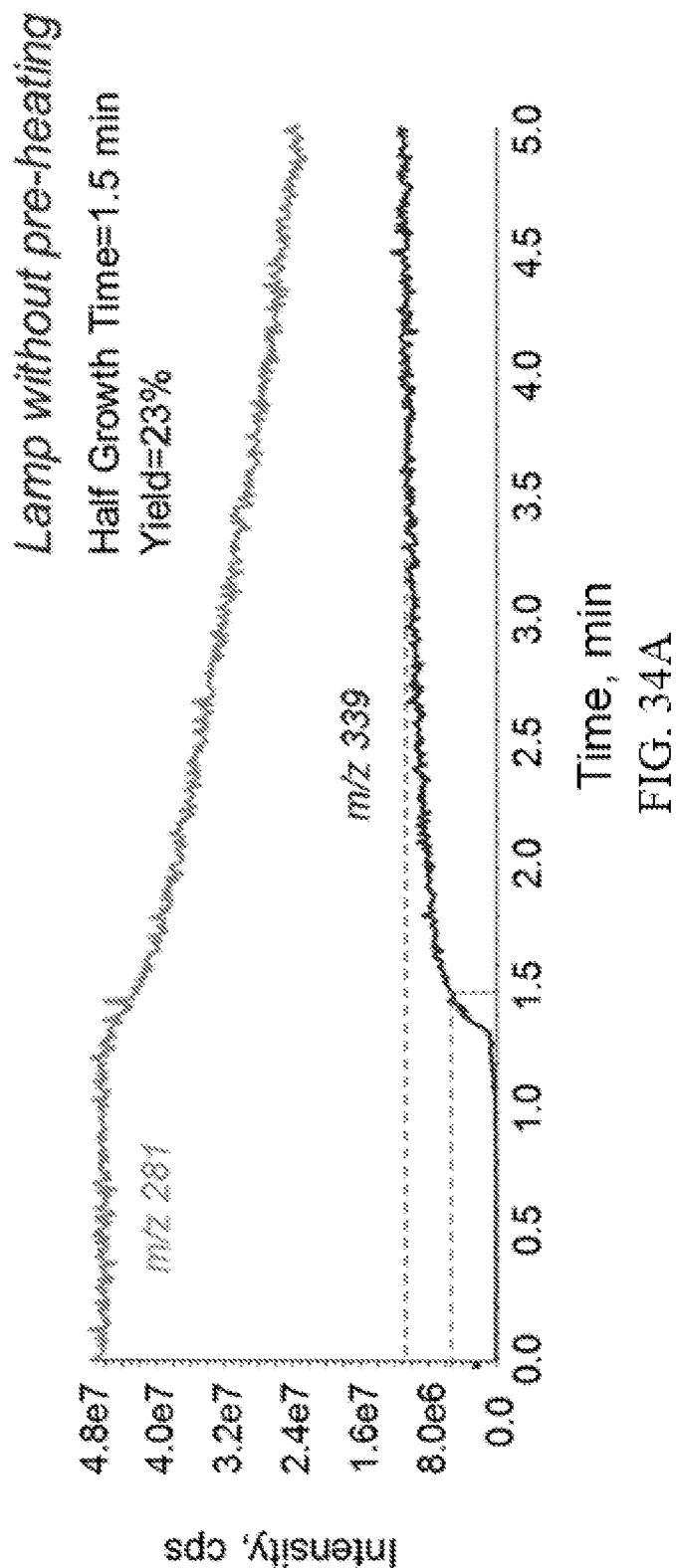
FIGS. 34A-B show optimization of lamp condition for P-B reaction of lipids and acetone. Total ion current of FA 18:1 [(M-H)–, m/z 281.3] and its P-B reaction product ion [(M+58-H)–, m/z 339.3] (FIG. 34A) with or (FIG. 34B) without pre-heating the UV lamp (λ=254 nm).
Figure 34B:
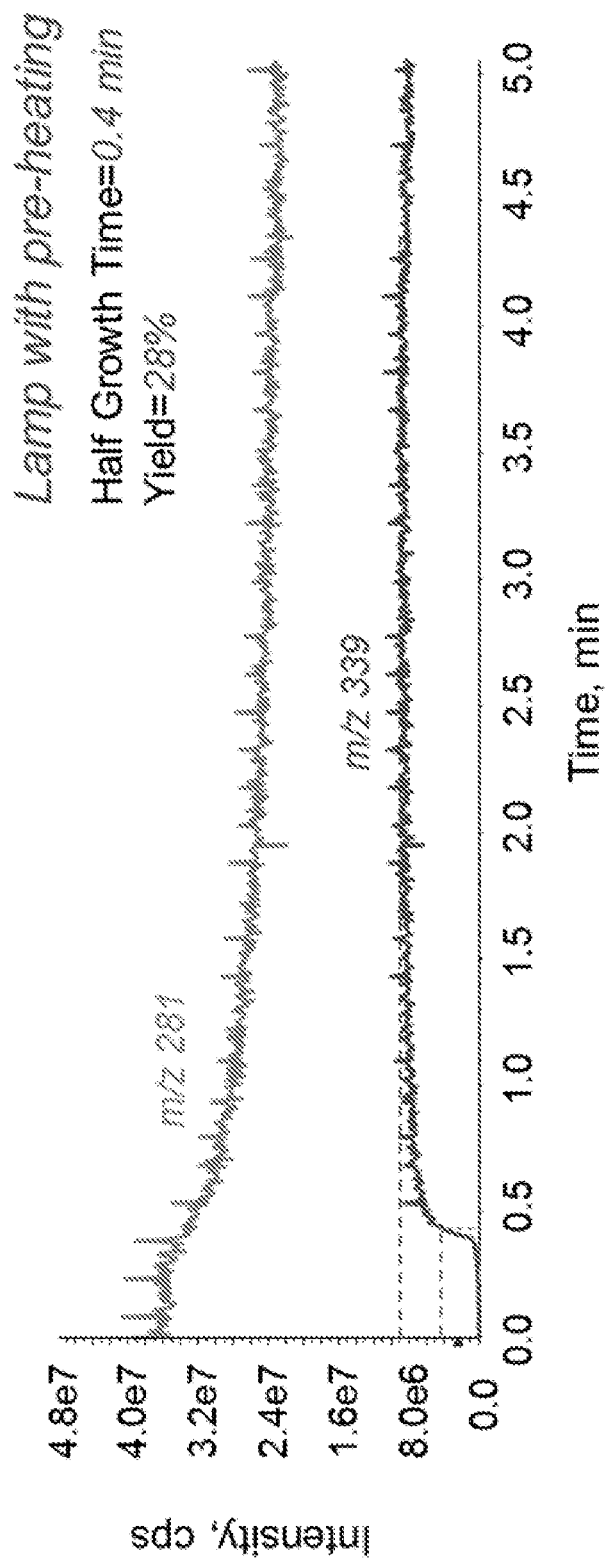

In order to localize individual double bond positions in each acyl chain of a lipid, P-B reaction was performed. As shown in FIGS. 31A-B, intensities of unsaturated fatty acids or phospholipids significantly decreased while many new peaks as product ions of P-B reactions appeared after radiation under the UV light. Double bond positions were indicated according to fingerprint fragments which were derived from retro P-B reaction by CID in an ion trap mass spectrometry. The $MS^2$ CID mass spectrum of m/z 339.3, as the product ion of fatty acid (FA) 18:1 in P-B reaction, was shown in FIG. 31C. Double bonds were designated to position in the ninth (n-9) or seventh (n-7) carbon from the methyl end of the lipid, respectively, based on two pairs of new generated fragments at m/z 171.0 & 197.1, as well as m/z 199.0 and 225.1 in comparison of $MS^2$ spectra before and after P-B reaction. The same result was also obtained in the acyl chain 18:1 of phosphatidylserine (PS) 18:0-18:1 based on the $MS^3$ CID spectrum of product ions of P-B reaction on cleaved unsaturated acyl chains (FIG. 31E). Addition of methanol (MeOH) or acetonitrile (ACN) helped extraction of phospholipids, but the yields of P-B reaction products were decayed in varying degrees due to UV absorption of MeOH or ACN to form radicals in the wavelength similar to 254 nm (FIGS. 33A-C). Interestingly, the half growth time of P-B reaction products was accelerated from 1.5 minutes to 0.5 minutes by pre-heating the lamp, for its quicker achievement of optimum condition in the light intensity and the wavelength (FIGS. 34A-B).

The reactive extraction spray showed a good performance in analyzing unsaturated lipids in a broad dynamic range of concentrations. Thirty one unsaturated lipids in concentrations across three orders of magnitudes in the rat brain were analyzed with good reproducibility of isomeric ratios (RSD<10%, sampling in the same region of one tissue, N=3), as shown in Tables 7-8.

TABLE 7

| Molecular Name | m/z before & after P—B reaction Before | m/z before & after P—B reaction After | Distribution of Fatty Acids in Brain | Isomers (n = 3) | | | | Isomeric Ratio in Prefrontal Cortex (right) (left/right) | Isomeric Ratio in Brain Stem (left/right) |
|---|---|---|---|---|---|---|---|---|---|
| FA 16:1 | 253.2 | 311.2 | 3.53% | n-7 | | | | | |
| FA 17:1 | 267.3 | 325.3 | 0.65% | n-8 | n-6 | | | 1.7 ± 0.1 | 0.9 ± 0.1 |
| FA 18:2 | 279.3 | 337.3 | 81.87% | n-9 | n-6 | | | | |
| FA 18:1 | 281.3 | 339.3 | | n-9 | n-7 | | | 2.8 ± 0.06 | 2.4 ± 0.1 |
| FA 19:1 | 295.3 | 353.3 | 0.34% | n-10 | n-8 | | | 1.2 ± 0.04 | 0.8 ± 0.05 |
| FA 20:1 | 309.4 | 367.4 | 4.42% | n-9 | n-7 | | | 1.5 ± 0.03 | 1.6 ± 0.1 |
| FA 21:1 | 323.3 | 381.3 | 0.14% | n-12 | n-10 | n-9 | n-8 | 54.4%:24.2%:11.4%:10.0% | 25.2%:49.1%:10.0%:15.7% |
| FA 22:1 | 337.4 | 395.4 | 0.47% | n-13 | n-11 | n-9 | | 58.3%:18.6%:23.1% | 37.9%:20.0%:42.1% |
| FA 24:1 | 365.4 | 423.4 | 5.20% | n-13 | n-11 | | | 1.3 ± 0.2 | 1.5 ± 0.2 |
| FA 26:1 | 393.4 | 451.4 | 1.45% | n-17 | | | | | |

TABLE 8

| Molecular Name | m/z before & after P—B reaction Before | m/z before & after P—B reaction After | Distribution of Phospholipids in Brain | Isomers (n = 3) | | Isomeric Ratio in Prefrontal Cortex (right) (n-9/n-7) | Isomeric Ratio in Brain Stem (n-9/n-7) |
|---|---|---|---|---|---|---|---|
| LPA 18:1 | 435.3 | 493.3 | 1.75 ± 0.38 nmol/g | n-9 | n-7 | 5.4 ± 0.4 | 4.6 ± 0.3 |
| cLPA 18:1 | 417.2 | 475.2 | N/A | n-9 | n-7 | 2.2 ± 0.04 | 1.7 ± 0.02 |
| LPG 18:1 | 509.3 | 567.3 | 1.70 ± 0.06 pmol in serum | n-9 | n-7 | 2.1 ± 0.2 | 1.4 ± 0.04 |
| LPI 18:1 | 597.3 | 655.3 | 5.0 ± 2.2 nmol/g | n-9 | n-7 | 2.4 ± 0.1 | 2.3 ± 0.04 |
| LPE 18:1 | 480.3 | 538.3 | 0.026% ± 0.002% | n-9 | n-7 | 3.2 ± 0.3 | 1.8 ± 0.2 |
| PA 18:1-18:1 | 699.4 | 757.4 | 0.047% ± 0.002% | n-9 | n-7 | 4.7 ± 0.3 | 2.3 ± 0.06 |
| PA 18:2-18:0 | | | | n-9 | n-7 | | |
| PA 18:0-18:1 | 701.4 | 759.4 | 0.111% ± 0.004% | n-9 | n-7 | 6.8 ± 0.2 | 8.4 ± 0.3 |
| PA 16:0-18:1 | 673.4 | 731.4 | 0.126% ± 0.007% | n-9 | n-7 | 3.0 ± 0.1 | 2.6 ± 0.1 |
| PA 16:1-18:0 | | | | n-9 | | | |
| PS (18:1)-16:1 | 758.4 | 816.4 | 0.002% ± 0.000% | n-9 | n-7 | 3.7 ± 0.04 | 3.1 ± 0.1 |
| PS 18:1-(16:1) | | | | n-9 | | | |
| PS 18:1-16:0 | 760.3 | 818.3 | 0.065% ± 0.005% | n-9 | n-7 | 4.6 ± 0.01 | 3.9 ± 0.2 |
| PS 18:1-18:0 | 788.5 | 846.5 | 0.556% ± 0.018% | n-9 | n-7 | 11.5 ± 0.5 | 9.5 ± 0.8 |
| PS 18:1-18:1 | 786.5 | 844.5 | 0.144% ± 0.011% | n-9 | n-7 | 5.3 ± 0.2 | 3.1 ± 0.1 |
| PS 18:2-18:0 | | | | N/A | | | |
| PS (20:1)-18:1 | 814.5 | 872.5 | 0.030% ± 0.002% | n-9 | n-7 | 2.3 ± 0.2 | 2.5 ± 0.1 |
| PS 20:1-(18:1) | | | | n-9 | n-7 | 3.4 ± 0.1 | 1.7 ± 0.04 |
| PS 20:0-18:1 | 816.5 | 874.5 | N/A | n-9 | n-7 | 4.4 ± 0.2 | 3.0 ± 0.04 |
| PS 20:1-18:0 | | | | n-9 | n-7 | 5.3 ± 0.6 | 7.9 ± 0.2 |
| PI 18:0-18:1 | 863.3 | 921.3 | 0.125% ± 0.002% | n-9 | n-7 | 3.0 ± 0.3 | 1.9 ± 0.1 |
| PI 18:1-18:1 | 861.3 | 919.3 | 0.025% ± 0.001% | n-9 | n-7 | 2.2 ± 0.2 | 1.7 ± 0.04 |
| PG 18:0-18:1 | 775.5 | 833.5 | 0.0090% ± 0.0005% | n-9 | n-7 | 1.2 ± 0.03 | 1.7 ± 0.1 |
| PG 18:1-18:1 | 773.5 | 831.5 | 0.0152% ± 0.0004% | n-9 | n-7 | 3.1 ± 0.1 | 2.1 ± 0.2 |
| PG 18:2-18:0 | | | | N/A | | | |
| PG (18:1)-16:1 | 745.5 | 803.5 | 0.0013% ± 0.0001% | n-9 | n-7 | 2.7 ± 0.2 | 2.4 ± 0.2 |

TABLE 8-continued

| Molecular Name | m/z before & after P—B reaction | | Distribution of Phospholipids in Brain | Isomers (n = 3) | | Isomeric Ratio in Prefrontal Cortex (right) (n-9/n-7) | Isomeric Ratio in Brain Stem (n-9/n-7) |
|---|---|---|---|---|---|---|---|
| | Before | After | | | | | |
| PG 18:1-(16:1) | | | | n-7 | | | |
| PG 18:2-16:0 | | | | N/A | | | |
| PE 18:0-18:1 | 744.5 | 802.5 | 0.405% ± 0.011% | n-9 | n-7 | 3.4 ± 0.01 | 3.2 ± 0.01 |
| PE 18:1-18:1 | 742.5 | 800.5 | 0.248% ± 0.008% | n-9 | n-7 | 4.8 ± 0.1 | 2.9 ± 0.1 |
| PE 18:2-18:0 | | | | N/A | | | |

Figure 35A:
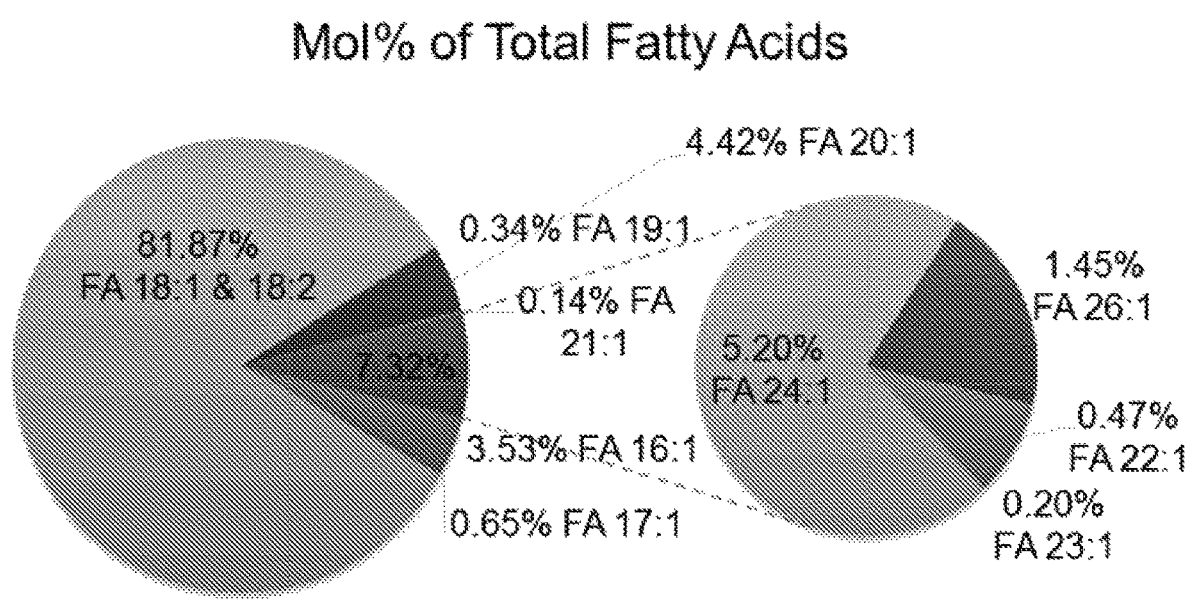
FIGS. 35A-C show dynamic range of lipids analyzed.
Figure 35B:
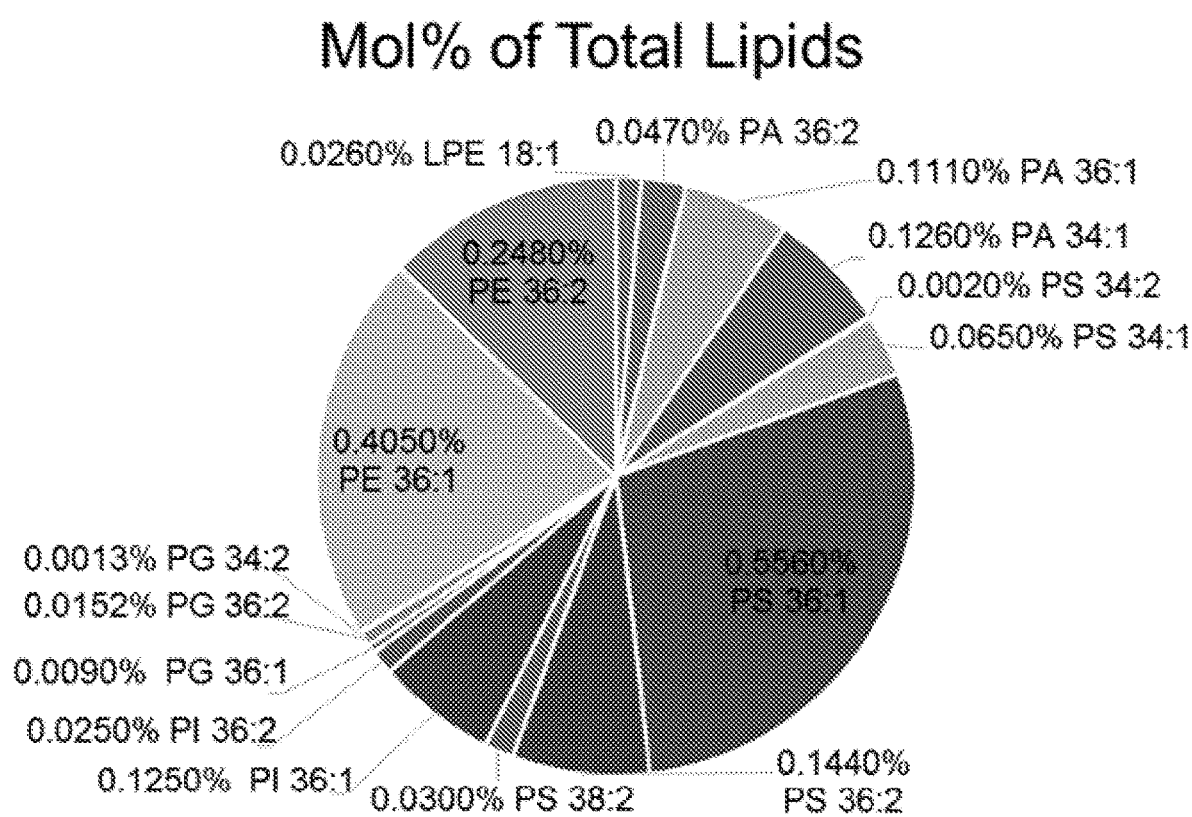
Figure 35C:
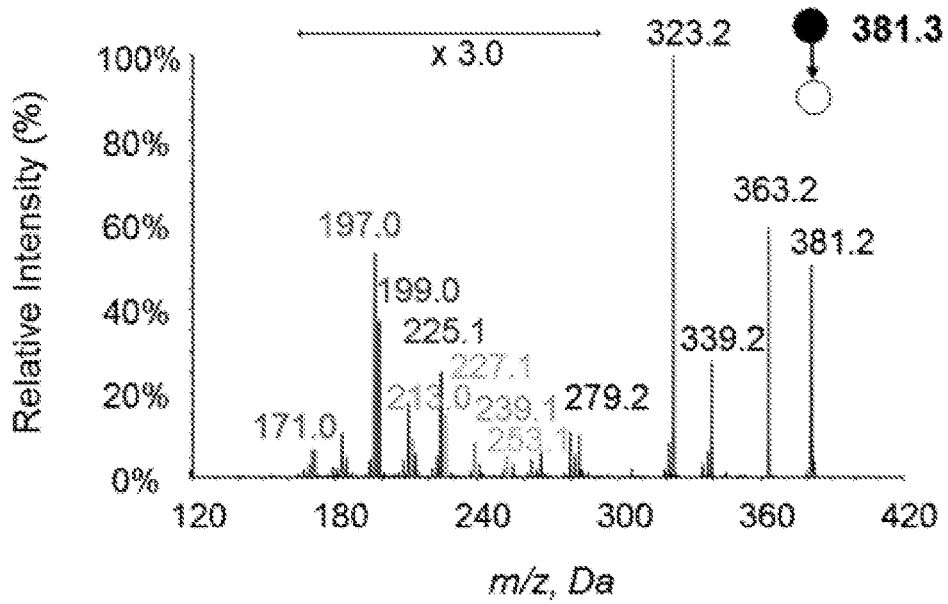
Figure 35D:
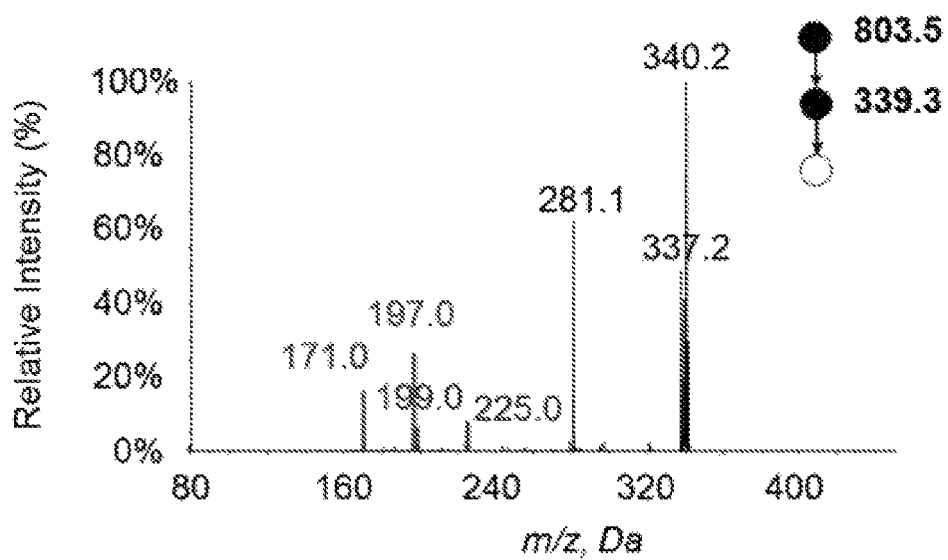
FIG. 35D shows MS3 CID spectra of PG 34:2 at m/z 339.3 in rat brain for determination of double bond positions.
Figure 36:
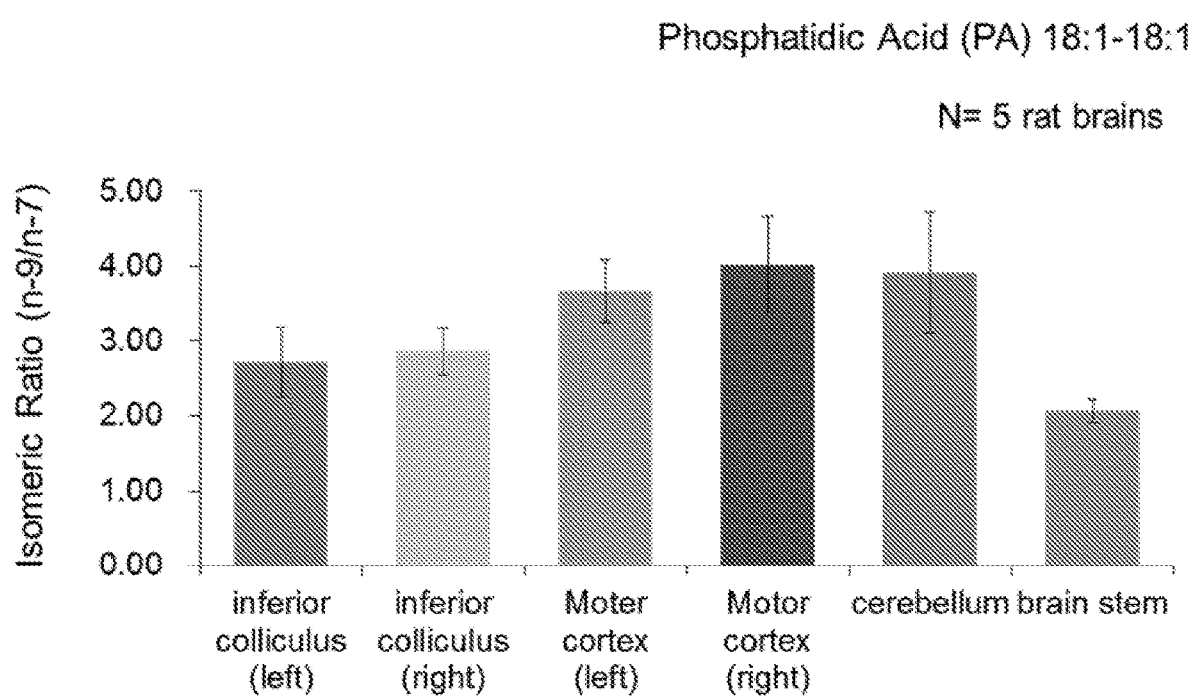
FIG. 36 shows isomeric ratios (±SD, N=5) of PA 18:1-18:1 (n-9 to n-7) in six regions of five rat brains, including inferior colliculus (left and right), moter cortex (left and right), cerebellum, and brain stem.
Figure 37A:
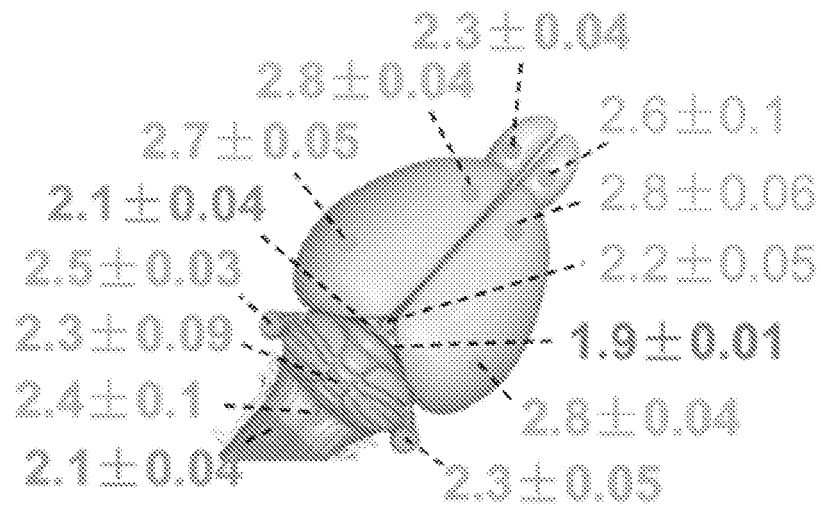
FIGS. 37A-D show 2D isomeric ratio (±SD, N=3) images of lipids in rat brain and kidney by reactive extraction spray mass spectrometry in negative ion mode. 2D isomeric ratio images of FA 18:1 (n-9 to n-7) distributed in (FIG. 37A) intact rat brains and (FIG. 37B) kidneys. 2D isomeric ratio (±SD, n=3) images of (FIG. 37C) LPA 18:1 (n-9 to n-7) and (FIG. 37D) PA 18:1-18:1 (n-9 to n-7) distributed in an intact rat brain.
Figure 37B:
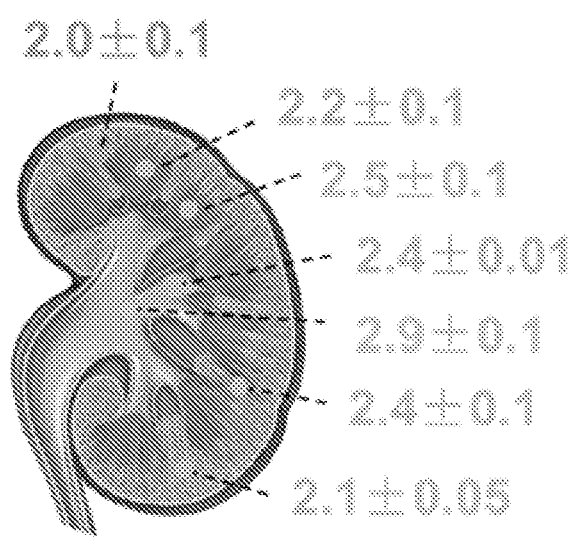
Figure 37C:
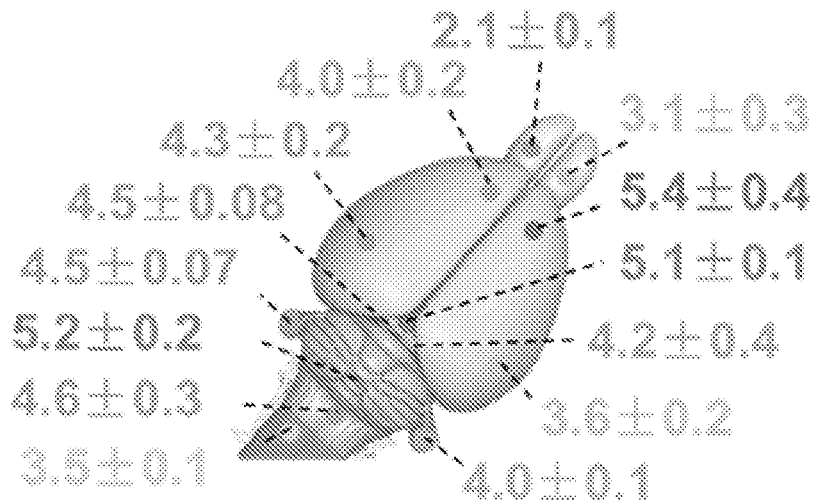
Figure 37D:
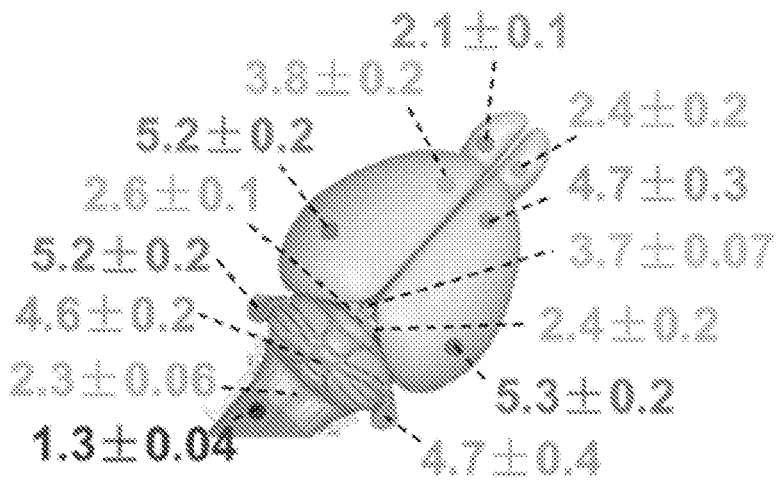

In addition, unsaturated lipids in trace level can also be analyzed with good signal-to-noise ratios. The lowest abundance of lipids, as 0.14% of total fatty acids for FA 21:1 and 0.0013% of total lipids for phosphatidylglycerol (PG) 34:2, have been achieved in direct analysis of rat brain (FIGS. 35A-D). FIGS. 35C-D showed typical CID spectra of FA 21:1 and PG 34:2 for determining double bonds after P-B reaction. Four possible positions (n-8, n-9, n-10, and n-12) of FA 21:1 and two possible positions (n-7 and n-9) were found according to fingerprint peaks.

Figure 38A:
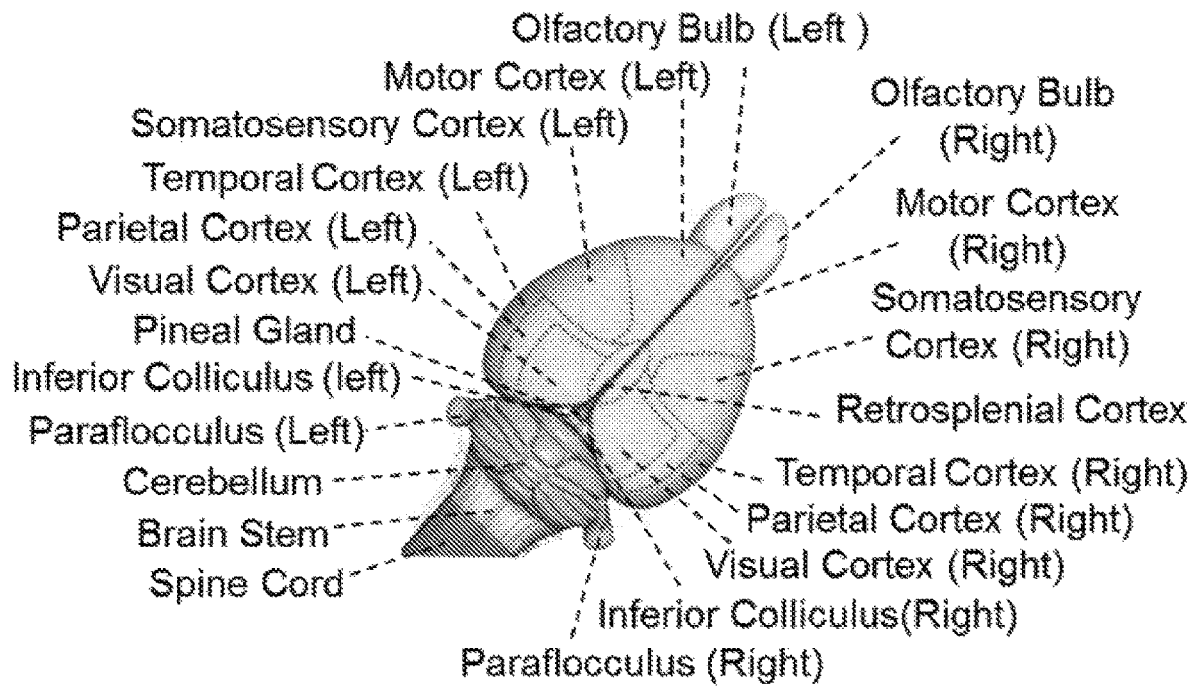
FIGS. 38A-D show two-dimensional isomeric ratio image of unsaturated lipid in rat brain by reactive extraction spray mass spectrometry in negative ion mode. Schematic representation of functional regions of (FIG. 38A) rat brain in dorsal aspect and (FIG. 38B) rat kidney section.
Figure 38B:
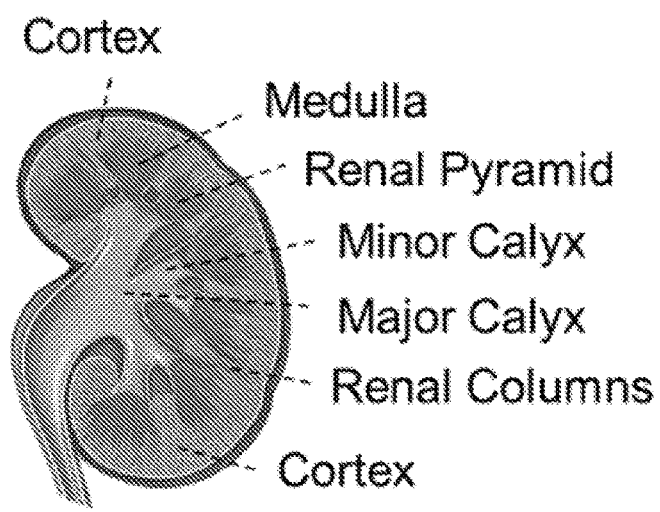
Figure 38C:
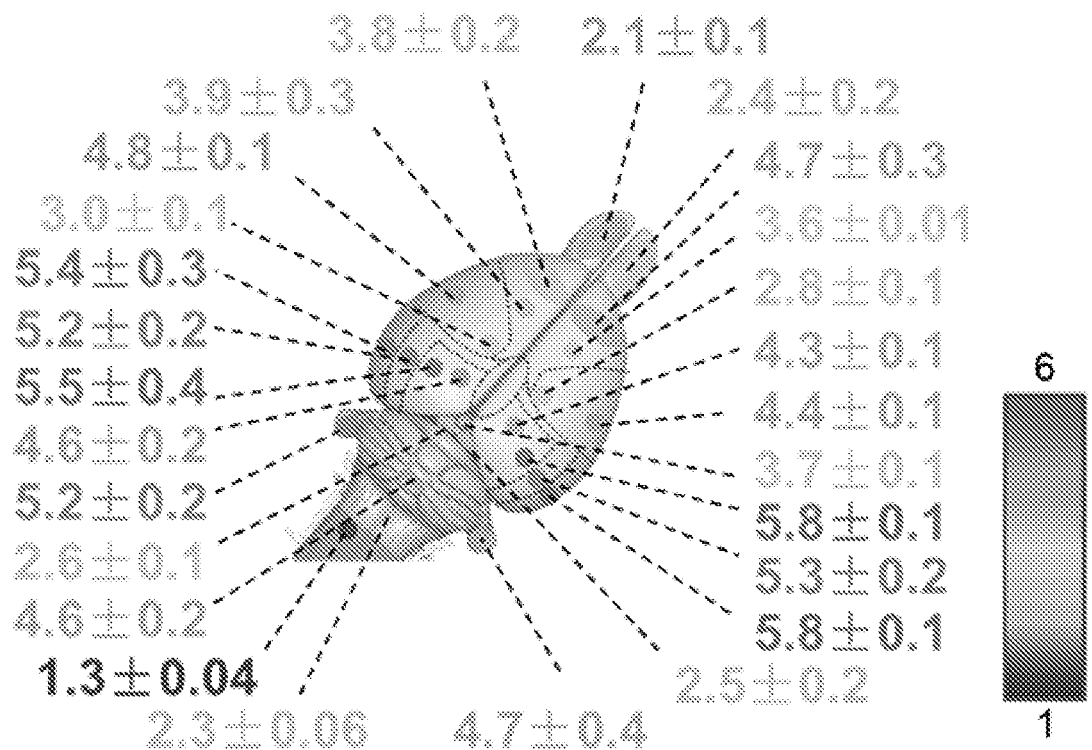
Figure 38D:
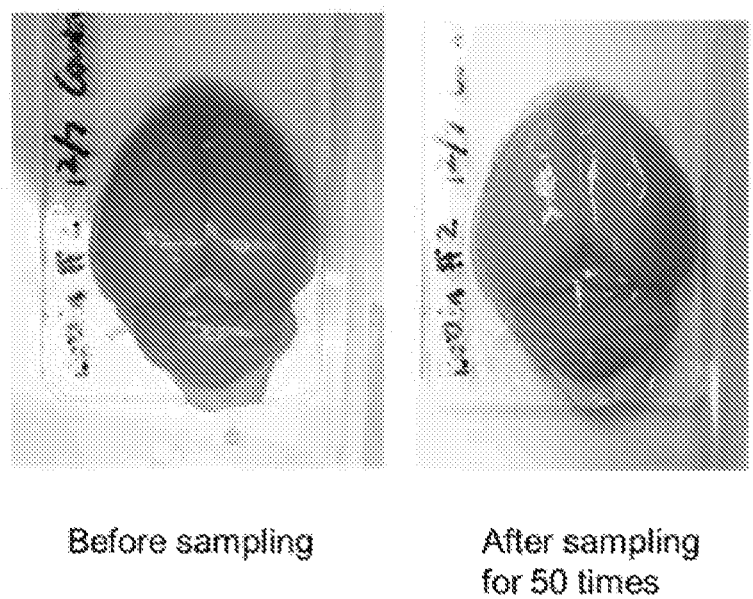
Figure 39A:
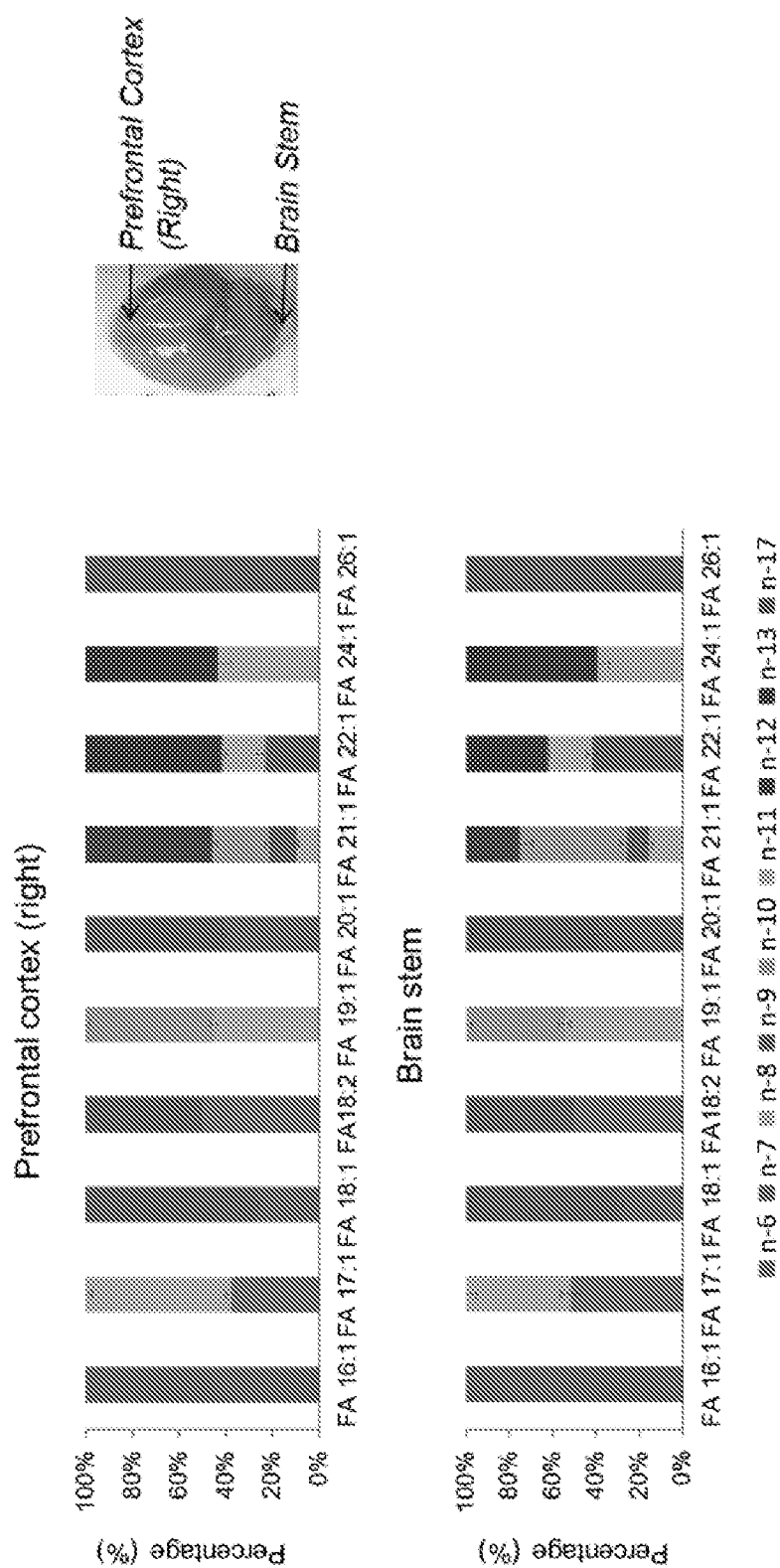
FIGS. 39A-D show unsaturation of fatty acids and phospholipids in prefrontal cortex and brain stem of rat brain.
Figure 39B:
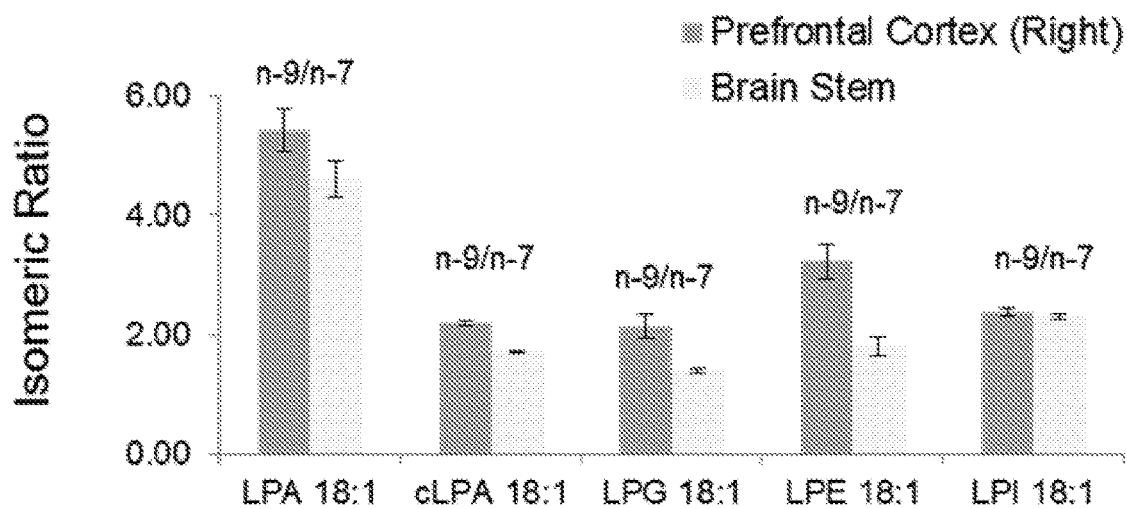
Figure 39C:
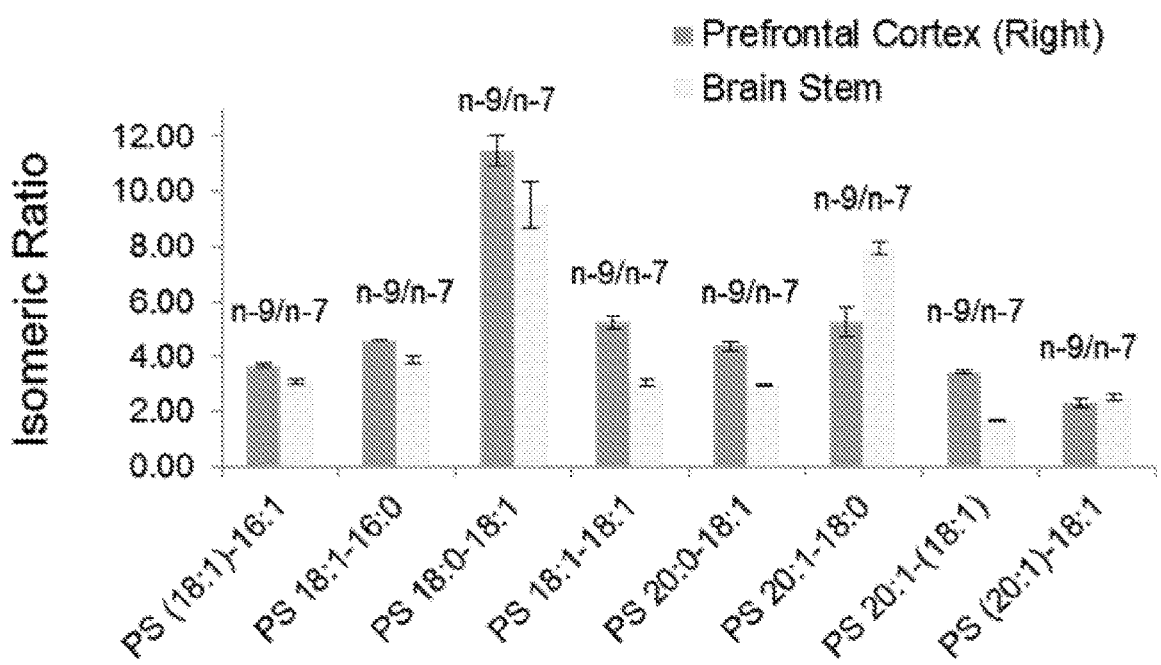
Figure 39D:
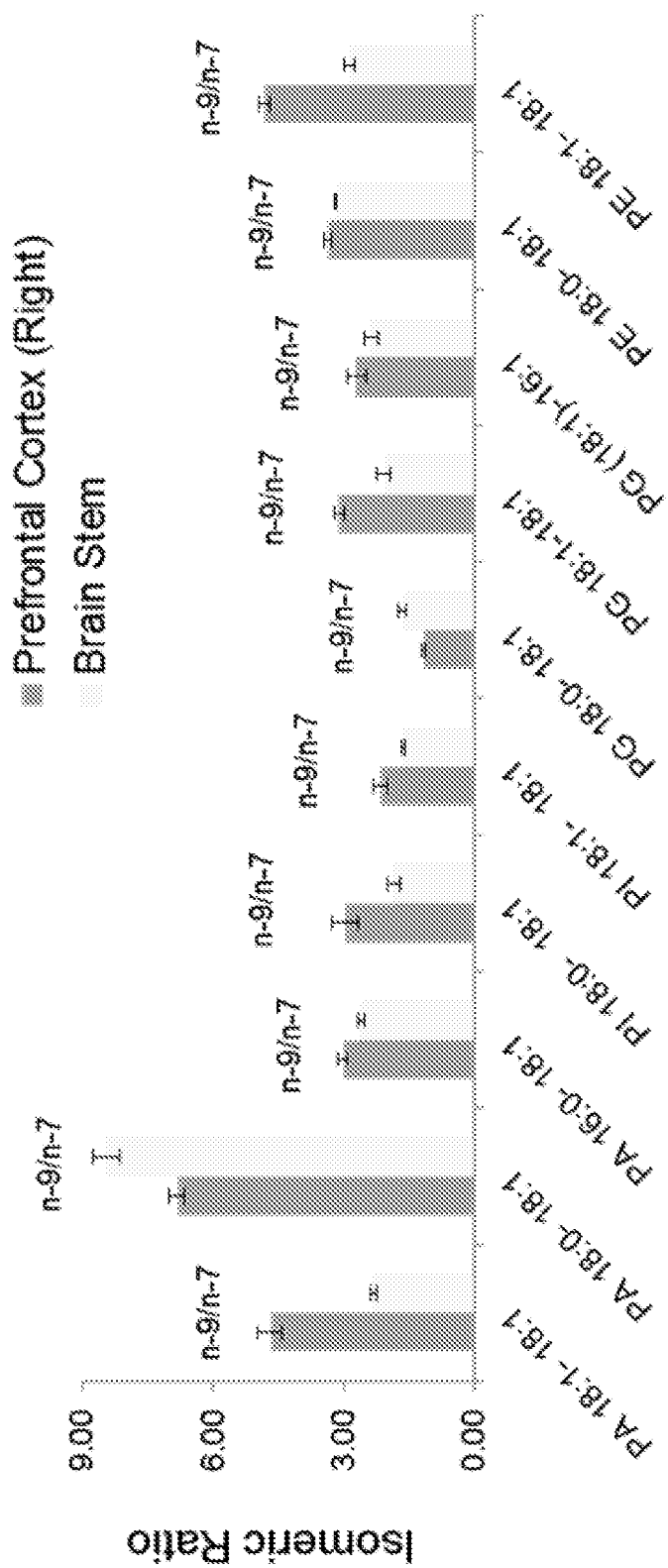
Figure 40:
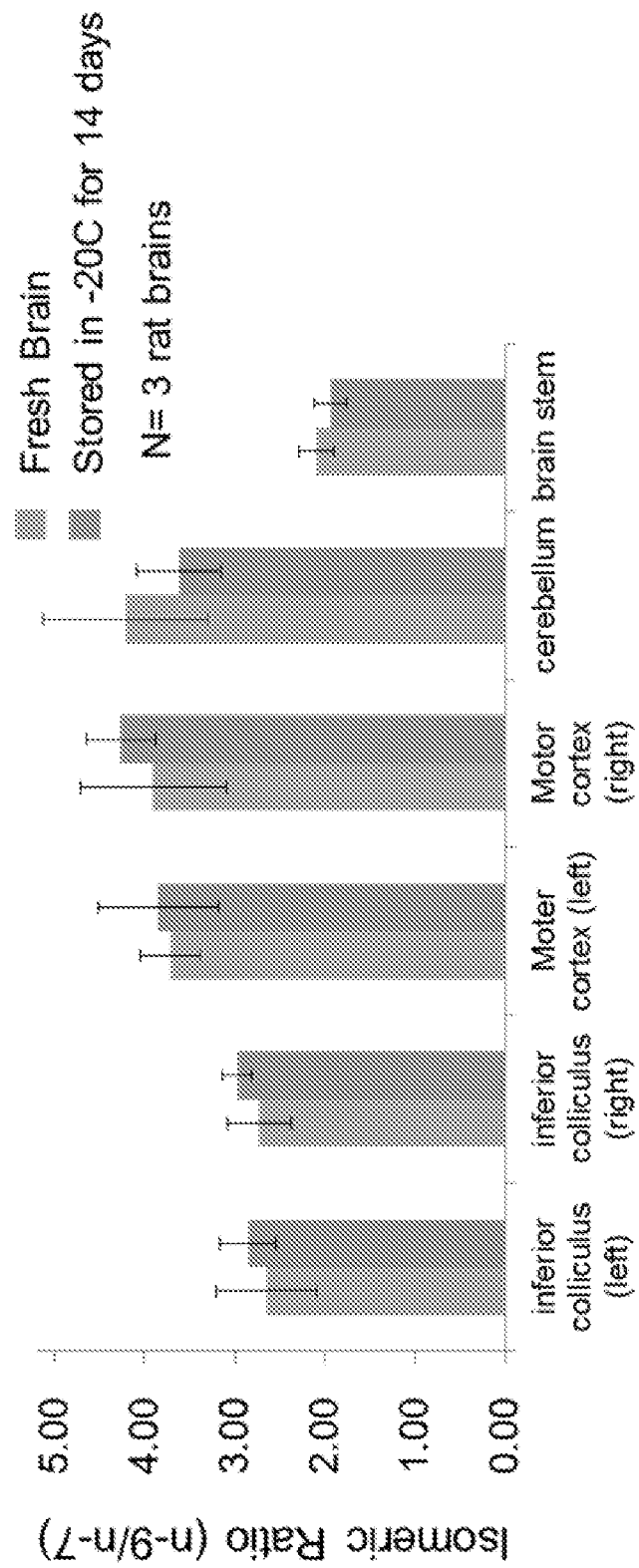
FIG. 40 shows impact of frozen and thaw on unsaturation of lipids. Isomeric ratios of PA 18:1-18:1 in six anatomy regions (including inferior colliculus left and right, moter cortex left and right, cerebellum and brain stem) of fresh rat brains and thawed brains frozen in –20° C. for 14 days.

In addition to high sensitivity, isomeric ratios of unsaturated lipids have also been first mapped for rat brain and kidney, benefiting from noteworthy advantages of small sampling area (0.04 cm$^2$) and low sample consumption (~10 μg). To perform the 2D imaging, an intact rat brain or a dissected kidney was positioned on a piece of graph paper in a resolution of 500 μm. A sampling probe was then inserted into the tissue with a precise coordinate position in a depth of ~2 mm. Each region was sampled at 1-3 locations with 3 duplicates at each location to obtain a representative isomeric ratio. Phosphatic acid (PA) 18:1-18:1, lysophosphatic acid (LPA) 18:1 and FA 18:1 were selected as target molecules due to their well-known messenger functions and their close relationship in molecular synthesis coordinated by glycerol-3-phosphate acyltransferase or lysophospatic acyltransferase. For rat brain imaging, the above three lipids in 14 selected anatomical regions, including spinal cord, brain stem, cerebellum, paraflocculus (left and right), inferior colliculus (left and right), pineal gland, parietal cortex (left and right), moor cortex (left and right), and olfactory (left and right), were symmetrically identified and quantitatively mapped (FIGS. 36 and 37A-D). A more comprehensive map of PA 18:1-18:1 were provided with isomeric ratios in 26 regions of rat brain in FIG. 38C. Profiting from small sample consumption, the brain was kept in good condition after it was sampled for 50 times (FIG. 38D). Interestingly, significant differences in isomeric ratios of LPA 18:1 and PA 18:1-18:1 were observed in different regions of the rat brain, while the isomeric ratio of FA 18:1 was relatively stable in both rat brain and kidney under investigation. A good consistency in isomeric ratio distribution of PA 18:1-18:1 was demonstrated as their RSDs were all below 21% when comparing among six selected anatomy regions of five brains in a similar condition but from different batches. In addition, distinctive isomeric ratios of 31 lipids were also observed to be different in various degrees between the right prefrontal cortex and brain stem of a same rat brain (FIGS. 39A-D and Tables 7-8). This result may indicate that the selection of isomeric FA 18:1 for synthesis of PA 18:1-18:1 and LPA 18:1 is not a random process and is closely related to regions of a tissue. Although the pathway is not clear, the present platform brings a big potential to reveal it and also provides a supportive platform to understand the effect of unsaturation of lipids on the function of a tissue. In addition, the effect of sample storage on unsaturation of lipids were also investigated by comparing isomeric ratios of PA 18:1-18:1 between three fresh rat brains and another three frozen in −20° C. for 14 days (FIG. 40). Six regions of rat brains were selected including inferior colliculus (left and right), moter cortex (left and right), cerebellum and brain stem. Stable and consistent unsaturation of PA 18:1-18:1 were demonstrated when the sample were frozen in −20° C. in a short time.

In conclusion, the combination of extraction spray with P-B reaction enabled direct identification of double bond locations within unsaturated FA chains for a more comprehensive characterization of unsaturated lipids in tissues. Sample pretreatment in multiple steps, which regularly require complex setups in the laboratory, can be simplified into a nanospray tip in only one step. Multiple types of unsaturated lipids in a broad dynamic range of concentrations can be profiled in good reproducibility of isomeric ratios with RSD<10%. More importantly, isomeric ratios of unsaturated lipids were first profiled in two dimensions benefiting from noteworthy advantages of small sampling area and low sample consumption. The reactive extraction spray provides a powerful imaging platform to study the impacts of unsaturated lipids on biological function and the disease state of the tissue.

Example 13: Direct Tissue Analysis and Characterization of Unsaturated Lipids Using a Miniature Mass Spectrometer Lipidomics has emerged as a potential field for biomarker discovery for human diseases. Direct tissue analysis as they can provide molecular information could be capable in clinical diagnosis. A desktop Mini 12 designed for point-of-care applications was used in this Example with direct sampling ionization for profiling fatty acids and lipids from biological tissues. Photochemical derivatization using Paternó-Büchi (PB) reactions was also implemented for quantifying the relative abundances of the unsaturated isomers of the lipids.

Figure 41:
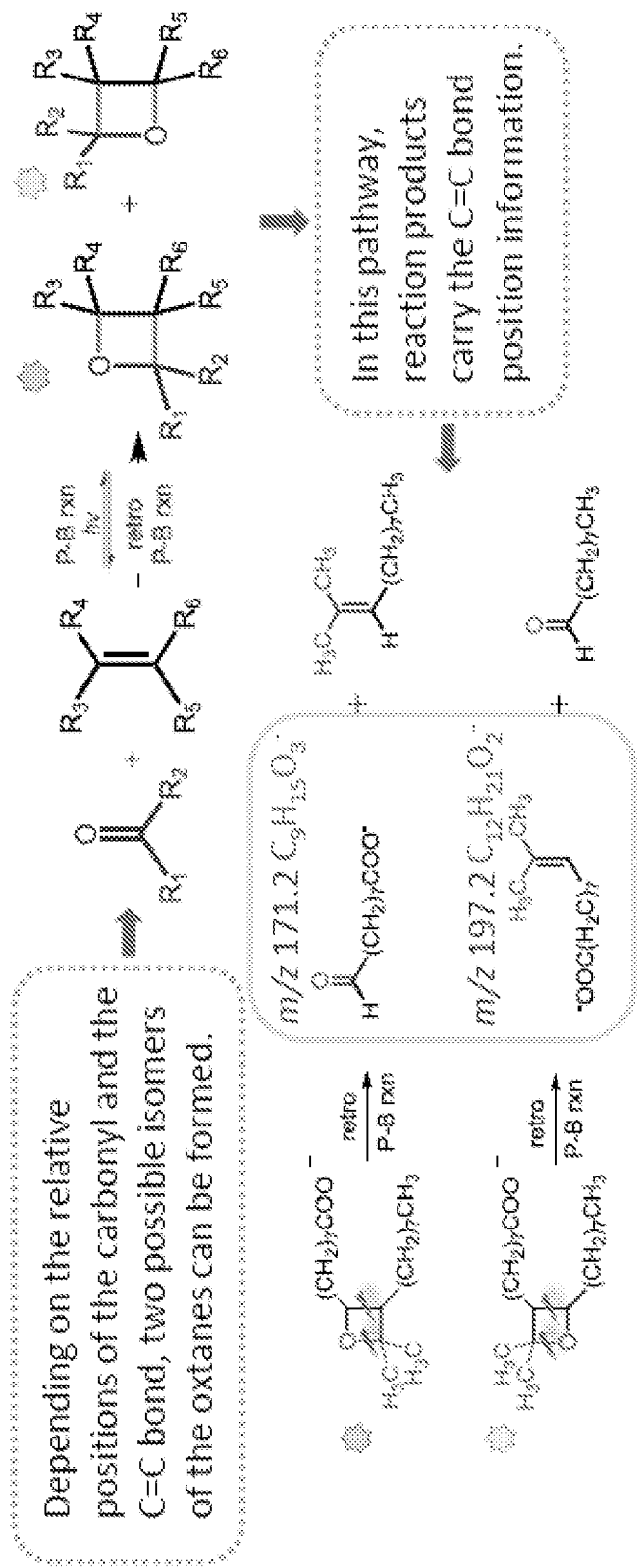
FIG. 41 shows a P-B reaction is a photochemical reaction.
Figure 42:
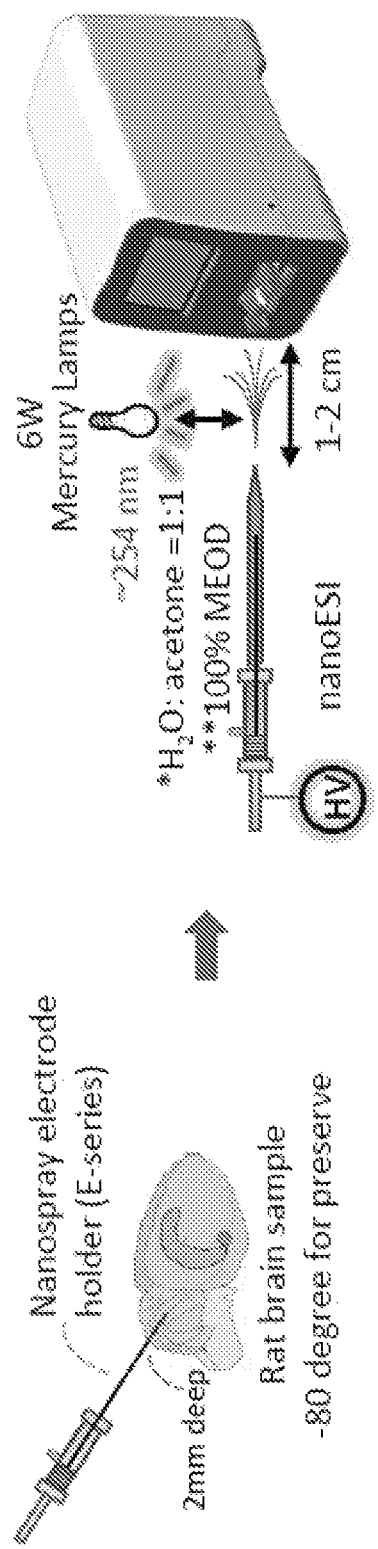
FIG. 42 shows an exemplary set-up used for tissue analysis using a miniature mass spectrometer.

P-B reaction is a photochemical reaction that forms four-membered oxetane rings from a carbonyl and an alkene. It has been widely used for many natural organic products (FIG. 41). FIG. 42 shows the set-up used for tissue analysis in this Example. Direct rat tissue analysis used Extraction Spray method. NanoESI spray solvent is 100% methanol. *$H_2O$:acetone=1:1 as the P-B reaction spray solvent.

Figures 43A, 43B:
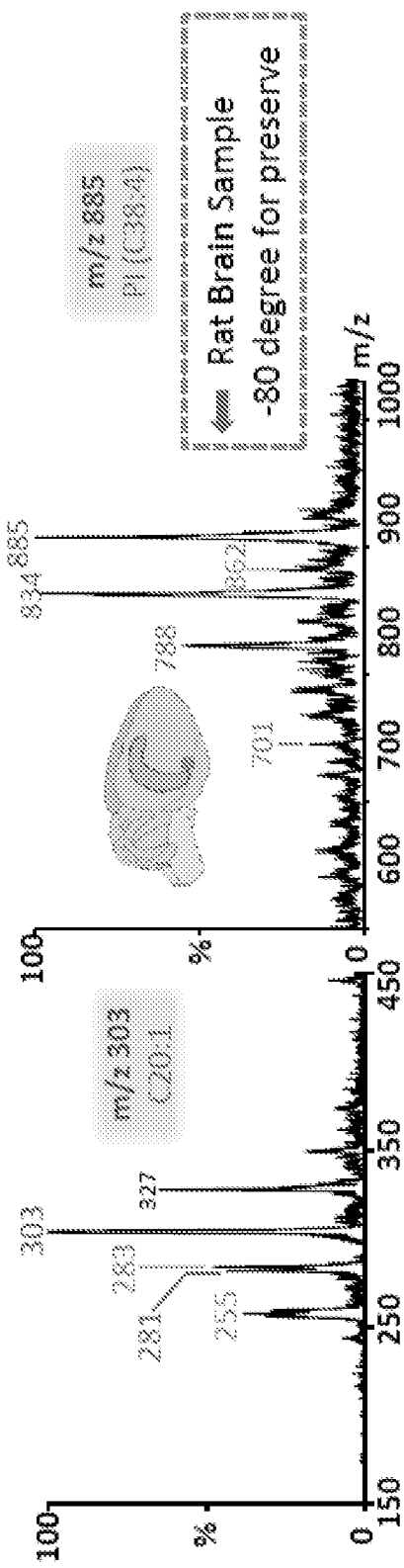
FIGS. 43A-F show lipid profiling results.
Figures 43C, 43D:
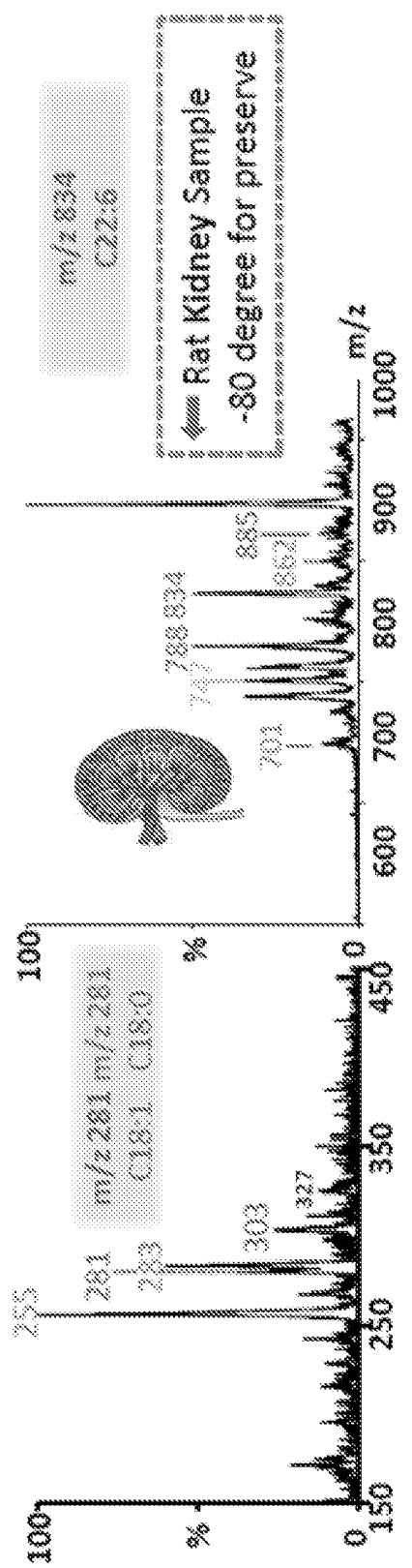
Figures 43E, 43F:
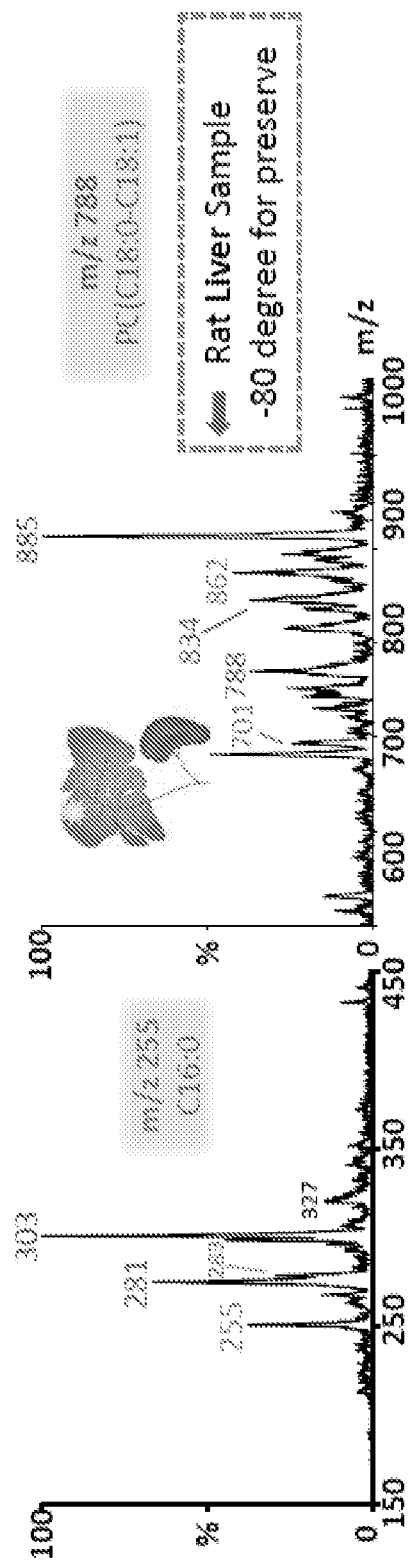
Figure 44:
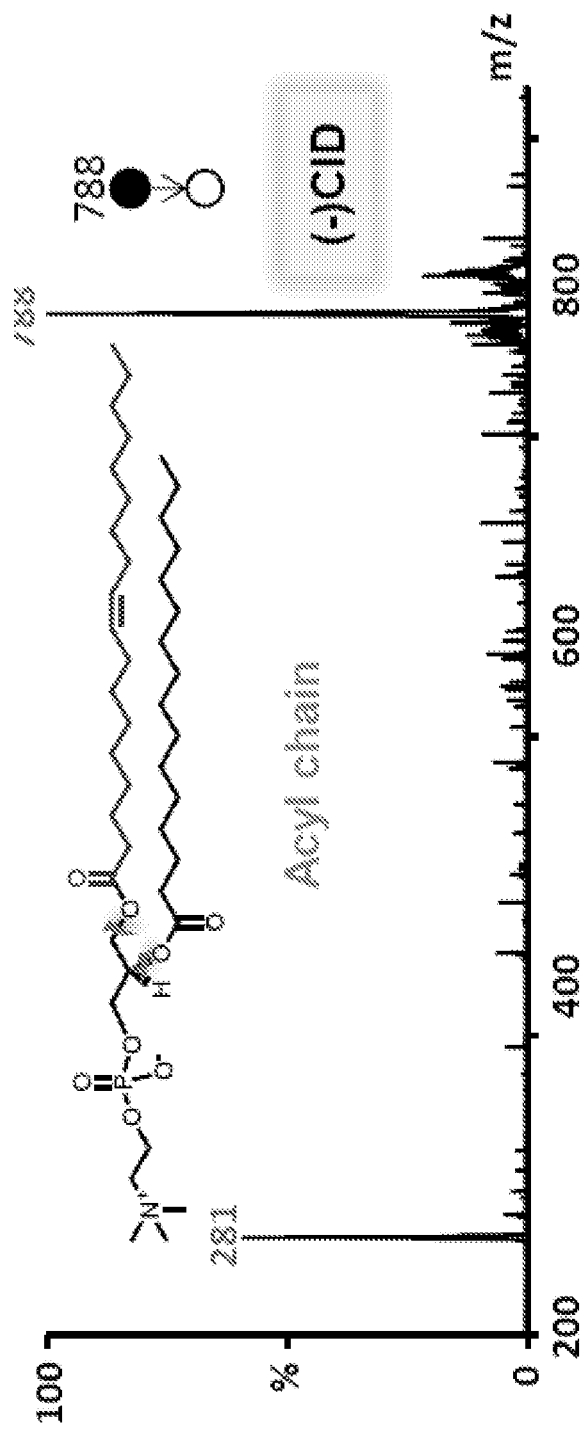
FIG. 44 shows CID of phosphocholine.
Figure 45:
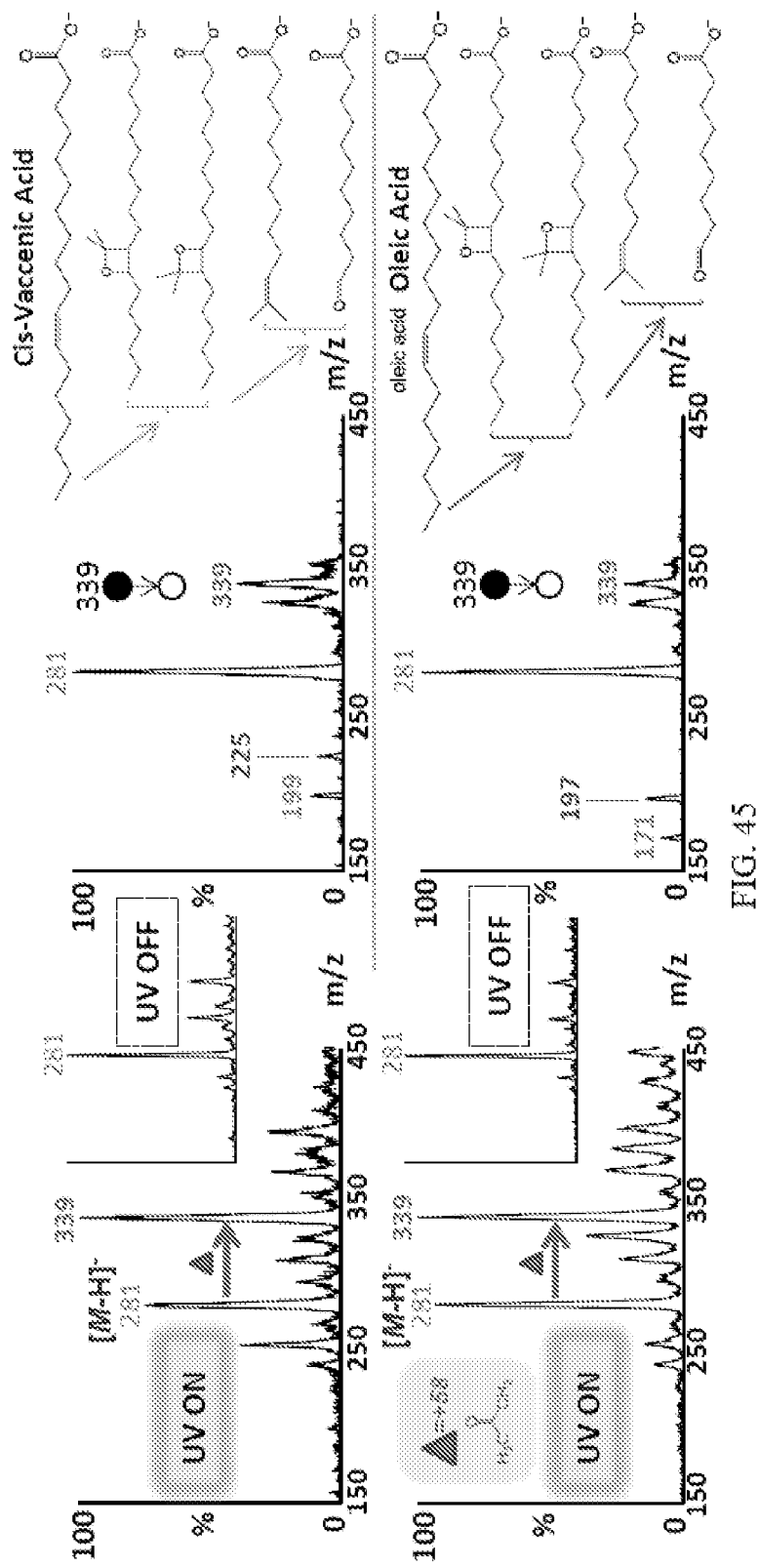
FIG. 45 shows an online P-B reaction using standard compounds.
Figure 46:
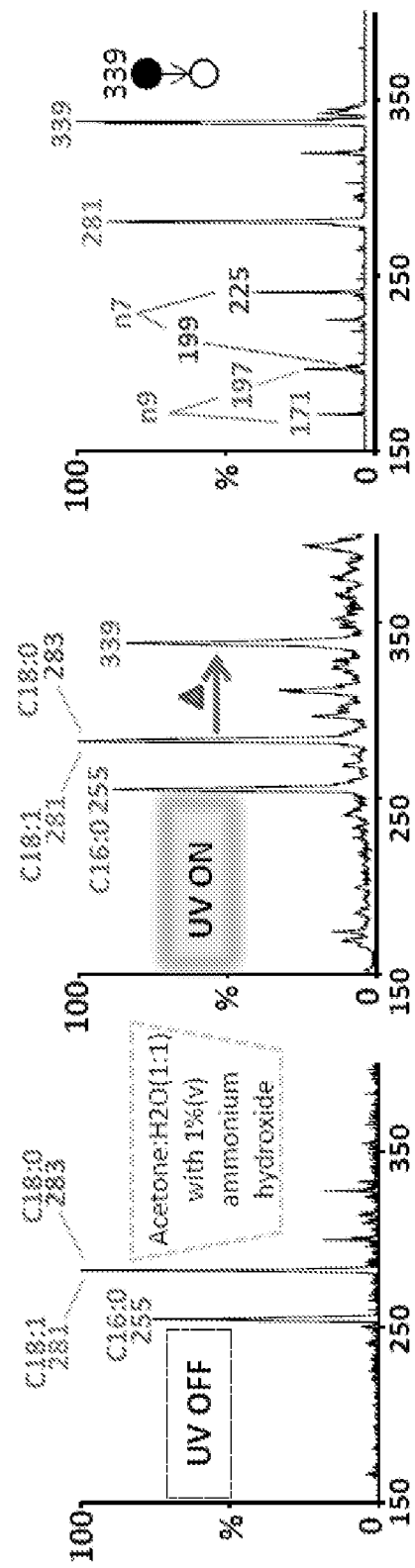
FIG. 46 shows an online P-B reaction using a rat brain sample.

FIG. 45 shows an online P-B reaction using standard compounds. FIG. 46 shows an online P-B reaction using a rat brain sample. Lipid profiling results are shown in FIGS. 43A-E. FIGS. 43A, 43C, and 43E show a lipid profile of Fatty Acid in three rat organ samples. FIG. 43B, FIG. 43D, and FIG. 43E show a lipid profile for phospholipids. Both of them were used nanoESI (−) mode. FIG. 44 shows CID of phosphocholine. The data show that lipid profiling can assist in identifying potential biomarkers for disease. The extraction spray method can find out a lipid profiling without sample preparation and vacuum environment.

In human body, 40% of total lipids are unsaturated. P-B reaction combined with mini MS system can confidently and efficiently determine the locations of C=C double bonds in fatty acid of Rat brain tissue.

Example 14: Mass Spectrometry Method with C=C Location Specificity for Qualitative and Quantitative Lipid Analysis This Example shows development of a method for determining carbon-carbon double bond (C=C) locations in lipids and its use for qualitative and quantitative lipidomics.

Lipids are a group of structurally diverse and complex compounds, which can be categorized into 8 major classes and many subclasses (terminology according to LIPID MAPS). Due to the structural diversity and large dynamic range of the lipids in cell, tissue, or organism, analysis of a complete lipid composition (lipidome) from biological samples has been traditionally difficult. The advances in MS, especially the development of soft ionization techniques (hyphenation with separations) and the tandem mass spectrometry (MS/MS), make MS-based lipid analysis the primary tool for lipidomic researches. Among many notable analytical figures of merits, high specificity in molecular structure is the distinct feature of the MS-based approach for lipid analysis. For instance, several levels of structural information of a lipid can be readily achieved from MS/MS including lipid class, bond type, fatty acyl/alkyl composition, and even some times the positions of the fatty acyl/alkyl chains. However, the information of the positions of C=C bonds and their configuration (cis vs. trans), is rarely obtained by MS/MS on most MS platforms and therefore it is either not reported or assumed in the majority of scientific reports on lipid analysis. Unsaturated lipids constitute a significant proportion of total lipids in biosystems and their physical properties, chemical reactivity, and bio-transformation are closely related to a variety of physiological and physiochemical functions. As lipid C=C bond position isomers do exist and are produced through various biosynthetic pathways, the lack of capability in determining C=C location or distinguishing and quantifying unsaturated lipid isomers significantly hampers our understandings on the biochemical and biological consequences that are associated with the difference in C=C locations.

This Example illustrates development of an MS platform that offers C=C location specificity as well as the capability of quantifying unsaturated lipid isomers for a broad range of lipid species in biological samples. The innovation of the technique resides on on-line coupling of a photochemical (Paternó-Büchi, PB) reaction, which has a highly specific reactivity toward C=C of a lipid, with ESI-MS/MS (ESI: electrospray ionization). The PB reaction product, when subjected to MS/MS produces C=C location specific fragment ions, which can be used for both structural identification and quantitation. In order to develop a robust and widely applicable platform for lipid analysis, a series of issues is addressed, which include the design of robust photo-reactors for on-line PB-ESI, development of a comprehensive MS/MS procedure for structural analysis of lipids, data analysis tool for automated identification and quantitation, and a comprehensive database of unsaturated lipid for different tissue types from small animals. This Example shows: development and optimization of reaction/ionization source for on-line coupling of Paternó-Büchi (PB) reaction with ESI-MS/MS; development of MS/MS methods for structural determination and quantitation of unsaturated lipids for a variety of lipid classes; development of PB-ESI-MS/MS workflows for shotgun and LC-MS/MS lipidomic analysis; and validation of the analysis platform for lipidomic analysis using tissue samples of different rat organs.

The outcome from the work herein is the establishment of a robust and widely applicable platform for qualitative and quantitative shotgun as well as LC-based lipidomic analysis. Data collected herein contributes to a first database of unsaturated lipids with the information of C=C location, composition and quantity of unsaturated lipid isoforms in rat tissues of different organs. This new lipid analysis capabilities advances research in many fields in biological science, including but not limited to lipid molecular biology, functional lipidomics, metabolomics, and biomarker discovery.

Background

Lipids as one important class of biomolecules serve diverse functions such as the earlier recognized roles of energy storage and cell membrane structural components and later established roles as regulatory and cell-cell signaling molecules. These diverse functions of lipids result from their diverse structures. About 40,000 (as of Apr. 2, 2015) unique lipid structures have been documented by LIPID MAPS database and they are not uniformly distributed within cells (i.e. membrane) and among organelles. One of the major challenges for lipid research is to understand how cells maintain and regulate lipid homeostasis. With the advances in biology and bio-analytical tools, characterization of a complete cellular lipid composition (lipidome) as well as lipid-lipid and lipid-protein interactions is now approachable in systems level. Mass spectrometry-based analysis for cellular lipids has been established as the primary tool in lipidomics for providing global lipid identification and quantitation. The thus obtained lipid profiles are increasingly used to study disease-bound alterations in overall lipid composition. Lipidomics is still at its relatively early stage and the development of high sensitivity, specificity, and throughput lipid analysis tools will greatly enhance studies on functional consequences of lipid diversity and lipid homeostasis.

MS-based lipidomic approaches: The high sensitivity and molecular specificity of MS as well as its hyphenation with separation techniques such as liquid chromatography (LC), have made it the most frequently used (80%) technique in lipid analysis. Two MS approaches are almost equally used for global lipid analysis: shotgun and LC-MS. For the shotgun approach, lipid extract is directly infused to a mass spectrometer typically using electrospray ionization (ESI) as the ionization source. Alternatively, the lipid extract can be separated by LC before MS analysis. The selection between the two approaches is dependent on the purpose of analysis. Due to the fast speed, the shotgun approach is attractive for disease diagnostics via comparison of global lipid profiles from normal/diseased samples. For accurate lipid quantitation, or identification of low-abundance lipid species from very complex samples, the hyphenated approach allows both high-fidelity structure identification and accurate quantitation Like ESI, matrix-assisted laser desorption ionization (MALDI) is another efficient method which can be used for lipid ionization. In recent years, MALDI-MS has received increasing research interests due to its imaging capability.

Lipid identification and quantitation by MS/MS: Simple mass measurement by a high resolution mass spectrometer provides elemental composition, however would not be able to provide detailed structural information due to the coexistence of many possible molecular isobaric and isomeric species. Tandem mass spectrometry (MS/MS) is the key technique used in lipid identification and quantitation. An MS/MS experiment contains at least three key elements: generation and isolation of the precursor ions, gas-phase reactions that dissociate the precursor ions, and the mass analysis of the product ions. Cumulative efforts from the past three decades have led to compressive development MS/MS methods for a broad range of lipid classes. The majority of these MS/MS methods have been established on MS instruments equipped with low energy collision-induced dissociation (CID). Tandem-in-space instruments, such as triple-quadrupole MS or highbred MS, can perform linked MS/MS experiments (neutral loss scan, precursor ion scan, product ion scan), which allow quick classification of lipids from complex mixtures as well as sensitive detection (reaction monitoring) and quantitation. Tandem-in-time mass spectrometers such as quadruple ion trap MS allows higher stages of MS/MS experiments (i.e. $MS^3$ or $MS^4$) and different types activation of to achieve detailed structural characterization.

Challenges in structural specific analysis: Lipids are structurally diverse molecules that can be divided into 8 classes and many subclasses. The major lipid classes detected in mammalian cells include fatty acid (FA), glycerolipid (GL), glycerolphospholipid (GP), spingolipid (SP), and sterol lipids (ST). GPs can be further divided into glycerolphosphocholine (PC), glycerophosphoethanolamine (PE), glycerophosphoserine (PS), glycerophosphoglycerol (PG), glycerophosphoinositol (PI), and glycerophosphate (PA). According to LIPID MAPS, there are five different levels of structural characterization listed from lowest to highest: Level 1. lipid class/species identification; Level 2. bond type/hydroxyl group identification; Level 3. fatty acyl/alkyl; Level 4. fatty acyl/alkyl position; and Level 5. defined chemical structure including stereochemistry and carbon-carbon double bond (C═C) positions/geometry. Currently, lipid structural analysis can be routinely achieved at level 3 to characterize fatty acyl or akyl compositions in a lipid. With careful data interpretation, level 4 information with regard to the location of acyl/alkyl chains can be drawn. For instance, a phosphatidylcholine (PC) with a molecular mass of 759.6 g/mol can be identified as PC 16:0/18:1 from the observation of characteristic m/z 184 (phosphocholine) fragment ion via MS/MS CID in positive ion mode and the detection of fatty acyl anions from MS/MS CID of PC acetate anion adduct ([PC+$CH_3COO$]⁻): m/z 257 (16:0, saturated acyl chain with 16 carbon atoms) and m/z 281 (18:1, 18 carbons and one C═C). Furthermore, the 16:0 and 18:1 acyl chains can be assigned to sn-1 and sn-2 positions, respectively, according to the empirical rule that sn-2 is typically produced at a higher intensity than the sn-1 acyl anion. However, level 5 identification such as C═C location and configuration is difficult to obtain by low energy CID equipped on most commercial MS platforms. This difficulty is fundamentally rooted in that significantly higher activation energies are required to break a C—C or C═C bond so that no fragment ions are created around C═C, leading no clue to for C═C location determination.

Existing methods for C═C determination: To address this issue, two distinct approaches have been taken in developing MS-based methods for C═C determination. One approach involves C═C selective reactions prior to MS analysis, such as ozonolysis, alkylthiolation, methoxymercuration, epoxidation, and etc. These reactions transform the C═C functional group into other groups which can be more readily analyzed by MS or low energy CID. Among these, off-line or on-line ozonolysis has the most impact due to its capability of coupling with HPLC, ESI, and applicability to a broader classes of lipids. However, inconclusive results are often reached for C═C locations when complex lipid mixtures are analyzed, since different lipid species can lead to the same ozonolysis products. Alternative to C═C derivatization before MS, several tandem-MS based methods have been developed for C═C determination, including charge remote fragmentation of intact lipids using high energy CID (~keV), multiple stage MS/MS CID of di-lithiated lipid adduct ions, and ozone-induced dissociation (OzID). These methods have not been widely applied to lipidomic studies due to the requirement of either specialized MS instrumentation or ionization conditions.

On-Line Paternó-Büchi (PB) Reaction Coupled with ESI-MS/MS

A unique chemical property of C═C is its susceptibility to radical attack, which prompts investigation by radical-involved MS analysis. The Example herein focuses on the development of radical reactions targeting C═C of lipids in the interface region of ESI and MS. This approach has two attractive characters for ESI-based lipidomics. First, radical reactions are fast (diffusion rate limited) and can be readily coupled with either direct ESI infusion methods or be performed online after separation and before ESI-MS. Secondly, since reactions happen outside the mass spectrometer, they can be applied to any types of MS consisting of an ESI interface. Among the large amount of reported radical reactions toward C═C from organic chemistry, good reaction candidates for lipid analysis however should satisfy the following factors: 1. High specificity toward C═C; 2. Reasonable reaction yield; 3. No direct cleavage of C═C so that there is a detectable link between the intact lipids and reaction modified lipids for further structural analysis; Reactants having minimum disturbance on MS analysis of lipids (e.g. ionization efficiency, charging property).

Figure 47A:
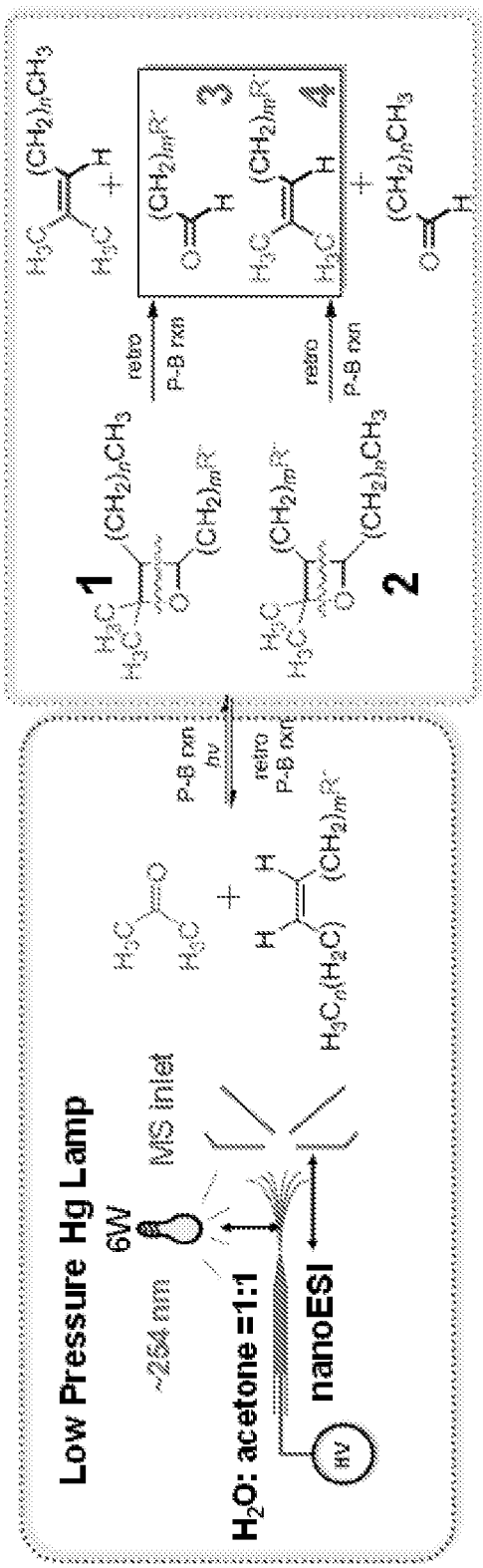
FIG. 47A shows a setup and principle of PB-MS/MS for C=C determination.
Figure 47B:
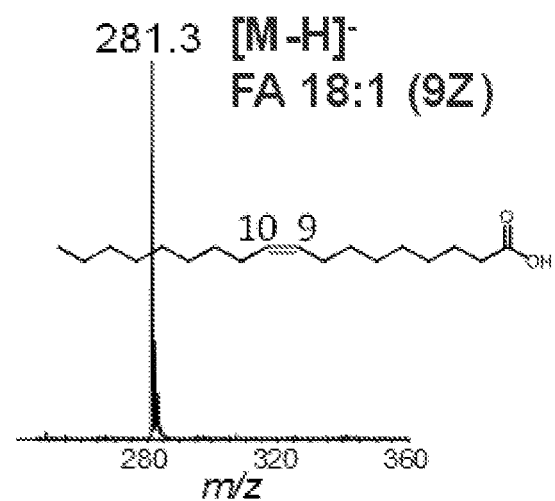
FIG. 47B shows NanoESI of FA 18:1 (9Z) at 10 µM in 1:1 acetone:H2O with 1% NH4OH added.
Figure 47C:
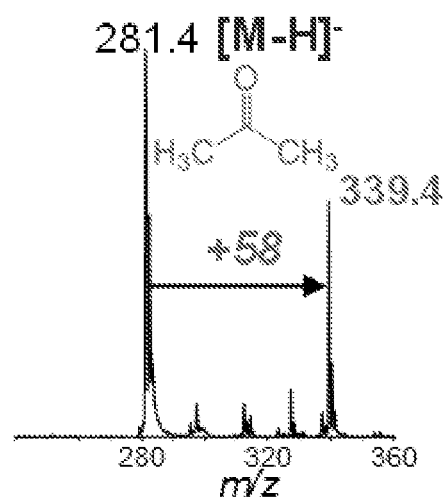

It is herein shown that the Paternó-Büchi (P-B) reaction, a classic [2+2] photochemical reaction, can be coupled with on-line ESI-MS/MS and provide fast and sensitive determination of C═C location from complex lipid extract. The reaction mechanism involves UV excitation of the carbonyl group within an aldehyde or ketone to its excited state, which subsequently adds on to the C═C and forms a diradical. Ring-closure of the diradical leads to the formation of four-membered oxetane ring. Depending on the relative positions of the carbonyl and the C═C bond, two oxtane position isomers (structures 1 and 2) are formed, as shown in FIG. 47A. The PB reaction product is stable and can be mass isolated and subjected to CID. In preliminary studies, lipid analyte was dissolved in 1:1 water/acetone, where acetone functions as the PB reaction reagent. The reaction was simply executed in the nanoESI source region and irradiated by a UV lamp emission wavelength centered at 254 nm (setup shown in the inset of FIG. 47A). FIG. 47C demonstrates PB reaction of oleic acid, FA 18:1 (9Z) (10 μM) analyzed on-line in negative mode nanoESI. Abundant PB reaction product (m/z 339) having mass increase of 58 Da (acetone's mass) relative to the intact FA anion (m/z 281) was observed only when UV irradiation was turned on (compared to FIG. 47B when UV is off). $MS^2$ CID of the PB reaction product (m/z 339.3) promoted retro-PB reactions (FIG. 47A). The product ion at m/z 281 resulted from the retro-PB pathway by losing a neutral acetone (58 Da). Product ions at m/z 171 (with a structure of 3) and 197 (with a structure of 4) resulted from retro-PB pathway of oxetane ring rupturing at the original C=O and C=C sites within P-B reaction products 1 and 2, respectively. Fragment ions having structures of 3 and 4 are always mass separated by 26 Da due to the difference of adding "0" vs. "$C_3H_6$" at the original C=C site. These ions are thus termed as C=C diagnostic ions. Their complementary fragments are not detected due to their existence as neutrals.

Figure 47D:
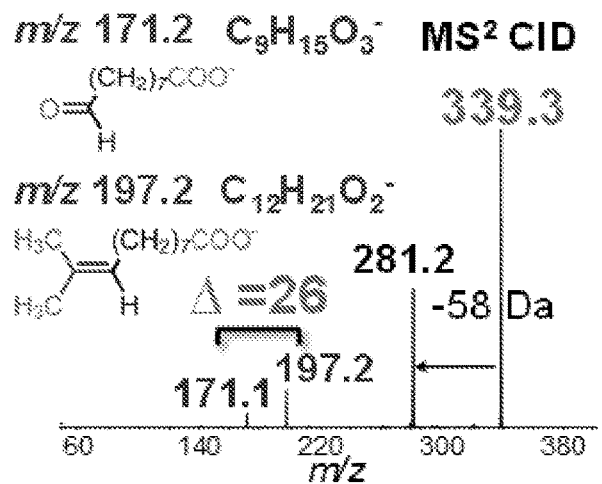
FIG. 47D shows $MS^2$ CID of PB product (m/z 339.3) leads the formation of C=C diagnostic ions at m/z 171 and 197.
Figure 48A:
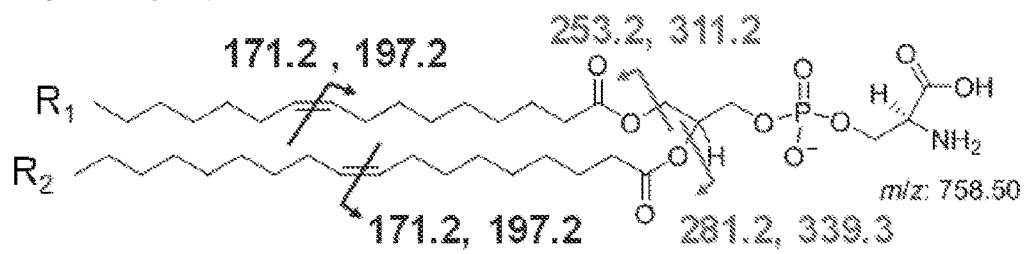
FIGS. 48A-D shows elucidation of double bond positions in PS 16:1(9Z)/18:1(9Z).
Figure 48B:
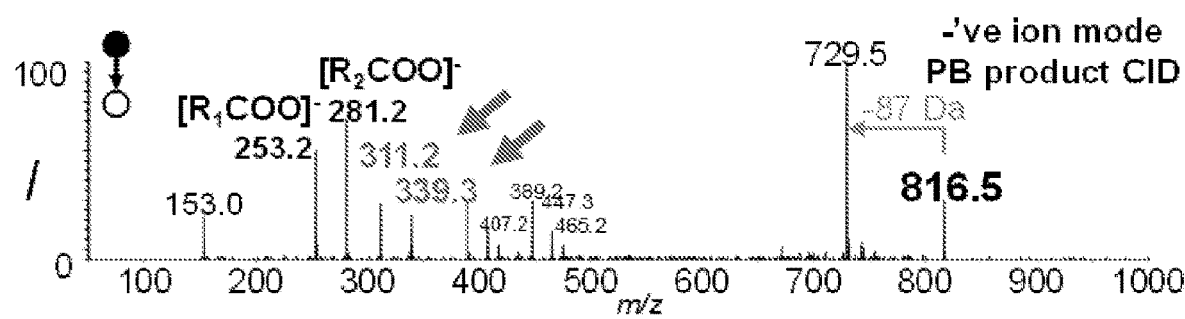
Figure 48C:
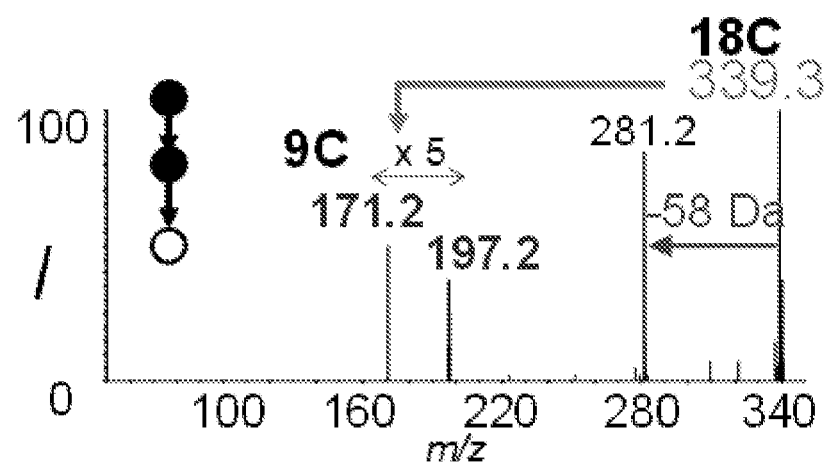
Figure 48D:
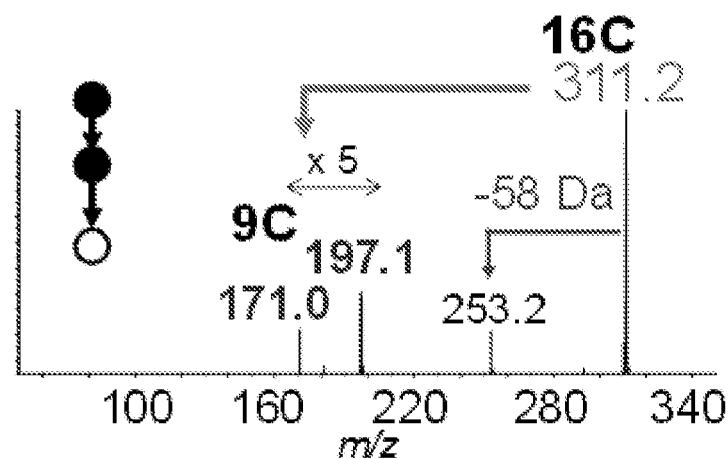

This PB-MS/MS strategy can also be applied to other classes of lipids such as GP as well as pinpointing individual C=C positions in different acyl chains. FIG. 48A shows an example of C=C determination from PS 16:1(9Z)/18:1(9Z) (m/z 758.6 of the deprotonated ions, structure shown in FIG. 47D). $MS^2$ CID of its PB reaction product at m/z 816.5 led to an 87 Da neutral loss (NL) specific to PS and ions corresponding to the two free acyl chains, $R_1COO^-$ and $R2COO^-$ at m/z 253.2 and 281.2. PB reaction modified two acyl chains were also observed, at m/z 311.2 and 339.3, respectively. $MS^3$ CID data of these PB reaction product ions are shown in FIGS. 48C and 48D. Based on the generic chemical formula of C=C diagnostic ion 3, $C_nH_{(2n-3)}O_3^-$, the double bond can be confidently determined to located between C9 and C10 for each acyl chain. Putting the acyl chain composition information together, it is straightforward to conclude that one acyl chain is C16 with a double bond between C9 and C10, and the other one is a C18 chain containing a double bond between C9 and C10. The above procedure also forms the basis for structural characterization of unsaturated lipids.

From studies on model FAs and GPs, obvious differences in reactivity or selectivity were not observed for acetone based PB reactions toward different classes of lipids or specific C=C locations or configurations. This character indicates that it has the potential to serve as a more general method for unsaturated lipid analysis. The other attractive features include its compatibility with "shotgun" lipidomics, simple and low cost experimental setup for reactions (UV lamp setup costs less than 200 dollars), no need to modify mass spectrometer, easy-to-interpret mass spectra, and inexpensive reprivatizing reagents. These aspects make PB reaction ideal candidate for further development as a robust and widely applicable tool for both shotgun and LC-MS based lipidomic approaches.

The lack of C=C location specific lipidomics tools leads to the inability in distinguishing and quantifying C=C isomers, thus causing missing links in studying unsaturated lipids, which contributes to a significant fraction of total lipids. The biological consequences that are associated with the difference in C=C locations are thus not understood and underappreciated in investigating altered lipidomes under pathological conditions. The methods herein provide an MS platform which offers C=C location specificity as well as the capability of quantifying unsaturated lipid isomers for a broad range of lipid species in biological samples. As discussed herein, online PB reaction coupled with ESI-MS/MS meets these needs. The data collected herein will also contribute to a first database of unsaturated lipids with the information of C=C location, composition and quantity of unsaturated lipid isoforms in different tissues of small animals. This new lipid analysis capabilities advances research in many fields in biological science, including but not limited to lipid molecular biology, functional lipidomics, metabolomics, and biomarker discovery.

Optimization of Reaction/Ionization Source for On-Line Coupling of Paternó-Büchi (PB) Reaction with ESI-MS/MS A PB reaction is traditionally conducted in bulk solution in organic synthesis. Given relatively low quantum yield of this type of reaction (0.01-0.1), high concentrations of reactants (in mM to M), long reaction times (in 3-24 hours UV irradiation), and non-polar solvents are employed in organic synthesis. These conditions are not directly compatible with typical lipid analysis conditions when using ESI-MS/MS nor the requirement of on-line coupling of the PB reaction with MS/MS. To address those issues, reactors and methods were developed that allow conducting on-line photochemical reactions and in situ reaction monitoring and product analysis by MS. The work allowed for characterizing factors that are important for achieving good PB reaction yield and sensitive lipid detection by MS.

Flow photochemistry in organic synthesis is a developing field where traditional batch reactors are replaced with continuously flowing solutions primarily in <1 mm i.d. capillaries (microreactor). Continuous solution flow in combination with microreactor dimensions enables precise control of solution UV exposure which results in enhanced product yields by reducing unwanted side products from over or uneven UV exposure. There are a few examples for conducting continuous flow photochemical reactions, such as intermolecular photo-addition and OH reaction with protein for "foot-printing". Based on these successful examples, PB reactions were developed in the source region of the nanoESI emitter and in the analyte solution transfer line for ESI (separate reaction and ESI).

Figure 49A:
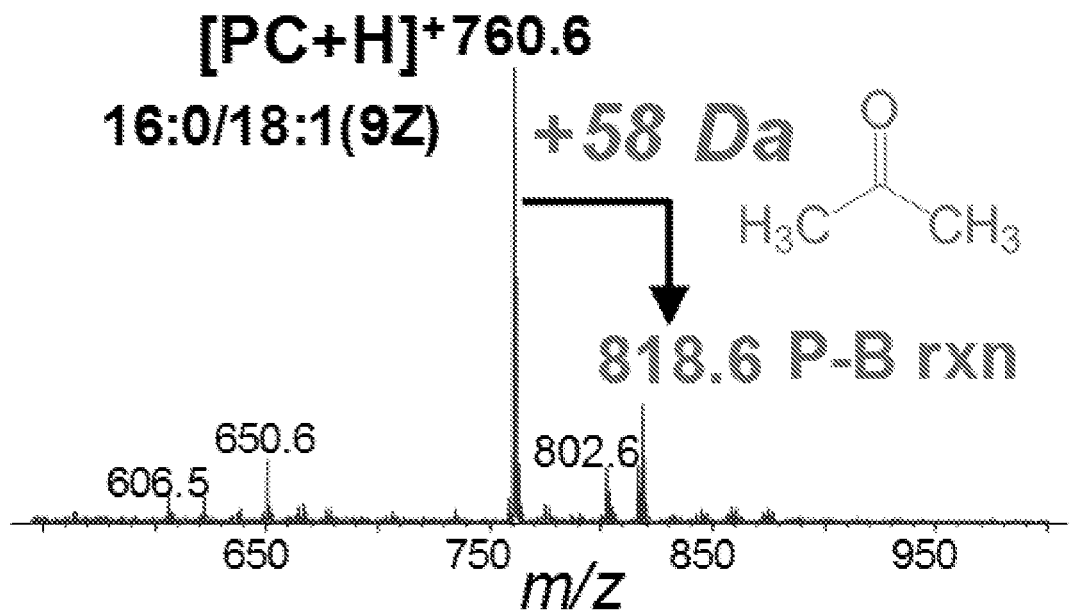
FIG. 49A shows a PB reaction MS spectrum of PC 16:0/18:1 prepared at 5 µM in 70:30 acetone/H2O.
Figure 49B:
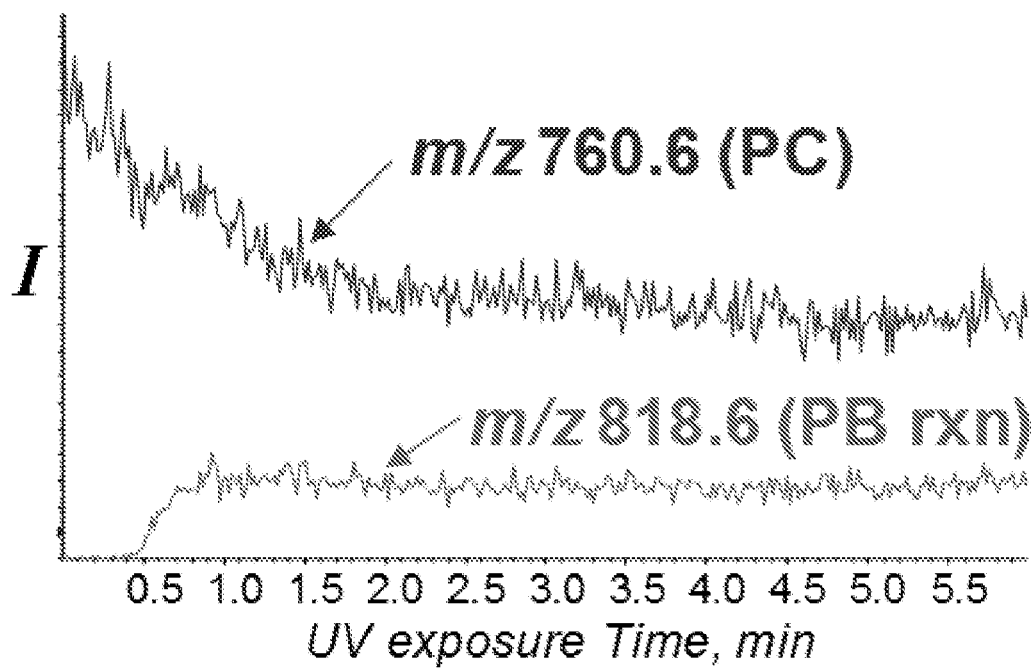
FIG. 49B shows XIC of intact PC ions (m/z 760.6) and its PB product (m/z 818.6).

A static nanoESI source without additional solvent pumping was initially used for PB reactions (FIG. 47A). PB reaction of a variety of lipid species have been implemented, however typically with low to medium reaction yields (10-40%). For instance, the PB reaction product of PC 16:0/8:1(9Z) (5 µM) is produced at m/z 818.6 with ~10% reaction yield (FIG. 49A). Moreover, a 30 s to 1 min lead-time is typically needed for the reaction to reach a steady-state as shown from the extracted ion chronogram (XIC) shown in FIG. 49B. This phenomenon clearly suggests that a significant portion of reaction happens within the nanoESI tip other than in the plume region of the nanoESI, which only permits~ms reaction time (droplet lifetime in the source region). The nanoESI spray emitter is made of borosilicate glass, which is partially transparent to 250 nm at the thin wall area at the tip head (estimated to be less than 100 µm). Given the low flow rate of the static nanoESI (10 nL/min) the change of the concentrations of molecules due to spray is negligible at the spray tip (~1 µL volume). Therefore, the reaction inside the nanoESI tip leads to an accumulation of P-B reaction product as a function of time and finally reaches a steady state in the first couple of minutes. This hypothesis is proven to be correct from an experiment that a much higher flow rate was used (~1-5 µL/min) and no obvious P-B reaction product was observed.

Since PB reaction happens mostly in the nanoESI tip, quartz glass or fused silica can be used as the nanoESI tip material to improve the reaction yield. These two types of material are transparent around 200 nm wavelength and therefore allow more photons to pass through. The impact of UV lamp position relative to the nanoESI tip and to the MS interface on reaction yield was also investigated. In preliminary studies, a low-pressure mercury (LP-Hg) lamp with 5 W, primary emission around 254 nm wavelength was used. Other types of UV lamps such as Xenon plasma flash-lamp which generates significant light intensity in the range of 200-300 nm, and LED UV lamps which allow the potential for miniaturization of the reaction region will be explored.

Figure 50A:
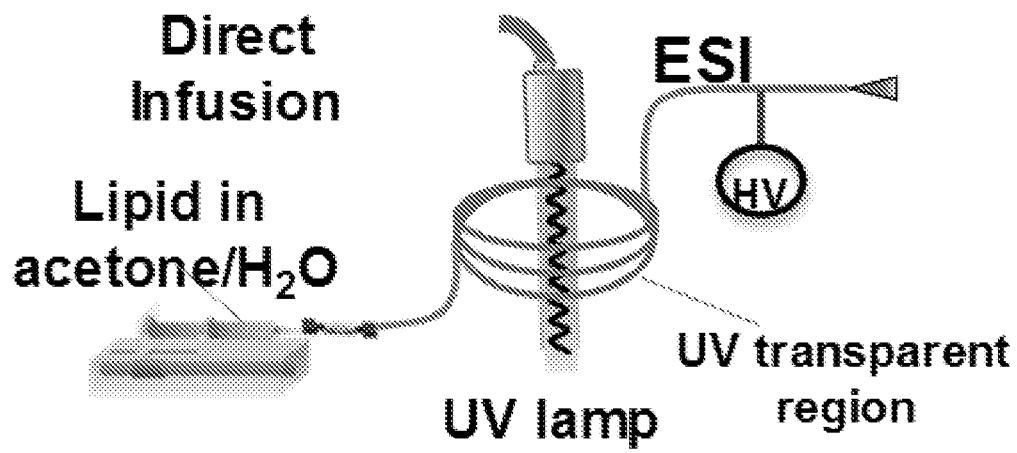
FIG. 50A shows a direct infusion setup for PB reaction.
Figure 50B:
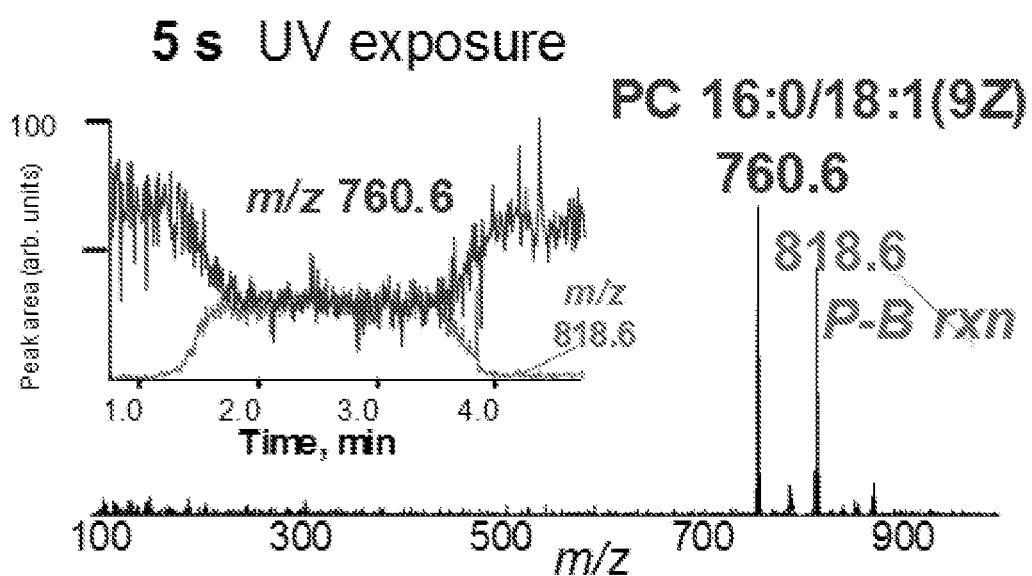
FIG. 50B shows PB reaction MS spectrum of 5 µM PC 16:0/18:1(9Z) (7:3 acetone: H2O with 1% acetic acid) at a flow rate 4.5 µL/min for 5 s UV exposure. Inset shows XID of intact PC and its PB product.
Figure 50C:
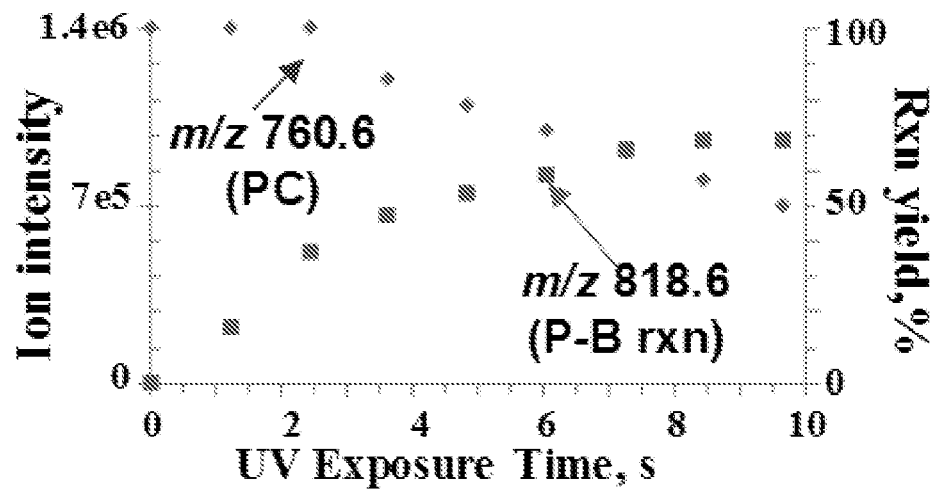
FIG. 50C shows Plots of intact PC and PB product as a function of UV exposure time.

For the purpose of making PB reaction compatible with infusion type ESI sources with a flow rate in the range of µL/min, it is more suitable to perform P-B reaction in the ESI transfer line. Fused silica capillary with UV transparent coating is chosen as the solution transfer line. For the reaction region, the capillary is coiled (3 cm in diameter) with the UV lamp placed in the center and 0.5 cm away from the capillary (FIG. 50A). For a solution flow rate of 4.5 µL/min, the 1 cm exposure corresponds to 1.1 s reaction time in the capillary. FIG. 50B shows the ESI MS spectrum of PC 16:0/18:1 (9Z) (5 µM in 7:3 acetone:$H_2O$, 1% acetic acid) after 5 s of UV exposure. The PB product (m/z 818.6) was formed at a yield of 45%, much higher than that was achieved from the nanoESI source (FIG. 47A). Moreover, PB reaction product signal was very stable during the UV on time as can be seen from XIC shown in the inset of FIG. 50B. This character is important to achieving good performance from MS/MS on PB products. This direct infusion setup allowed one to vary the UV exposure time through changing solution flow rate or the length of the capillary exposed to UV so that the kinetic information can be obtained. It has been found that PB reaction of PC 16:0/18:1 (9Z) could reach 68% yield within 10 s using 7:3 acetone:$H_2O$, 1% acetic acid as the solvent. Based on this promising result, it was planned to further optimize the configuration (lamp distance, lamp power) of the "direct infusion" setup for a range of ESI flow speeds (100 nL-50 µL) which has been commonly employed for ESI based lipid analysis.

Figure 50D:
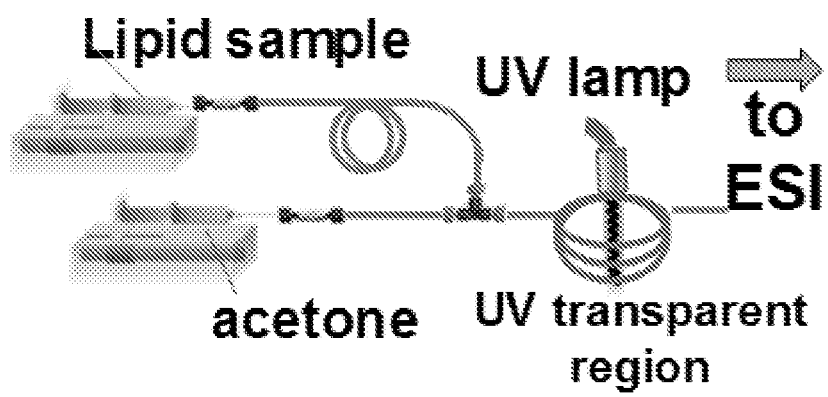
FIG. 50D shows flow injection setup for PB reaction. Lamp is placed 0.5 cm away from the capillary.

For the Direct Infusion setup, the P-B reaction reagent, i.e., acetone is used as a co-solvent for ESI, which is however not commonly employed as an elution solvent for normal phase or reversed phase HPLC separations. To overcome this limitation, the "flow injection concept" was used to Tee-in the PB reaction reagent through the sample transfer line to the ESI source, while the photochemical reaction region is located after the "T" junction. A schematic setup of the "flow injection" is shown in FIG. 50D. This device was tested using PC 16:0/18:1 (9Z). This lipid was dissolved in isopropanol/$H_2O$, 70%/30% which is a common solvent composition from normal phase LC separation, and was pumped to an ESI source at a flow speed of 1 µL/min. Acetone was delivered by another syringe pump at 1 µL/min and Tee-d in to the lipid solution transfer line. The composition of the solution is acetone:isopropanol:$H_2O$ (50%/35%/15%) after mixing. The subsequent P-B reaction (5 s) provided a very similar spectrum to FIG. 50B. This setup was further investigated for its coupling with on-line HPLC and ESI-MS/MS as discussed below.

The reaction setup shown in FIG. 50D was used to characterize experimental parameters important to the performance of PB reaction as well as lipid detection using model lipid compounds representative of the major lipid classes (FA, GL, GP, SP, ST) from mammalian cells. Important aspects will be evaluated include conditions to minimize side reactions, solvent systems that are suitable for PB and compatible with ESI of lipids, and the analytical utility of using different types of carbonyl compounds as PB reagent.

Figure 51A:
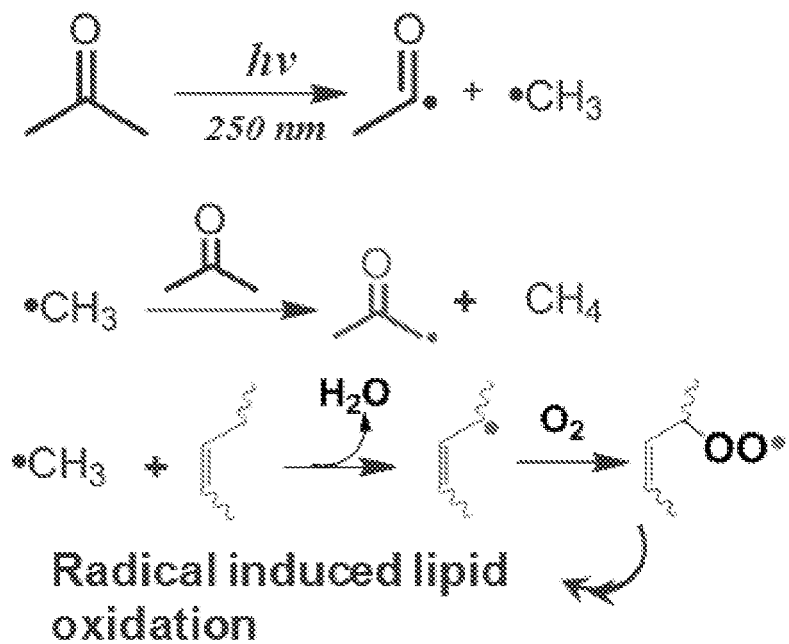
FIG. 51A shows a Norrish Type I reaction and subsequent radical reactions involving oxidation of lipids. Eliminating O2 from solvent system for improved PB reaction yield: MS spectra of 10 s PB reaction of PC16:0/18:1(9Z).
Figure 51B:
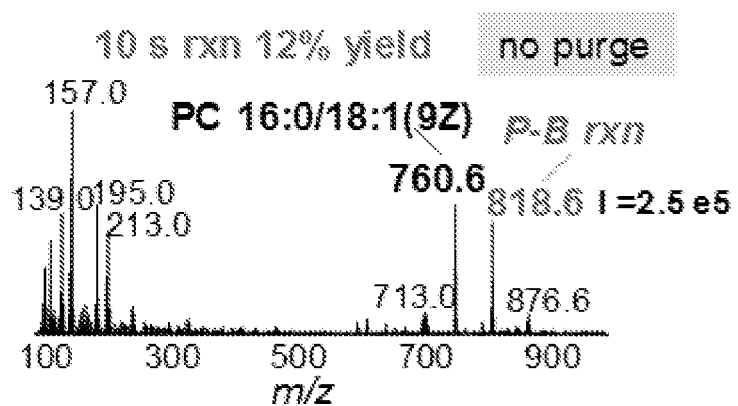
Figure 51C:
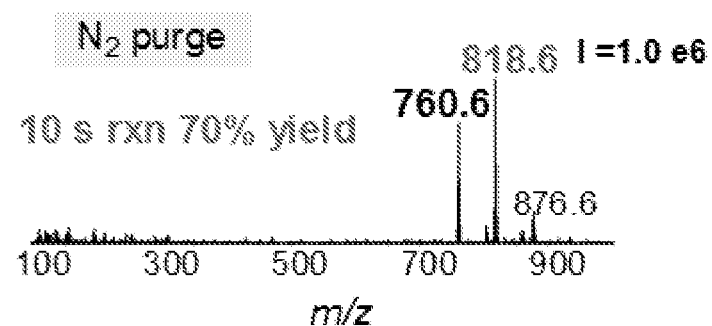

The UV excitation wavelength triggering PB reaction can also initiate Norrish Type I reaction, which results in photochemical cleavage of the α-carbon bond of the acetone and formation of acetyl radical and methyl radical (FIG. 51A). These two radicals can abstract H atoms from organic solvent and lipid to form a variety of secondary radicals or add onto the C=C bond. When the solution consists of trace $O_2$, the secondary lipid radicals proceed through the well characterized lipid peroxidation pathways, leading to the formation of oxidized and degraded lipid products. This is indeed observed for solutions which are even freshly made. FIG. 51B shows a 10 s PB reaction of 5 µM PC16:0/18:1 (9Z) in acetone: water (1:1). A cluster of new peaks at low m/z range (100-300) results from radical induced lipid degradation, causing a significant loss of lipid ion signal and the PB reaction yield is only 12% (normalized to intact lipid signal before UV irradiation). $N_2$ purge of this lipid solution was tried to remove trace $O_2$ and a high PB reaction yield at 70% was achieved (FIG. 51C). These preliminary results signify the importance of controlling competing side reactions in order to achieve good PB reaction yield. For the experiments involved herein, $N_2$ purge will be performed for lipid solutions right before PB reactions. The degree of involvement and impact of Norrish Type II reaction will be characterized with model lipids from different classes. The impact of organic solvent on the degree of side reactions will be examined.

In preliminary studies, aqueous solvent systems consisting of 50-70% acetone (volume %) were used for maximizing PB reaction yield and reducing possible side radical reactions when organic solvent was employed. The above conditions, however are not necessarily the best conditions for ionization and detection via ESI. Besides, organic solvents such as $CHCl_3$, hexane, acetonitrile, and aliphatic alcohols are commonly used in lipid extraction, separation, and ESI; therefore, it is necessary to investigate the effect of organic solvent composition on the performance of both P-B reaction and ESI. The following solvent compositions were tested: acetone:$H_2O$:X=70:15:15 (v:v:v), with X being the organic solvent. Only the condition of 15% of $CHCl_3$ showed a significant interference for PB reaction when PC 16:0/18:1(9Z) was used as a model compound for positive ion mode ESI ("direct infusion setup), all the other organic solvent showed acceptable PB reaction yields (20-30%) for 6 s UV exposure. Standard compounds from the major classes will be tested and the suitable solution compositions will be determined for both PB reaction and ESI analysis. The key evaluating criteria include the PB reaction yield, the absolute ion counts of the intact lipid and P-B reaction product, the degree of side reactions, compatibility with LC solvent.

Acetone as the PB reagent has advantages of good co-solubility in both polar and non-polar lipids and solvents, as well as no interference with ESI-MS detection. For the above reasons, acetone will be used in most of our proposed studies for method development and optimization. In order to further explore the utility of PB reaction for lipid analysis, it is beneficial to survey a larger pool of carbonyl compounds as PB reagents. Some properties that the candidates should have include high PB reaction selectivity, good reaction yield, preferential formation of C=C diagnostic ions from low energy CID of the PB reaction products. It would also be interesting to find PB reagents that are compatible with longer wavelengths (300-500 nm) so that different types of light sources can be used. Table 9 lists several candidates that will be investigated, their maximum adsorption wavelengths (λmax) for n→π* transitions, which is responsible for PB reaction, and the Δmass between the pair diagnostic ions characteristic for C=C location determination.

TABLE 9

| Reagents/<br>Mass (Da) | Structure | λ(absorb)<br>(nm) | Δ mass (Da)<br>(diagnostic<br>ions) |
|---|---|---|---|
| acetone<br>58.04 |  | 280[24] | 26.06 |

TABLE 9-continued

| Reagents/Mass (Da) | Structure | λ(absorb) (nm) | Δ mass (Da) (diagnostic ions) |
|---|---|---|---|
| 3-pentanone 86.07 | (structure: pentan-3-one) | ~280[24] | 54.09 |
| Benzaldehyde 106.04 | (structure: benzaldehyde) | 330[25] | 74.06 |
| Acetophenone 120.06 | (structure: acetophenone, C$_6$H$_5$-CO-CH$_3$) | 319[24] | 88.09 |
| Benzophenone 182.07 | (structure: benzophenone) | 330[26] | 150.09 |
| Charged Reagents | (H$_3$C)$_3$N$^+$-C$_6$H$_4$-CO-CH$_3$ Mass: 178.12 | | |
| | (H$_3$C)$_3$N$^+$-(CH$_2$)$_4$-CO-CH$_3$ Mass: 158.15 | | |
| | HOOC-(CH$_2$)$_4$-CO-CH$_3$ Mass: 144.08 | | |

Figure 52A:
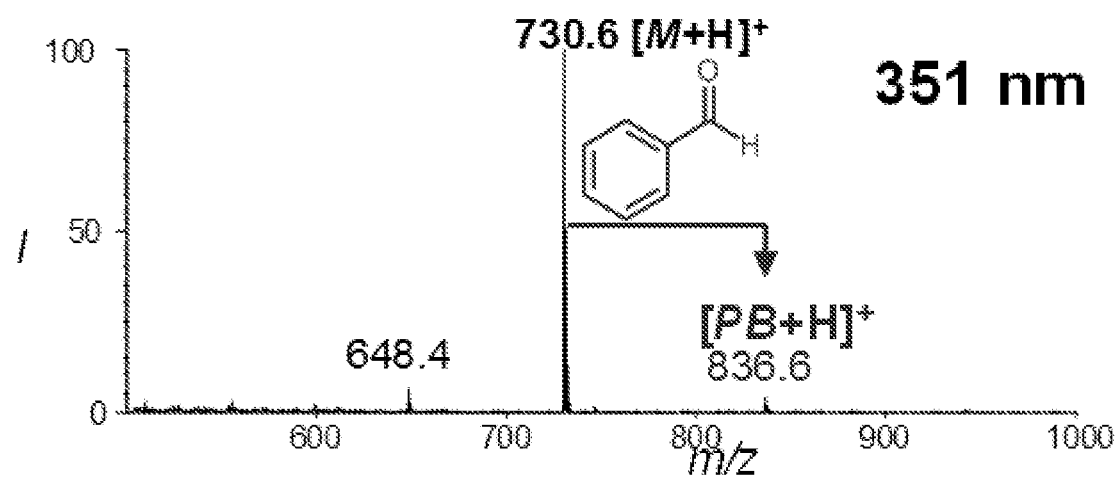
FIG. 52A shows PB reaction of PC 18:1(6Z)/18:1(6Z) using benzaldehyde as PB reagent under 351 nm UV irradiation.
Figure 52B:
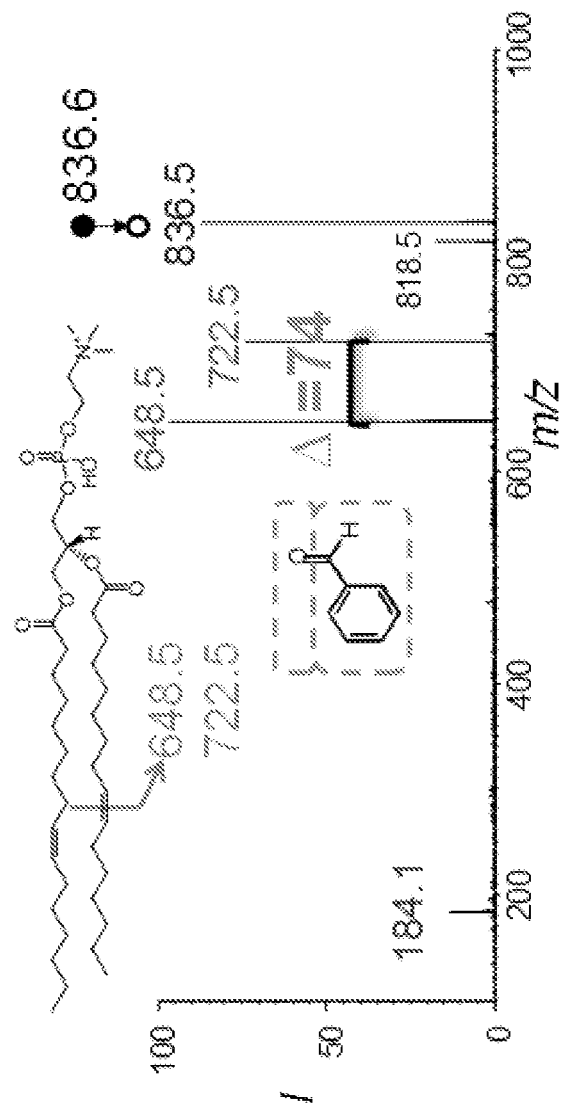
FIG. 52B shows MS2 CID of PB product produces C=C diagnostic ions at m/z 648.4 and 722.5.

Preliminary studies showed that benzaldehyde could react with PC 18:1(6Z)/18:1(6Z) with reasonable efficiency using a UV 350 nm lamp (FIG. 52A). MS$^2$ CID of the PB product (m/z 836.6, FIG. 52B) produced abundant C=C diagnostic ions at m/z 648.5 and 722.5 with a characteristic Δmass of 74 Da. Compared to the use of acetone as PB reagent, side reactions are lower when using benzaldehyde, which may relate to the lower energy UV photons used. The reagents listed in Table 9 will be applied to reactions with representative model compounds from different lipid classes and their performance for unsaturated lipid C=C analysis will be investigated. In addition to the neutral PB reagents, we will also explore charge functioned ketones for the purpose of increasing ionization efficiency for neutral lipids such as cholesterol and glycerol lipids.

In certain alternative set-ups, the PB reaction can be uncoupled from the ESI-MS so that conditions can be optimized independently. For instance, the coiled UV-transparent fused silica setup for PB reaction can be used off-line as a flow micro-reactor. Lipid molecules can be dissolved with high concentrations in pure acetone to maximize PB reaction yield. After reaction, acetone will be removed from drying and the remaining lipid can be dissolved in proper solvent for ESI.

Additionally, methods of the invention can be conducted using MALDI. Several of the PB reagents (i.e. benzaldehyde, benzophenone, and acetophenone) we proposed to study in Table 9 have UV absorption bands overlapping with UV MALDI wavelengths (337 or 355 nm). These reagents if co-dissolved in matrix with unsaturated lipid molecules can be UV exited and react with C=C during desorption and ionization. The PB reaction capability could dramatically enhance structural characterization of the unsaturated lipids for many applications in bio-MS imaging.

Development MS/MS Methods for Structural Determination and Quantitative Analysis of Unsaturated Lipids The analytical capability of PB-MS/MS for C=C determination highly depends on the gas-phase fragmentation behavior of the PB reaction product of a specific unsaturated lipid. Given the structural diversity of different lipid classes, we will tailor the tandem MS methods for each specific lipid class in terms of maximizing the amount of structural information that can be obtained including head group, acyl chain, C=C location determination. We will also focus on method development for characterizing lipid C=C location isomers and their quantitation based on the established MS/MS conditions. Pure unsaturated lipids with known C=C locations from the major lipid classes will be used as models for method development. This Example provides a standard guideline for using CID based MS/MS to gain both structural and quantitative information of unsaturated lipids.

MS/MS methods based on collisional activation have been well established for analyzing different classes of lipids. Rich structural information is regularly obtained from class/substructure specific fragmentation channels (termed linked-scans from MS/MS). Therefore, it is of high interest to have the add-on capability of determining C=C location to these existing MS/MS methods so that multi-levels of structural information can be obtained. In preliminary studies, PB-MS/MS for a small set of standard compounds from FA and GP were investigated using the ionization and CID conditions that have been established for these two classes of lipids. Two phenomena are commonly observed for the formation of C=C diagnostic ions: 1) it is a facile fragmentation channel, which can be generated from various ionic forms of lipids; and 2) it does not interfere or suppress structural informative fragment ions using the MS/MS conditions established for intact lipid ions. The latter is advantageous since all the established knowledge can be directly applied for data interpretation. It was also noticed that the ionic form of the PB product indeed affects the formation of C=C diagnostic ions. CID of PB product of α-linolenic acid, FA 18:3 (9Z,12Z,15Z) as a lithium ion adduct in the positive ion mode (m/z 343.3) produced three pairs of diagnostic ions of the three C=C bonds in high abundances. However, CID of the deprotonated PB product (m/z 335.3) only produced one pair of diagnostic ions from the 9Z position with relatively high intensity; the other two pairs either exist in relative low intensities or overlapping with the major 58 Da loss. Clearly, the CID of lithium adduct is more preferable for C=C characterization.

In the Examples, an expanded study was undertaken using lipids representing five major lipid classes (FA, GL, GP, SP, ST) and their subclasses (listed in Table 10).

TABLE 10

| Lipid Class | PB-MS/MS method (CID) | Structure infor from PB-MS/MS | |
|---|---|---|---|
| | | C=C | Other infor |
| MUFA 18:1 (9Z) | [FA − H]⁻, MS² | ✓ | NL58 |
| PUFA 18:3 (9Z, 12Z, 15Z) | [FA+Li]⁺ MS² | ✓ | NL58 |
| PC, LPC | [PC + H]⁺ MS² | ✓ | m/z 184 |
| PC 16:0/18:1 (9Z) | [PC + Ac]⁻ MS³ | ✓ | [RCOO]⁻ |
| LPC 18:1 (9Z) | | | |
| PS, LPS | [PS + H]⁺ MS² | ✓ | NL 185 Da |
| PS 16:0/18:1 (9Z) | [PS − H]⁻ MS³ | ✓ | NL 87 Da |
| LPS 18:1 (9Z) | | | m/z 153, [RCOO]⁻ |
| PI, LPI | [PI − H]⁻ MS³ | ✓ | m/z 241 [RCOO]⁻ |
| PI 18:0/18:1 (9Z) | | | |
| LPI 18:1 (9Z) | | | |
| PE, LPE | [PE + H]⁺ MS² | ✓ | NL 141 Da |
| PE 16:0/18:1 (9Z) | [PE − H]⁻ MS³ | ✓ | m/z 196, NL 87 Da [RCOO]⁻ |
| LPE 18:1 (9Z) | | | |
| PA, LPA | [PA − H]⁻ MS³ | ✓ | m/z 153 [RCOO]⁻ |
| PA 16:0/18:1 (9Z) | | | |
| LPA 18:1 (9Z) | | | |
| CE 18:1 (9Z) 18:2 (10Z, 12Z) | [CE+Li]⁺ MS², MS³ | ✓ | NL 58, 368 m/z 369 [RCOOH + Li]⁺ |
| MG 18:1(9Z)/0:0/0:0 | [MG+Li]⁺ | ✓ | NL 58 |
| PG 16:0/18:1 (9Z) | | | |
| CL (1′ − [18:1 (9Z)/18:1(9Z)], 3′ − [18:1(9Z)/18:1(9Z)]) | [CL − H]⁻ | | |
| Cer d18:1/18:1(9Z)[M + H]⁺ | | | |
| SM d18:1/18:1(9Z), [M + H]⁺ or [M+Li]⁺ | | | |
| DG 18:1(9Z)/0:0/18:1 (9Z), [DG+Li]⁺ | | | |
| TG 18:1(9Z)/18:1(9Z)/18:1 (9Z) [TG+Li]⁺ | | | |

The amount of structural information such as head group, acyl chain, C=C location that can be obtained from PB-MS/MS using the well accepted MS/MS conditions was evaluated. These conditions will be further improved by manipulating the nature of ions, i.e. ion charge polarity (positive ions vs. negative ions) and the identity of charge carrier (e.g. H+ vs. Li+). Different types of CID such as beam-type collisional activation vs. on-resonance collisional activation will be compared using a triple quadrupole/linear ion trap mass spectrometer.

Figure 53A:
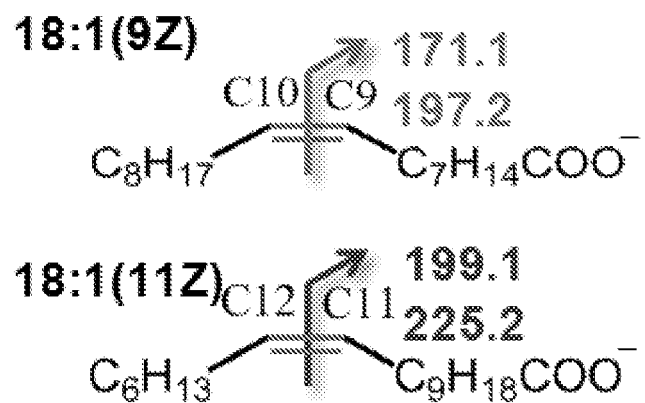
FIG. 53A shows predicted C=C diagnostic ions of FA 18:1 (9Z) and (11Z).
Figure 53B:
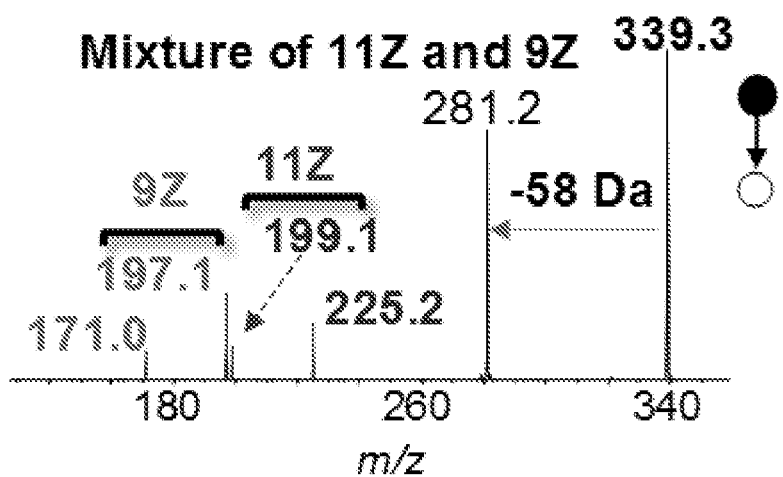
FIG. 53B shows MS2 CID of PB product of FA 18:1 (9Z) and (11Z) mixture.

PB-MS/MS has the unique property of producing diagnostic fragment ions carrying the C=C bond location information; therefore, it allows distinction of each C=C region-isomers based on observation of characteristic diagnostic ions. In preliminary studies, this was tested with FA 18:1 C=C isomers, i.e. oleic acid (9Z) and cis-vaccenic acid (11Z), which have been observed from mouse and human brain tissue analysis. A 2:1 molar ratio mixture of 11Z and 9Z was subjected to PB-MS/MS (m/z 339.3, FIGS. 53A-B). As expected, distinct pairs of C=C diagnostic ions were formed for 11Z (m/z 199, 225) and 9Z (m/z 171,197), respectively, allowing unambiguous detection of 9Z and 11Z C=C regio-isomers even though their PB reaction products do not have any mass difference. This set of data clearly demonstrates the potential of PB-MS/MS in C=C isomeric structural characterization. In this Example, a series of commercially available model C=C bond isomers, including MUFA (FA 20:1 9Z vs. 11Z), PUFA (FA 20:4 n-6 vs. n-3) and phospholipids (PC 18:1(6Z)/18:1(6Z) vs. PC 18:1(9Z)/18:1(9Z)) were examined. Attentions was given to the CID conditions for the formation of diagnostic ions using breakdown curve method and its effect on isomeric mixture analysis. The PB-MS/MS method was not limited by the number of C=C bond isomers that coexisted in the mixture since each C=C location isomer provided diagnostic ions with distinct masses. That was tested using FA 18:1(9Z), (11Z), and (6Z) isomeric mixtures.

The capability of producing C=C diagnostic ions also opens up the possibility of unsaturated lipid quantitation using PB-MS/MS. This Example illustrates development of quantitative methods for the following two situations: 1) absolute quantitation of unsaturated lipid without C=C position isomers or total quantitation if C=C isomers exist and 2) relative and absolute quantitation of C=C position isomers.

Figure 54:
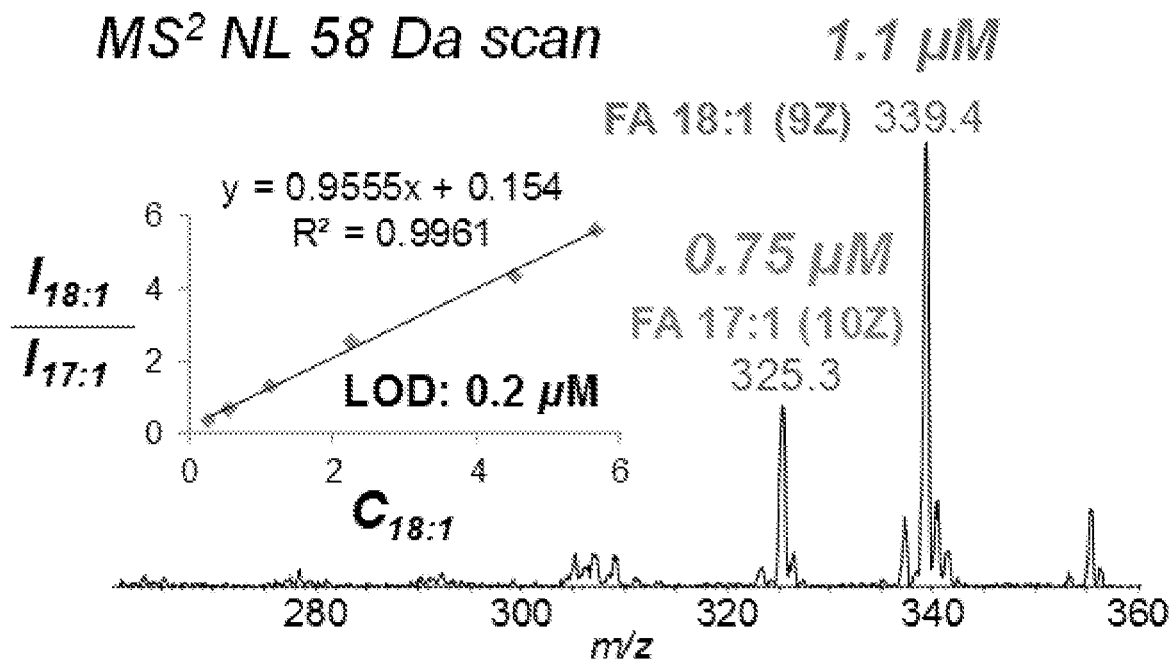
FIG. 54 shows NL 58 scan for quantitation of FA 18:1(9Z) using FA 17:1(10Z) as the internal standard. Inset: calibration curve.

Tandem MS is widely used for lipid quantitation by using class or sub-class specific fragmentation channels (linked scans) to achieve high molecular specificity and high sensitivity. The development of MS/MS for FA quantitation lags behind because it is difficult to form structural informative fragment ions from intact FA ions under low energy CIDs, the mostly available fragmentation method. GC-MS or HPLC-MS are the current choices of analysis for FA quantitation; however off-line sample derivatization is always required before analysis. Therefore, developing MS/MS based method for quantitation FA mixture analysis stage could greatly enhance molecular specificity, sensitivity, quantitative accuracy, and linear dynamic range. NL 58 Da is common fragmentation channel observed from PB-MS/MS of MUFAs with different chain lengths and it accounts for 60-70% of total fragment ion intensity. These two aspects suggest that NL of 58 Da should be a good candidate for quantitation purpose. Testing was performed for quantitation of FA 18:1(9Z) using FA 17:1(10Z) as an internal standard. FIG. 54 shows the NL of 58 Da spectrum of the PB products of FA 18:1 (9Z) (1.1 µM, m/z 339.4) and FA 17:1 (m/z 325.3, 0.75 µM). A calibration curve was obtained from a range of 0.4 to 6 µM and a limit of detection (LOD) of 0.2 µM. This result compares favorably to the commonly used GC-MS method. NL 58 scan was further evaluated for quantitation of MUFAs and PUFAs with carbon numbers in the range from 16 to 24, which are naturally occurred in mammalian cells. The effect of choice of internal standard (chain length and degree of unsaturation), collision energy, and other parameters will be characterized for its analytical figures of merits. The applicability of NL 58 Da for total quantitation of FA C=C isomers was evaluated using FA 18:1 (9Z) and (11Z).

Figure 55A:
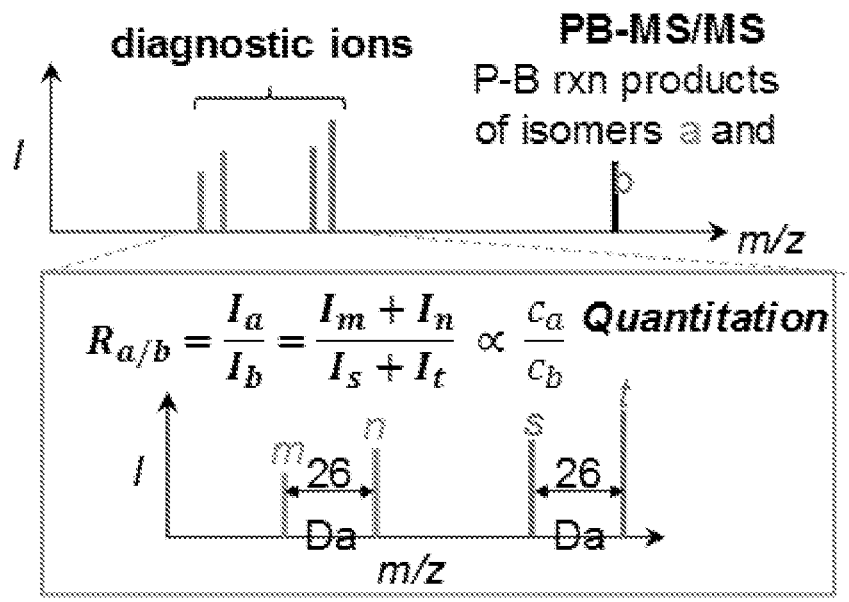
FIG. 55A shows the use of C=C diagnostic ion intensity for quantitation.
Figure 55B:
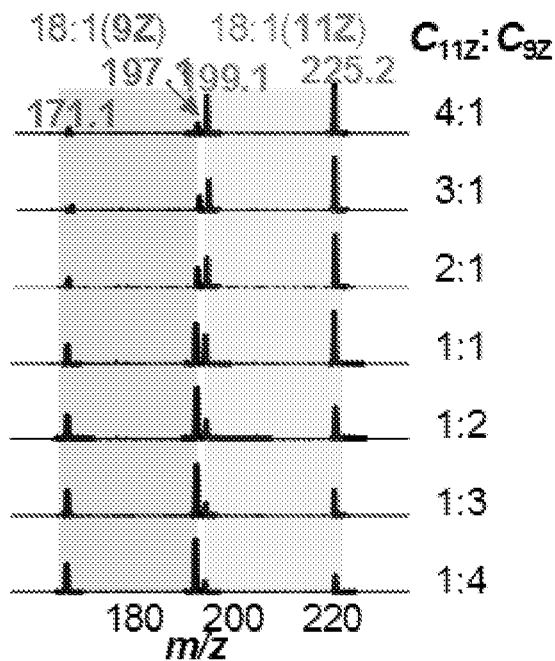
FIG. 55B shows MS2 CID spectra of FA 18:1 (9Z) and (11Z) mixtures.
Figure 55C:
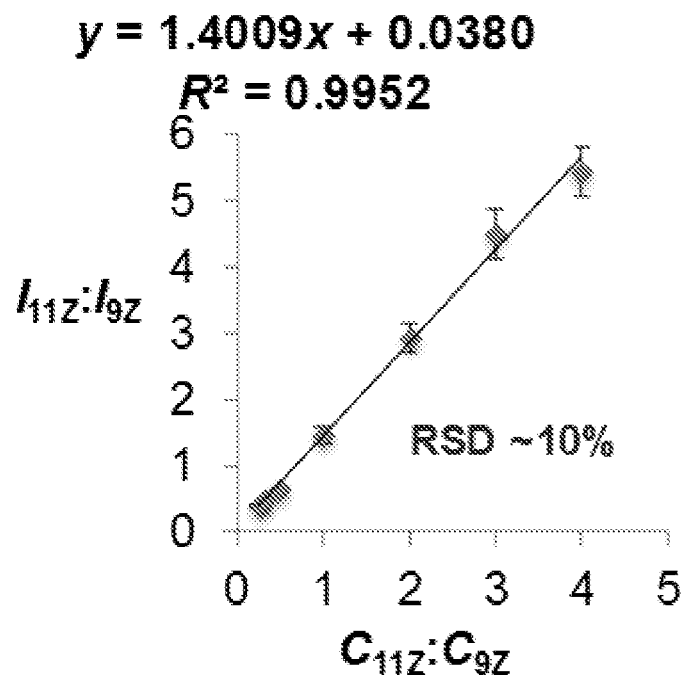
FIG. 55C shows relative quantitation from C=C diagnostic ion intensity ratios vs. molar ratios.

Given that distinct diagnostic ions are formed from CID of different C=C bond location isomers, a straightforward approach is to use the ion intensity of diagnostics ions as the measurable for quantitation as illustrated in FIG. 55A. FA18:1 (9Z) and FA18:1 (11Z) were used to test the feasibility of this idea. FIG. 55B shows zoomed-in PB-MS² CID of m/z 339.3 spectra resulting from mixture of 9Z and 11Z, with total concentration kept at 10 µM however with different molar ratios (C11Z:C9Z=4:1 to 1:4). The ion intensities of the each pair of diagnostic ions are summed and the ion intensity ratios (I11Z:I9Z) are plotted against the concentration ratios (C11Z:C9Z). Such a calibration curve is shown in FIG. 55C. The linear fit has an R2 value of 0.9952 and relative standard deviation (RSD) less than 10%. This result shows that diagnostic ion intensities can be used for quantitation of the C=C isomers.

The activation energy used in CID and the type of CID (on-resonance CID vs. beam-type CID) on the relative standard deviation of calibration curves was investigated. That established the optimized CID conditions of each group of isomeric lipids for quantitative analysis. This knowledge is directly transferable for complex mixture analysis.

Since the calibration curve is established from the ion intensity ratios and concentration ratios, it is important to evaluate if the same linear relationship holds for different concentration ranges. Our preliminary studies based on FA 18:1(9Z) and (11Z) showed little variation for the calibration curve within the total concentration range of 0.1 uM to 100 uM. The extent of linear dynamic range for the isomeric ratios was also estimated.

Figure 55D:
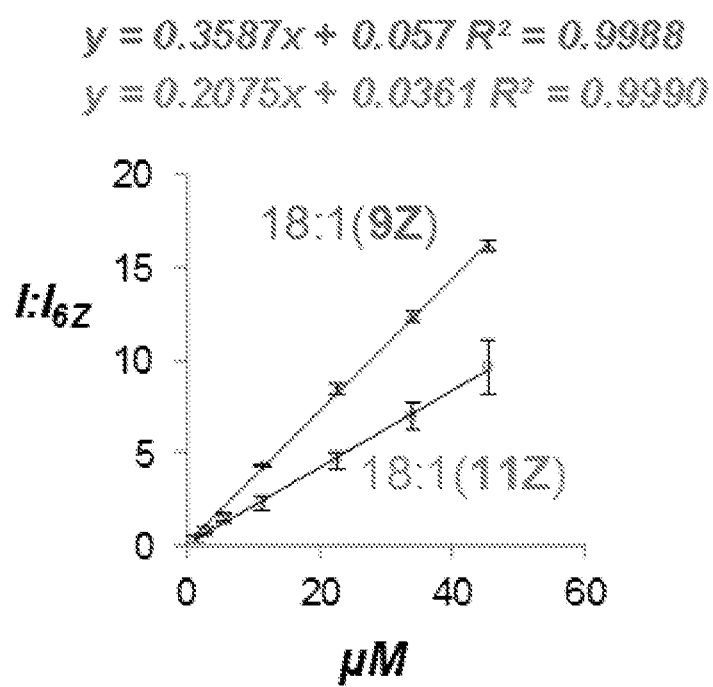
FIG. 55D shows absolute quantitation with the use of FA 18:1(6Z) as internal standard for FA 18:1(9Z) and (11Z).

Two different approaches were tested and compared in terms of their analytical figures of merits for lipid isomer quantitative analysis. FA 18:1 C=C isomers was used for method development. Since the principle of using PB-MS/MS for unsaturated lipid quantitation (FIG. 55C) is based on C=C diagnostic ion intensities, the best internal standard (IS) should be a C=C bond isomer which is not naturally occurred in the system. Petroselinic acid FA18:1(6Z) is not commonly detected in mouse or human cells, and therefore is a good choice of internal standard for the quantitation of FA 18:1 (9Z) and (11Z) isomers. Collisional activation of the PB reaction product of 6Z produces diagnostic ions at m/z 155 and 181. Based on the diagnostic ion intensity ratios of 9Z/6Z and 11Z/6Z, two calibration curves for 9Z and 11Z were obtained as shown in FIG. 55D with 6Z's concentration kept constant at 10 μM and the concentrations of 9Z and 11Z varied in the range of 1.5-45 μM. Excellent linear relationships were obtained for both 9Z and 11Z isomers. This IS method is advantageous by avoiding experimental variations due to PB reaction, ionization, and CID efficiencies.

Depending on the availability, one of the C=C isomers can be used as a reference for standard addition. The use of FA 18:1 (11Z) was tested to perform standard addition to a mock mixture of FA 18:1 9Z and 11Z isomers. PB-MS$^2$ CID were recorded before and after the standard addition. This information was used to calculate the concentration ratios of 11Z vs. 9Z before and after standard addition by using the relative calibration curved described in FIG. 55C. Combining the above information with the known quantity from standard addition, the absolute concentrations of both 9Z and 11Z were be determined with good accuracy, respectively.

Development of PB-ESI-MS/MS Platforms for Lipidomic Studies

MS based lipidomic analysis can be performed directly on lipid extract from biological sample (so-called shotgun lipidomics) or it can be coupled with LC separations. A shotgun method facilities high throughput global profiling of the lipidome by providing both structural and quantitative information and it becomes a powerful tool for biomarker detection and validation. Identification and quantitation of low abundance lipids, lipids with low ionization efficiencies, and lipid isomers are always challenging for shotgun approach in analyzing lipid extracts from biological samples due to the large complexity (200-400 lipid species), different chemical-physical property, and wide dynamic range (4-6 orders of concentration differences). This issue is effectively addressed when separations such as LC are performed before or online with MS analysis. Currently, shotgun and LC-MS(/MS) methods are employed with almost equal frequency and together account for 80% of scientific reports on lipidomics. It is of high interest to implement PB-MS/MS strategy on both of these two platforms to enhance C=C specificity from complex lipid mixture analysis.

Figure 56:
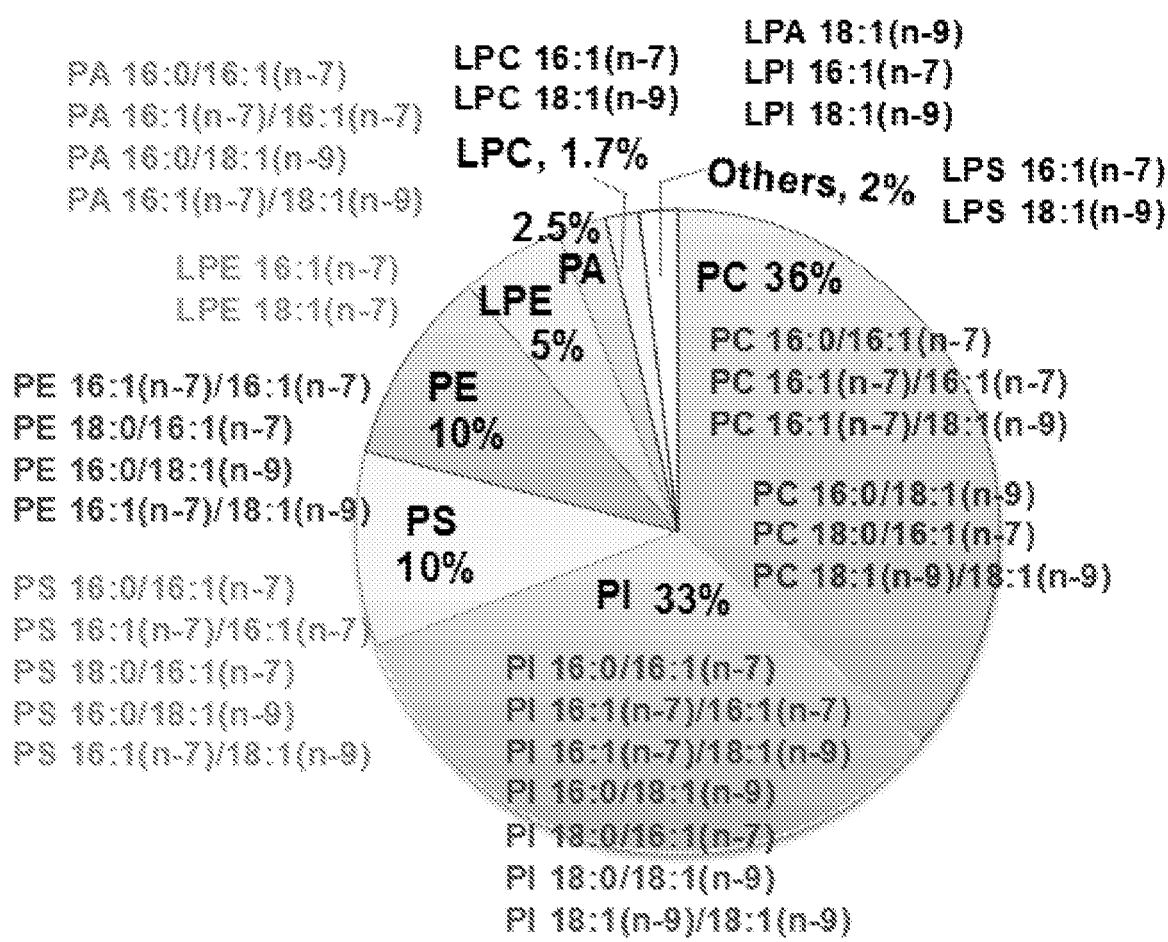
FIG. 56 shows C=C Identified GP from yeast polar extract from PB-MS/MS applied on shotgun analysis.

Both nanoESI and ESI setups were used for implementing PB-MS/MS for shotgun analysis of commercially obtained yeast polar extract from yeast (Avanti). The yeast polar extract mainly consists of FAs and GPs and the relative composition of each sub-classes have been documented. PB-MS/MS coupled with the direct infusion ESI setup (allowed the identification of 35 unsaturated GP species, including PC, PE, PI, PA, PS, LPC, LPE, LPA, LPS with the C=C location being determined (detailed molecular information is shown in FIG. 56). Since PB-MS/MS methods cannot provide the absolute configuration of the C=C, nomenclature counting C=C was followed from the methyl end (e.g. n-7 or n-9) of an acyl chain for detecting C=C location for lipids identified from biological samples. The identified GPs contained a combination of acyl chains of 16:0, 18:0, 16:1(n-7), and 18:1(n-9). It is important to note that some low concentration species with mol % ~0.1%, such as LPA 18:1(n-9) and LPS 16:1(n-7), can be confidently identified. Interestingly, no C=C location isomers have been observed from this system. The preliminary results demonstrate the feasibility of applying on-line PB-MS/MS for shotgun lipid analysis.

Figure 57:
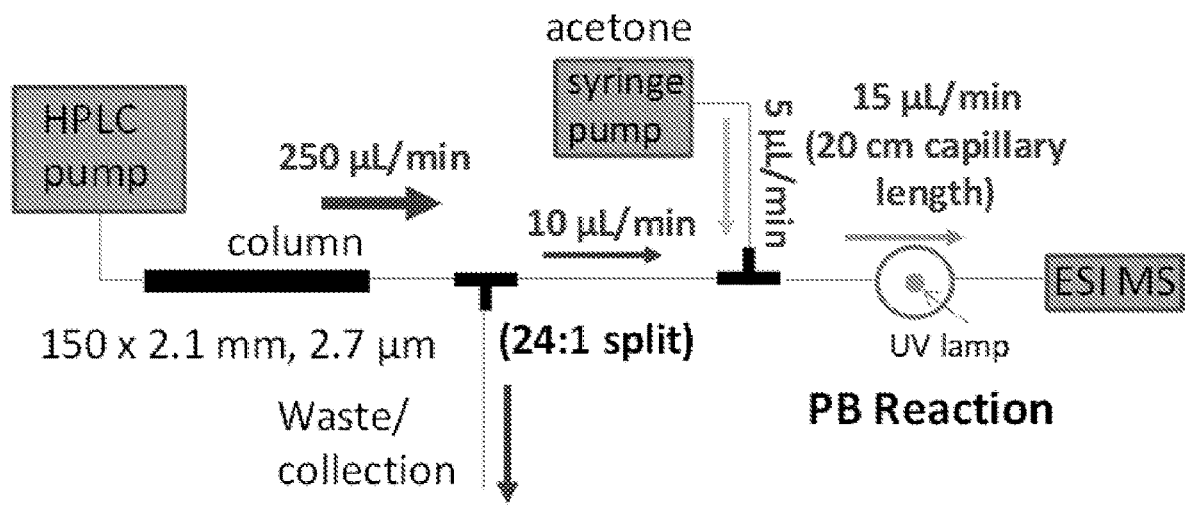
FIG. 57 shows scheme of coupling PB in post column separation and ESI-MS.

An Agilent 1200 HPLC will be coupled to the TurboESI-QTRAP 4000 MS interface (both available in the PI's lab). PB reaction was implemented after LC separation and before ESI-MS/MS analysis using the "flow injection device" described above, in which the PB reagent (acetone), which will be Tee-d into the eluents. A schematic of the whole setup is shown in FIG. 57. This arrangement will introduce least disturbance to the separation process. The conditions described above for this Example were used to provide guidance on choosing initial parameters for testing. These include lipid eluent/acetone ratios for mixing, PB reaction time (UV exposure time) under such a solvent condition, and the necessary length of fused silica capillary for UV exposure. The lowest flow rate that can be managed by the current HPLC system is 250 μL/min. This flow rate will require about 3 m exposure of the fused silica capillary for a 10 s UV exposure time under optimized solvent conditions. For the initial test, a 24:1 split of the HPLC eluent was performed, so that 10 μL/min eluent was Tee-d with 5-10 μL/min of acetone solution for 10 s PB reaction, which is equivalent to 20 cm capillary length for exposure. This condition was mimicked using the "flow injection" setup. One syringe was pumping at 10 μL/min for the standard PC dissolved in $H_2O$:ACN:IPA (43:42:15), 5 mM ammonium formate (AF), a common LC isocratic separation condition. Acetone was delivered at 10 uL/min and good PB reaction yield of PC was achieved.

CID based PB-MS/MS method can provide C=C specific structural information and quantitative information for different classes of unsaturated lipids. In order to apply such a method for large scale lipidomic research, it is important to rationally design MS/MS data acquisition workflows based on the unique CID fragmentation chemistry of PB reaction products for both discovery mode and targeted lipid analysis.

Facile identification of PB product for subsequent MS/MS is an important step for obtaining both C=C bond location information and quantitation. This is helpful for shotgun approach given that PB reaction creates additional m/z peaks (molecular species) from unsaturated lipids, making it even worse for already congested MS spectrum derived from lipid extract of biological samples. Two methods were tested to meet this challenge, including neutral loss of 58 Da (NL 58) scan and data dependent PB search. NL 58 scan preliminary studies above show that NL 58 (acetone loss from the oxetane ring) is characteristic to PB reaction products and is commonly observed for FAs and neutral lipids (i.e. CE, MG). Therefore, NL 58 MS/MS scan should allow quick and sensitive discovery of PB reaction products of those lipid classes. Since only the P-B reaction products are detected, the spectrum is greatly simplified with enhanced sensitivity. The NL 58 scan was further optimized with the use of yeast extract as a model system. Assessment was based on the number of lipid species that can be identified and detection limit. Virtue PB search for lipid classes that NL 58 is not an abundant fragmentation channel, such as for GPs, we will first target GPs consisting of unsaturated acyl chains by using "multiple precursor ion scattering (MPIS)" approach, such as PIS m/z 279 (FA 18:2), 281 (FA 18:1), 301 (FA 20:5), in the negative ion mode. A PB m/z list will be computer generated by adding 58 Da to those unsaturated lipid species and further selected for PB-MS/MS analysis.

For many lipidomics studies, it is of interest to target a selection of known lipid species for detection and quantitation. This is typically performed using selected reaction monitoring (SRM, also known as MRM, multiple reaction monitoring) on tandem-in-space mass spectrometers, such as the triple quadrupole MS. The defined relationship between the parent ion and fragment ions, coined as "transition", ultimately determines analytical figures of merit of this method. Given the unique fragments associated with the PB reaction products, i.e. the formation of C=C diagnostic ions NL 58 Da, it is straight forward to use them in transitions. These transitions were tested by targeting a lipid standard which is spiked into the yeast extract with the aim to determine the optimum number of transitions for specific and sensitive detection.

Data processing tools will be developed to facilitate automatic C=C location determination from the CID spectra of the PB reaction products. The program will be written by matlab and initial tests will be performed on data acquired from model lipid species and then optimized with lipid extracts from biological samples. The program will have the following layers of functions: 1) Diagnostic ion selection rules. In addition to standard selecting algorithm (3× noise level), peaks with a mass difference of 26 Da (due to the use of acetone as PB reagent) will be chosen. 2) Determination of C=C locations. Class specific algorithm will employed for C=C bond location determination. For MUFA and GPs, PB-MS2 or $MS^3$ CID data collected in negative ion mode will be used. The location of C=C bond can be calculated from the lower mass peak ($C_nH(2_{n-3})O_3^-$) of the pair of diagnostic ions for simplicity. The number n represents the location of the C=C bond counting from carboxylic acid. For PUFA, CE, and GL, PB-$MS^2$/$MS^3$ CID data collected in positive ion mode with alkaline metal adduct as charge carrier will be used and the C=C determination formula will be modified accordingly to reflect the diagnostic ion structures. For PUFA, the C=C determination will be cross-checked with the spacing of 40 Da ($C_3H_4$) of the same sires of diagnostic ions, which is a signature for C=C separated with a methylene group.

The C=C identified species will be compared to the MS/MS spectral database generated from lipid standards and manually interpreted data acquired from lipid extract. Spectral similarity score will be reported together with the C=C location to as a scoring system and the ones with low similarity scores will be manually evaluated.

Validation and Application to Rat Lipid Analysis

Based on the optimized parameters for conducting PB-MS/MS, lipid extract from rat tissues was used to validate its utility for unsaturated lipid analysis with an emphasis on its unique capability of C=C location isomer detection and quantitation. This type of information has not been achieved for many lipid classes endogenous from mammalian lipidomes and therefore would form a benchmark for further method development and cross-comparisons to other analytical methods which allow C=C determination (e.g. OzID). Another goal of this project is to establish a database of unsaturated lipids from biological samples with confident C=C assignments as well as the composition of C=C isomers if they exist. This database will be also be employed for automatic unknown lipid C=C.

Figure 58A:
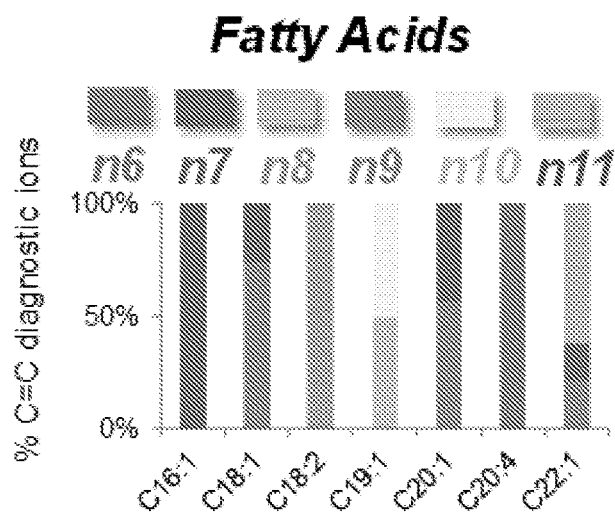
FIGS. 58A-C show composition of C=C isomers for (FIG. 58A) FAs, GPs (FIG. 58B) and (FIG. 58C) from rat brain.
Figures 58B, 58C:
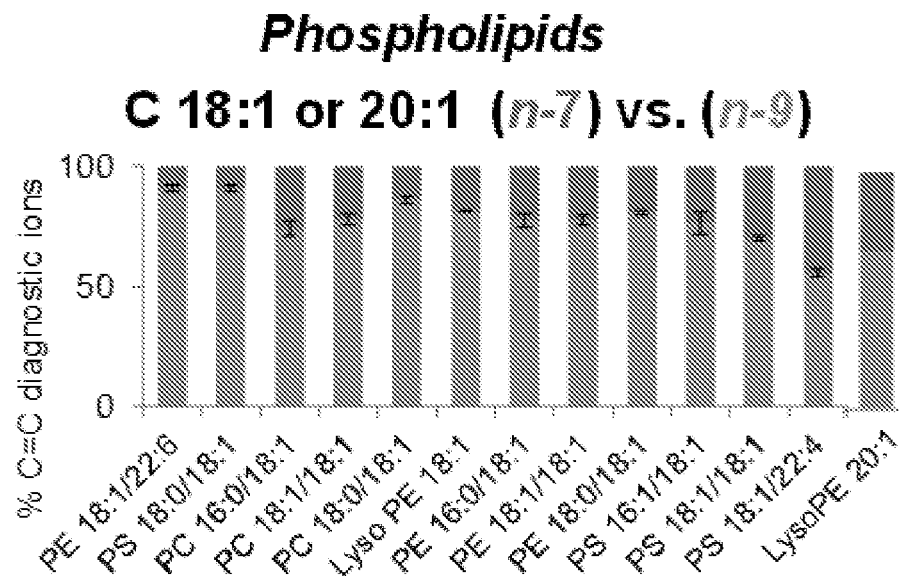

Using the nanoESI setup described above, initial shotgun lipid analysis for polar lipid extract from rat brain was performed. Lipid extraction was performed on 20-50 mg tissue using established extraction conditions. The $N_2$ dried extract was reconstituted in 1:1 acetone/$H_2O$ solution with 1% acid or base added for conducting PB-MS/MS in either positive or negative ionization mode. It was found that except for FA 16:1 (n-7), 18:2 (n-6) and 20:4 (n-6), all detected free FAs have C=C position isomers. For instance, FA 19:1 is a mixture of n-8 and n-10 isomers, FAs 18:1 and 20:1 are mixtures of n-7 and n-9 isomers, and FA 22:1 consists of three isomers with C=C located at n-7, n-9, or n-11 (FIG. 58A). Their relative compositions were established based on C=C specific diagnostic ion intensity ratios discussed above. It is important to note that the observed C=C composition by PB-MS/MS is consistent with earlier reports using GC-MS for free FA identification and quantitation from rat brain, however with much less sample consumption and shorter analysis time. In agreement with free FA 18:1 C=C isomeric composition, all 18:1-containing GPs in rat brain are mixtures of n-7 and n-9 isomers, although the relative ratios of these tow C=C isomers varied from different species. The consistency of C=C isomeric composition between free FA and GPs contain the same acyl chain was generally observed. The rat brain GP analysis led to full structural assignment of 85 molecular species from (L)/PS, PE, PC, PI, PA, 50% of which have at least one C=C isomeric forms. This is the first time documentation of a wide spectrum of GP with a molecular specificity of C=C location as well as C=C isomeric composition from biological samples.

Using rat brain tissue lipid extracts, PB-MS/MS for shotgun lipidomics was further validated using conditions identified above with the goal to expand structural characterization of other classes of lipids (CL, GL, CE, SM), perform quantitative analysis, and push the limits for low abundance lipid analysis. The rat brain lipid extracts were also used for the validation of the HPLC-PB-MS/MS platform described above. The data collected from these two approaches will be cross-compared and a relatively complete lipid profile will be constructed by pooling identified unsaturated lipids from both approaches. The manually annotated mass spectral data will be used to construct a searchable database and evaluate or train computer assisted C=C determination and relative quantitation for C=C isomers. The analysis of rat brain lipids will also lead the establishment of a series protocols covering aspects of sample preparation, lipid extraction, separation, PB-MS/MS, and data interpretation.

Figure 58D:
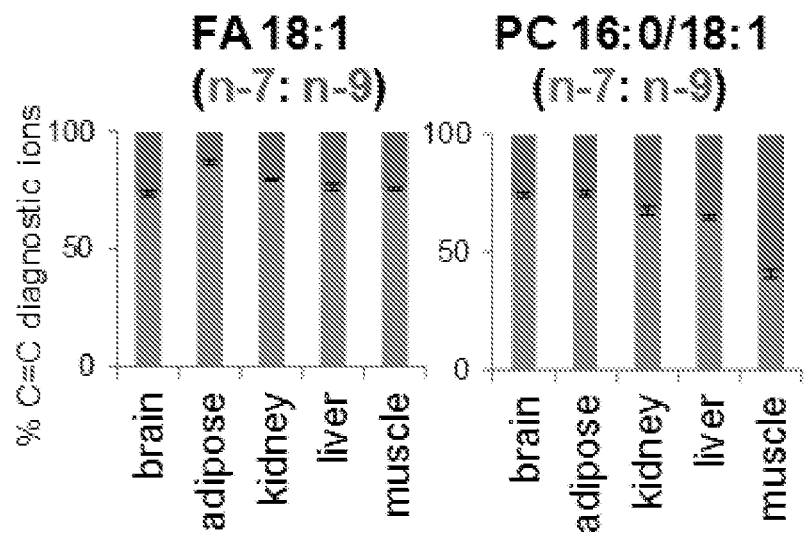
FIG. 58D shows distribution C=C isomer of FA 18:1 and PC 16:0/18:1 among different tissue types.

This data illustrate that PB-MS/MS can be applied for different types of biological samples, such as plasma and various tissue types using shotgun or separation-based platforms. The data show that although the n-7 and n-9 C=C isomeric forms of free FA 18:1 and PC 16:0/18:1 are consistently observed for different types of rate tissues, such as brain, adipose, kidney, liver, and muscle; the relative ratios of these two isomeric forms vary among different tissues (note the much higher contribution of PC 16:0/18:1 (n-7) isomer from muscle as compared to others, FIG. 58D).

These findings are important since they demonstrate for the first time that C═C isomeric distributions are not the same for different types of tissues, which is tied into their unique biological functions in their local environment.

Example 15: Photochemical Tagging for Rapid Quantitation of Unsaturated Fatty Acids by Mass Spectrometry Fatty acid (FA) profiling provides phenotypic information and is of a significant interest for a broad range of biological and biomedical studies. Quantitation of unsaturated FAs, especially with confident carbon-carbon double bond (C═C) location assignment, is both sample and time consuming using traditional gas chromatography-mass spectrometry analysis. In this study, we developed a rapid, sensitive, and quantitative method for profiling unsaturated FAs without resorting to chromatographic separations. This method was based on a combination of in-solution photochemical tagging of a C═C in FAs and a following gas-phase de-tagging via neutral loss scan tandem mass spectrometry. This method allowed direct quantitation of a series of unsaturated FAs from biological samples (blood, plasma, and cell lines). Quantitative information of FA C═C location isomers, which was traditionally overlooked, could now be obtained and applied to studying FA changes between normal and cancerous human prostate cells.

Fatty acids are essential for all living organisms by serving critical roles in a wide range of biological functions. They facilitate energy storage, they play essential functions in signaling, and they are the building blocks for complex lipids such as phospholipids, glycolipids, cholesterol esters. The structures and biophyiscal properties of FAs are dictated by length of the chain and the number, location, and configuration of the carbon-carbon double bonds (C═Cs). Many unsaturated FAs are known to have C═C location isomers, each performing distinct biological functions. For instance, omega-6 polyunsaturated fatty acids (ω-6 PUFAs) have the first C═C located at the sixth carbon, counting from the methyl end; they are reported to play different pro-inflammatory and anti-inflammatory functions as compared to their ω-3 C═C location isomers. There are strong evidences showing correlations between unsaturated FA composition changes and the development and progression of a number of chronical diseases.

Although gas chromatography-mass spectrometry (GC-MS) is still the mainstream method for FA analysis, shotgun lipid analysis has been increasingly used because of the ease of operation, fast speed, and the capability of obtaining lipid profiles for multiple classes. In a shotgun approach, FAs in crude lipid extracts are ionized by electrospray ionization (ESI) and analyzed by MS without separation. Molecular information, such as the FA chain length and the degree of unsaturation, can be readily deduced from accurate mass measurements. Unfortunately, tandem mass spectrometry (MS/MS), proved as a powerful technique for both qualitative and quantitative analysis, is not directly applicable to analysis of intact FAs. This is because few structure-informative fragment ions can be produced from FA anions through collision-induced dissociation (CID) at low energy conditions. This situation also makes it impossible to pinpoint the locations of C═C bonds in the unsaturated FAs, especially for monounsaturated FAs (MUFAs).

Alternative approaches have been explored. Charge-switch derivatization of carboxylic acid functional group of FAs has been shown to have several advantages in FA analysis. First, it greatly improves the ionization efficiency of FAs in positive ESI mode, improving the sensitivity of the analysis. More importantly, CID of the derived FA ions could now provide abundant signature fragment ions, which enables the detection and quantitation of the unsaturated FAs. By choosing proper derivatization groups, structural informative fragment ions can be generated from MS/MS, providing clues of C═C locations. The scientific literature has reported the identification of FA 18:3 C═C location isomers, α- and γ-linolenic acids (also frequently referred as ω-3 and ω-6 FA 18:3), which were at relatively low concentrations in human plasma, via charge-switch derivatization and shotgun analysis.

In this study, we explored a new approach of fishing and quantifying the unsaturated FAs in complex samples using an in-solution photochemical tagging followed by a gas-phase de-tagging by MS/MS. Our research recently showed that the coupling photochemical reaction, viz. Paternó-Büchi (PB) reaction, with online MS/MS allowed confident assignments of C═C locations for various classes of lipids. In this approach, each C═C in a fatty acyl chain is tagged by acetone electronically excited upon UV irradiation during an electrospray (ESI) process. Acetone-tagged lipids ionized by ESI are then analyzed by MS/MS, which generates fragment ions (termed as C═C diagnostic ions) specific to the locations of C═C bonds. The MS measurement of the C═C diagnostic ions provides information for both identification and quantitation of the C═C location isomers. Besides the production of C═C diagnostic ions, the loss of tag (-58 Da viz. acetone loss) is found to be a dominant fragmentation channel upon CID of tagged unsaturated FAs. This high abundance of acetone loss limits sensitivity of FA analysis based on detecting C═C diagnostic ions. However, in the newly developed approach to be reported here, this acetone loss fragment channel was utilized to derive an effective means of fishing and quantifying unsaturated FAs from complex biological samples. Neutral loss scans was used to select the unsaturated FAs that had been specifically tagged by the acetone and quantitation of them can now be easily performed.

Figure 59A:
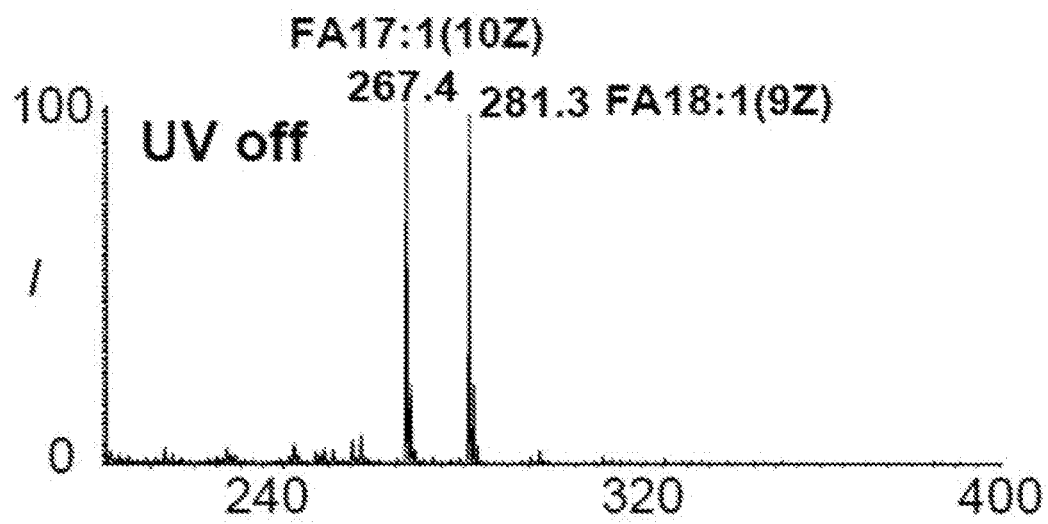
FIGS. 59A-F show Negative ion mode nanoESI mass spectra of an equal molar mixture of FA 17:1(10Z) and FA 18:1(9Z) (3.5 µM each in acetone/H2O=50/50, v/v with 0.1% NH4OH added)
Figure 59B:
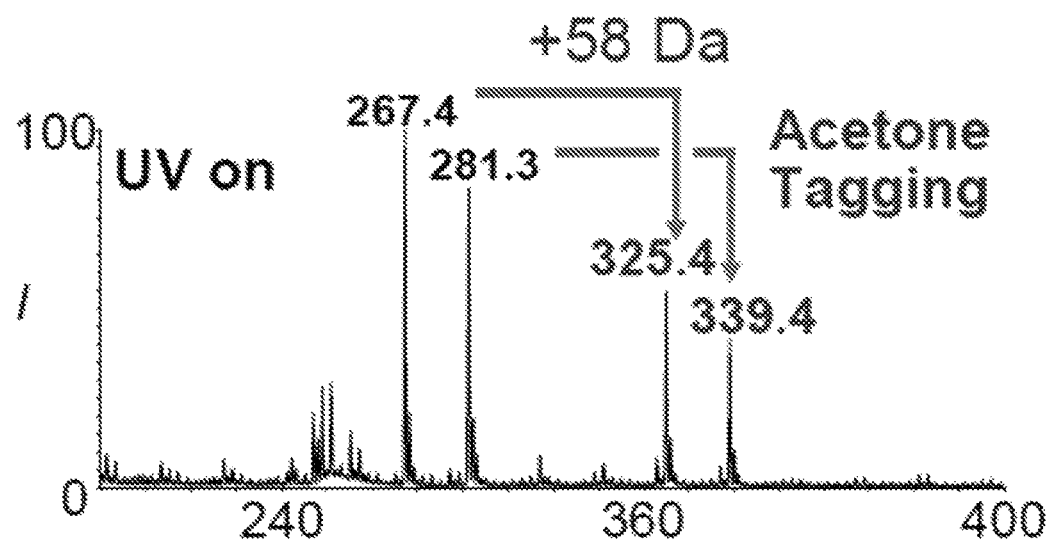
Figure 59C:
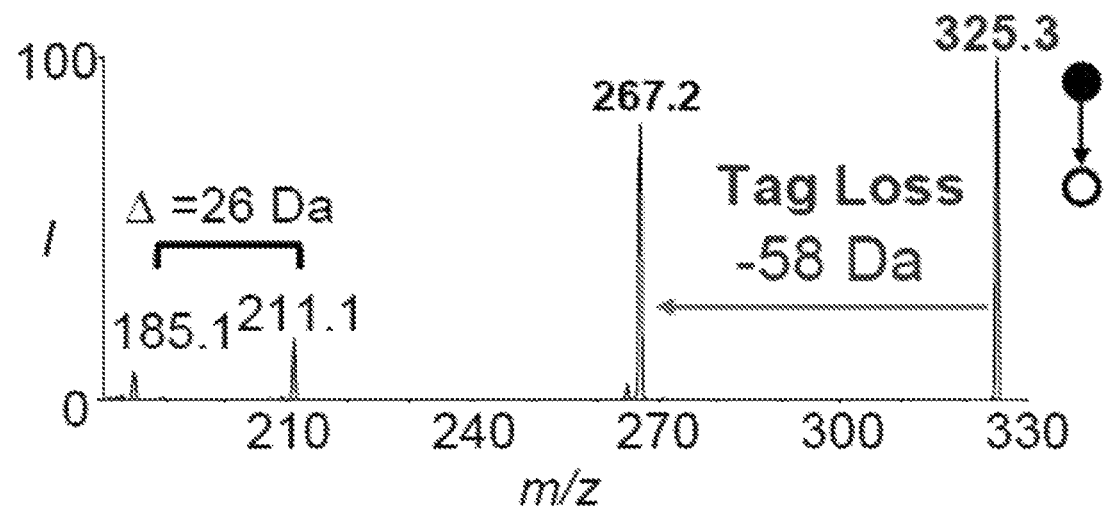

In order to test this idea, an equimolar mixture of FA 18:1(9Z) (oleic acid) and FA 17:1(10Z)) (cis-10-heptadecenoic acid) was subjected to acetone photochemical tagging via PB reaction. FIGS. 59A and 59B show negative ion mode nanoESI spectra of such a mixture (each at 3.5 µM in acetone/H2O (50/50, v/v) with 0.1% NH4OH) before and after photochemical tagging, respectively. Formation of acetone-tagged FAs at m/z 325 and 339 were clearly detected in good intensities, each with a 58 Da mass increase from the corresponding intact FAs (FA 17:1 at m/z 267 and FA 18:1 at m/z 281). MS2 CID of tagged FAs (also referred as PB-MS/MS), i.e. tagged FA 17:1 (m/z 325), led to dominant tag loss (-58 Da) and a pair of C═C diagnostic ions with a signature 26 Da mass separation (FIG. 59C). This set of experiments demonstrates that the processes of acetone tagging in solution and acetone de-tagging in gas phase are efficient.

Figure 59D:
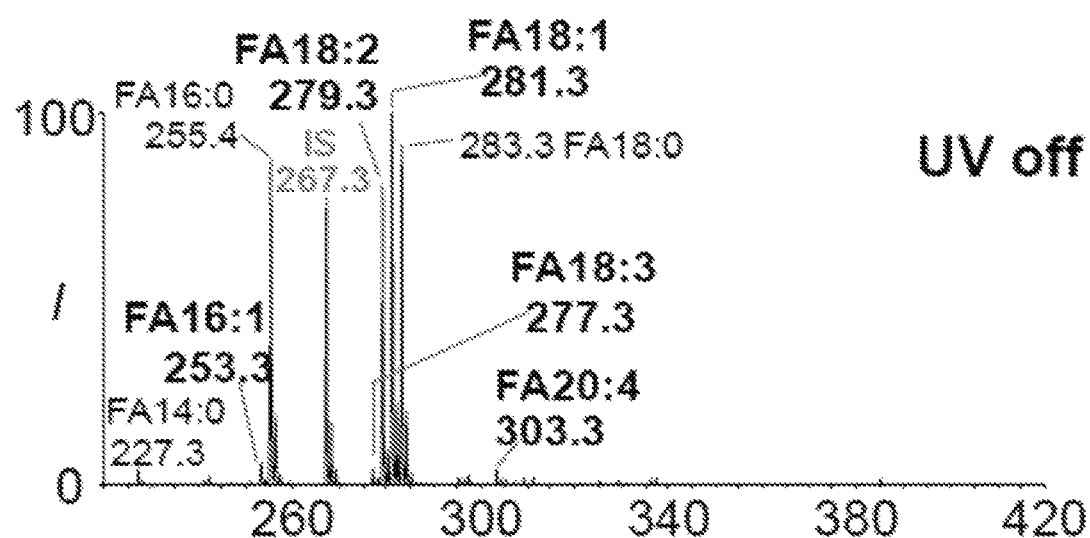
Figure 59E:
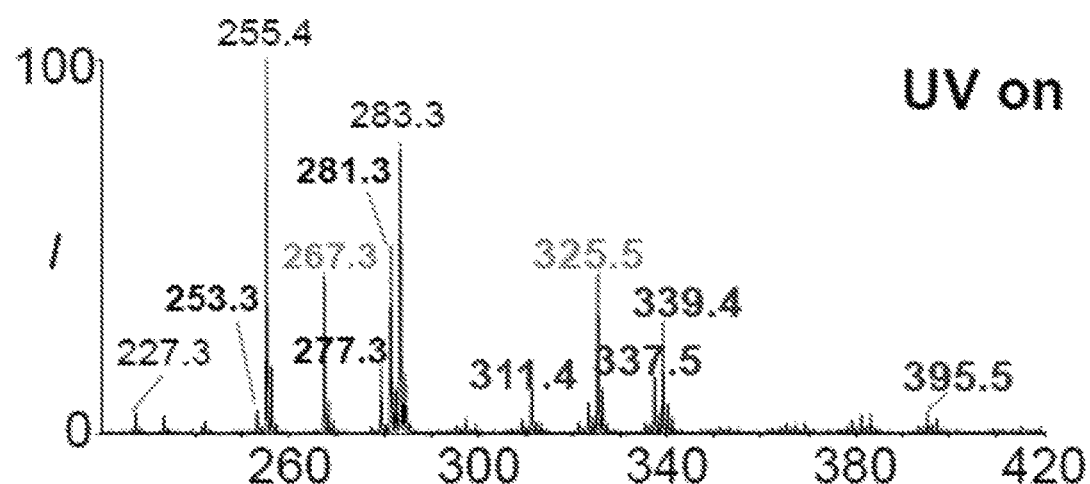
Figure 59F:
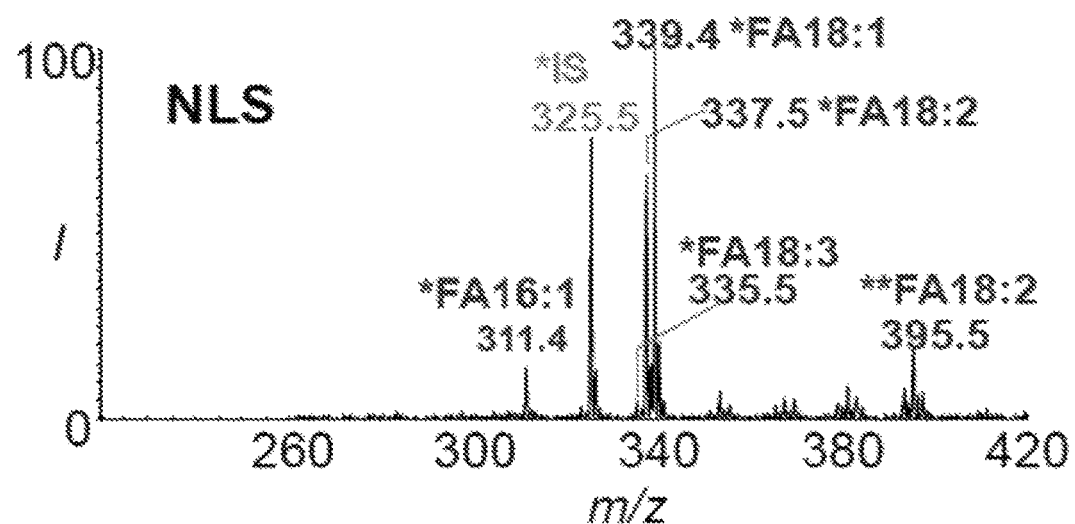

This method was then applied to analysis of FA extract from human plasma (20 µL). FA 17:1(10Z) was added to the exact as an internal standard (IS) given its negligible abundance in human plasma. NanoESI-MS revealed that the extract contained a variety of saturated and unsaturated FAs (FIG. 59D). Major species included FAs 14:0 (m/z 227.3), 16:1 (m/z 253.3), 16:0 (m/z 225.4), 18:2 (m/z 279.3), 18:1 (m/z 281.3), 18:0 (m/z 283.3), and 20:4 (m/z 303.3). After photochemical tagging (FIG. 59E), the relative intensities of unsaturated FAs decreased significantly with a concomitant appearance of tagged FAs (indicated with "*", e.g. m/z 311.4 for FA 16:1, m/z 337.5 and 395.5 for FA 18:2, m/z 339.3 for FA 18:1, m/z 325.2 for IS). Since the tagging reaction (PB reaction) is not 100% in yield, this leads to a more complicated spectrum. However, by taking advantage of the neutral loss scan via CID, the reaction spectrum was greatly simplified with detection of only unsaturated FAs from mixtures (FIG. 59F). It is worth noting that saturated FAs do not appear in the NLS (58 Da) spectrum (FIG. 59F) at all, an evidence of the high selectivity of the tagging by PB reaction towards the unsaturated FAs.

Figure 60A:
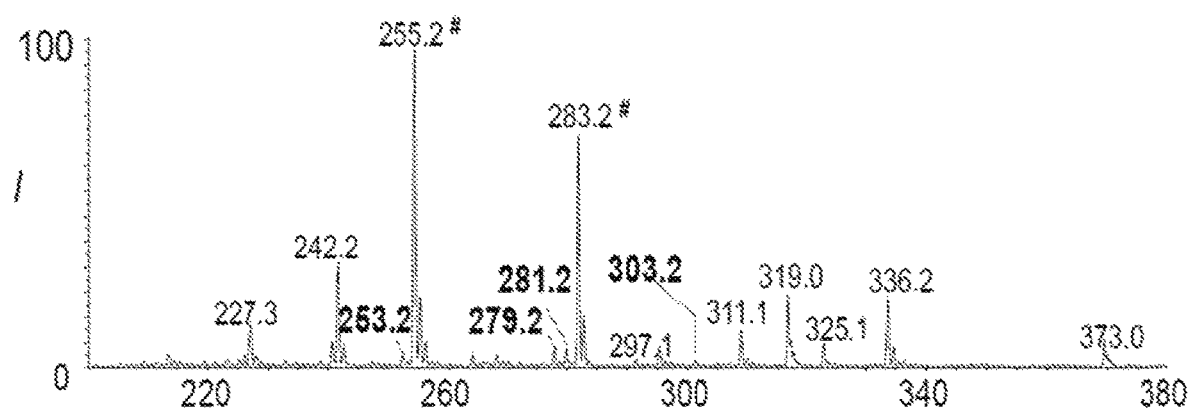
Figure 60B:
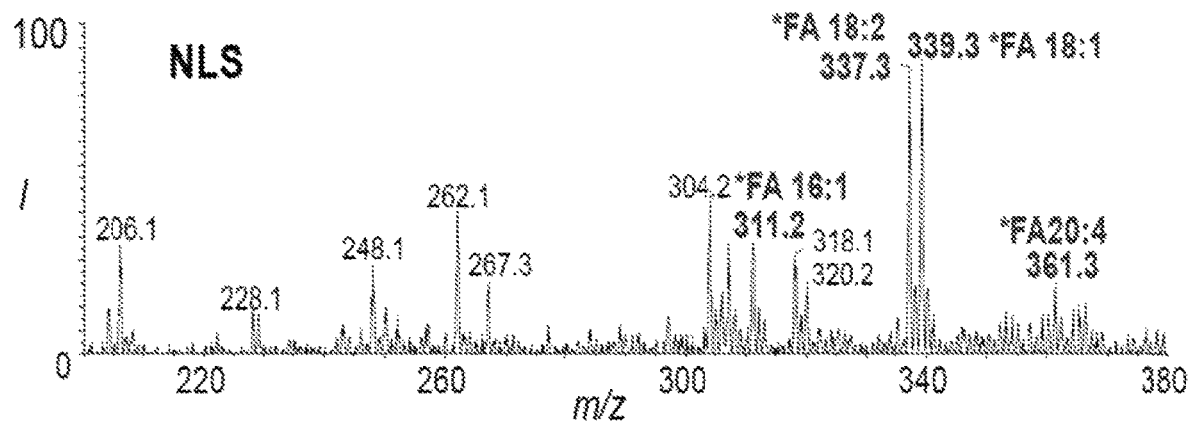

With the MS/MS incorporated in the analysis workflow, detection and identification of unsaturated FAs are more sensitive and specific as compared to MS only analysis. FIGS. 60A and B summarize such a comparison for analysis of 2 µL rat whole blood sample. A 25 time-dilution occurred for the FA extract and the most abundant peaks in the MS spectrum such as m/z 255 and 283 were in fact due to background chemical interference (annotated with "#" in FIG. 60A). The low intensity peaks at m/z 253, 279, 281, and 303 had mass matches with FA 16:1, 18:2, 18:1, and 20:4; however, without accurate mass measurement their identities were questionable. By applying a 58 Da NLS, tagged FA 16:1, 18:2, and 18:1 were clearly identified as shown in FIG. 60B. The confidence for assigning identities to these FAs is high because of the tagging and de-tagging process specific to unsaturated FAs.

Figure 61A:
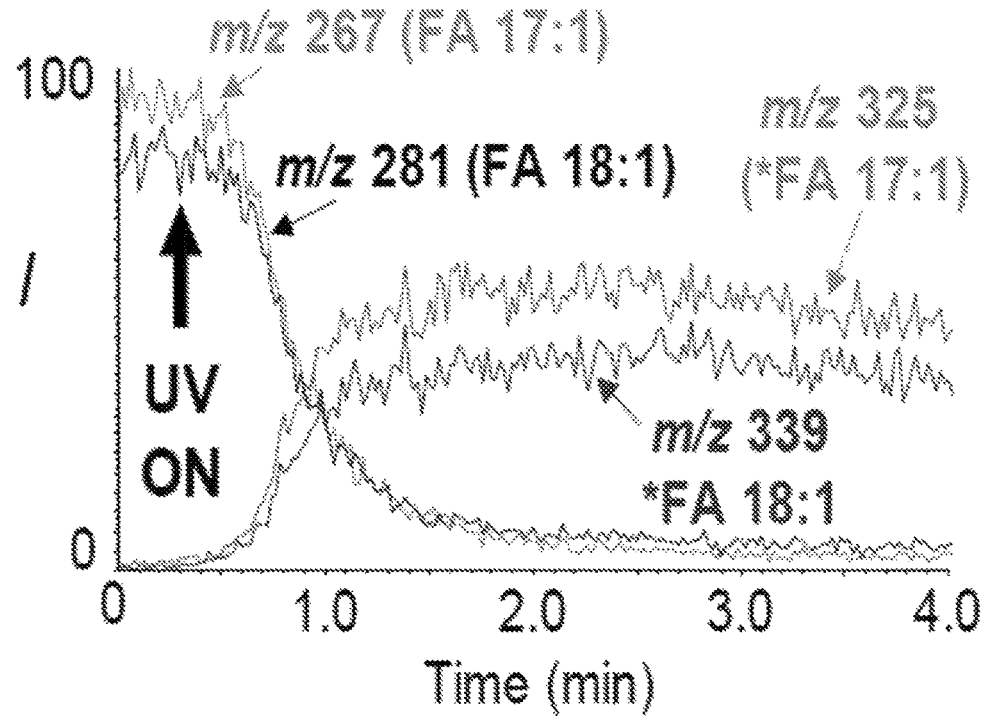
FIG. 61A shows Extracted ion chromatogram of intact and acetone-tagged FA 17:1 and FA 18:1 during photochemical reaction.
Figure 61B:
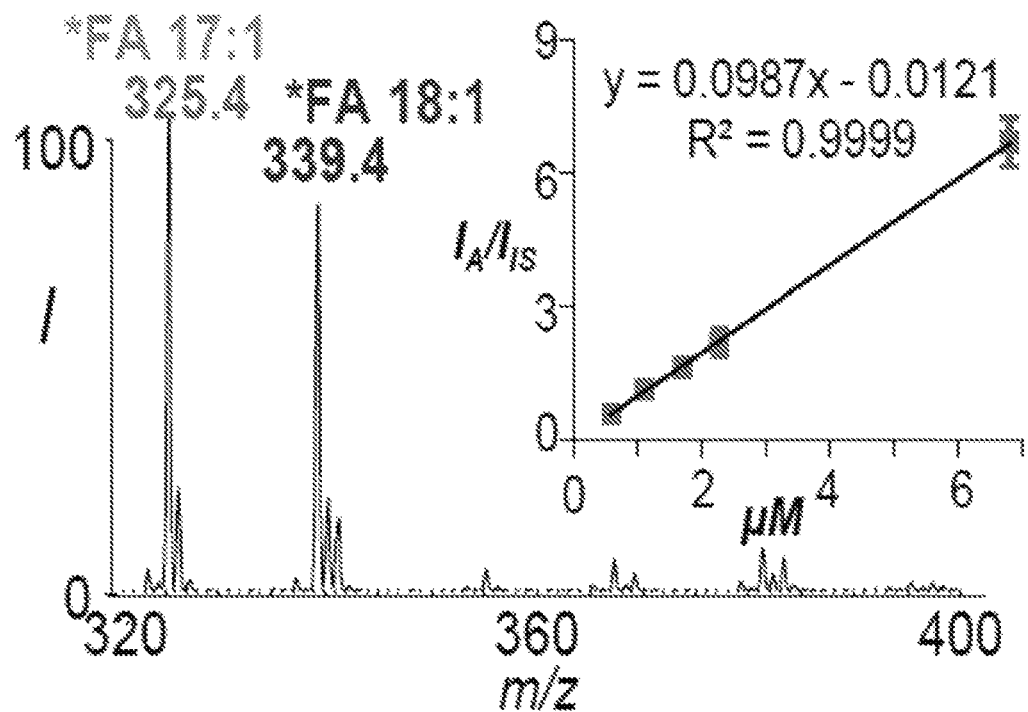
FIG. 61B shows NLS (58 Da) of tagged FA 17:1 and FA 18:1. Inset shows the calibration curve for FA 18:1(9Z) based on NLS (FA 17:1(10Z) was used as the IS).

With the achievement of selective detection for unsaturated FAs, we further evaluated its application for quantitative analysis. Limited by the quantum yield of acetone in PB reaction, tagging can only be achieved with 30-60% yield for MUFAs. Under this situation, maintaining a relatively steady tagging efficiency is important for quantitative analysis. FIG. 61A shows the extracted ion chromatograms of intact and tagged FAs for an equal molar mixture of FA 18:1(9Z) and 17:1(10Z). It is clear that both FAs reacted with similar kinetics: tagging reached a plateau within 30 s of UV irradiation and the tagged FA signals were stable during the period of analysis (10-20 minutes). Interestingly, FA 17:1(10Z) had a slightly higher reaction yield (~58%) than FA 18:1(9Z) (~50%). Based on 58 Da NLS (FIG. 61B), a calibration curve for FA 18:1(9Z) using FA 17:1(10Z) as the IS (7.5 µM) was obtained. It showed both excellent linearity ($R2=0.9999$) and sensitive detection (limit of detection, LOD=15 nM), which is comparable to conventional GC-MS analysis. Calibration curves with good linearity and detection limit were consistently obtained for MUFAs from 16 to 24 carbons (See Table 11).

TABLE 11

| Fatty Acid | Calibration curve | $R^2$ | LOD (µM) | LOQ (µM) |
|---|---|---|---|---|
| palmitoleic acid (FA 16:1) | y = 0.1007 x + 0.0262 | 0.9972 | 0.039 | 0.39 |
| linoleic acid (FA 18:2) | y = 0.1116 x + 0.0149 | 0.9948 | 0.071 | 0.36 |
| oleic acid/ cis-vaccenic acid[a] (FA 18:1) | y = 0.1274 x + 0.0324 | 0.9996 | 0.035 | 0.35 |
| arachidonic acid[b] (FA 20:4) | y = 0.2774 x − 0.0621 | 0.9961 | 0.33 | 0.66 |
| α-linoleic acid (FA 18:3) | y = 0.1887 x − 0.0416 | 0.9912 | 0.10 | 0.31 |

The molar composition of FA 18:1 was pre-determined to be 91.5% oleic acid and 8.5% cis-vaccenic acid, and used to make standard solutions to prepare the calibration curve for FA 18:1. Solvent conditions for FA 16:1, FA 18:1, and FA 18:2 is 5% ethanol in acetone/H2O. Solvent conditions for FA 18:2, 18:3, and 20:4: 40% ethanol in acetone/H2O.

Figure 61C:
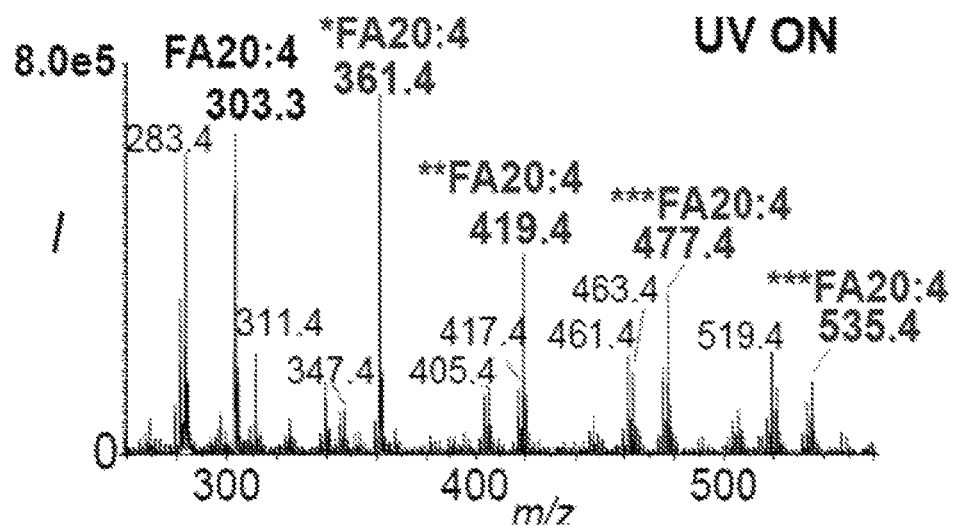
FIGS. 61C and 61D show photochemical reaction MS spectrum of FA 20:4 (5Z, 8Z, 11Z, 14Z) using different reaction solvent conditions.
Figure 61D:
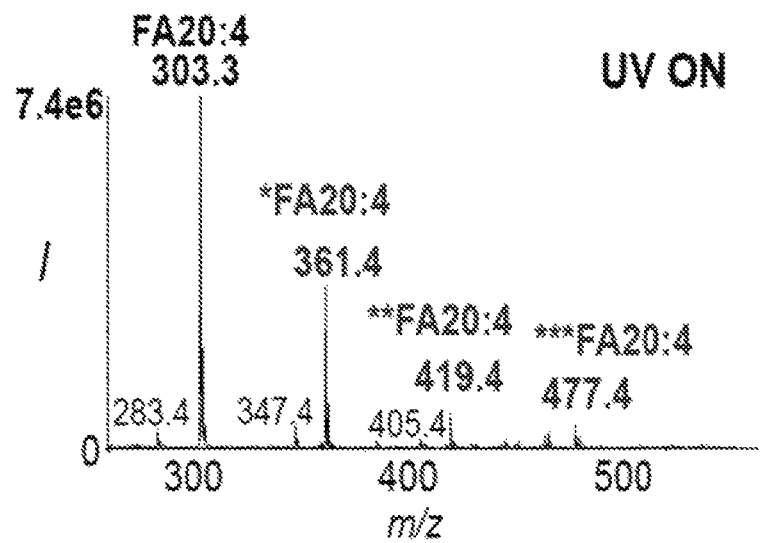
Figure 66A:
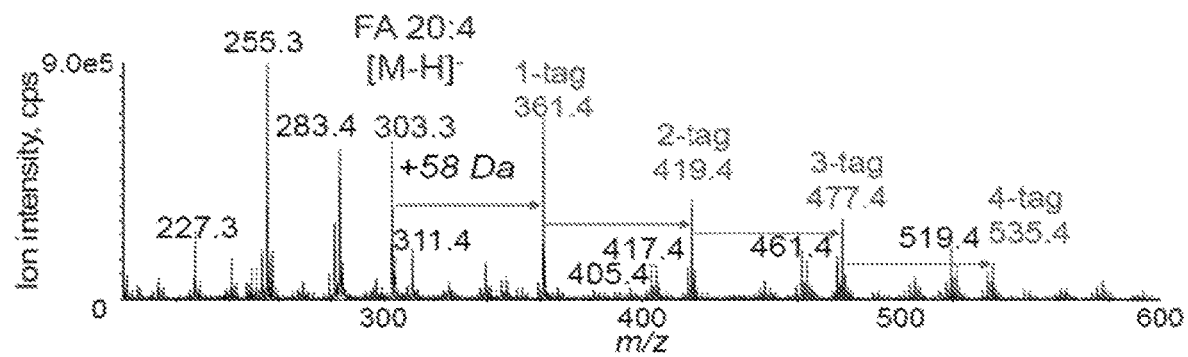
FIGS. 66A-C show photochemical tagging of arachidonic acid (FA 20:4 (5Z, 8Z, 11Z, 14Z)) by PB reaction under different solvent conditions.
Figure 66B:
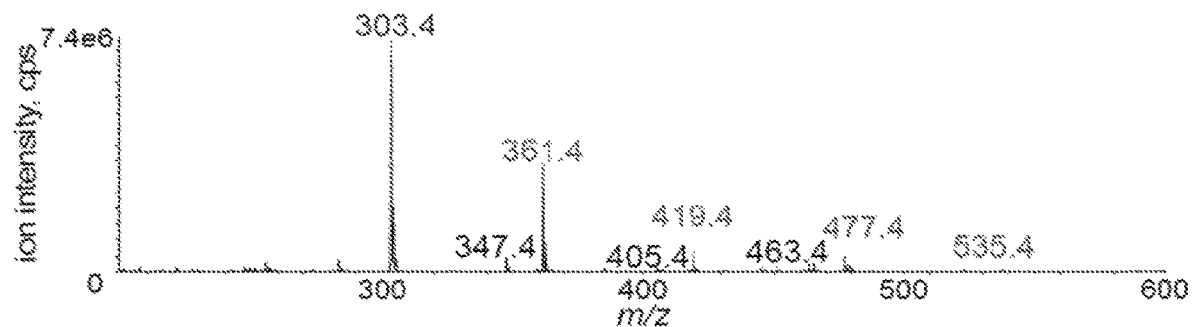
Figure 66C:
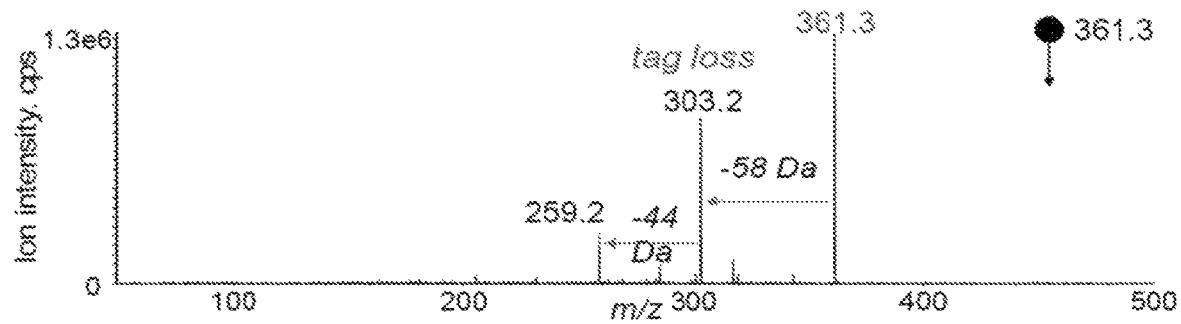
Figure 67:
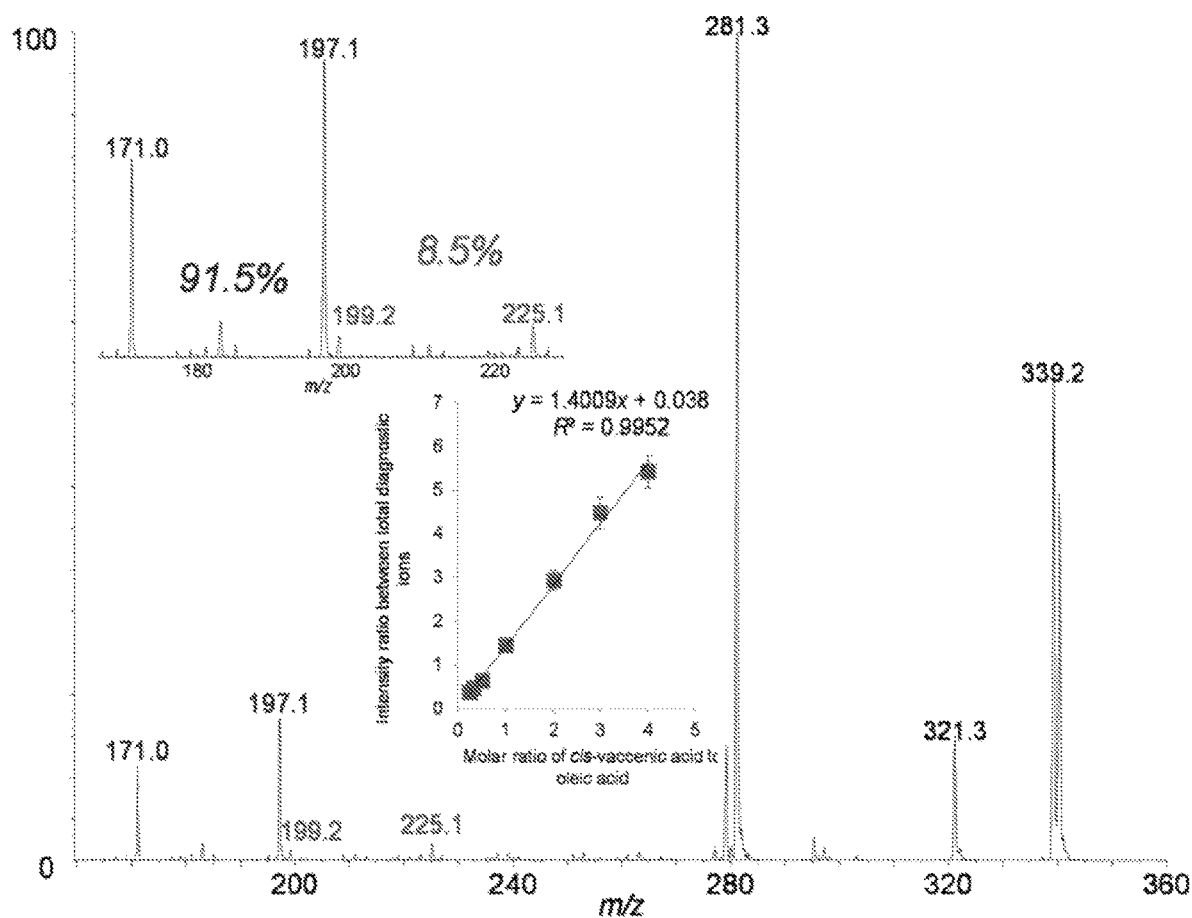
FIG. 67 shows determination of FA 18:1 C=C isomer composition through the relative intensities of the two diagnostic ions of each isomer. Insets are a zoomed-in view of the mass range for diagnostic ions and calibration curve that converts diagnostic ion intensity ratio to isomer composition.

Acetone/water (50/50, v/v) is a good reaction solvent system for tagging MUFAs due to its fast reaction kinetics. This condition, however, leads to a sequential tagging of multiple C═Cs in PUFAs. For instance, arachidonic acid (FA 20:4(5Z, 8Z, 11Z, 14Z)) has four C═Cs and therefore four acetone-tagged products (at m/z 361, 419, 477, 535) could be formed as shown in FIG. 61C. This excessive degree of reaction, however, is undesirable since it reduces the amount of singly-tagged products, which is most useful for structural identification. Moreover, side reactions, e.g. Norrish Type I reactions (forming ions at m/z 347.4, 405.4, 463.4, 519.4), were found to be more competitive, which interfered the detection and quantitation of unsaturated FAs. Ethanol has been shown to slow down PB reactions through photo-reduction of electronically excited acetone. We found that addition of ethanol into the reaction solvent system, i.e., ethanol/acetone/water (40/30/30, v/v/v), maximized the single-acetone tagged products for PUFAs. As shown in FIG. 61D, the single acetone tagged product of FA 20:4 (at m/z 361) accounted for ~80% of all tagged products and its absolute intensity increased about 5 times as compared to FIG. 61C where acetone/water (50/50) was used. MS2 CID of this product (m/z 361) showed a dominant tag loss and a small sequential 44 Da loss commonly observed for PUFAs (FIG. 66). Quantitation of FA 20:4 using FA 17:1(10Z) as the IS was achieved via 58 Da NLS with good linearity and an LOD of 80 nM obtained with a solvent condition of ethanol/acetone/water (40/30/30, v/v/v).

Figure 68A:
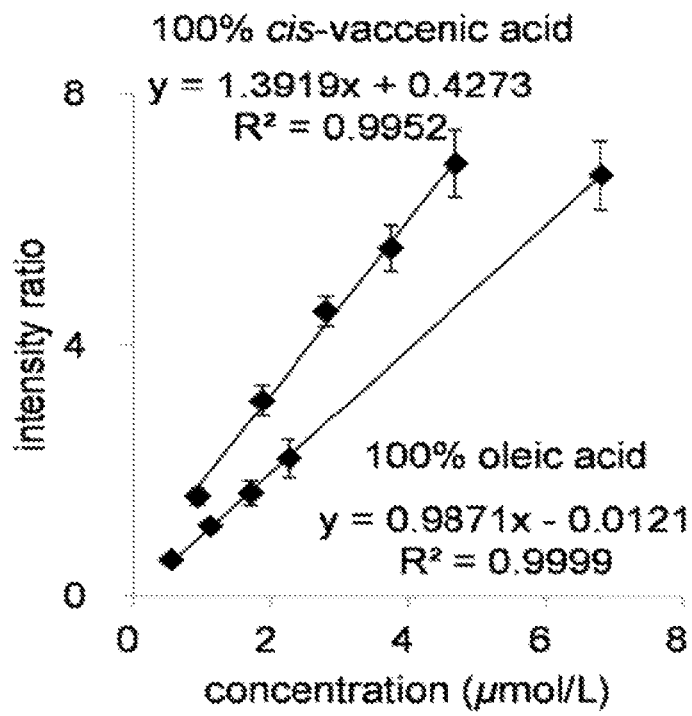
FIG. 68A shows calibration curves for pure oleic acid (FA 18:1 (9Z)) and cis-vaccenic acid (FA 18:1 (11Z)). Note that these two calibration curves do not overlay with each other because tagged products of each isomer show different degrees of tag loss.
Figure 68B:
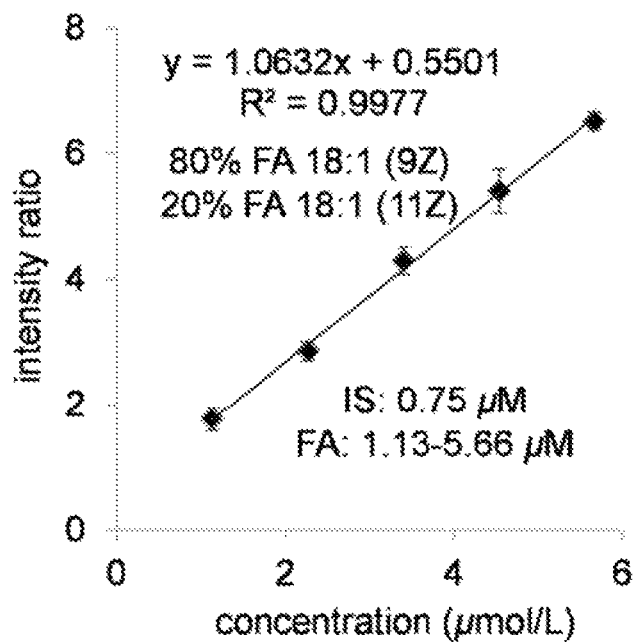
FIG. 68B shows a calibration curve of a mixture of 80% FA 18:1 (9Z) and 20% FA 18:1 (11Z).

In a mammalian lipidome many unsaturated FAs exist as a mixture of C═C location isomers, which calls for a powerful analytical method to achieve quantitation for each C═C location isomer. Through photochemical tagging and 58 Da NLS, the total amount of C═C location isomers can be quantified in a more sensitive fashion. The molar ratio of C═C location isomers can be obtained using our previously established method, by measuring C═C diagnostic ion intensity ratios from PB-MS/MS data. Quantitation for each isomer can then be achieved by combining the total quantity with the molar ratio information of C═C location isomers. This approach was found to be successful for experiments performed on a series of mixtures of FA 18:1 Δ9 and Δ11 isomers. It is worth noting that C═C location isomers can have different degrees of tag loss under the same CID conditions. Therefore, the calibration curves for pure isomers do not overlay with each other (FIG. 68). This phenomenon suggests that in order to achieve good accuracy for the quantitation of a mixture of FA C═C location isomers, calibration solutions should be prepared using the same isomeric composition as detected from the real sample.

Unsaturated FA Analysis in Human Plasma

Figure 62A:
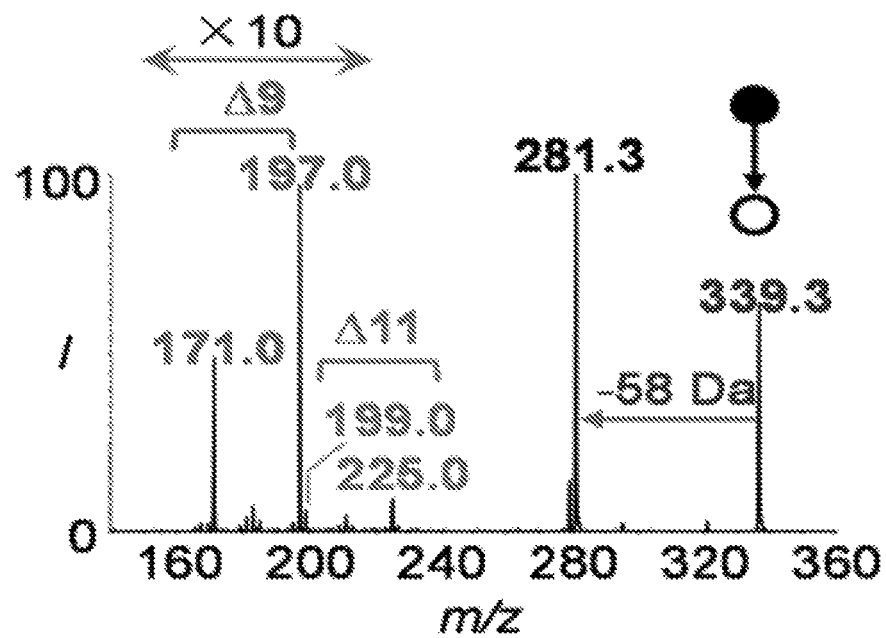
FIGS. 62A-E show analysis of FA C=C location isomers from human plasma.
Figure 62B:
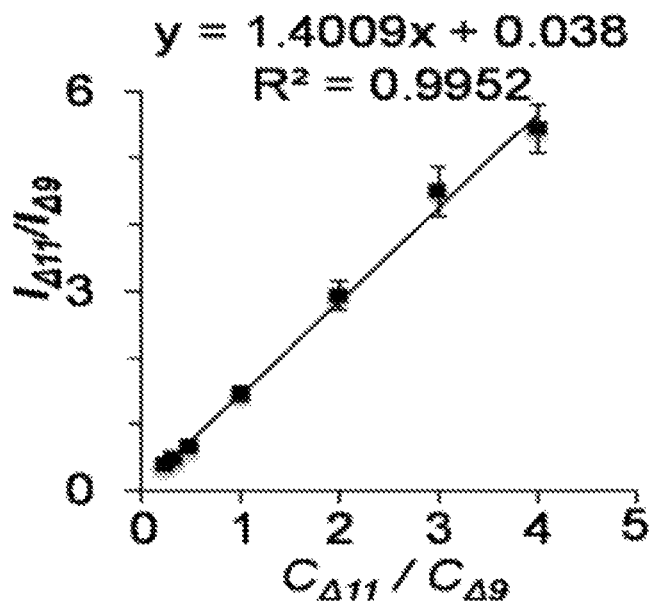
Figure 69A:
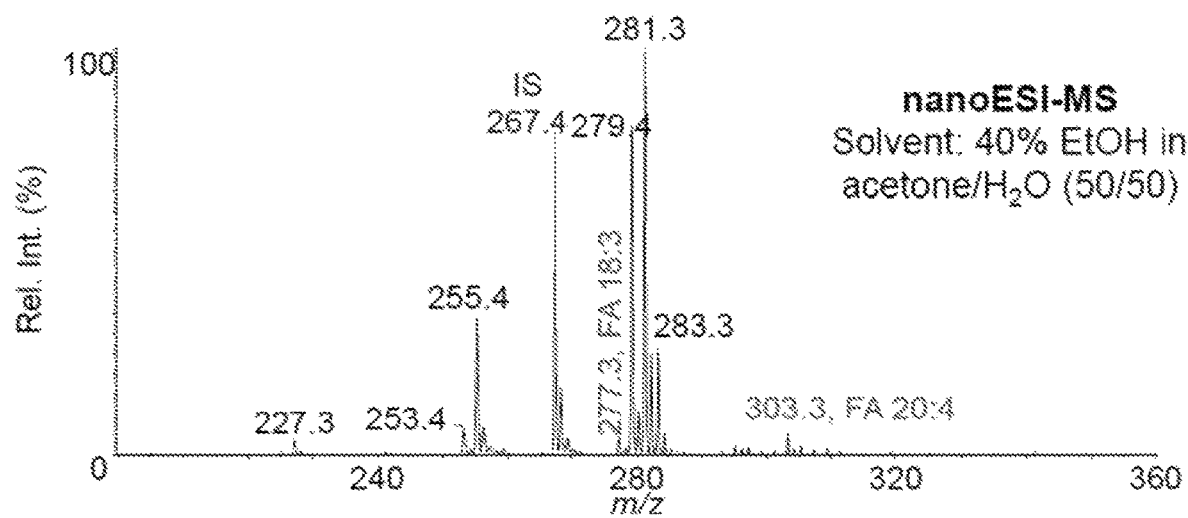
FIGS. 69A-B show analysis of PUFAs (FA 18:3 and FA 20:4) in human plasma.
Figure 69B:
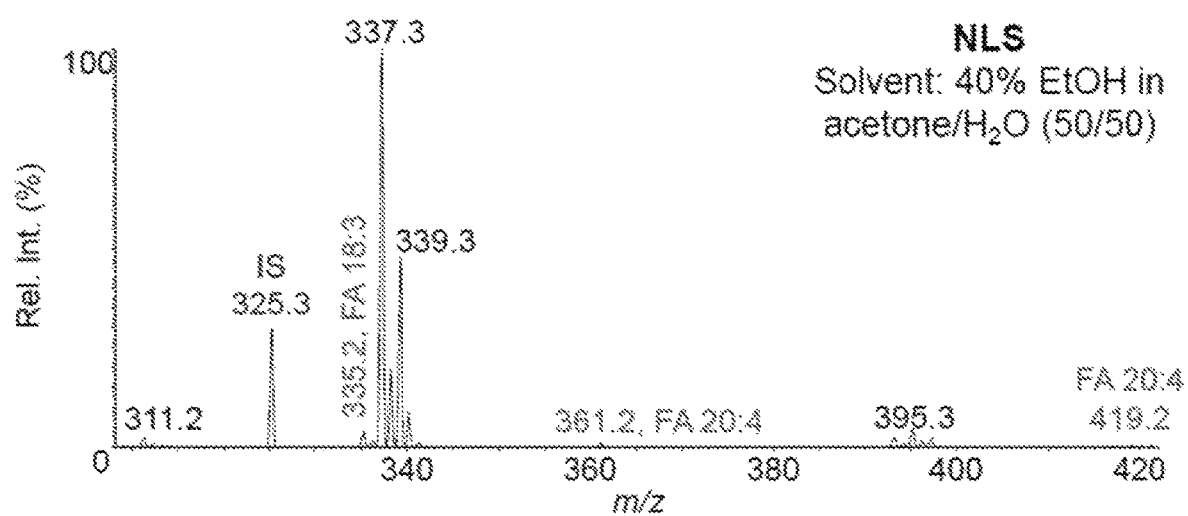
Figure 70A:
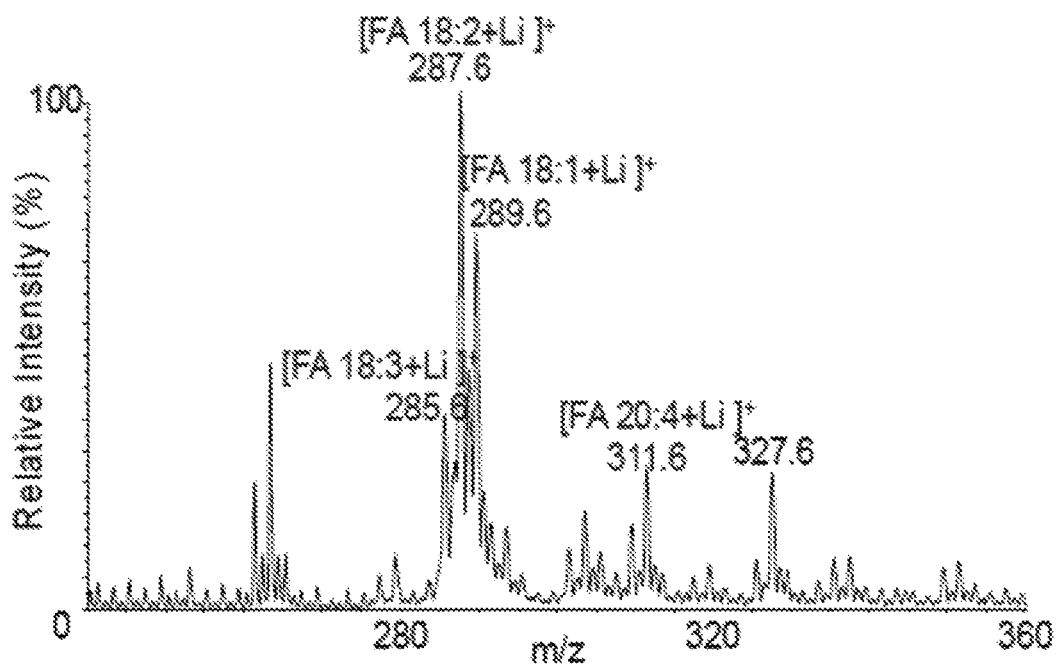
FIGS. 70A-D show where FA 18:3 in human plasma is a mixture of ω-3 (FA 18:3 (9Z, 12Z, 15Z), α-linoleic acid, ALA) and ω-6 (FA 18:3 (6Z, 9Z, 12Z), γ-linoleic acid, GLA) isomers. Since FA 18:3 is a PUFA, no abundant diagnostic ions in MS/MS can be produced after tagging, due to the more dominant 44 Da loss (in negative ion mode). We therefore made the analysis of FA 18:3 possible by +nanoESI-MS by adding lithium chloride (5 mM). Abundant diagnostic ions can be produced accordingly, and the 44 Da neutral loss is suppressed.
Figure 70B:
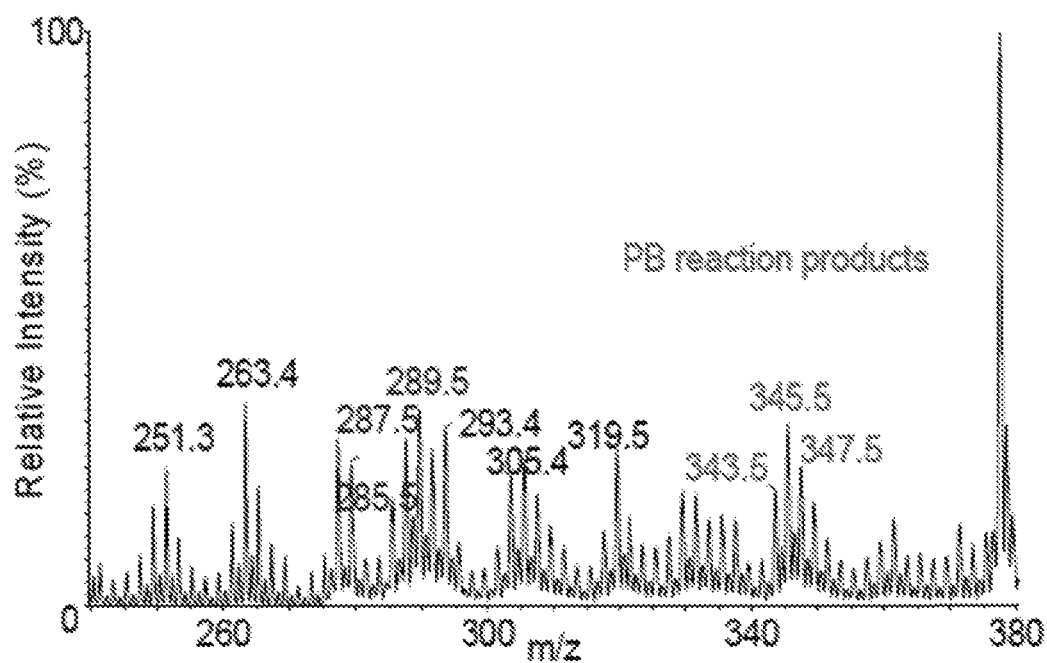
Figure 70C:
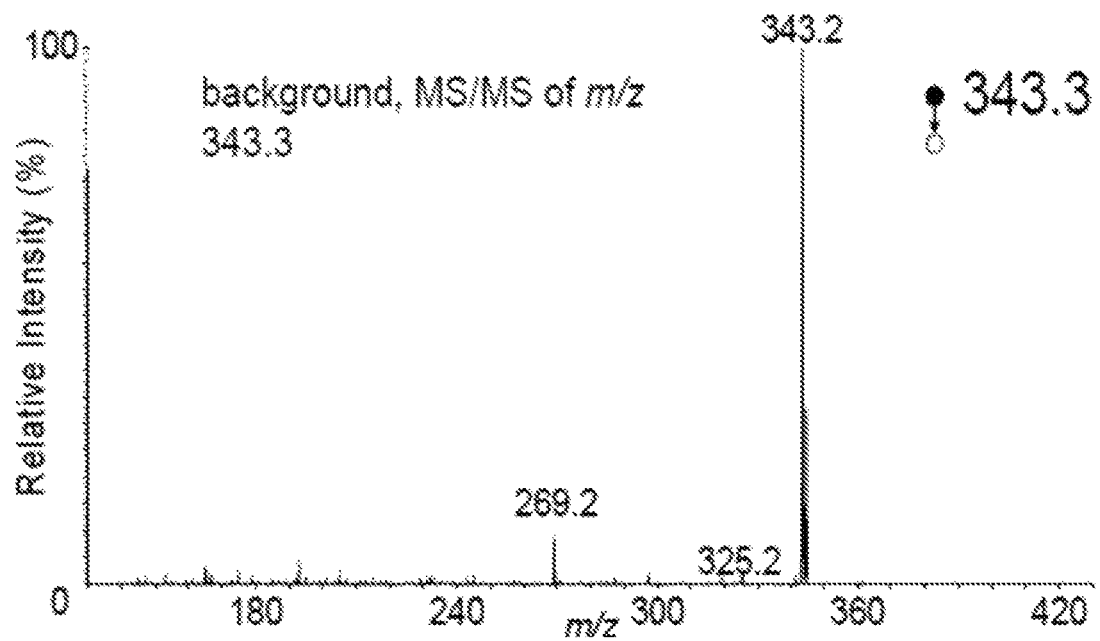
Figure 70D:
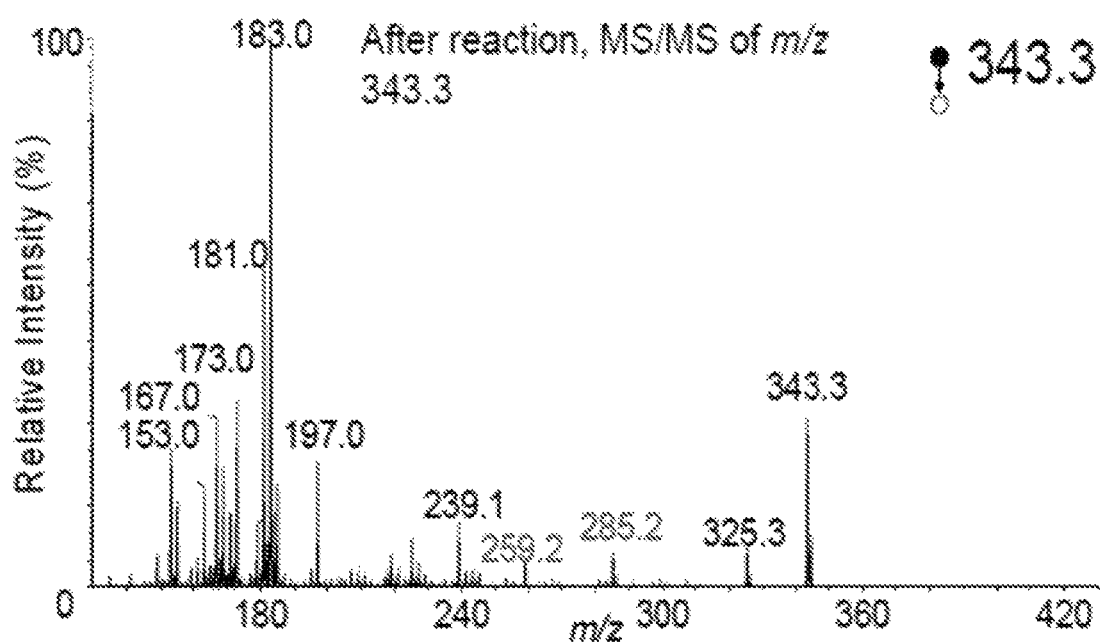

The method of photochemical tagging followed by 58 Da NLS was applied for FA analysis in human plasma (20 µL). FA 17:1(10Z) (7.5 µM) was added to the extract as an IS. FA profile from nanoESI-MS is shown in FIG. 59D, while the unsaturated FA profile can be found from 58 Da NLS (FIG. 59F). Prior to quantitative study, PB-MS/MS was applied to each individual unsaturated FAs (single acetone tagged FAs) in order to determine C═C locations and the existence of any C═C location isomers. We found that FA 16:1(9), 18:2 (9, 12), and 20:4 (5, 8, 11, 14) existed as pure forms, with the numbers in parenthesis indicating the C═C locations. Quantitation of these FAs was then obtained from 58 Da NLS and determined as follows: 28.9±1.6 µM of FA 16:1, 193±20 µM of FA 18:2, and 18.2±2.3 µM of FA 20:4 (FIG. 69). PB-MS/MS revealed that FA 18:1 and FA 18:3 consisted of C=C location isomers. As shown in FIG. 62A, MS/MS CID of tagged FA 18:1 (at m/z 339) produced two pairs of diagnostics ions at m/z 171, 197 and m/z 199, 225. Detection of these diagnostic ions clearly suggested the existence of C=C location isomers at Δ9 and Δ11, respectively. Based on C=C diagnostic ion intensity ratio (Δ11/Δ9=0.0662) and the established molar ratio calibration curve of the two isomers (FIG. 62B), FA 18:1 was found to consist of 91.5% Δ9 and 8.5% Δ11 isomers.

Figure 62C:
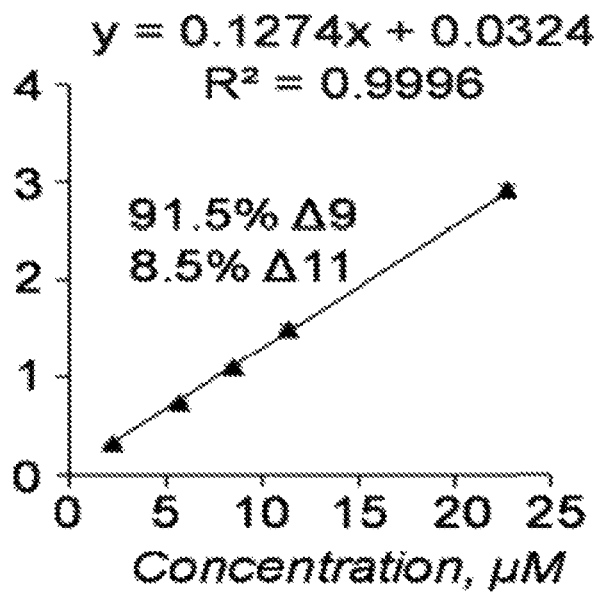
Figure 62D:
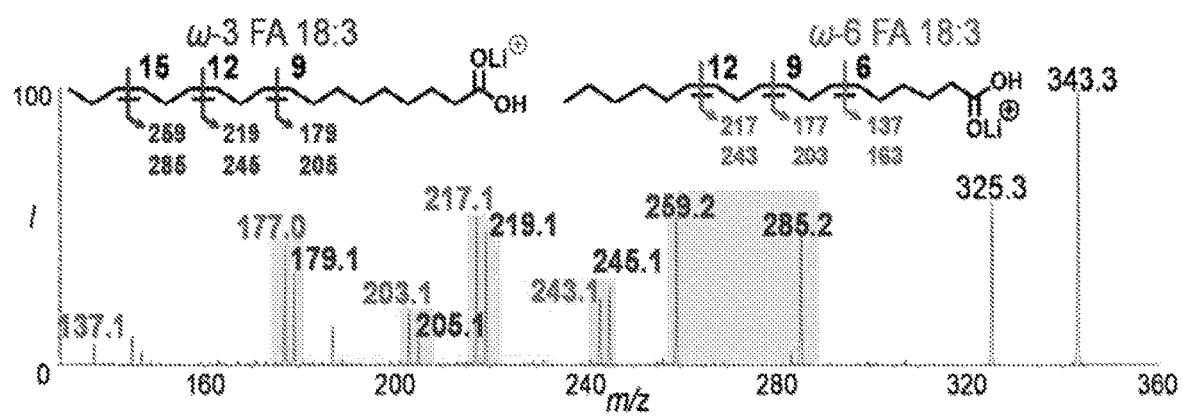
Figure 62E:
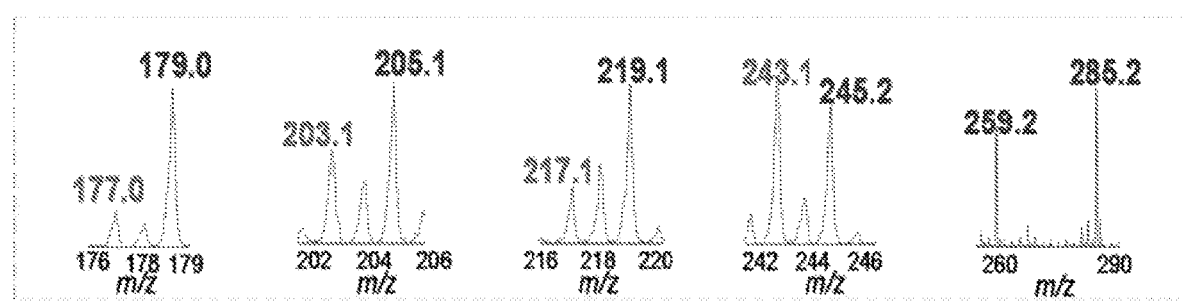
Figure 71:
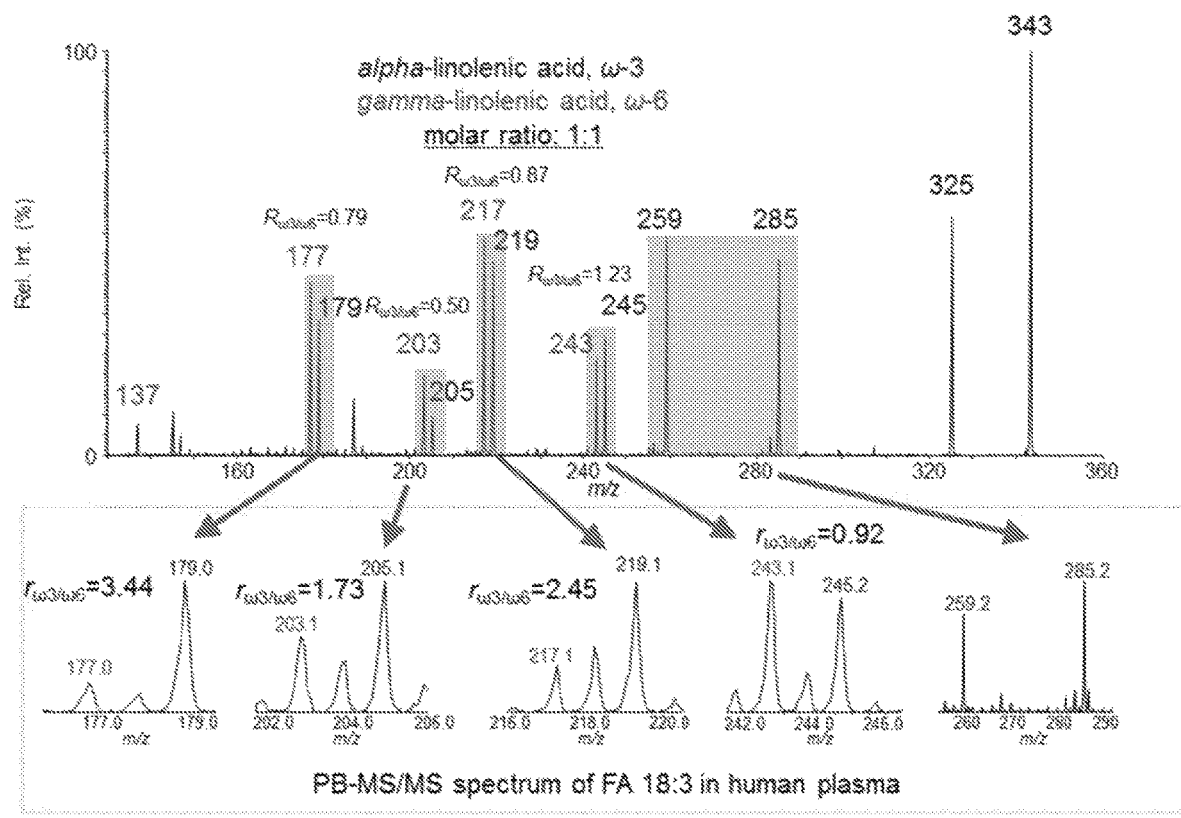
FIG. 71 shows CID spectrum of a 1:1 mixture of FA 18:3 ω-3/ω-6 isomers. Peaks in red belong to the ω-6 isomer, and peaks in blue belong to the ω-3 isomer. The same sets of peaks are zoomed in below to show the presence of FA 18:3 ω-3/ω-6 isomers, whose relative intensities were used for quantitation.

A set of calibration solutions consisting of the same composition of C=C location isomers but varying in total concentrations was prepared and used for producing the 58 Da NLS calibration curve as shown in FIG. 62C. The total concentration of FA 18:1 was found to be 276±36 corresponding to 253±33 µM Δ9 isomer and 23±3 µM Δ11 isomer. PB-MS/MS showed that FA 18:3 was a mixture of ω-3 (C=C at Δ9, 12, 15) and ω-6 (C=C at Δ6, 9, 12) isomers (FIG. 70). Limited by its relatively low abundance (7.5±1.5 µM) in human plasma, the accurate determination of the molar ratio between these two isomers was difficult. Nevertheless, by comparing the C=C diagnostic ions observed from a 1:1 (molar ratio) mixture of FA 18:3 ω-3 and ω-6 standards (FIG. 62D) to those from human plasma (FIG. 62E), ω-3 isomer was found to be the more abundant than ω-6 isomer (FIG. 71). This finding is consistent with previous reports in the literature.

Figure 63A:
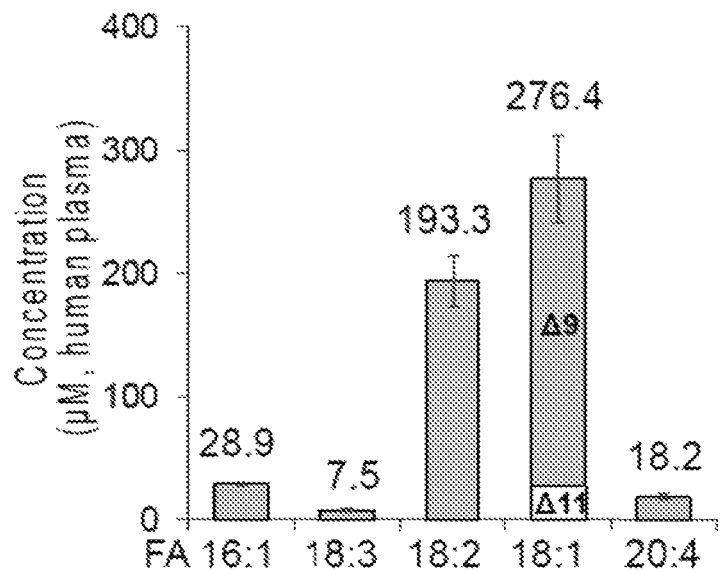
FIG. 63A shows quantitation of unsaturated FAs in human plasma.
Figure 72A:
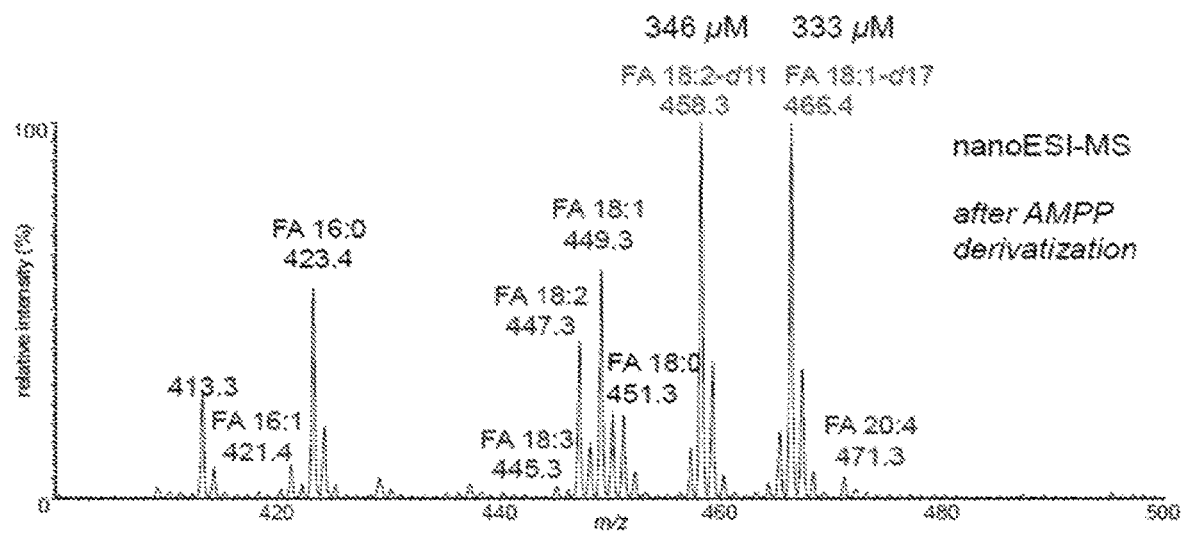
FIGS. 72A-B show quantitation of unsaturated FAs in human plasma using the AMPP method.
Figure 72B:
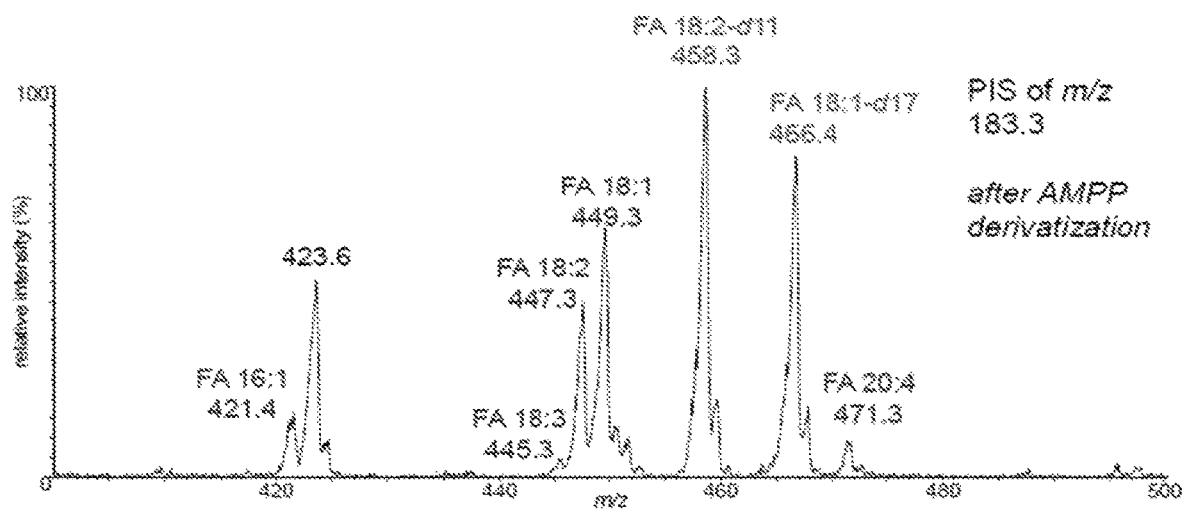

The quantitative data of six major species of unsaturated FA in human plasma are summarized in FIG. 63A. The charge-switch method reported in the literature was also applied to the same set of human plasma sample for cross-validation. The two methods provided consistent quantitation measurements within 10% relative error (FIG. 72). The online photochemical tagging coupled with 58 Da NLS method however offered distinct advantage of confident identification and quantitation of unsaturated FAs and their C=C location isomers. For instance, FA 18:1 C=C location isomers was not reported by charge switch methods, likely due to the low relative concentration (<10%) of the Δ11 isomer in FA 18:1.

Quantitation of Unsaturated FAs in Normal and Cancerous Human Prostate Cells

Quantitative monitoring of changes of metabolites, such as fatty acids, has been increasingly used to aid studies in cancer biology. It has been shown that FA profiles change significantly from normal to cancel cells due to altered cell metabolism. However, the identities of unsaturated FAs are typically not determined at the level of C=C location specificity; therefore, the changes of individual C=C location on isomers are not known. By using our method of photochemical tagging followed by 58 Da NLS, quantitation with high molecular specificity for unsaturated FAs could be achieved. Normal (RWPE1) and cancerous human prostate cells (PC3 cells) were used as model systems for a comparative study. The major FA species were found to include FA 16:0, 16:1, 18:0, 18:1 and 18:2 (FA profiles of the two cell lines summarized in FIG. 73). FA 16:1 and FA 18:2 were determined to be pure using our method, with C=C located at Δ9 and Δ9,12, respectively, for both cell lines, while FA 18:1 consisted of Δ9 and Δ11 isomers (FIG. 74).

Figure 63B:
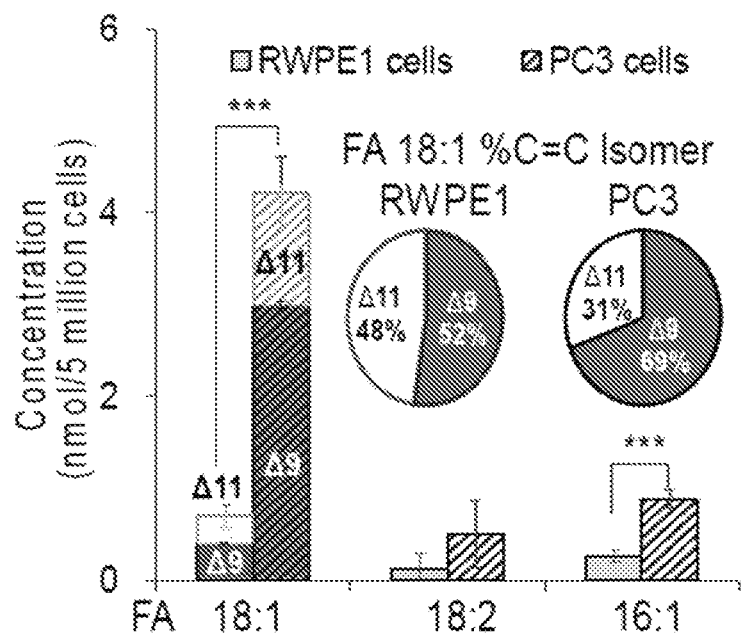
FIG. 63B shows a comparison of the amounts of major unsaturated FAs in RWPE1 and PC3 cells. (d) Amounts of Δ9 and Δ11 isomers of FA 18:1 in RWPE1 and PC3 cells.

Significantly elevated quantity of unsaturated FAs (16:1, 18:1, and 18:2) were detected in prostate cancer cells (PC3, FIG. 63B), consistent with literature reports. Specifically, as the most abundant unsaturated FA species in both cell lines, the total amount of FA 18:1 in PC3 cells is 6.0±1.7 times of that in RWPE1 cells (FIG. 63C). FA 16:1 and FA 18:2 also increased by 3.4±0.5 and 3.7±0.7 times in PC3 cells as compared to RWPE1 cells, respectively. Interestingly, although the absolute quantity of Δ9 and Δ11 isomers of FA 18:1 both increased in PC3 cells, the relative contribution of the Δ11 isomer decreased in FA 18:1. As shown in the pie charts of FIG. 63B inset, % composition of the Δ11 isomer decreased from 48.0±1.3% in RWPE1 cells to 31.0±0.9% in PC3 cells. The Δ9 and Δ11 isomers of FA 18:1 are biosynthesized from FA 16:0 (palmitic acid), however with the opposite sequences of chain elongation and desaturation. The significant changes in both absolute quantities and relative concentrations of FA 18:1 C=C location isomers from normal to cancerous prostate cancer cells indicate variations in biosynthesis or metabolism pathways of FA 18:1 between the two cell lines.

A new method is developed to enable a fast and sensitive quantitation of unsaturated FAs and their C=C location isomers, taking advantage of the combination of a in-solution photochemical tagging and online tandem MS (58 Da NLS). This method is compatible with shotgun lipidomics workflow for analysis of complex FA mixtures from biological samples. Using this method, quantitation of unsaturated FAs was achieved for human plasma and cell lines with performance comparable to traditional GC-MS and charge-switch derivatization methods. More importantly, FA C=C location isomer analysis can now be performed with high confidence. Information such as composition and relative abundancies of the unsaturated FA isomers, as demonstrated with FA 18:1 and FA 18:3 ω-3/ω-6, respectively, can now be readily obtained for biological studies. The application of this method for disease study is expected to provide another level of understanding of the biological processes of regulating the FA isomers, which might well lead to the discovery of the lipid biomarkers.

Fatty acid standards, rat whole blood, and human plasma sample were purchased from commercial vendors. FA extractions were performed following LIPID-MAPS protocol (http://www.lipidmaps.org/protocols/PP0000005301.pdf). A low-pressure mercury lamp with a primary emission band at 254 nm was placed 1.0 cm away from the nanoESI emitter to initiate photochemical reactions. All MS experiments were performed on a 4000 QTRAP triple quadrupole/linear ion trap mass spectrometer (Sciex).

Chemicals and Materials

All FAs and deuterium-labeled FA standards were purchased from Cayman Chemical (Ann Arbor, Mich.) and used without further purification. Pooled human plasma (Li Heparin as anticoagulant) was purchased from Innovative Research (Novi, Mich.). Other chemicals were purchased from Sigma Aldrich (St. Louis, Mo.).

Cell Culture

All cells were cultured in 37° C. moisture incubator with 5% CO2 supply. Prostate cancer PC3 cells were maintained in F-12K medium supplemented with 10% fetal bovine serum (FBS), 100 units/mL penicillin and 100 µg/mL streptomycin. Normal prostate epithelial RWPE1 cells were cultured in Keratinocyte Serum Free Medium supplemented with 30 µg/ml bovine pituitary extract and 0.2 ng/ml human recombinant epidermal growth factor (Invitrogen, Carlsbad, Calif.).

Protocols for the Extraction of FAs from Human Plasma and Cells

The following method was used to extract FAs from human plasma:

Add 30 µL dPBS to 20 µL human plasma in a 16 mm×125 mm glass tube, followed by addition of 60 µL methanol. The mixture was then acidified with 1 M HCl to reach a final concentration of 25 mM.

After the addition of 0.1 mL isooctane, the sample is vortexed and centrifuged at 3000 g for 1 minute to separate layers. The top layer is removed and transferred to a 10 mm×75 mm glass tube.

Repeat step 2 for one time.

Combine the organic layers. Dry down the extract under vacuum or using nitrogen flow.

The following method was used to extract FAs from cells:

Five million cells in 1 mL $H_2O$ in a 16 mm×125 mm glass tube was centrifuged for 2 minutes at 3000 rpm, after which the upper aqueous layer was discarded.

Into the cells was added 300 µL dPBS, followed by addition of 600 µL methanol. The cell suspension was acidified with HCl to reach a final concentration of 25 mM.

After the addition of 1 mL isooctane (2,2,4-trimethylpentane), the sample was vortexed and centrifuged at 3000 g for 1 minute to separate layers. The top layer was removed and transferred to a 10 mm/75 mm glass tube.

Repeat step 3.

Combine the organic layers. Dry down the extract under vacuum or nitrogen flow.

Photochemical Tagging and Tandem MS Analysis

Figure 64:
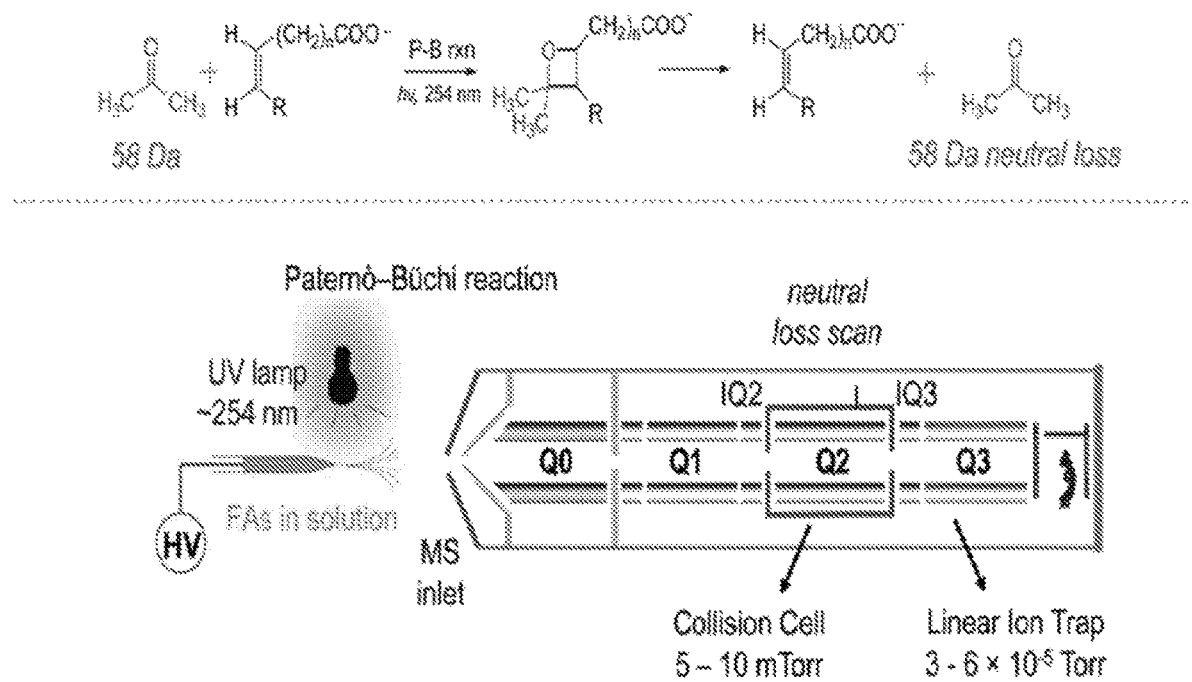
FIG. 64 shows the reaction scheme of PB reaction and retro-PB reactions during MS/MS at the top. The bottom of FIG. 64 shows the experimental setup coupling PB reaction with nanoESI-MS/MS on an AB Sciex Qtrap 4000 MS for the quantitation of unsaturated FAs by NLS.

For quantitation, MUFAs were dissolved in 5% ethanol in acetone/water (50/50 v/v) prior to MS analysis, whereas PUFAs were dissolved in 40% ethanol in acetone/water (50/50 v/v). To facilitate FA detection by negative mode nanoESI-MS, 0.5% (v/v) NH4OH (28%-30% as NH3) was added into all FA solutions. NanoESI tips of ~10 µm outer diameter were pulled using borosilicate glass capillary tips (1.5 mm o.d. and 0.86 mm i.d.) by a P-1000 Flaming/Brown micropipette puller (Sutter Instrument, Novato, Calif., USA). Lipid solution was loaded from the back opening of the borosilicate glass tip. A stainless steel wire was inserted to the tip to serve as the electric contact, with the nanoESI tip aligned with the MS sampling orifice. To initiate photochemical tagging via PB reactions1, A low-pressure mercury (LP-Hg) lamp (254 nm, Model No.: 80-1057-01, BHK, Inc., CA, USA) was placed 1.0 cm from the nanoESI emitter. All MS experiments were performed on a 4000 QTRAP triple quadrupole/linear ion trap (LIT) hybrid mass spectrometer (Applied Biosystems/Sciex, Toronto, Canada), and its schematics is shown in FIG. 64. The instrument parameters were as follows: ESI voltage, −1200-1800V; curtain gas, 10 psi; interface heater temperature, 40° C.; declustering potential: −20 V. For MS/MS analysis of selected PB reaction products, the isolation width was set to 1.5 Th, and the precursor intensity was kept at around 4×106 counts. The ion injection time was 10-200 ms. The collision energy (CE) used for PB reaction products of FAs was optimized to be 35 V (beam-type CID) or 50 a.u. (resonance trap CID). For neutral loss scan (NLS), a CE of 35 V was used.

Analysis of Free FAs in Human Plasma

Figure 65:
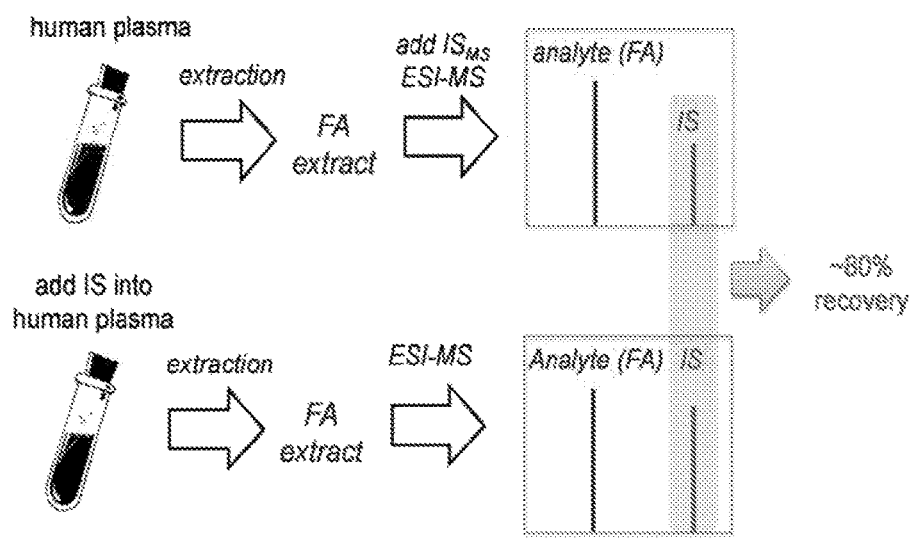
FIG. 65 illustrates the principle to estimate the recovery of FAs in human plasma (using a LIPID-MAPS FAs extraction protocol).

FA extraction efficiency was estimated (using isotope-labelled internal standards) according to the scheme shown in FIG. 65. Results are shown in table 12.

TABLE 12

| stds added before extraction | ratio (D/H) | stds added after extraction | ratio (D/H) | Recovery (%) |
|---|---|---|---|---|
| C16:1-d14/C16:1 | 6.43 | C16:1-d14/C16:1 | 8.09 | 79.53 |
| C18:1-d17/C18:1 | 0.84 | C18:1-d17/C18:1 | 1.05 | 80.19 |
| C18:2-d11/C18:2 | 1.27 | C18:2-d11/C18:2 | 1.62 | 78.19 |
| C20:4-d8/C20:4 | 1.61 | C20:4-d8/C20:4 | 2.00 | 80.51 |

Tagging conditions for PUFA's were optimized as shown in FIG. 66. FA C=C isomer composition was determined as follows. The mass-to-charge ratios of diagnostic ions can be used to accurately determine the C=C location in each FA C=C isomer. In addition, our recent study has shown that the total intensities of diagnostic ions can also be used to quantify lipid C=C isomers. FIG. 66 shows a CID mass spectrum of PB products of FA 18:1 (m/z 339.3) in pooled human plasma, whereby the two pairs of diagnostic ions (m/z 171, 197 and m/z 199, 225) clearly indicate the presence of two FA 18:1 C=C isomers (Δ9 and Δ11). By inputting the ratio between the two pairs of diagnostic ions into the calibration curve (inset in FIG. 66), we determined that FA 18:1 in the pooled human plasma consists of 91.5% Δ9 isomer and 8.5% Δ11 isomer.

Low-abundance PUFAs and their isomers were quantitated as shown in FIGS. 69-72.

Cross-validation was performed by charged-switched AMPP derivatization of FAs. AMPP derivatization has been developed as an effective method to improve the detection sensitivity for fatty acids. Here in this study, we employed this strategy for the quantitation of fatty acids in human plasma to validate the developed PB/NLS method, using linoleic acid-d11 and oleic acid-d17 as the internal standards. The isotopologue has the same ionization efficiency as the corresponding fatty acid. After derivatization, all fatty acids and internal standards can be detected with high sensitivity by positive nanoESI-MS, and each AMPP-derivatized fatty acid produce a characteristic ion at m/z 183.3 upon CID (FIG. 70). By comparing the peak ratio between the fatty acid and its corresponding isotopologue in the precursor ion scan (PIS) spectrum, the concentrations of FA 18:1 and FA 18:2 in human plasma were determined to be 254 µM and 180 µM, consistent with the results obtained by the PB/NLS method (276.4±35.6 µM and 193.3±20.3 µM).

Figure 73A:
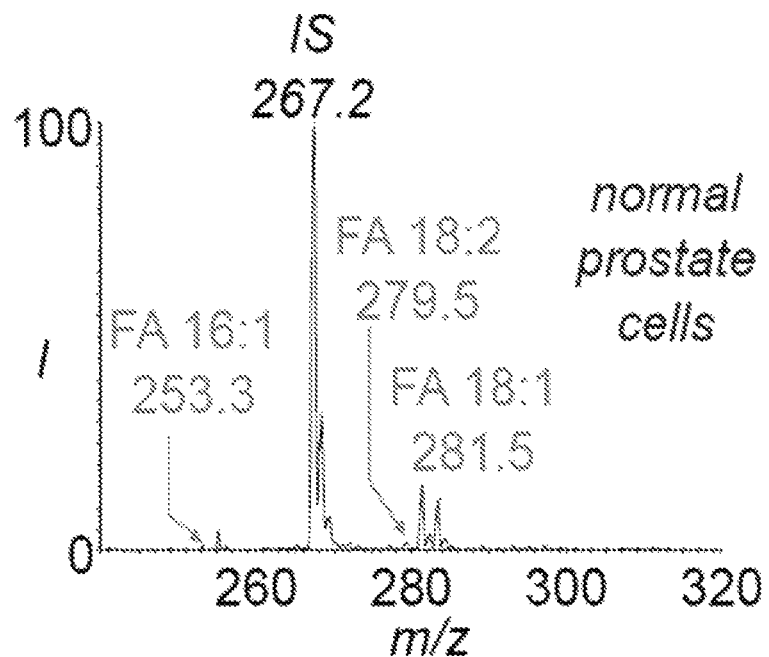
FIGS. 73A-B show FA profiles of normal and cancerous prostate cells.
Figure 73B:
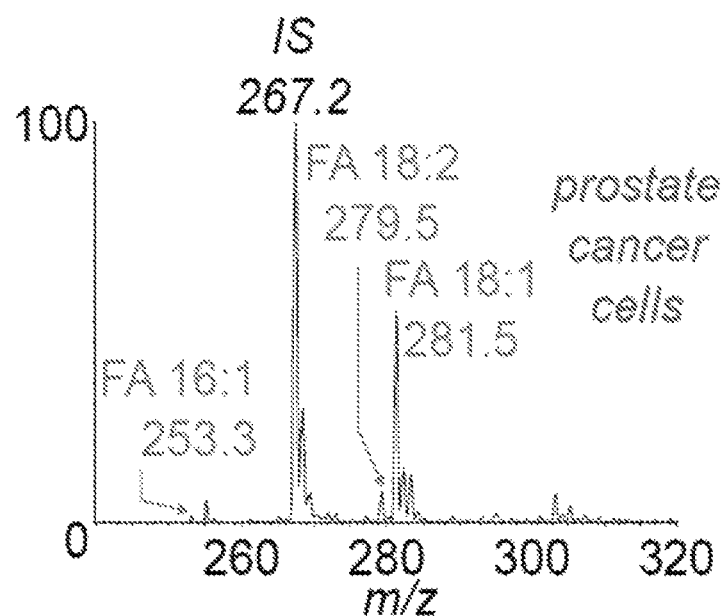
Figure 74A:
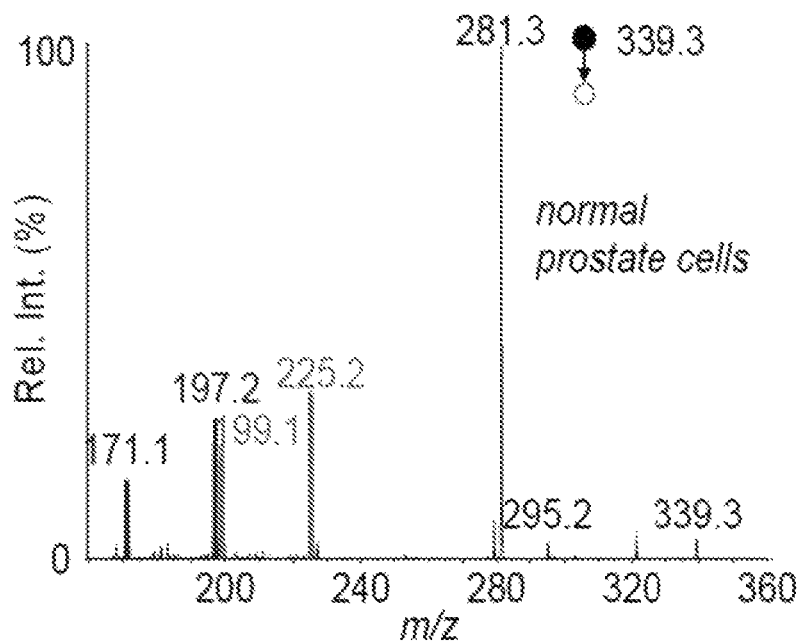
FIGS. 74A-B show FA 18:1 in normal and cancerous human prostate cells is a mixture of 9Z and 11Z isomers.
Figure 74B:
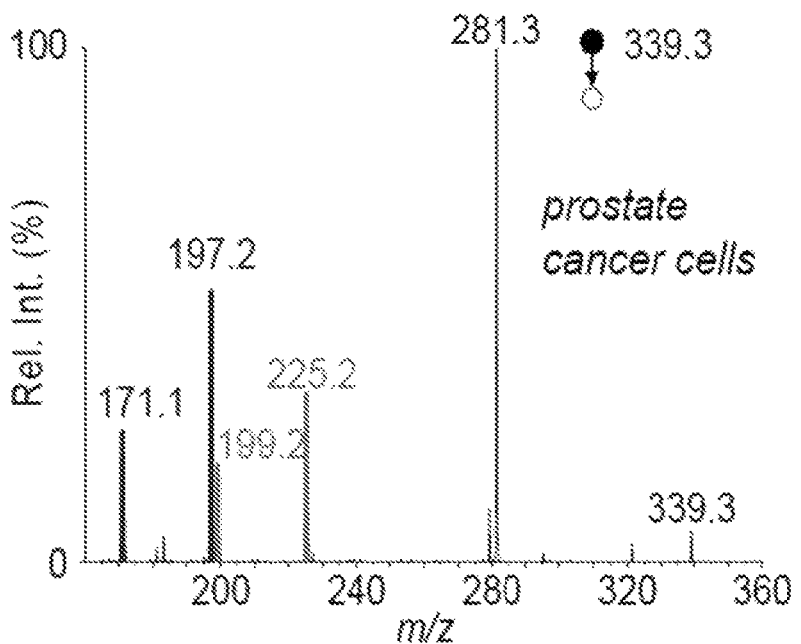
Figure 75:
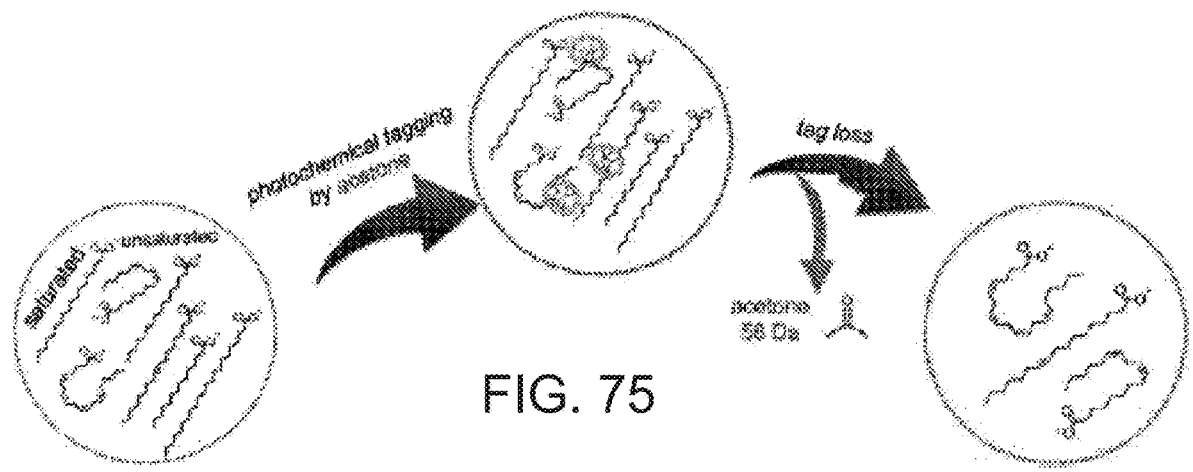
FIG. 75 illustrates a method for the highly selective quantitation of unsaturated fatty acids entails the use of photochemical reaction and tandem mass spectrometry. Such a method can be directly applied to fatty acid analysis in complex bio-samples in a shotgun lipidomics approach.

Unsaturated FAs in normal and cancerous prostate cells were analyzed as shown in FIGS. 73 and 74.

What is claimed:

1. A method for analyzing a tissue sample, the method comprising:
   obtaining a tissue sample comprising an unsaturated compound;
   conducting a radical reaction on the tissue sample that targets a carbon-carbon double bond within the unsaturated compound to thereby produce a plurality of compound isomers;
   subjecting the plurality of compound isomers to mass spectrometry analysis to identify a location of the carbon-carbon double bond within the unsaturated compound; and
   quantifying the plurality of compound isomers in order to distinguish normal tissue from diseased tissue.

2. The method according to claim 1, wherein the unsaturated compound is a lipid or a fatty acid.

3. The method according to claim 1, wherein the radical reaction comprises exposing the unsaturated compound and reagents for the radical reaction to ultraviolet light.

4. The method according to claim 3, wherein the radical reaction is conducted while the unsaturated compound is within a mass spectrometry probe.

5. The method according to claim 4, wherein at least a portion of the mass spectrometry probe is transparent to ultraviolet light.

6. The method according to claim 5, wherein the mass spectrometry probe is composed of a material that is transparent to ultraviolet light at approximately 200 nm wavelength.

7. The method according to claim 3, wherein the radical reaction is conducted in a vessel and subsequent to the reaction, the compound isomers are transferred to a mass spectrometry probe.

8. The method according to claim 1, wherein the radical reaction is conducted in association with a high-pressure liquid chromatography system and reagents for the radical reaction are within an elution solvent.

9. The method according to claim 1, wherein the radical reaction is a Paternò-Büchi (PB) reaction.

10. The method according to claim 8, wherein the Paternò-Büchi (PB) reaction is conducted in a solvent mixture comprising acetone.

11. A method for analyzing a tissue sample, the method comprising:
   contacting a sampling probe to a tissue comprising an unsaturated compound in a manner in which the unsaturated compound is retained on the sampling probe;
   inserting the sampling probe into a hollow body, wherein reagents for a radical reaction are present within the hollow body and the radical reaction targets a carbon-carbon double bond within the unsaturated compound;
   conducting the radical reaction within the hollow body to produce reaction products;
   emitting the reaction products from a distal tip of the hollow body; and
   analyzing the emitted reaction products in a mass spectrometer in order to identify a location of the carbon-carbon double bond within the unsaturated compound.

12. The method according to claim 11, wherein the unsaturated compound is a lipid or a fatty acid.

13. The method according to claim 11, wherein the sampling probe comprises a needle.

14. The method according to claim 13, wherein the radical reaction comprises exposing the unsaturated compound and reagents for the radical reaction to ultraviolet light.

15. The method according to claim 14, wherein the unsaturated compound is flowing through the hollow body while the reaction is being conducted.

16. The method according to claim 15, wherein at least some of the hollow body is transparent to ultraviolet light.

17. The method according to claim 16, wherein the hollow body composed of a material that is transparent to ultraviolet light at approximately 200 nm wavelength.

18. The method according to claim 17, wherein the hollow body is composed of quartz glass or fused silica.

19. The method according to claim 11, wherein the radical reaction is a Paternò-Büchi (PB) reaction.

20. The method according to claim 19, wherein the Paternò-Büchi (PB) reaction is conducted in a solvent mixture comprising acetone.

* * * * *